(12) United States Patent
Liu et al.

(10) Patent No.: US 11,169,101 B2
(45) Date of Patent: Nov. 9, 2021

(54) OLIGOSACCHARIDE COMPOSITIONS AND METHODS OF USE THEREOF

(71) Applicant: Kaleido Biosciences, Inc., Lexington, MA (US)

(72) Inventors: Christopher Matthew Liu, Somerville, MA (US); Anastasia Lioubomirov, San Jose, CA (US); John M. Geremia, Watertown, MA (US); Mitchell Antalek, Lexington, MA (US); Jonathan Lawrence, Lexington, MA (US); Tatyana Yatsunenko, Lexington, MA (US); Brian Meehan, Lexington, MA (US)

(73) Assignee: Kaleido Biosciences, Inc., Lexington, MA (US)

( * ) Notice: Subject to any disclaimer, the term of this patent is extended or adjusted under 35 U.S.C. 154(b) by 0 days.

(21) Appl. No.: 17/157,292

(22) Filed: Jan. 25, 2021

(65) Prior Publication Data
US 2021/0164926 A1    Jun. 3, 2021

Related U.S. Application Data

(63) Continuation of application No. PCT/US2019/060626, filed on Nov. 8, 2019.

(60) Provisional application No. 62/845,299, filed on May 8, 2019, provisional application No. 62/757,716, filed on Nov. 8, 2018.

(51) Int. Cl.
G01N 24/08   (2006.01)
C07H 1/00    (2006.01)
C07H 3/06    (2006.01)

(52) U.S. Cl.
CPC ............. G01N 24/088 (2013.01); C07H 1/00 (2013.01); C07H 3/06 (2013.01)

(58) Field of Classification Search
CPC ... C07H 3/04; C07H 3/06; C07H 1/00; G01N 24/088
See application file for complete search history.

(56) References Cited

U.S. PATENT DOCUMENTS

| | | | |
|---|---|---|---|
| 5,085,883 A | 2/1992 | Garleb et al. | |
| 6,559,302 B1 | 5/2003 | Shah et al. | |
| 9,079,171 B2 | 7/2015 | Geremia et al. | |
| 9,487,764 B2 | 11/2016 | Falb et al. | |
| 9,492,473 B2 | 11/2016 | von Maltzahn et al. | |
| 9,757,403 B2 | 9/2017 | von Maltzahn et al. | |
| 9,901,595 B2 | 2/2018 | von Maltzahn et al. | |
| 10,314,853 B2 | 6/2019 | von Maltzahn et al. | |
| 10,702,542 B2 | 7/2020 | von Maltzahn et al. | |
| 10,881,676 B2 | 1/2021 | von Maltzahn et al. | |
| 2004/0235789 A1 | 11/2004 | Day et al. | |
| 2005/0004070 A1 | 1/2005 | Stahl et al. | |
| 2006/0257977 A1 | 11/2006 | Hamaker et al. | |
| 2016/0007642 A1 | 1/2016 | Geremia et al. | |
| 2016/0213702 A1 | 7/2016 | von Maltzahn et al. | |
| 2016/0366909 A1 | 12/2016 | Geremia et al. | |
| 2017/0151268 A1 | 6/2017 | von Maltzahn et al. | |
| 2018/0037599 A1 | 2/2018 | Duflot et al. | |
| 2021/0113596 A1 | 4/2021 | von Maltzahn et al. | |

FOREIGN PATENT DOCUMENTS

| | | | |
|---|---|---|---|
| EP | | 2248907 A1 | 11/2010 |
| WO | WO | 1998/041544 A1 | 9/1998 |
| WO | WO | 2004/052121 A1 | 6/2004 |
| WO | WO | 2005/003329 A1 | 1/2005 |
| WO | WO | 2009/082214 A1 | 7/2009 |
| WO | WO | 2012/118767 A1 | 9/2012 |
| WO | WO | 2014/031956 A1 | 2/2014 |
| WO | WO | 2016/007778 A1 | 1/2016 |
| WO | WO | 2016/122884 A1 | 8/2016 |
| WO | WO | 2016/122885 A1 | 8/2016 |
| WO | WO | 2016/122889 A1 | 8/2016 |
| WO | WO | 2016/172657 A2 | 10/2016 |
| WO | WO | 2016/172658 A2 | 10/2016 |
| WO | WO | 2017/035412 A1 | 3/2017 |
| WO | WO | 2018/013871 A1 | 1/2018 |
| WO | WO | 2018/106845 A1 | 6/2018 |
| WO | WO | 2019/090181 A1 | 5/2019 |

OTHER PUBLICATIONS de Souza et al., Chemical Engineering and Processing, 2010, 49, p. 1137-1143. (Year: 2010).*
Lundborg et al., Anal. Chem. 2011, 83, p. 1514-1517, URL: http:/www.casper.organ.su.se/casper/. (Year: 2011).*
Schulze et al., Nahrung., 1991, 35(9), p. 903-920, English abstract only. (Year: 1991).*
Invitation to Pay Additional Fees for Application No. PCT/US2019/060626, mailed Feb. 19, 2020.
International Search Report and Written Opinion for Application No. PCT/US2019/060626, dated Jul. 1, 2020.
International Preliminary Report on Patentability for Application No. PCT/US2019/060626, dated May 20, 2021.
Arn et al., Hyperammonemia in women with a mutation at the ornithine carbamoyltransferase locus. A cause of postpartum coma. N Engl J Med. Jun. 7, 1990;322(23): 1652-5. doi: 10.1056/NEJM199006073222307.
Boltje et al., Opportunities and challenges in synthetic oligosaccharide and glycoconjugate research. Nat Chem. Nov. 2009; 1(8):611-22. doi: 10.1038/nchem.399. Author Manuscript.

(Continued)

*Primary Examiner* — Jonathan S Lau

(74) *Attorney, Agent, or Firm* — Wolf, Greenfield & Sacks, P.C.

(57) ABSTRACT

Aspects of the disclosure relate to oligosaccharide compositions and methods of making the same. Also provided are methods of using oligosaccharide compositions as microbiome metabolic therapies for reducing ammonia levels and for the treatment of related diseases.

22 Claims, 13 Drawing Sheets

(56) References Cited

OTHER PUBLICATIONS

Braissant et al., Current concepts in the pathogenesis of urea cycle disorders. Mol Genet Metab. 2010;100 Suppl 1:S3-S 12. doi: 10.1016/j.ymgme.2010.02.010. Epub Feb. 14, 2010.

Burton, Inborn errors of metabolism in infancy: a guide to diagnosis. Pediatrics. Dec. 1998;102(6):E69. doi: 10.1542/peds.102.6.e69.

Caporaso et al., Ultra-high-throughput microbial community analysis on the Illumina HiSeq and MiSeq platforms. ISME J. Aug. 2012;6(8):1621-4. doi: 10.1038/ismej.2012.8. Epub Mar. 8, 2012.

Cavicchi et al., Hypocitrullinemia in expanded newborn screening by LC-MS/MS is not a reliable marker for ornithine transcarbamylase deficiency. J Pharm Biomed Anal. Jul. 12, 2009;49(5): 1292-5. doi: 10.1016/j.jpba.2009.03.001. Epub Mar. 20, 2009.

Cordwell et al., Exploring and exploiting bacterial proteomes. Methods Mol Biol. 2004;266:115-35. doi: 10.1385/1-59259-763-7:115.

Darmaun et al., Phenylbutyrate-induced glutamine depletion in humans: effect on leucine metabolism. Am J Physiol. May 1998;274(5):E801-7. doi: 10.1152/ajpendo.1998.274.5.E801.

De Preter et al., Effect of lactulose and *Saccharomyces boulardii* administration on the colonic urea-nitrogen metabolism and the bifidobacteria concentration in healthy human subjects. Aliment Pharmacol Ther. Apr. 1, 2006;23(7):963-74. doi: 10.1111/j.1365-2036.2006.02834.x.

Díez-Municio et al., Synthesis of novel bioactive lactose-derived oligosaccharides by microbial glycoside hydrolases. Microb Biotechnol. Jul. 2014;7(4):315-31. doi: 10.1111/1751-7915.12124. Epub Apr. 1, 2014.

Gibson et al., Dietary modulation of the human colonic microbiota: introducing the concept of prebiotics. J Nutr. Jun. 1995;125(6):1401-12. doi: 10.1093/jn/125.6.1401.

Guerrero et al., Purification of highly concentrated galacto-oligosaccharide preparations by selective fermentation with yeasts. International Dairy Journal. Nov. 2014;39(1):78-88. doi.org/10.1016/j.idairyj.2014.05.011.

Heiss et al., The structure of Cryptococcus neoformans galactoxylomannan contains beta-D-glucuronic acid. Carbohydr Res. May 12, 2009;344(7):915-20. doi: 10.1016/j.carres.2009.03.003. Epub Mar. 10, 2009.

Huang et al., Tandem mass neonatal screening in Taiwan—report from one center. J Formos Med Assoc. Nov. 2006;105(11):882-6. doi: 10.1016/S0929-6646(09)60173-X.

Kailemia et al., Oligosaccharide analysis by mass spectrometry: a review of recent developments. Anal Chem. Jan. 7, 2014;86(1):196-212. doi: 10.1021/ac403969n. Epub Dec. 16, 2013. Author Manuscript. 31 pages.

Kuechel et al., Short communication: Development of a rapid laboratory method to polymerize lactose to nondigestible carbohydrates. J Dairy Sci. Apr. 2018;101(4):2862-2866. doi: 10.3168/jds.2017-13813. Epub Feb. 7, 2018.

Lee et al., In vivo urea cycle flux distinguishes and correlates with phenotypic severity in disorders of the urea cycle. Proc Natl Acad Sci U S A. Jul. 5, 2000;97(14):8021-6. doi: 10.1073/pnas.140602197.

Maestri et al., The phenotype of ostensibly healthy women who are carriers for ornithine transcarbamylase deficiency. Medicine (Baltimore). Nov. 1998;77(6):389-97.

McCleary et al., Determination of insoluble, soluble, and total dietary fiber (CODEX definition) by enzymatic-gravimetric method and liquid chromatography: collaborative study. J AOAC Int. May-Jun. 2012;95(3):824-44. doi: 10.5740/jaoacint.cs2011_25.

McCleary et al., Determination of total dietary fiber (CODEX definition) by enzymatic-gravimetric method and liquid chromatography: collaborative study. J AOAC Int. Jan.-Feb. 2010;93(1):221-33.

Miles et al., Hepatocyte glycogen accumulation in patients undergoing dietary management of urea cycle defects mimics storage disease. J Pediatr Gastroenterol Nutr. Apr. 2005;40(4):471-6. doi: 10.1097/01.mpg.0000157200.33486.ce.

Niroomand et al., Fate of bacterial pathogens and indicator organisms in liquid sweeteners. J Food Prot. Mar. 1998;61(3):295-9. doi: 10.4315/0362-028x-61.3.295.

Paik et al., Comparison of rifaximin and lactulose for the treatment of hepatic encephalopathy: a prospective randomized study. Yonsei Med J. Jun. 30, 2005;46(3):399-407. doi: 10.3349/ymj.2005.46.3.399.

Palframan et al., Development of a quantitative tool for the comparison of the prebiotic effect of dietary oligosaccharides. Lett Appl Microbiol. 2003;37(4):281-4. doi: 10.1046/j.1472-765x.2003.01398.x.

Pinelo et al., Membrane technology for purification of enzymatically produced oligosaccharides: Molecular and operational features affecting performance. Separation and Purification Technology. Nov. 19, 2009;70(1):1-11. doi.org/10.1016/j.seppur.2009.08.010.

Quinonez et al., Citrullinemia Type I. GeneReviews. Adam MP, Ardinger HH, Pagon RA, et al., editors. Seattle (WA): University of Washington, Seattle; 1993-2021. Retrieved from www.ncbi.nlm.nih.gov/books/NBK1458. Accessed on Jun. 14, 2011. 19 pages.

Romero-Gomez et al., Gut ammonia production and its modulation. Metab Brain Dis. Mar. 2009;24(1):147-57. doi: 10.1007/s11011-008-9124-3. Epub Dec. 10, 2008.

Sajilata et al., Resistant Starch—A Review. Compr Rev Food Sci Food Saf. Jan. 2006;5(1):1-17. doi: 10.1111/j.1541-4337.2006.tb00076.x.

Scaglia et al., Clinical consequences of urea cycle enzyme deficiencies and potential links to arginine and nitric oxide metabolism. J Nutr. Oct. 2004;134(10 Suppl):2775S-2782S; discussion 2796S-2797S. doi: 10.1093/jn/134.10.2775S.

Schaefer et al., Dialysis in neonates with inborn errors of metabolism. Nephrol Dial Transplant. Apr. 1999;14(4):910-8. doi: 10.1093/ndt/14.4.910.

Seeberger et al., Solid-phase oligosaccharide synthesis and combinatorial carbohydrate libraries. Chem Rev. Dec. 13, 2000;100(12):4349-94. doi: 10.1021/cr9903104.

Sen et al., Galactosyl oligosaccharide purification by ethanol precipitation. Food Chemistry. Oct. 1, 2011;128(3):773-777. doi.org/10.1016/j.foodchem.2011.03.076.

Sharma et al., Randomized controlled trial comparing lactulose plus albumin versus lactulose alone for treatment of hepatic encephalopathy. J Gastroenterol Hepatol. Jun. 2017;32(6):1234-1239. doi: 10.1111/jgh.13666.

Shchelochkov et al., High-frequency detection of deletions and variable rearrangements at the ornithine transcarbamylase (OTC) locus by oligonucleotide array CGH. Mol Genet Metab. Mar. 2009;96(3):97-105. doi: 10.1016/j.ymgme.2008.11.167. Epub Jan. 12, 2009.

Sreenath Nagamani et al., Argininosuccinate Lyase Deficiency. GeneReviews. Adam MP, Ardinger HH, Pagon RA, et al., editors. Seattle (WA): University of Washington, Seattle; 1993-2021. Retrieved from www.ncbi.nlm.nih.gov/books/NBK51784. Accessed on Jun. 14, 2011. 24 pages.

Summar et al., Current strategies for the management of neonatal urea cycle disorders. J Pediatr. Jan. 2001;138(1 Suppl):S30-9. doi: 10.1067/mpd.2001.111834.

Summar et al., Diagnosis, symptoms, frequency and mortality of 260 patients with urea cycle disorders from a 21-year, multicentre study of acute hyperammonaemic episodes. Acta Paediatr. Oct. 2008;97(10):1420-5. doi: 10.1111/j.1651-2227.2008.00952.x. Epub Jul. 17, 2008. Author Manuscript.

Summar et al., Proceedings of a consensus conference for the management of patients with urea cycle disorders. J Pediatr. Jan. 2001;138(1 Suppl):S6-10. doi: 10.1067/mpd.2001.111831.

Sun et al., Arginase Deficiency. GeneReviews. Adam MP, Ardinger HH, Pagon RA, et al., editors. Seattle (WA): University of Washington, Seattle; 1993-2021. Retrieved from ncbi.nlm.nih.gov/books/NBK1159. Accessed on Jun. 14, 2011. 23 pages.

Theriot et al., Antibiotic-induced shifts in the mouse gut microbiome and metabolome increase susceptibility to Clostridium difficile infection. Nat Commun. 2014;5:3114. doi: 10.1038/ncomms4114. Author Manuscript.

(56) References Cited

OTHER PUBLICATIONS

Titgemeyer et al., Fermentability of various fiber sources by human fecal bacteria in vitro. Am J Clin Nutr. Jun. 1991;53(6):1418-24. doi: 10.1093/ajcn/53.6.1418.

Tuchman et al., Blood levels of ammonia and nitrogen scavenging amino acids in patients with inherited hyperammonemia. Mol Genet Metab. Jan. 1999;66(1):10-5. doi: 10.1006/mgme.1998.2783.

Vanneste et al., Techno-economic evaluation of membrane cascades relative to simulated moving bed chromatography for the purification of mono- and oligosaccharides. Separation and Purification Technology. Aug. 18, 2011;80(3):600-609. doi.org/10.1016/j.seppur.2011.06.016.

Vera et al., Synthesis and purification of galacto-oligosaccharides: state of the art. World J Microbiol Biotechnol. Dec. 2016;32(12):197. doi: 10.1007/s11274-016-2159-4. Epub Oct. 18, 2016. 20 pages.

Wang et al., Naive Bayesian classifier for rapid assignment of rRNA sequences into the new bacterial taxonomy. Appl Environ Microbiol. Aug. 2007;73(16):5261-7. doi: 10.1128/AEM.00062-07. Epub Jun. 22, 2007.

Xiao et al., Chemical synthesis of polysaccharides and polysaccharide mimetics. Prog Poly Science. Nov. 2017;74:78-116. doi: 10.1016/j.progpolymsci.2017.07.009.

Zeuner et al., Methods for improving enzymatic trans-glycosylation for synthesis of human milk oligosaccharide biomimetics. J Agric Food Chem. Oct. 8, 2014;62(40):9615-31. doi: 10.1021/jf502619p. Epub Sep. 23, 2014.

Zhao et al., Rapid, sensitive structure analysis of oligosaccharides. Proc Natl Acad Sci U S A. Mar. 4, 1997;94(5):1629-33. doi: 10.1073/pnas.94.5.1629.

\* cited by examiner

OLIGOSACCHARIDE COMPOSITIONS AND METHODS OF USE THEREOF

RELATED APPLICATIONS

This application is a continuation of International PCT Application No. PCT/US2019/060626, filed Nov. 8, 2019, which claims priority under 35 U.S.C. § 119(e) of U.S. Provisional Application No. 62/845,299, filed May 8, 2019, and U.S. Provisional Application No. 62/757,716, filed Nov. 8, 2018, each of which is incorporated by reference herein in its entirety.

FIELD OF THE INVENTION

The present disclosure relates to oligosaccharide compositions and uses thereof.

BACKGROUND OF INVENTION

The gut microbiome, the ecosystem of about one hundred trillion ($1 \times 10^{14}$) microbial cells in the intestine, can be regarded as an important organ of the human body, responsible for functions that human cells cannot carry out independently. The gut microbiota play a key role in human health and disease by affecting nutrient utilization, colonization resistance, development of the immune system, modulation of the host metabolism, and other diverse aspects of the host's physiology.

One example of the gut microbiota's contribution to the host's metabolic capabilities concerns nitrogen utilization. The colon is rich in nitrogen sources, which include mucin, urea, and dietary amino acids that have escaped host digestion. Some gut microbes can liberate ammonia from these molecules and incorporate this ammonia into bacterial biomolecules like proteins and nucleic acids. However, the amount of ammonia liberated often exceeds the metabolic requirements of these gut bacteria, which causes ammonia to accumulate in the gut. Under non-acidic conditions this ammonia diffuses across the gut epithelium into the portal circulation, potentially making a significant contribution to the elevated ammonia levels in hyperammonemic patients, including patients with hepatic encephalopathy. These patients can have serious neurological symptoms and are more susceptible to infections by pathogens. As a result, there is a need for additional treatment options for hyperammonemic patients.

SUMMARY OF INVENTION

According to some aspects, provided herein are microbiome metabolic therapies utilizing oligosaccharide compositions that are useful for driving functional outputs of the gut microbiome organ, e.g., to treat disease and improve overall health. In some embodiments, such oligosaccharide compositions are particularly effective for reducing ammonia levels in a subjects. Accordingly, in some embodiments oligosaccharide compositions disclosed herein are useful for treating subject having disorders associated with hyperammonemia, hepatic encephalopathy (HE) and/or cirrhosis. In some embodiments, such oligosaccharide compositions are particularly effective for reducing the acquisition of, colonization of, or reducing the reservoir of a pathogen (e.g., a drug or antibiotic resistant pathogen, or an MDR pathogen) in a subject, e.g., by modulating the relative abundance of commensal microbial populations. For example, in some embodiments oligosaccharide compositions disclosed herein are useful for treating subject having intestinal colonization with a pathogen, e.g., extended-spectrum beta-lactamase (ESBL) producing microorganisms, carbapenem-resistant Enterobacteriaceae (CRE), and/or vancomycin-resistant Enterococci (VRE).

In some aspects, provided herein are oligosaccharide compositions comprising a plurality of oligosaccharides, each composition being characterized by a multiplicity-edited gradient-enhanced $^{1}\text{H}$-$^{13}\text{C}$ heteronuclear single quantum correlation (HSQC) NMR spectrum comprising signals 1 to 11:

| Signal | Center Position (ppm) $^{1}\text{H}$ | $^{13}\text{C}$ | Area under the curve (AUC) (% of total areas of signals 1-11) |
|---|---|---|---|
| 1 | 3.67 | 63.35 | 18.67-26.54 |
| 2 | 3.97 | 66.25 | 4.46-7.34 |
| 3 | 3.88 | 67.13 | 2.39-4.52 |
| 4 | 3.71 | 67.34 | 6.06-8.68 |
| 5 | 3.83 | 71.27 | 5.18-8.84 |
| 6 | 3.96 | 71.58 | 5.40-8.38 |
| 7 | 3.72 | 72.4 | 5.57-11.87 |
| 8 | 3.33 | 73.76 | 12.44-19.14 |
| 9 | 4.06 | 77.39 | 4.19-9.48 |
| 10 | 4.11 | 81.73 | 4.01-6.81 |
| 11 | 4.51 | 103.34 | 7.98-11.84 |

In some embodiments, any one or all of signals 1-11 are defined as follows:

| Signal | Center Position (ppm) $^{1}\text{H}$ | $^{13}\text{C}$ | Area under the curve (AUC) (% of total areas of signals 1-11) |
|---|---|---|---|
| 1 | 3.67 | 63.35 | 20.25-24.97 |
| 2 | 3.97 | 66.25 | 5.03-6.76 |
| 3 | 3.88 | 67.13 | 2.82-4.09 |
| 4 | 3.71 | 67.34 | 6.59-8.15 |
| 5 | 3.83 | 71.27 | 5.91-8.11 |
| 6 | 3.96 | 71.58 | 5.99-7.78 |
| 7 | 3.72 | 72.4 | 6.83-10.61 |
| 8 | 3.33 | 73.76 | 13.78-17.80 |
| 9 | 4.06 | 77.39 | 5.25-8.42 |
| 10 | 4.11 | 81.73 | 4.57-6.25 |
| 11 | 4.51 | 103.34 | 8.75-11.07 |

In some embodiments, any one or all of signals 1-11 are defined as follows:

| Signal | Center Position (ppm) $^{1}\text{H}$ | $^{13}\text{C}$ | Area under the curve (AUC) (% of total areas of signals 1-11) |
|---|---|---|---|
| 1 | 3.67 | 63.35 | 20.23-21.61 |
| 2 | 3.97 | 66.25 | 5.26-6.25 |
| 3 | 3.88 | 67.13 | 3.13-3.57 |
| 4 | 3.71 | 67.34 | 6.72-7.41 |
| 5 | 3.83 | 71.27 | 6.96-8.43 |
| 6 | 3.96 | 71.58 | 6.84-7.62 |
| 7 | 3.72 | 72.4 | 9.07-10.88 |
| 8 | 3.33 | 73.76 | 16.01-17.29 |
| 9 | 4.06 | 77.39 | 5.56-6.60 |
| 10 | 4.11 | 81.73 | 4.75-5.02 |
| 11 | 4.51 | 103.34 | 9.78-11.14 |

In some aspects, provided herein are oligosaccharide compositions comprising a plurality of oligosaccharides, each composition being characterized by a multiplicity-edited gradient-enhanced $^1$H-$^{13}$C heteronuclear single quantum correlation (HSQC) NMR spectrum comprising at least one or all signal(s) selected from signals 1, 2, 4, 5, 7, 9, 10, and 11:

| | Center Position (ppm) | | Area under the curve (AUC) |
|---|---|---|---|
| Signal | $^1$H | $^{13}$C | (% of total areas of signals 1-11) |
| 1 | 3.67 | 63.35 | 18.67-26.54 |
| 2 | 3.97 | 66.25 | 4.46-7.34 |
| 3 | 3.88 | 67.13 | 2.39-4.52 |
| 4 | 3.71 | 67.34 | 6.06-8.68 |
| 5 | 3.83 | 71.27 | 5.18-8.84 |
| 6 | 3.96 | 71.58 | 5.40-8.38 |
| 7 | 3.72 | 72.4 | 5.57-11.87 |
| 8 | 3.33 | 73.76 | 12.44-19.14 |
| 9 | 4.06 | 77.39 | 4.19-9.48 |
| 10 | 4.11 | 81.73 | 4.01-6.81 |
| 11 | 4.51 | 103.34 | 7.98-11.84 |

In some embodiments, any or all of signals 1, 2, 4, 5, 7, 9, 10, and 11 are defined as follows:

| | Center Position (ppm) | | Area under the curve (AUC) |
|---|---|---|---|
| Signal | $^1$H | $^{13}$C | (% of total areas of signals 1-11) |
| 1 | 3.67 | 63.35 | 20.25-24.97 |
| 2 | 3.97 | 66.25 | 5.03-6.76 |
| 4 | 3.71 | 67.34 | 6.59-8.15 |
| 5 | 3.83 | 71.27 | 5.91-8.11 |
| 7 | 3.72 | 72.4 | 6.83-10.61 |
| 9 | 4.06 | 77.39 | 5.25-8.42 |
| 10 | 4.11 | 81.73 | 4.57-6.25 |
| 11 | 4.51 | 103.34 | 8.75-11.07 |

In some embodiments, any or all of signals 1, 2, 4, 5, 7, 9, 10, and 11 are defined as follows:

| | Center Position (ppm) | | Area under the curve (AUC) |
|---|---|---|---|
| Signal | $^1$H | $^{13}$C | (% of total areas of signals 1-11) |
| 1 | 3.67 | 63.35 | 20.23-21.61 |
| 2 | 3.97 | 66.25 | 5.26-6.25 |
| 4 | 3.71 | 67.34 | 6.72-7.41 |
| 5 | 3.83 | 71.27 | 6.96-8.43 |
| 7 | 3.72 | 72.4 | 9.07-10.88 |
| 9 | 4.06 | 77.39 | 5.56-6.60 |
| 10 | 4.11 | 81.73 | 4.75-5.02 |
| 11 | 4.51 | 103.34 | 9.78-11.14 |

In some embodiments, the NMR spectrum of the oligosaccharide composition comprises 2, 3, 4, 5, 6, 7, or 8 signals selected from signals 1, 2, 4, 5, 7, 9, 10, and 11, wherein the NMR spectrum comprises at least signals 4 and 5. In some embodiments, the NMR spectrum further comprises 1-3 signals selected from signals 3, 6, and 8.

In some aspects, provided herein are oligosaccharide compositions comprising a plurality of oligosaccharides, each composition being characterized by a multiplicity-edited gradient-enhanced $^1$H-$^{13}$C heteronuclear single quantum correlation (HSQC) NMR spectrum comprising at least one or all signal(s) selected from signals 5, 6, 7, 8, and 11:

| | Center Position (ppm) | | Area under the curve (AUC) |
|---|---|---|---|
| Signal | $^1$H | $^{13}$C | (% of total areas of signals 1-11) |
| 5 | 3.83 | 71.27 | 5.18-8.84 |
| 6 | 3.96 | 71.58 | 5.40-8.38 |
| 7 | 3.72 | 72.4 | 5.57-11.87 |
| 8 | 3.33 | 73.76 | 12.44-19.14 |
| 11 | 4.51 | 103.34 | 7.98-11.84 |

In some embodiments, the NMR spectrum further comprises:

| | Center Position (ppm) | | Area under the curve (AUC) |
|---|---|---|---|
| Signal | $^1$H | $^{13}$C | (% of total areas of signals 1-11) |
| 1 | 3.67 | 63.35 | 18.67-26.54 |
| 4 | 3.71 | 67.34 | 6.06-8.68 |

In some embodiments, signals 1-11 are each further characterized by an $^1$H integral region and a $^{13}$C integral region, defined as follows:

| | $^1$H Position (ppm) | | | $^{13}$C Position (ppm) | | |
|---|---|---|---|---|---|---|
| | Center | $^1$H Integral Region | | Center | $^{13}$C Integral Region | |
| Signal | Position | from | to | Position | from | to |
| 1 | 3.67 | 3.607 | 3.742 | 63.35 | 63.78 | 62.92 |
| 2 | 3.97 | 3.925 | 4.008 | 66.25 | 66.78 | 65.73 |
| 3 | 3.88 | 3.848 | 3.910 | 67.13 | 67.50 | 66.76 |
| 4 | 3.71 | 3.674 | 3.753 | 67.34 | 68.02 | 66.65 |
| 5 | 3.83 | 3.791 | 3.864 | 71.27 | 71.70 | 70.84 |
| 6 | 3.96 | 3.906 | 4.014 | 71.58 | 71.91 | 71.24 |
| 7 | 3.72 | 3.669 | 3.777 | 72.4 | 72.78 | 72.02 |
| 8 | 3.33 | 3.262 | 3.404 | 73.76 | 74.29 | 73.23 |
| 9 | 4.06 | 4.022 | 4.108 | 77.39 | 77.89 | 76.90 |
| 10 | 4.11 | 4.066 | 4.147 | 81.73 | 82.15 | 81.32 |
| 11 | 4.51 | 4.461 | 4.556 | 103.34 | 103.95 | 102.72 |

In some embodiments, the NMR spectrum of an oligosaccharide composition of the disclosure is obtained by subjecting a sample of the composition to a multiplicity-edited gradient-enhanced $^1$H-$^{13}$C heteronuclear single quantum coherence (HSQC) experiment using an echo-antiecho scheme for coherence selection using the pulse sequence diagram as described in FIG. 10, and the following acquisition parameters and processing parameters:

Acquisition Parameters
$^1$H Carrier Frequency=4 ppm
$^{13}$C Carrier Frequency=65 ppm
Number of points in acquisition dimension=596
Spectral range in acquisition dimension=6.00 ppm to 2.03 ppm
Number of points in indirect dimension=300 complex points
Spectral range in indirect dimension=120 ppm to 10 ppm
Recycle delay=1 second
One-bond $^1$H-$^{13}$C coupling constant=$J_{CH}$=146 Hz
Number of scans=8
Temperature=298 K
Solvent=$D_2O$
  Processing Parameters
Window function in direct dimension=Gaussian broadening, 7.66 Hz
Window function in indirect dimension=Gaussian broadening 26.48 Hz Processing=512 complex points in direct dimension, 1024 complex points in indirect dimension In some embodiments, the NMR spectrum is obtained by subjecting a sample of the composition to HSQC NMR, wherein the sample is dissolved in D$_2$O.

In some embodiments, the mean degree of polymerization (DP) of the oligosaccharide composition is from about DP6 to about DP14. In some embodiments, the mean degree of polymerization (DP) of the oligosaccharide composition is from about DP6 to about DP12. In some embodiments, the mean degree of polymerization (DP) of the oligosaccharide composition is from about DP6 to about DP11. In some embodiments, the mean degree of polymerization (DP) of the oligosaccharide composition is from about DP8 to about DP14. In some embodiments, the mean degree of polymerization (DP) of the oligosaccharide composition is from about DP8 to about DP9.

In some embodiments, the oligosaccharides in the oligosaccharide composition have a MWw (g/mol) in a range of about 970 to about 2270. In some embodiments, the oligosaccharides in the oligosaccharide composition have a MWw (g/mol) in a range of about 970 to about 1950. In some embodiments, the oligosaccharides in the oligosaccharide composition have a MWw (g/mol) in a range of about 1300 to about 1450. In some embodiments, the oligosaccharides in the oligosaccharide composition have a MWn (g/mol) in a range of about 680-1200. In some embodiments, the oligosaccharides in the oligosaccharide composition have a MWn (g/mol) in a range of about 725-1215.

In some embodiments, the oligosaccharide composition comprises 5% to 40% dextrose equivalent (dry basis). In some embodiments, the oligosaccharide composition comprises 15% to 25% dextrose equivalent (dry basis). In some embodiments, the oligosaccharide composition comprises 55% to 95% total dietary fiber (dry basis). In some embodiments, the oligosaccharide composition comprises at least 75% and less than 90% total dietary fiber (dry basis). In some embodiments, the oligosaccharide composition comprises at least 55%, 60%, 70%, 80%, or 90% total dietary fiber (dry basis).

In some embodiments, the oligosaccharide composition comprises oligosaccharides comprising glucose and galactose. In some embodiments, the ratio of glucose to galactose monomer units of the oligosaccharides in the composition is about 1:1. In some embodiments, the molar ratio of dextrose (e.g., dextrose monohydrate) to galactose (e.g., anhydrous galactose) is about 1:1.

In some embodiments, at least one oligosaccharide of the plurality of oligosaccharides comprises an at least one internal monomer unit selected from glucose.

In some embodiments, the oligosaccharide composition comprises at least 60% of oligosaccharides with a degree of polymerization (DP) of equal or greater than 3. In some embodiments, greater than 75% and less than 90% of the oligosaccharides of the oligosaccharide composition comprise a degree of polymerization (DP) of equal or greater than 3. In some embodiments, the oligosaccharide composition comprises at least 50% of oligosaccharides with a degree of polymerization (DP) of equal or greater than 4.

In some aspects, provided herein are oligosaccharide compositions comprising a plurality of oligosaccharides that comprise Formula (I) and Formula (II):

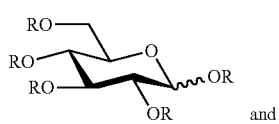

(I)

and

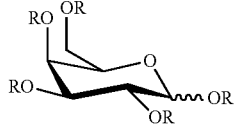

(II)

wherein R in Formula (I) and Formula (II) is independently selected from hydrogen, and Formulae (Ia), (Ib), (Ic), (Id), (IIa), (IIb), (IIc), (IId):

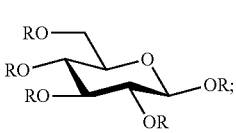

(Ia)

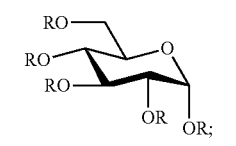

(Ib)

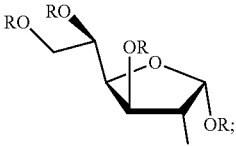

(Ic)

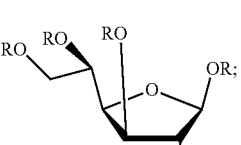

(Id)

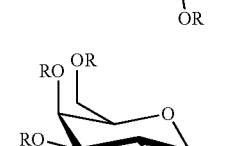

(IIa)

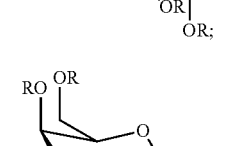

(IIb)

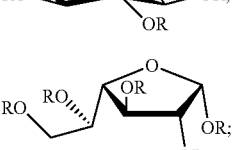

(IIc)

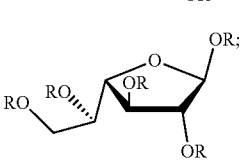

(IId)

wherein R in Formulae (Ia), (Ib), (Ic), (Id), (IIa), (IIb), (IIc), and (IId) is independently defined as above in Formula (I) and Formula (II);

wherein at least one oligosaccharide of the plurality of oligosaccharides comprises at least one internal monomer unit selected from the group consisting of Formulae (Ia), (Ib), (Ic), and (Id).

In some embodiments, at least 10% of the oligosaccharides comprise one or more internal monomer unit selected from the group consisting of Formulae (Ia), (Ib), (Ic), and (Id). In some embodiments, at least one oligosaccharide comprises two or more internal monomer units selected from the group consisting of Formulae (Ia), (Ib), (Ic), and (Id).

In some embodiments, the oligosaccharide composition is produced by a non-enzymatic catalyst. In some embodiments, the oligosaccharide composition further comprises an acid catalyst. In some embodiments, the oligosaccharide composition is produced in the presence of the acid catalyst. In some embodiments, the acid catalyst is a soluble acid catalyst. In some embodiments, the acid catalyst is citric acid.

In some embodiments, the plurality of oligosaccharides comprises about 50% (e.g., 40-60%) dextrose and about 50% (e.g., 40-60%) galactose.

In some embodiments, the oligosaccharide composition is a heterogenous preparation of oligosaccharides. In some embodiments, the oligosaccharide composition does not consist of oligonucleotides of the formula Galactose-(Galactose)n-Glucose. In some embodiments, the oligosaccharide composition does not consist of and does not consist essentially of oligonucleotides of the formula Galactose-(Galactose)n-Glucose. In some embodiments, the oligosaccharide composition does not consist of the formula Galactose-(Galactose)n-Glucose, wherein n is an integer reflecting the number of noted Galatose subunits. In some embodiments, n is in in the range of 0 to 8. In some embodiments, the oligosaccharide composition does not consist essentially of the formula Galactose-(Galactose)n-Glucose, optionally wherein n is an integer in the range of 0 to 8. In some embodiments, greater than 50% of the oligosaccharides in the oligosaccharide composition are not of the formula Galactose-(Galactose)n-Glucose, optionally wherein n is an integer in the range of 0 to 8. In some embodiments, greater than 50% of the oligosaccharides in the oligosaccharide composition are not of the formula Galactose-(Galactose)$_n$-Glucose, wherein n is an integer in the range of 0 to 8. In some embodiments, greater than 50% of the oligosaccharides in the oligosaccharide composition have a degree of polymerization (DP) of 3 or more. In some embodiments, greater than 60% of the oligosaccharides in the oligosaccharide composition have a degree of polymerization (DP) of 3 or more. In some embodiments, greater than 70% of the oligosaccharides in the oligosaccharide composition have a degree of polymerization (DP) of 3 or more. In some embodiments, greater than 75% and less than 90% of the oligosaccharides in the oligosaccharide composition have a degree of polypolymerization (DP) of 3 or more. In some embodiments, the oligosaccharide composition does not consist one or more of N-acetylglucosamine, N-acetylgalactosamine, fucose or sialic acid. In some embodiments, the mean degree of polymerization (DP) of the oligosaccharide composition is from about DP6 to about DP14. In some embodiments, the composition comprises 55% to 95% total dietary fiber (dry basis). In some embodiments, the composition comprises at least 75% and less than 90% total dietary fiber (dry basis).

In some embodiments, provided herein are oligosaccharide compositions comprising a plurality of oligosaccharides that comprise Formula (I) and Formula (II):

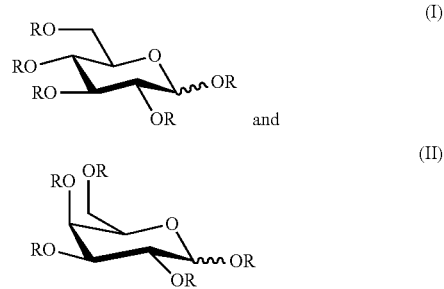

wherein R in Formula (I) and Formula (II) is independently selected from hydrogen, and Formulae (Ia), (Ib), (Ic), (Id), (IIa), (IIb), (IIc), (IId):

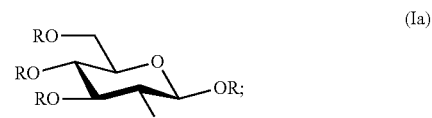

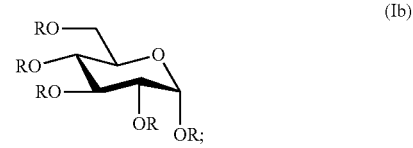

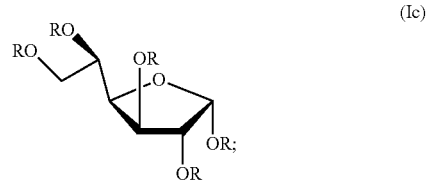

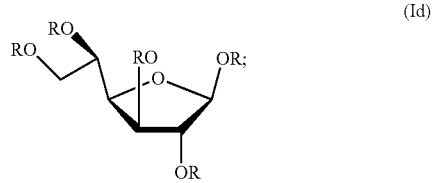

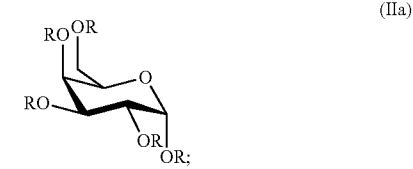

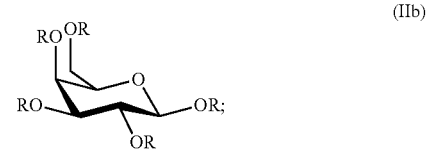

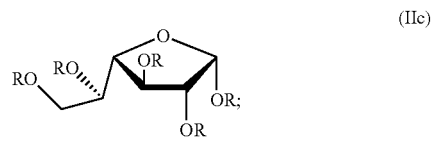

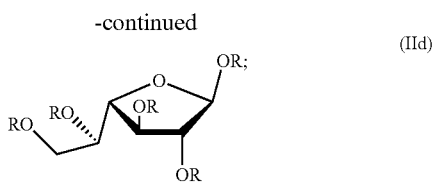

(IId)

wherein R in Formulae (Ia), (Ib), (Ic), (Id), (IIa), (IIb), (IIc), and (IId) is independently defined as above in Formula (I) and Formula (II);
wherein the oligosaccharide composition is produced by a process comprising:
(a) forming a reaction mixture comprising a dextrose preparation and a galactose preparation with a catalyst comprising acidic protons; and
(b) promoting acid catalyzed oligosaccharide formation in the reaction mixture by transferring sufficient heat to the reaction mixture to maintain the reaction mixture at its boiling point until the molar ratio of net water condensate produced by the reaction mixture relative to the total dextrose and galactose in the dextrose and galactose preparations prior to loading in (a) is in a range of 0.1-1.0, wherein the reaction mixture is maintained at a pressure in a range of 0.5-1.5 atm; and optionally
wherein at least one oligosaccharide of the plurality of oligosaccharides comprises at least one internal monomer unit selected from the group consisting of Formulae (Ia), (Ib), (Ic), and (Id).

In some embodiments, at least 10% of the oligosaccharides comprise one or more internal monomer unit selected from the group consisting of Formulae (Ia), (Ib), (Ic), and (Id). In some embodiments, at least one oligosaccharide comprises two or more internal monomer units selected from the group consisting of Formulae (Ia), (Ib), (Ic), and (Id).

In some embodiments, the process further comprises (c) quenching the reaction mixture using water while bringing the temperature of the reaction mixture to below 100° C. In some embodiments, step (b) further comprises removing water from the reaction mixture by evaporation. In some embodiments, in step (c) the water is deionized water. In some embodiments, in step (c) the water has a temperature of about 60-100° C. In some embodiments, in step (c) the water is added to the reaction mixture under conditions sufficient to avoid solidifying the mixture. In some embodiments, the reaction mixture is maintained at its boiling point until the molar ratio of net water condensate produced by the reaction mixture relative to the total dextrose and galactose in the dextrose and galactose preparations prior to loading in (a) is in a range of 0.3-0.9. In some embodiments, prior to step (b), the temperature of the reaction mixture is gradually increased from room temperature to the boiling point of the reaction mixture under suitable conditions to achieve homogeneity and uniform heat transfer. In some embodiments, the reaction mixture in step (a) comprises a molar ratio of glucose to galactose of about 1:1. In some embodiments, the reaction mixture in step (a) comprises a molar ratio of dextrose (e.g., dextrose monohydrate) and galactose (anhydrous galactose) of about 1:1.

In some embodiments, the catalyst is a solid acid catalyst. In some embodiments, the catalyst is a strong acid cation exchange resin having one or more physical and chemical properties according to Table 1 and/or wherein the catalyst comprises >3.0 mmol/g sulfonic acid moieties and <1.0 mmol/gram cationic moieties. In some embodiments, the catalyst has a nominal moisture content of 45-50 weight percent.

In some embodiments, the process further comprises: (d) separating at least a portion of the oligosaccharides from the acid catalyst. In some embodiments, in step (d) said separating comprises removing the catalyst by filtration. In some embodiments, step (d) comprises cooling the reaction mixture to below about 85° C. before filtering. In some embodiments, the process further comprises diluting the oligosaccharide composition of (d) with deionized water to a concentration of about 5-65 weight percent.

In some embodiments, the catalyst is a soluble acid catalyst. In some embodiments, the catalyst is citric acid. In some embodiments, in step (a), the catalyst is present in an amount such that the molar ratio of acidic protons to total dextrose and galactose is in a range of 0.001-0.25. In some embodiments, in step (a), the catalyst is present in an amount such that the molar ratio of acidic protons to total dextrose and galactose is in a range of 0.0016-0.022. In some embodiments, in step (a), the dextrose preparation comprises dextrose monomer. In some embodiments, in step (a), the galactose preparation comprises galactose monomer. In some embodiments, in step (a), the dextrose preparation comprises dextrose monohydrate or corn syrup (e.g., 70DS corn syrup). In some embodiments, in step (a), the galactose preparation comprises anhydrous galactose. In some embodiments, the reaction mixture of step (a) comprises dextrose monohydrate and anhydrous galactose. In some embodiments, in step (a), the dextrose preparation comprises lactose. In some embodiments, in step (a), the galactose preparation comprises lactose. In some embodiments, in step (a), the dextrose preparation and the galactose preparation comprise lactose.

In some embodiments, the plurality of oligosaccharides that comprise Formula (I) and Formula (II) comprise at least 60%, at least 70%, at least 80%, or at least 90% of the oligosaccharide composition. In some embodiments, the plurality of oligosaccharides that comprise Formula (I) and Formula (II) comprise at least 95% of the oligosaccharide composition. In some embodiments, the plurality of oligosaccharides that comprise Formula (I) and Formula (II) comprise at least 98% of the oligosaccharide composition. In some embodiments, the plurality of oligosaccharides that comprise Formula (I) and Formula (II) comprise 100% of the oligosaccharide composition.

In some embodiments, no more than 0.5%, 1%, 2%, 3%, 5%, 7%, or 10% of the oligosaccharide composition or the plurality of oligosaccharides—does not comprise Formula (I), Formula (II), or Formulae (Ia), (Ib), (Ic), (Id), (IIa), (IIb), (IIc), and (IId). In some embodiments, no more than 0.5% of the oligosaccharide composition or the plurality of oligosaccharides does not comprise Formula (I), Formula (II), or Formulae (Ia), (Ib), (Ic), (Id), (IIa), (IIb), (IIc), and (IId). In some embodiments, no more than 1% of the oligosaccharide composition or the plurality of oligosaccharides does not comprise Formula (I), Formula (II), or Formulae (Ia), (Ib), (Ic), (Id), (IIa), (IIb), (IIc), and (IId). In some embodiments, no more than 5% of the oligosaccharide composition or the plurality of oligosaccharides does not comprise Formula (I), Formula (II), or Formulae (Ia), (Ib), (Ic), (Id), (IIa), (IIb), (IIc), and (IId). In some embodiments, the oligosaccharide composition or the plurality of oligosaccharides do not comprise derivatized or chemically altered (e.g., degraded) sugar units (e.g., anhydro-forms). In some embodiments, the oligosaccharide composition comprises less than 0.5% derivatized or chemically altered (e.g., degraded) sugar units (e.g., anhydro-forms). In some embodiments, the plurality of oligosaccharides of the oligosaccharide composition comprise less than 0.5% anhydro-form sugar subunits, e.g., as determined by relative abundance or as measured by mass spectrometry. In some embodiments, the oligosaccharide composition comprises less than 1% derivatized or chemically altered (e.g., degraded) sugar units (e.g., anhydro-forms). In some embodiments, the plurality of oligosaccharides of the oligosaccharide composition comprise less than 1% anhydro-form sugar subunits, e.g., as determined by relative abundance or as measured by mass spectrometry. In some embodiments, the oligosaccharide composition comprises less than 2% derivatized or chemically altered (e.g., degraded) sugar units (e.g., anhydro-forms). In some embodiments, the plurality of oligosaccharides of the oligosaccharide composition comprise less than 2% anhydro-form sugar subunits, e.g., as determined by relative abundance or as measured by mass spectrometry. In some embodiments, the oligosaccharide composition comprises less than 3% derivatized or chemically altered (e.g., degraded) sugar units (e.g., anhydro-forms). In some embodiments, the plurality of oligosaccharides of the oligosaccharide composition comprise less than 3% anhydro-form sugar subunits, e.g., as determined by relative abundance or as measured by mass spectrometry. In some embodiments, the oligosaccharide composition comprises less than 5% derivatized or chemically altered (e.g., degraded) sugar units (e.g., anhydro-forms). In some embodiments, the plurality of oligosaccharides of the oligosaccharide composition comprise less than 5% anhydro-form sugar subunits, e.g., as determined by relative abundance or as measured by mass spectrometry. In some embodiments, the oligosaccharide composition comprises less than 7% derivatized or chemically altered (e.g., degraded) sugar units (e.g., anhydro-forms). In some embodiments, the plurality of oligosaccharides of the oligosaccharide composition comprise less than 7% anhydro-form sugar subunits, e.g., as determined by relative abundance or as measured by mass spectrometry. In some embodiments, the oligosaccharide composition comprises less than 10% derivatized or chemically altered (e.g., degraded) sugar units (e.g., anhydro-forms). In some embodiments, the plurality of oligosaccharides of the oligosaccharide composition comprise less than 10% anhydro-form sugar subunits, e.g., as determined by relative abundance or as measured by mass spectrometry. In some embodiments, the oligosaccharide composition comprises less than 0.5% levoglucosan, e.g., as determined by relative abundance or as measured by mass spectrometry. In some embodiments, the plurality of oligosaccharides of the oligosaccharide composition comprise less than 1% anhydro-form sugar subunits, e.g., as determined by relative abundance or as measured by mass spectrometry. In some embodiments, the oligosaccharide composition comprises less than 1% levoglucosan, e.g., as determined by relative abundance or as measured by mass spectrometry. In some embodiments, the plurality of oligosaccharides of the oligosaccharide composition comprise less than 3% anhydro-form sugar subunits, e.g., as determined by relative abundance or as measured by mass spectrometry. In some embodiments, the oligosaccharide composition comprises less than 3% levoglucosan, e.g., as determined by relative abundance or as measured by mass spectrometry. In some embodiments, less than 0.5%, 1%, 2%, 3%, 5%, 7%, or 10% of the oligosaccharide composition or the plurality of oligosaccharides comprise monomers or oligomer subunits that are different from Formula (I), Formula (II), or Formulae (Ia), (Ib), (Ic), (Id), (IIa), (IIb), (IIc), and (IId), e.g., comprised of derivatized or chemically altered (e.g., degraded) sugar units (e.g., anhydro-forms).

In some embodiments, the plurality of oligosaccharides comprises about 50% (e.g., 40-60%) dextrose and about 50% (e.g., 40-60%) galactose.

In some embodiments, the process further comprises one or more (e.g., two or more, or three) of steps (e) to (g):
(e) passing the diluted composition through a cationic exchange resin;
(f) passing the diluted composition through an anionic exchange resin; and
(g) passing the diluted composition through a decolorizing polymer resin;
wherein each of (e), (f), and (g) can be performed one or more times in any order.

In some embodiments, the composition comprises total water content at a level below that which is necessary for microbial growth upon storage at room temperature. In some embodiments, the composition comprises total water content in a range of 24-33 weight percent. In some embodiments, the composition comprises a total water content of about 30% or less. In some embodiments, the composition comprises a total water content of about 10% or less, e.g., 9% or less, 7% or less, 5% or less, 4% or less, or 3% or less.

In some embodiments, the mean degree of polymerization (DP) of the oligosaccharide composition is from about DP6 to about DP14. In some embodiments, the mean degree of polymerization (DP) of the oligosaccharide composition is from about DP6 to about DP12. In some embodiments, the mean degree of polymerization (DP) of the oligosaccharide composition is from about DP6 to about DP11. In some embodiments, the mean degree of polymerization (DP) of the oligosaccharide composition is from about DP8 to about DP14. In some embodiments, the mean degree of polymerization (DP) of the oligosaccharide composition is from about DP8 to about DP9.

In some embodiments, the oligosaccharides in the oligosaccharide composition have a MWw (g/mol) in a range of about 970 to about 2270. In some embodiments, the oligosaccharides in the oligosaccharide composition have a MWw (g/mol) in a range of about to about 1950. In some embodiments, the oligosaccharides in the oligosaccharide composition have a MWw (g/mol) in a range of about 1300 to about 1450. In some embodiments, the oligosaccharides in the oligosaccharide composition have a MWn (g/mol) in a range of about 680-1200. In some embodiments, the oligosaccharides in the oligosaccharide composition have a MWn (g/mol) in a range of about 725-1215.

In some embodiments, the oligosaccharide composition has a pH in a range of 2.5-7.5. In some embodiments, the oligosaccharide composition has a pH in a range of 2.5-5.0. In some embodiments, about 75 to 95 weight percent (dry basis) of the oligosaccharide composition comprises oligosaccharides having a degree of polymerization of two or more monomers (DP2+). In some embodiments, about 80 to 90 weight percent (dry basis) of the oligosaccharide composition comprises oligosaccharides having a degree of polymerization of two or more monomers (DP2+). In some embodiments, greater than 75% and less than 90% of the oligosaccharides in the oligosaccharide compostions have a degree of polymerization (DP) of 3 or more.

In some embodiments, the oligosaccharide composition comprises less than 25% monomer (DP1). In some embodiments, the oligosaccharide composition comprises less than 15% monomer (DP1). In some embodiments, wherein the oligosaccharide composition comprises less than 3% monomer (DP1). In some embodiments, the oligosaccharide composition comprises less than 1% monomer (DP1). In some embodiments, the oligosaccharide composition comprises less than 3% w/w impurities. In some embodiments, the composition comprises less than 1% total impurities.

In some embodiments, the oligosaccharide composition is substantially non-absorbable in a human. In some embodiments, the oligosaccharide composition is minimally digestible by a human. In some embodiments, the oligosaccharide composition comprises 5% to 40% dextrose equivalent (dry basis). In some embodiments, the oligosaccharide composition comprises 15% to 25% dextrose equivalent (dry basis). In some embodiments, the oligosaccharide composition comprises at least 55%, at least 60%, at least 70%, at least 80%, at least 90% total dietary fiber (dry basis). In some embodiments, the oligosaccharide composition comprises 55% to 95% total dietary fiber (dry basis). In some embodiments, the oligosaccharide composition comprises at least 75% and less than 90% total dietary fiber (dry basis).

In some embodiments, the composition does not contain detectable quantities of soluble dietary fiber precipitate (SDFP), insoluble dietary fiber (IDF), and/or high molecular weight dietary fiber (HMWDF).

In some embodiments, provided herein are oligosaccharide compositions comprising a plurality of glycans selected from Formula (I) and Formula (II):

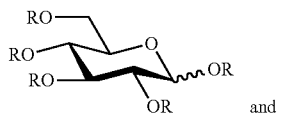
(I)

and

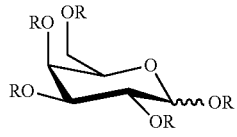
(II)

wherein each R independently is selected from hydrogen, and Formulae (Ia), (Ib), (Ic), (Id), (IIa), (IIb), (IIc), (IId):

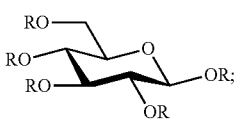
(Ia)

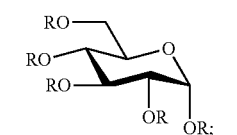
(Ib)

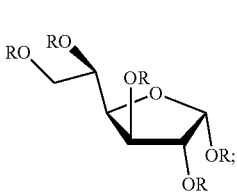
(Ic)

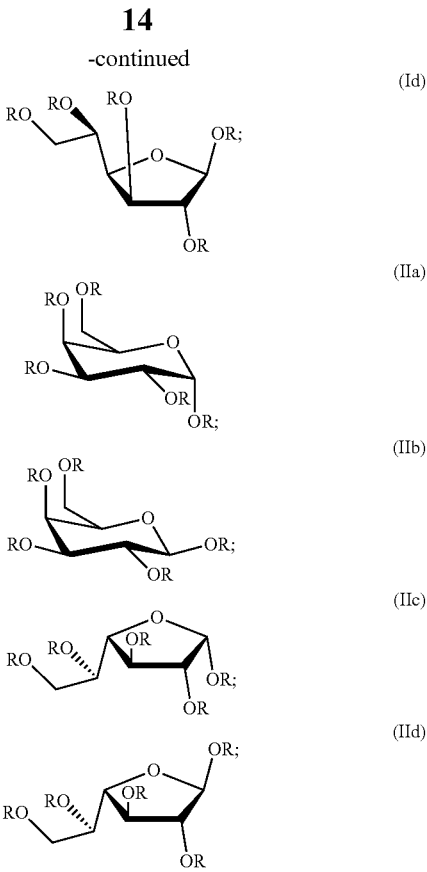

wherein each R independently is as defined above;
wherein the oligosaccharide composition is produced by a process comprising:

(a) heating a preparation comprising dextrose and galactose wherein the molar ratio of glucose to galactose is about 1:1 under agitation conditions, to a temperature in a range of 110° C. to 160° C.;

(b) loading the preparation with a catalyst comprising acidic protons, in an amount such that the molar ratio of acidic protons to total dextrose and galactose content is in a range of 0.001-0.25, thereby forming a reaction mixture; and (c) maintaining the reaction mixture at its boiling point, at a pressure in the range of 0.5-1.5 atm, under conditions that promote acid catalyzed oligosaccharide formation, until the weight percent of dextrose monomer and galactose monomer in the oligosaccharide composition is in a range of 12-16;

(d) quenching the reaction mixture using water while bringing the temperature of the reaction mixture to below 100° C.; and (e) separating oligosaccharides from the acid catalyst; thereby obtaining the oligosaccharide composition.

In some embodiments, step (a) involves heating to a temperature in a range of about 128° C. to 150° C. In some embodiments, step (c) involves maintaining a temperature in a range of about 128° C. to 150° C. In some embodiments, wherein steps (a) and (b) occur simultaneously. In some embodiments, wherein step (a) comprises gradually increasing the temperature (e.g., from room temperature) to about 130° C., about 135° C., or about 148° C., under suitable conditions to achieve homogeneity and uniform heat transfer. In some embodiments, said heating comprises melting the preparation and/or heating the preparation under suitable conditions to achieve homogeneity and uniform heat transfer. In some embodiments, the process further comprises removing water from the reaction mixture by evaporation. In some embodiments, step (c) further comprises maintaining the reaction mixture at 93-94 weight percent dissolved solids.

In some embodiments, in (d) the water is deionized water. In some embodiments, in (d) the water has a temperature of about 95° C. In some embodiments, in (d) the water is added to the reaction mixture under conditions sufficient to avoid solidifying the mixture. In some embodiments, in (e) said separating comprises removing the catalyst by filtration. In some embodiments, in (e) comprises cooling the reaction mixture to below about 85° C. before filtering.

In some embodiments, the process further comprises:
(f) diluting the oligosaccharide com€ition of (e) with water to a concentration of about 45-55 weight percent and passing the diluted composition through a cationic exchange resin;
(g) passing the diluted composition through an anionic exchange resin; and
(h) passing the diluted composition through a decolorizing polymer resin;
wherein each of (f), (g), and (h) can be performed one or more times in any order.

In some embodiments, the process further comprises diluting the oligosaccharide composition of (e) with water to a concentration of about 45-55 weight percent and passing the diluted composition through a 45 μm filter.

In some embodiments, the catalyst is a solid acid catalyst. In some embodiments, the catalyst is a strong acid cation exchange resin having one or more physical and chemical properties according to Table 1 and/or wherein the catalyst comprises >3.0 mmol/g sulfonic acid moieties and <1.0 mmol/gram cationic moieties. In some embodiments, the catalyst has a nominal moisture content of 45-50 weight percent. In some embodiments, the catalyst is a soluble acid catalyst. In some embodiments, the catalyst is citric acid. In some embodiments, in step (a), the acid catalyst is present in an amount such that the molar ratio of acidic protons to dextrose and galactose is in a range of 0.0016-0.022. In some embodiments, in step (a), the acid catalyst is present in an amount such that the molar ratio of acidic protons to dextrose is in a range of 0.050 to 0.052.

In some embodiments, in step (a), the dextrose preparation comprises dextrose monomer. In some embodiments, in step (a), the galactose preparation comprises galactose monomer. In some embodiments, in step (a), the dextrose preparation comprises dextrose monohydrate or corn syrup. In some embodiments, in step (a), the galactose preparation comprises anhydrous galactose. In some embodiments, the reaction mixture of step (a) comprises dextrose monohydrate and anhydrous galactose. In some embodiments, in step (a), the dextrose preparation comprises lactose. In some embodiments, in step (a), the galactose preparation comprises lactose. In some embodiments, in step (a), the dextrose preparation and the galactose preparation comprise lactose. In some embodiments, the reaction mixture of step (a) comprises a molar ratio of dextrose (e.g., dextrose monohydrate) to galactose (e.g., anhydrous galactose) of about 1:1.

In some embodiments, the plurality of oligosaccharides that comprise Formula (I) and Formula (II) comprise at least 60%, at least 70%, at least 80%, or at least 90% of the oligosaccharide composition. In some embodiments, the plurality of oligosaccharides that comprise Formula (I) and Formula (II) comprise at least 95% of the oligosaccharide composition. In some embodiments, the plurality of oligosaccharides that comprise Formula (I) and Formula (II) comprise at least 98% of the oligosaccharide composition. In some embodiments, the plurality of oligosaccharides that comprise Formula (I) and Formula (II) comprise 100% of the oligosaccharide composition.

In some embodiments, the plurality of oligosaccharides comprises about 50% (e.g., 40-60%) dextrose and about 50% (e.g., 40-60%) galactose.

In some embodiments, the process further comprises water at a level below that which is necessary for microbial growth upon storage at room temperature. In some embodiments, the composition comprises water in a range of 45-55 weight percent. In some embodiments, the mean degree of polymerization (DP) of the oligosaccharide composition is from about DP6 to about DP14. In some embodiments, the mean degree of polymerization (DP) of the oligosaccharide composition is from about DP6 to about DP12. In some embodiments, the mean degree of polymerization (DP) of the oligosaccharide composition is from about DP6 to about DP11. In some embodiments, the mean degree of polymerization (DP) of the oligosaccharide composition is from about DP8 to about DP14. In some embodiments, the mean degree of polymerization (DP) of the oligosaccharide composition is from about DP8 to about DP9.

In some embodiments, the oligosaccharides in the oligosaccharide composition have a MWw (g/mol) in a range of about 970 to about 2270. In some embodiments, the oligosaccharides in the oligosaccharide composition have a MWw (g/mol) in a range of about to about 1950. In some embodiments, the oligosaccharides in the oligosaccharide composition have a MWw (g/mol) in a range of about 1300 to about 1450. In some embodiments, the oligosaccharides in the oligosaccharide composition have a MWn (g/mol) in a range of about 680-1200. In some embodiments, the oligosaccharides in the oligosaccharide composition have a MWn (g/mol) in a range of about 725-1215.

In some embodiments, the oligosaccharide composition has a pH in a range of 2.5-7.5. In some embodiments, the oligosaccharide composition has a pH in a range of 2.5-5.0. In some embodiments, about 75 to 95 weight percent (dry basis) of the oligosaccharide composition comprises oligosaccharides having a degree of polymerization of two or more monomers (DP2+). In some embodiments, about 80 to 90 weight percent (dry basis) of the oligosaccharide composition comprises oligosaccharides having a degree of polymerization of two or more monomers (DP2+). In some embodiments, greater than 75% and less than 90% of the oligosaccharides in the oligosaccharide composition have a degree of polymerization of 3 or more.

In some embodiments, the oligosaccharide composition comprises less than 25% monomer (DP1). In some embodiments, the oligosaccharide composition comprises less than 15% monomer (DP1). In some embodiments, wherein the oligosaccharide composition comprises less than 3% monomer (DP1). In some embodiments, the oligosaccharide composition comprises less than 1% monomer (DP1). In some embodiments, the oligosaccharide composition comprises less than 3% w/w impurities. In some embodiments, the composition comprises less than 1% total impurities.

In some embodiments, the oligosaccharide composition is substantially non-absorbable in a human. In some embodiments, the oligosaccharide composition is minimally digestible by a human. In some embodiments, the oligosaccharide composition comprises 5% to 40% dextrose equivalent (dry basis). In some embodiments, the oligosaccharide composition comprises 15% to 25% dextrose equivalent (dry basis). In some embodiments, the oligosaccharide composition comprises at least 55%, at least 60%, at least 70%, at least 80%, at least 90% total dietary fiber (dry basis). In some embodiments, the oligosaccharide composition comprises 55% to 95% total dietary fiber (dry basis). In some embodiments, the oligosaccharide composition comprises at least 75% and less than 90% total dietary fiber (dry basis).

In some embodiments, the composition does not contain detectable quantities of soluble dietary fiber precipitate (SDFP), insoluble dietary fiber (IDF), and/or high molecular weight dietary fiber (HMWDF).

In some aspects, provided herein are oligosaccharide compositions comprising a plurality of oligosaccharides, each oligosaccharide comprising a plurality of monomer radicals; the plurality of oligosaccharides comprising two or more of the following monomer radicals:

(1) t-glucopyranose monoradicals, representing 7.2-26.77 mol % of monomer radicals in the plurality of oligosaccharides;
(2) t-galactofuranose monoradicals, representing 0.0-10.3 mol % of monomer radicals in the plurality of oligosaccharides;
(3) t-galactopyranose monoradicals, representing 7.3-17.4 mol % of monomer radicals in the plurality of oligosaccharides;
(4) 3-glucopyranose monoradicals, representing 2.3-6.2 mol % of monomer radicals in the plurality of oligosaccharides;
(5) 2-glucopyranose monoradicals, representing 2.4-4.1 mol % of monomer radicals in the plurality of oligosaccharides;
(6) 2-galactofuranose and/or 2-glucofuranose monoradicals, representing 0.0-5.2 mol % of monomer radicals in the plurality of oligosaccharides;
(7) 3-glucofuranose monoradicals, representing 0.0-0.9 mol % of monomer radicals in the plurality of oligosaccharides;
(8) 3-galactopyranose monoradicals, representing 1.7-5.1 mol % of monomer radicals in the plurality of oligosaccharides;
(9) 3-galactofuranose monoradicals, representing 0.8-3.6 mol % of monomer radicals in the plurality of oligosaccharides;
(10) 2-galactopyranose monoradicals, representing 0.8-4.2 mol % of monomer radicals in the plurality of oligosaccharides;
(11) 6-glucopyranose monoradicals, representing 5.1-16.2 mol % of monomer radicals in the plurality of oligosaccharides;
(12) 4-galactopyranose and/or 5-galactofuranose monoradicals, representing 2.1-4.9 mol % of monomer radicals in the plurality of oligosaccharides;
(13) 4-glucopyranose and/or 5-glucofuranose monoradicals, representing 2.2-5.6 mol % of monomer radicals in the plurality of oligosaccharides;
(14) 2,3-galactofuranose diradicals, representing 0.0-1.2 mol % of monomer radicals in the plurality of oligosaccharides;
(15) 6-glucofuranose monoradicals, representing 0.0-2.4 mol % of monomer radicals in the plurality of oligosaccharides;
(16) 6-galactofuranose monoradicals, representing 0.4-5.7 mol % of monomer radicals in the plurality of oligosaccharides;
(17) 6-galactopyranose monoradicals, representing 4.2-11.5 mol % of monomer radicals in the plurality of oligosaccharides;
(18) 3,4-galactopyranose and/or 3,5-galactofuranose and/or 2,3-glucopyranose diradicals, representing 0.3-2.3 mol % of monomer radicals in the plurality of oligosaccharides;
(19) 3,4-glucopyranose and/or 3,5-glucofuranose diradicals, representing 0.0-1.8 mol % of monomer radicals in the plurality of oligosaccharides;
(20) 2,3-glucopyranose diradicals, representing 0.0-1.8 mol % of monomer radicals in the plurality of oligosaccharides;
(21) 2,4-glucopyranose and/or 2,5-glucofuranose and/or 2,4-galactopyranose and/or 2,5-galactofuranose diradicals, representing 0.7-1.7 mol % of monomer radicals in the plurality of oligosaccharides;
(22) 3,6-glucopyranose diradicals, representing 1.1-3.3 mol % of monomer radicals in the plurality of oligosaccharides;
(23) 3,6-glucofuranose diradicals, representing 0.0-0.8 mol % of monomer radicals in the plurality of oligosaccharides;
(24) 2,6-glucopyranose and/or 4,6-glucopyranose and/or 5,6-glucofuranose diradicals, representing 0.0-5.6 mol % of monomer radicals in the plurality of oligosaccharides;
(25) 3,6-galactofuranose diradicals, representing 0.6-1.8 mol % of monomer radicals in the plurality of oligosaccharides;
(26) 4,6-galactopyranose and/or 5,6-galactofuranose diradicals, representing 0.4-4.8 mol % of monomer radicals in the plurality of oligosaccharides;
(27) 2,3,4-glucopyranose and/or 2,3,5-glucofuranose triradicals, representing 0.0-0.5 mol % of monomer radicals in the plurality of oligosaccharides;
(28) 3,6-galactopyranose diradicals, representing 0.9-3.7 mol % of monomer radicals in the plurality of oligosaccharides;
(29) 2,6-galactopyranose diradicals, representing 0.4-1.9 mol % of monomer radicals in the plurality of oligosaccharides;
(30) 3,4,6-galactopyranose and/or 3,5,6-galactofuranose and/or 2,3,6-galactofuranose triradicals, representing 0.0-2.2 mol % of monomer radicals in the plurality of oligosaccharides;
(31) 3,4,6-glucopyranose and/or 3,5,6-glucofuranose triradicals, representing 0.0-1.6 mol % of monomer radicals in the plurality of oligosaccharides;
(32) 2,3,6-glucofuranose triradicals, representing 0.0-0.2 mol % of monomer radicals in the plurality of oligosaccharides;
(33) 2,4,6-glucopyranose and/or 2,5,6-glucofuranose triradicals, representing 0.0-1.2 mol % of monomer radicals in the plurality of oligosaccharides;
(34) 2,3,6-galactopyranose and/or 2,4,6-galactopyranose and/or 2,5,6-galactofuranose triradicals, representing 0.0-1.8 mol % of monomer radicals in the plurality of oligosaccharides;
(35) 2,3,6-glucopyranose triradicals, representing 0.0-1.2 mol % of monomer radicals in the plurality of oligosaccharides; and
(36) 2,3,4,6-glucopyranose and/or 2,3,5,6-glucofuranose tetraradicals, representing 0.0-0.7 mol % of monomer radicals in the plurality of oligosaccharides.

In some embodiments, the plurality of oligosaccharides comprise three or more monomer radicals selected from radicals (1)-(36). In some embodiments, the plurality of oligosaccharides comprise four or more monomer radicals selected from radicals (1)-(36). In some embodiments, the plurality of oligosaccharides comprise each of the monomer radicals selected from radicals (1)-(36).

In some embodiments, the molar percentages of monomer radicals are determined using a permethylation assay, wherein the permethylation assay comprises gas chromatography-mass spectroscopy (GC-MS) analysis. In some embodiments, the oligosaccharide composition comprises a plurality of oligosaccharides that consist essentially of Formula (I) and Formula (II):

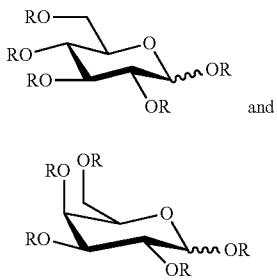

wherein R in Formula (I) and Formula (II) is independently selected from hydrogen, and Formulae (Ia), (Ib), (Ic), (Id), (IIa), (IIb), (IIc), (IId):

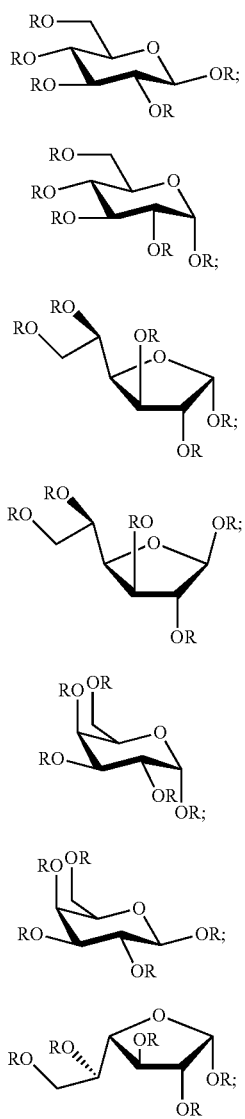

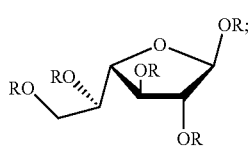

wherein R in Formulae (Ia), (Ib), (Ic), (Id), (IIa), (IIb), (IIc), and (IId) is independently defined as above in Formula (I) and Formula (II).

In some embodiments, the mean degree of polymerization (DP) of the oligosaccharide composition is from about DP6 to about DP14. In some embodiments, the mean degree of polymerization (DP) of the oligosaccharide composition is from about DP6 to about DP12. In some embodiments, the mean degree of polymerization (DP) of the oligosaccharide composition is from about DP6 to about DP11. In some embodiments, the mean degree of polymerization (DP) of the oligosaccharide composition is from about DP8 to about DP14. In some embodiments, the mean degree of polymerization (DP) of the oligosaccharide composition is from about DP8 to about DP9.

In some embodiments, greater than 75% and less than 90% of the oligosacchsirdes in the oligosaccharide composition have a degree of polymerization of 3 or more.

In some embodiments, the oligosaccharides in the oligosaccharide composition have a MWw (g/mol) in a range of about 970 to about 2270. In some embodiments, the oligosaccharides in the oligosaccharide composition have a MWw (g/mol) in a range of about to about 1950. In some embodiments, the oligosaccharides in the oligosaccharide composition have a MWw (g/mol) in a range of about 1300 to about 1450. In some embodiments, the oligosaccharides in the oligosaccharide composition have a MWn (g/mol) in a range of about 680-1200. In some embodiments, the oligosaccharides in the oligosaccharide composition have a MWn (g/mol) in a range of about 725-1215.

In some embodiments, the plurality of oligosaccharides comprises about 50% (e.g., 40%-60%) glucose and 50% (e.g., 40%-60%) galactose.

In some embodiments, the oligosaccharide composition comprises 5% to 40% dextrose equivalent (dry basis). In some embodiments, the oligosaccharide composition comprises 15% to 25% dextrose equivalent (dry basis). In some embodiments, the oligosaccharide composition comprises at least 55%, at least 60%, at least 70%, at least 80%, at least 90% total dietary fiber (dry basis). In some embodiments, the oligosaccharide composition comprises 55% to 95% total dietary fiber (dry basis). In some embodiments, the oligosaccharide composition comprises at least 75% and less than 90% total dietary fiber (dry basis).

In some aspects, provided herein are co-formulations of an oligosaccharide composition as described herein and a second pharmaceutical agent (e.g. a drug). In some embodiments, the drug is an antibiotic (e.g., rifaximin). In some embodiments, the drug is lactulose.

In some aspects, provided herein are co-formulations of an oligosaccharide composition as described herein and one or more commensal or probiotic bacterial taxa.

In some aspects, provided herein are methods of reducing ammonia levels in a human subject, comprising administering to the human subject an effective amount of an oligosaccharide composition described herein. In some embodiments, the ammonia levels are blood ammonia levels in the human subject. In some embodiments, ammonia levels are reduced by at least 10% compared to the ammonia levels in the human subject prior to administration of the oligosaccharide composition to the human subject.

In some embodiments, the subject has or has been diagnosed as having hepatic encephalopathy (HE). In some embodiments, the subject has or has been diagnosed as having a cirrhosis. In some embodiments, the subject has been diagnosed as having had a hepatic encephalopathy (HE) event or is at risk of having a hepatic encephalopathy (HE) event. In some embodiments, the subject has or has been diagnosed as having an infection or is at risk of developing an infection. In some embodiments, the subject is of a geriatric population. In some embodiments, the subject has or has been diagnosed as having minimal hepatic encephalopathy (MHE). In some embodiments, the subject has or has been diagnosed as having overt hepatic encephalopathy (OHE). In some embodiments, the subject has been or is being treated with lactulose and/or rifaximin. In some embodiments, administering to the human subject an effective amount of an oligosaccharide composition is performed prior to, contemporaneously with, or after treatment with lactulose and/or rifaximin.

In some embodiments, the disclosure provides methods of reducing the frequency of hepatic encephalopathy (HE) events in a human subject having or having been diagnosed with a disease or condition associated with hyperammonemia, comprising administering to the human subject an effective amount of an oligosaccharide composition. In some embodiments, frequency of hepatic encephalopathy (HE) events is reduced by at least 10% compared to the frequency of hepatic encephalopathy (HE) events in the human subject prior to administration of the oligosaccharide composition.

In some embodiments, the subject has or has been diagnosed as having hepatic encephalopathy (HE). In some embodiments, the subject has or has been diagnosed as having a cirrhosis. In some embodiments, the subject has or has been diagnosed as having an infection or is at risk of developing an infection. In some embodiments, the subject is of a geriatric population. In some embodiments, the subject has or has been diagnosed as having minimal hepatic encephalopathy (MHE). In some embodiments, the subject has or has been diagnosed as having overt hepatic encephalopathy (OHE). In some embodiments, the subject has or is being treated with lactulose and/or rifaximin. In some embodiments, administering to the human subject an effective amount of an oligosaccharide composition is performed prior to, contemporaneously with, or after treatment with lactulose and/or rifaximin.

In some embodiments, the disclosure provides methods for preventing a hepatic encephalopathy (HE) event in a human subject in need thereof (e.g., in a subject with cirrhosis and/or MHE), or preventing the reoccurrence of a hepatic encephalopathy (HE) event in a human subject in need thereof (e.g., in a subject with cirrhosis and/or OHE), comprising administering to the subject an effective amount of an oligosaccharide composition. In some embodiments, the human subject has or has been diagnosed as having hepatic encephalopathy (HE). In some embodiments, the subject has or has been diagnosed as having a cirrhosis. In some embodiments, the subject has or has been diagnosed as having decompensated liver cirrhosis. In some embodiments, the subject has or has been diagnosed as having compensated liver cirrhosis.

In some embodiments, the subject has or has been diagnosed as having an infection. In some embodiments, the subject is of a geriatric population. In some embodiments, the subject has or has been diagnosed as having minimal hepatic encephalopathy (MHE). In some embodiments, the subject has or has been diagnosed as having overt hepatic encephalopathy (OHE). In some embodiments, the subject has or is being treated with lactulose and/or rifaximin.

In some embodiments, the disclosure provides methods of treating or preventing a disease symptom associated with liver cirrhosis in a human subject who has or has been diagnosed as having liver cirrhosis, comprising administering to the human subject an oligosaccharide composition. In some embodiments, the human subject has or has been diagnosed as having hepatic encephalopathy (HE). In some embodiments, the subject has or has been diagnosed as having decompensated liver cirrhosis. In some embodiments, the subject has or has been diagnosed as having an infection or is at risk of developing an infection. In some embodiments, the subject is of a geriatric population. In some embodiments, the subject has or has been diagnosed as having minimal hepatic encephalopathy (MHE). In some embodiments, the subject has or has been diagnosed as having overt hepatic encephalopathy (OHE). In some embodiments, the subject has or is being treated with lactulose and/or rifaximin. In some embodiments, administering the oligosaccharide composition prevents a hepatic encephalopathy (HE) event or reduces the frequency of hepatic encephalopathy (HE) events. In some embodiments, administering the oligosaccharide composition prevents the subject from developing an infection or reduces the severity of an infection.

In some embodiments, the disclosure provides methods of reducing the relative abundance of a pathogen and/or increasing the relative abundance of a commensal bacterium in a human subject, relative to a control, comprising administering to the human subject an effective amount of an oligosaccharide composition. In some embodiments, the control can be the abundance of the pathogen relative to the abundance of a commensal bacterium in the human subject prior to being administered the oligosaccharide composition. In some embodiments, the control can be the abundance of the pathogen relative to the abundance of a commensal bacterium in a different human subject that has not been administered the oligosaccharide composition and/or an antibiotic. In some embodiments, the control can be the average abundance of the pathogen relative to the average abundance of a commensal bacterium in a population of human subjects that have not been administered the oligosaccharide composition and/or an antibiotic.

In some embodiments, the oligosaccharide composition is administered in an amount effective to modulate colonization by and/or to modulate (e.g. increase) decolonization by the pathogen in the gut of the human subject. In some embodiments, the colonization or decolonization of the gut of the subject can be determined by culturing fecal samples before and after oligosaccharide composition administration on a solid agar plate to attain colony counts (CFU plating) and/or using quantitative PCR on the samples.

In some embodiments, administration of the oligosaccharide composition reduces or inhibits colonization by the pathogen in the gut of the human subject. In some embodiments, administration of the oligosaccharide composition increases decolonization by the pathogen in the gut of the human subject. In some embodiments, administration of the oligosaccharide composition reduces or inhibits colonization by the pathogen and increases decolonization by the pathogen in the gut of the human subject.

In some embodiments, the oligosaccharide composition is administered in an amount effective to (a) decrease the relative abundance of a pathogen and/or a drug- or antibiotic-resistance gene or an MDR element carrier; and (b) increase the relative abundance of a commensal or beneficial bacterium.

In some embodiments, the oligosaccharide composition reduces the relative abundance of the pathogen in the human subject by at least 10%, at least 20%, at least 30%, at least 40%, or at least 50%. In some embodiments, the oligosaccharide composition increases the relative abundance of the commensal or beneficial bacterium in the human subject by at least 10%, at least 20%, at least 30%, at least 40%, or at least 50%.

In some embodiments, the pathogen comprises a bacterium or a fungus. In some embodiments, the pathogen comprises a drug or antibiotic resistant pathogen. In some embodiments, the pathogen comprises a vancomycin-resistant *Enterococcus* (VRE), extended spectrum beta-lactamase producing Enterobacteriaceae or a carbapenem-resistant Enterobacteriaceae (CRE). In some embodiments, the pathogen comprises VRE *Enterococcus faecium*. In some embodiments, the pathogen comprises CRE *Escherichia coli* or CRE *Klebsiella pneumoniae*. In some embodiments, the pathogen comprises an extended-spectrum beta-lactamase (ESBL) producing bacterium. In some embodiments, the pathogen comprises an extended spectrum beta lactamase (ESBL) producing Enterobacteriaceae. In some embodiments, the pathogen comprises a fungus. In some embodiments, the pathogen comprises a *Candida* fungus. In some embodiments, the pathogen comprises *Candida albicans, Candida auris, Candida glabrata, Candida krusei, Candida tropicalis*, or *Candida lusitaniae*. In some embodiments, the pathogen comprises *Clostridium difficile*. In some embodiments, the pathogen comprises a gram-positive bacterium or a gram-negative bacterium.

In some embodiments, the commensal bacterium is a *Bacteroides* or a *Parabacteroides*.

In some embodiments, the human subject: (i) has received a cancer treatment; (ii) has received a transplant; (iii) has received immunosuppression, and/or (iv) has an auto-immune disease (e.g., systemic lupus erythematosus, rheumatoid arthritis, Sjögren's syndrome, or Crohn's disease). In some embodiments, the human subject has received a cancer treatment, wherein the cancer treatment is chemotherapy. In some embodiments, the human subject has received a transplant, and wherein the transplant comprises hematopoietic stem cells. In some embodiments, the human subject has received an immunosuppressant. In some embodiments, the human subject has an autoimmune disease (e.g., the autoimmune disease is system lupus erythematosus, rheumatoid arthritis, Sjögren's syndrome, or Crohn's disease). In some embodiments, the human subject has a depleted microbiome, e.g., the subject has a reduced diversity and/or biomass of commensals. In some embodiments, the human subject has a detectable amount of commensal bacteria in the gut.

In some embodiments, a process further comprises administering to the human subject a population of commensal or probiotic bacteria. In some embodiments, the population of commensal or probiotic bacteria are administered to the human subject before, concurrently with, or after the oligosaccharide composition. In some embodiments, the human subject does not have a detectable amount of commensal bacteria in the gut.

In some embodiments, provided herein is an oligosaccharide composition comprising a plurality of oligosaccharides, wherein: the oligosaccharide composition comprises or consists essentially of any of the oligosaccharide compositions described herein, and wherein the oligosaccharide composition comprises any of the NMR spectra described herein.

In some embodiments, provided herein is an oligosaccharide composition comprising a plurality of oligosaccharides, wherein: the oligosaccharide composition comprises or consists essentially of any of the oligosaccharide compositions described herein, and wherein the oligosaccharide composition is produced by any of the processes described herein.

In some embodiments, provided herein is an oligosaccharide composition comprising a plurality of oligosaccharides, wherein: the oligosaccharide composition comprises any of the NMR spectra described herein, and wherein the oligosaccharide composition is produced by any of the processes described herein.

In some embodiments, provided herein is an oligosaccharide composition comprising a plurality of oligosaccharides, wherein: the oligosaccharide composition comprises or consists essentially of any of the oligosaccharide compositions described herein, wherein the oligosaccharide composition comprises any of the NMR spectra described herein, and wherein the oligosaccharide composition is produced by any of the processes described herein.

In some embodiments, provided herein is an oligosaccharide composition comprising a plurality of oligosaccharides, wherein: the oligosaccharide composition comprises or consists essentially of any of the oligosaccharide compositions described herein, and wherein the oligosaccharide composition comprises any of the plurality of monomer radicals described herein. In some embodiments, provided herein is an oligosaccharide composition comprising a plurality of oligosaccharides, wherein: the oligosaccharide composition comprises any of the plurality of monomer radicals described herein, and wherein the oligosaccharide composition is produced by any of the processes described herein.

In some embodiments, provided herein is an oligosaccharide composition comprising a plurality of oligosaccharides, wherein: the oligosaccharide composition comprises or consists essentially of any of the oligosaccharide compositions described herein, wherein the oligosaccharide composition comprises any of the plurality of monomer radicals described herein, and wherein the oligosaccharide composition is produced by any of the processes described herein.

BRIEF DESCRIPTION OF THE DRAWINGS

FIG. 5A is a graph showing reduction of pathogens in fecal samples spiked with carbapenem-resistant Enterobacteriaceae. FIG. 5B is a graph showing reduction of pathogens in fecal samples spiked with vancomycin-resistant Enterococcaceae.

FIG. 6A is a graph showing reduction of pathogens in fecal samples spiked with carbapenem-resistant Enterobacteriaceae. FIG. 6B is a graph showing reduction of pathogens in fecal samples spiked with vancomycin-resistant Enterococcaceae.

FIG. 8A is a HSQC NMR spectrum of the selected oligosaccharide composition. Integrated peaks that correspond to the selected oligosaccharide composition, as denoted in Table 3, are circled in green. FIG. 8B is a HSQC NMR spectrum of Galacto-oligosaccharide (GOS).

DETAILED DESCRIPTION OF INVENTION

Figure 1:
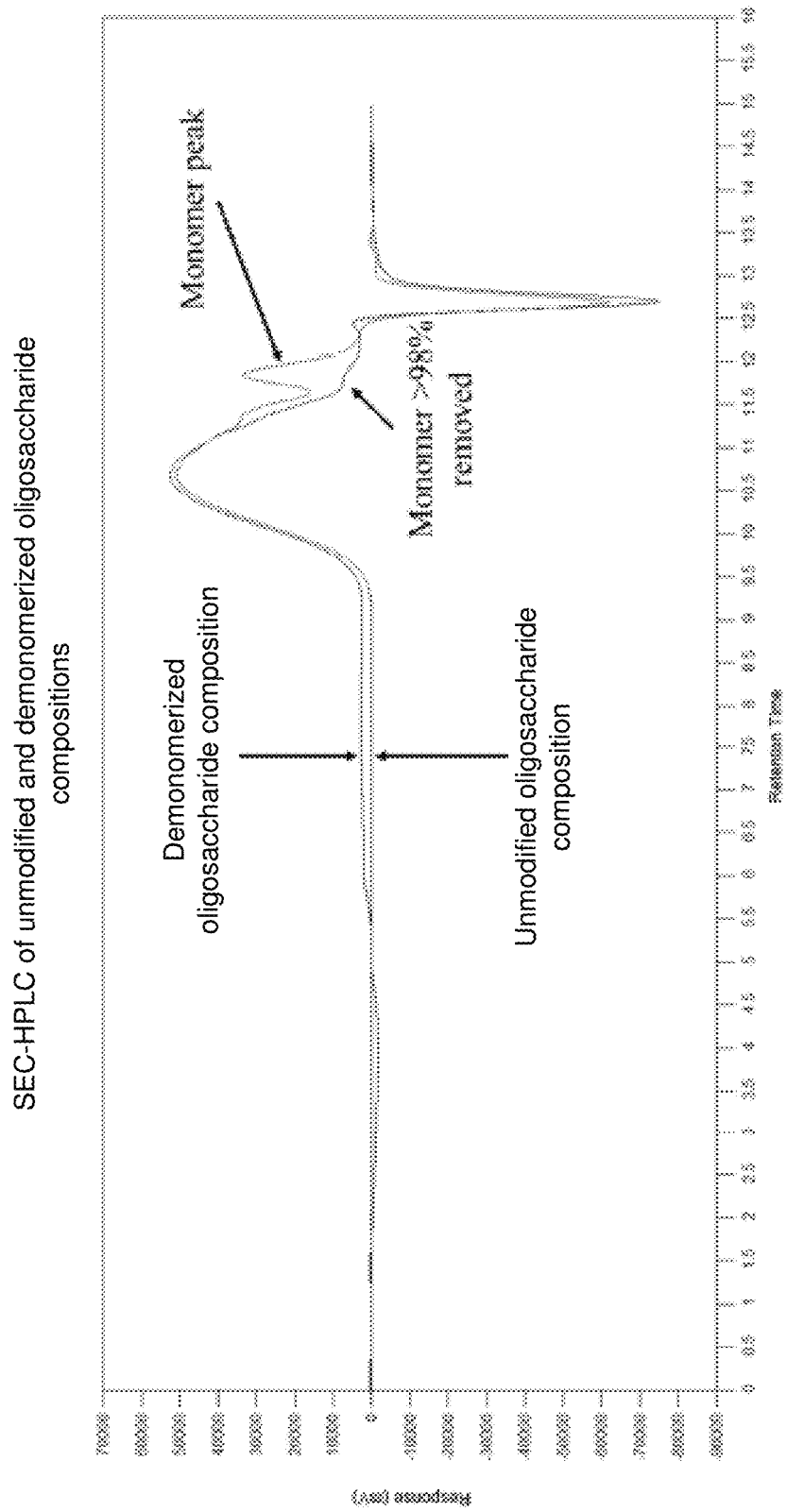
FIG. 1 depicts overlaid SEC-HPLC chromatograms of an unmodified oligosaccharide composition and an oligosaccharide composition that has been de-monomerized by amine column flash chromatography, as described in Example 4.

Aspects of the disclosure relate to oligosaccharide compositions that are effective for reducing ammonia levels and/or reducing pathogen leves, abundance, and/or colonization in a subject, e.g., a subject with hyperammonemia, hepatic encephalopathy (HE), and/or cirrhosis.

Some aspects of the disclosure are based on the results of an extensive screening effort that was performed to identify oligosaccharide compositions that are capable of modulating, e.g., reducing, levels of ammonia in a subject. Some aspects of the disclosure are based on the results of an extensive screening effort that was performed to identify oligosaccharide compositions that are capable of modulating, e.g., reducing, levels of pathogens in a subject. Hundreds of unique oligosaccharide compositions were assayed for their effect on ammonia levels and/or levels of pathogens. The oligosaccharide compositions examined in the screens were produced using different saccharide monomers, e.g., dextrose monomers, xylose monomers, etc., and under conditions involving differing reaction temperatures, for varying periods of time, and/or in the presence of different catalysts.

From these screening efforts, a selected oligosaccharide composition was identified as a highly effective modulator of ammonia levels and as a highly effective modulator of pathogen levels. Accordingly, in some embodiments, this oligosaccharide composition is particularly useful for treating subjects having disorders associated with hyperammonemia. Further, this oligosaccharide composition is particularly useful for treating subjects having high levels of pathogens in their GI tract (e.g., subjects colonized with pathogens in their intestines) and/or receiving broad spectrum antibiotics. Further aspects of the disclosure, including a description of defined terms, are provided below.

I. Definitions

Agitation conditions: As used herein, the term "agitation conditions" refers to conditions that promote or maintain a substantially uniform or homogeneous state of a mixture (e.g., a reaction mixture comprising dextrose monomer and galactose monomer) with respect to dispersal of solids (e.g., solid catalysts), uniformity of heat transfer, or other similar parameters. Agitation conditions generally include stirring, shaking, and/or mixing of a reaction mixture. In some embodiments, agitation conditions may include the addition of gases or other liquids into a solution. In some embodiments, agitation conditions are used to maintain substantially uniform or homogenous distribution of a catalyst, e.g., an acid catalyst. In some embodiments, a reaction mixture comprising dextrose monomer and galactose monomer is heated in the presence of an acid catalyst under suitable conditions to achieve homogeneity and uniform heat transfer in order to synthesize an oligosaccharide composition.

Approximately: As used herein, the term "approximately" or "about," as applied to one or more values of interest, refers to a value that is similar to a stated reference value. In certain embodiments, the term "approximately" or "about" refers to a range of values that fall within 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Dextrose monomer: As used herein, the term "dextrose monomer" refers to a D-isomer of a glucose monomer, known as $_D$-glucose. In some embodiments, dextrose monomers are compliant under good manufacturing practices (GMP) conditions.

Dextrose preparation: As used herein, the term "dextrose preparation" refers to a preparation that comprises at least two dextrose molecules, e.g., a preparation comprising at least two saccharide units that comprise dextrose. In some embodiments, a saccharide unit that comprises dextrose is a dextrose monomer. In some embodiments, a dextrose preparation comprises dextrose monohydrate. In some embodiments, the dextrose preparation comprises dextrose monohydrage. In some embodiments, a dextrose preparation comprises corn syrup (e.g., 70DS corn syrup). In some embodiments, a dextrose preparation comprises a starch hydrolysate, such as, e.g., a corn syrup (e.g., a corn syrup with a reducing sugar content of greater than 20% dextrose equivalent (DE)) or a maltodextrin (e.g., a maltodextrin with a reducing sugar content of less than 20% DE). In some embodiments, a dextrose preparation can be a solid, e.g., a powder, or a syrup, e.g., a liquid comprising greater than 70% solids.

Effective amount: As used herein, the term "effective amount" refers to an administered amount or concentration of an oligosaccharide composition that is necessary and sufficient to elicit a biological response, e.g., in a subject or patient. In some embodiments, an effective amount of an oligosaccharide composition is capable of modulating, e.g., increasing or decreasing, the activity or levels of an enzyme in a subject. In some embodiments, an effective amount of an oligosaccharide composition is capable of modulating, e.g., increasing or decreasing, the processing of a metabolite. In some embodiments, an effective amount of an oligosaccharide composition is capable of modulating, e.g., increasing or decreasing, the concentration or number of at least one microbial species. In some embodiments, an effective amount of an oligosaccharide composition is capable of modulating, e.g., decreasing, the symptoms of a disease associated with hyperammonemia in a subject (e.g., the severity or number of symptoms). In some embodiments, an effective amount of an oligosaccharide composition is capable of treating a disease associated with hyperammonemia in a subject. In some embodiments, an effective amount of an oligosaccharide composition is an amount capable of modulating, e.g., decreasing, or mitigating one or more symptoms of a disease associated with elevated pathogen abundance or colonization in a subject (e.g., the severity or number of symptoms). In some embodiments, an effective amount of an oligosaccharide composition is an amount capable of reducing the acquisition of, colonization of, and/or reducing the reservoir of a pathogen (e.g., a drug or antibiotic resistant pathogen, or an MDR pathogen) in a subject. In some embodiments, an effective amount of an oligosaccharide composition is capable of treating a subject having intestinal colonization with a pathogen, e.g., CRE or VRE.

Galactose monomer: As used herein, the term "galactose monomer" refers to a D-isomer of a galactose monomer, known as $_D$-galactose. In some embodiments, galactose monomers are compliant under good manufacturing practices (GMP) conditions.

Galactose preparation: As used herein, the term "galactose preparation" refers to a preparation that comprises at least two galactose molecules, e.g., a preparation comprising at least two saccharide saccharide units that comprise galactose. In some embodiments, a saccharide unit that comprises galactose is a galactose monomer. In some embodiments, the galactose preparation comprises anhydrous galactose. In some embodiments, the galactose preparation comprises galactose monohydrage. In some embodiments, a galactose preparation can be a solid, e.g., a powder, or a syrup, e.g., a liquid comprising greater than 70% solids.

Hyperammonemia: As used herein, the term "hyperammonemia" refers to a condition in a subject (e.g., a human subject) associated with elevated levels of ammonia. Generally, a subject having hyperammonemia has elevated levels of ammonia in circulation, e.g., in blood. In some embodiments, the duration and severity of hyperammonemia is positively correlated with brain damage. In some embodiments, patients who have experienced an extended duration of hyperammonemia or high peak ammonia, particularly pediatric patients, may develop profound and chronic neurologic morbidity, including developmental delay, severe intellectual disability, deficits in executive function impacting daily activities, cerebral palsy, and seizure disorder.

As used herein, the term "internal monomer unit" refers to a monomer unit IN of the following formula: $(M)_n$-IN-$(M)_n$, wherein n is an integer of 1 or greater, M is a monomer unit linked (e.g., by glycosidic linkage) to at least one other monomer unit. In some embodiments, an internal monomer unit is linked to at least two other monomer units. In some embodiments, IN is selected from Formulae (Ia), (Ib), (Ic), or (Id), and M is any of Formulae (I) or (II). In some embodiments, an internal monomer unit comprises dextrose monomer.

Monosaccharide preparation: As used herein, the term "monosaccharide preparation" refers to a preparation that comprises at least two monosaccharides (e.g., at least two free molecules, e.g., dextrose monomer and galactose monomer). In some embodiments, a monosaccharide preparation comprises dextrose monomer and galactose monomer.

Oligosaccharide: As used herein, the term "oligosaccharide" (which may be used interchangeably with the term "glycan" in some contexts) refers to a saccharide molecule comprising at least two monosaccharides (e.g., dextrose monomer and galactose monomer) linked together via a glycosidic bond (having a degree of polymerization (DP) of at least 2 (i.e., DP2+)). In some embodiments, an oligosaccharide comprises at least two, at least three, at least four, at least five, at least six, at least seven, at least eight, at least nine, or at least ten monosaccharide subunits linked by glycosidic bonds. In some embodiments, an oligosaccharide in the range of 10-25, 20-50, 40-80, 75-100, 100-150, or at least 100 monosaccharides linked by glycosidic bonds. In some embodiments, an oligosaccharide comprises at least one 1,2; 1,3; 1,4; and/or 1,6 glycosidic bond. Oligosaccharides may be linear or branched. Oligosaccharides may have one or more glycosidic bonds that are in alpha-configurations and/or one or more glycosidic bonds that are in beta-configurations.

Pharmaceutical Composition: As used herein, a "pharmaceutical composition" refers to a composition having pharmacological activity or other direct effect in the mitigation, treatment, or prevention of disease, and/or a finished dosage form or formulation thereof and is for human use. A pharmaceutical composition or pharmaceutical preparation is typically produced under good manufacturing practices (GMP) conditions. Pharmaceutical compositions or preparations may be sterile or non-sterile. If non-sterile, such pharmaceutical compositions or preparations typically meet the microbiological specifications and criteria for non-sterile pharmaceutical products as described in the U.S. Pharmacopeia (USP) or European Pharmacopoeia (EP). Any oligosaccharide composition described herein may be formulated as a pharmaceutical composition.

Subject: As used herein, the term "subject" refers to a human subject or patient. Subjects may include a newborn (a preterm newborn, a full-term newborn), an infant up to one year of age, young children (e.g., 1 yr to 12 yrs), teenagers, (e.g., 13-19 yrs), adults (e.g., 20-64 yrs), and elderly adults (65 yrs and older). In some embodiments, a subject is of a pediatric population, or a subpopulation thereof, including neonates (birth to 1 month), infants (1 month to years), developing children (2-12 years), and adolescents (12-16 years). In some embodiments, a subject is a healthy subject. In some embodiments, a subject is a patient having higher abundance of pathogen relative to a healthy subject, e.g., a subject colonized with a pathogen (e.g., CRE and/or VRE pathogens) in their intestines. In some embodiments, a subject is a patient receiving broad spectrum antibiotics. In some embodiments, the subject is particularly susceptible to pathogen infection, e.g., the subject is critically-ill and/or immunocompromised.

Treatment and Treating: As used herein, the terms "treating" and "treatment" refer to the administration of a composition to a subject (e.g., a symptomatic subject afflicted with an adverse condition, disorder, or disease) so as to affect a reduction in severity and/or frequency of a symptom, eliminate a symptom and/or its underlying cause, and/or facilitate improvement or remediation of damage, and/or preventing an adverse condition, disorder, or disease in an asymptomatic subject who is susceptible to a particular adverse condition, disorder, or disease, or who is suspected of developing or at risk of developing the condition, disorder, or disease.

II. Oligosaccharide Compositions

Provided herein are oligosaccharide compositions, and their methods of use for modulating levels of ammonia in a human subject and for treatment of hyperammonemia and/or hepatic encephalopathy (HE).

In one aspect, oligosaccharide compositions are provided herein that comprise a a plurality of oligosaccharides selected from Formula (I) and Formula (II):

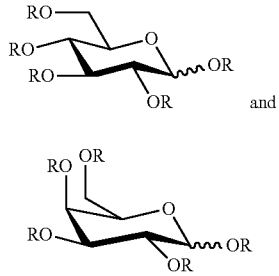

wherein each R independently is selected from hydrogen, and Formulae (Ia), (Ib), (Ic), (Id), (IIa), (IIb), (IIc), (IId):

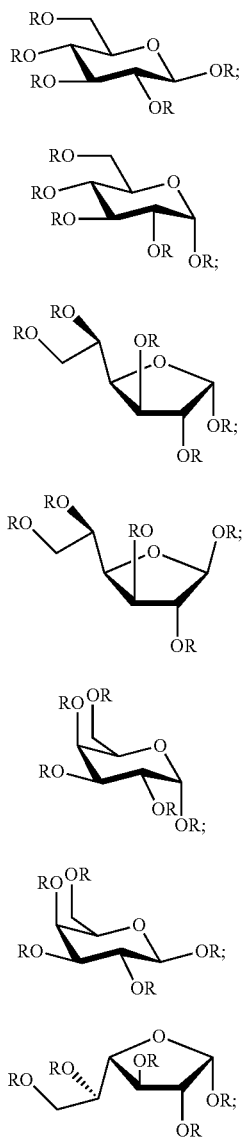

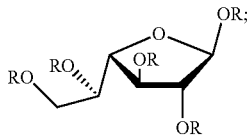

wherein each R independently is as defined above.

In some embodiments, the oligosaccharide composition is minimally digestible by a human. In some embodiments, the oligosaccharide composition contains a plurality of oligosaccharides that are minimally digestible in humans. In some embodiments, the oligosaccharide composition contains a plurality of oligosaccharides that are resistant to degradation by human digestive enzymes (e.g., amylases, glucosidases, galactosidases and other digestive enzymes encoded by human cells), and/or are resistant to hydrolytic digestion, e.g., in the upper GI tract (e.g., the small intestines and stomach).

In some embodiments, the oligosaccharide composition contains a plurality of oligosaccharides selected from Formula (I) and Formula (II), wherein each R in Formula (I) and Formula (II) is selected from hydrogen and Formulae (Ia), (Ib), (Ic), (Id), (IIa), (IIb), (IIc), (IId), and wherein approximately 5% to 95% of the Rs are selected from Formulae (Ia), (Ib), (Ic), and (Id), e.g., approximately 10% to 90%, 15% to 85%, 20% to 80%, 25% to 75%, 30% to 70%, 35% to 65%, 40% to 60%, 45% to 55%, 5% to 15%, 5% to 25%, 10% to 50%, 10% to 25%, 20% to 50%, 25% to 50%, 30% to 50%, or 40% to 80% of the Rs are selected from Formulae (Ia), (Ib), (Ic), and (Id). In some embodiments, the oligosaccharide compositions contain a plurality of oligosaccharides selected from Formula (I) and Formula (II), wherein each R in Formula (I) and Formula (II) is selected from hydrogen and Formulae (Ia), (Ib), (Ic), (Id), (IIa), (IIb), (IIc), (IId), and wherein approximately 5% to 95% of the Rs are selected from Formulae (IIa), (IIb), (IIc), and (IId), e.g., approximately 10% to 90%, 15% to 85%, 20% to 80%, 25% to 75%, 30% to 70%, 35% to 65%, 40% to 60%, 45% to 55%, 5% to 15%, 5% to 25%, 10% to 50%, 10% to 25%, 20% to 50%, 25% to 50%, 30% to 50%, or 40% to 80% of the Rs are selected from Formulae (IIa), (IIb), (IIc) and (IId). In some embodiments, the oligosaccharide compositions contain a plurality of oligosaccharides selected from Formula (I) and Formula (II), wherein each R independently is selected from hydrogen and Formulae (Ia), (Ib), (Ic), (Id), (IIa), (IIb), (IIc), (IId), and wherein approximately 50% of the Rs are selected from Formulae (Ia), (Ib), (Ic), and (Id), and approximately 50% of the Rs are selected from Formulae (IIa), (IIb), (Ic) and (IId).

In some embodiments, the oligosaccharide compositions contain a plurality of oligosaccharides that comprise approximately 5% to 95% glucose saccharides, e.g., approximately 10% to 90%, 15% to 85%, 20% to 80%, 25% to 75%, 30% to 70%, 35% to 65%, 40% to 60%, 45% to 55%, 5% to 15%, 5% to 25%, 10% to 50%, 10% to 25%, 20% to 50%, 25% to 50%, 30% to 50%, or 40% to 80% glucose saccharides. In some embodiments, the remaining saccharides (i.e., non-glucose saccharides) of the plurality of oligosaccharides comprise galactose monomers. In some embodiments, the oligosaccharide compositions contain a plurality of oligosaccharides that comprise approximately 5% to 95% galactose saccharides, e.g., approximately 10% to 90%, 15% to 85%, 20% to 80%, 25% to 75%, 30% to 70%, 35% to 65%, 40% to 60%, 45% to 55%, 5% to 15%, 5% to 25%, 10% to 50%, 10% to 25%, 20% to 50%, 25% to 50%, 30% to 50%, or 40% to 80% galactose saccharides. In some embodiments, the remaining saccharides (i.e., non-galactose saccharides) of the plurality of oligosaccharides comprise glucose saccharides. In some embodiments, the oligosaccharide compositions contain a plurality of oligosaccharides that comprise approximately 50% glucose saccharides and approximately 50% galactose saccharides.

Generation of Oligosaccharide Compositions

Provided herein are methods for generating oligosaccharide compositions, by: a) providing one or more oligosaccharide unit(s), b) contacting the oligosaccharide unit(s) with a catalyst described herein and, optionally, a suitable solvent (e.g., water or a non-aqueous solvent), for a period of time sufficient to produce oligosaccharide compositions comprising polymers of the oligosaccharide units with a desired average degree of polymerization; and, optionally, c) isolating and/or recovering at least a portion of the polymerized oligosaccharide compositions. In certain embodiments, the oligosaccharide compositions produced using the methods described herein reduce ammonia levels and/or the abundance of pathogens in subjects in need thereof, e.g., subjects having or at risk of having a disease, disorder, or condition associated with elevated ammonia levels and/or pathogen infection or colonization.

In certain embodiments, the oligosaccharide compositions described herein comprise polymers of glucose and galactose monomer units. In certain embodiments, the starting material of the oligosaccharide production methods described herein (comprising, e.g., preparations of glucose and galactose monomer units, such as dextrose and galactose monosaccharides) is contacted with a catalyst in a reaction mixture under conditions that promote the formation of one or more glycosidic bonds between oligosaccharide units, thereby producing a preparation of oligosaccharide polymers. In some embodiments, a non-enzymatic catalyst is used to prepare the oligosaccharide compositions described herein. In some embodiments, a catalyst comprising acidic protons, such as a solid or soluble acid catalyst, is added to the starting material preparation (e.g., during or following heating) to promote the formation of one or more glycosidic bonds between the dextrose and/or galactose units, thereby leading to the formation of oligosaccharides. In some embodiments, the catalyst comprises acidic protons. In some embodiments, the catalyst is an organic acid, an inorganic acid, or an anhydride. In some embodiments, the catalyst is a homogenous acid catalyst. In some embodiments, the catalyst is a heterogeneous acid catalyst. In some embodiments, the catalyst is a monocarboxylic acid. In some embodiments, the catalyst is a polycarboxylic acid. In some embodiments, the catalyst is a cross-linkable acid catalyst. In some embodiments, the catalyst is not a cross-linkable acid catalyst. In some embodiments, a solid acid catalyst is used to prepare the oligosaccharide compositions. In certain embodiments, suitable catalysts comprise acidic monomers, optionally, wherein each acidic monomer has at least one Bronsted-Lowry acid. In some embodiments, the catalyst is a strong acid cation exchange resin having one or more physical and chemical properties according to Table 1. In some embodiments, the catalyst comprises >3.0 mmol/g sulfonic acid moieties and <1.0 mmol/gram cationic moieties. In certain embodiments, the catalyst has a nominal moisture content of 45-50 weight percent. In some embodiments, a soluble acid catalyst is used to prepare the oligosaccharide compositions.

TABLE 1

Non-Limiting Example of Strong Acid Cation Exchange Resin Properties

| Property | Unit | Value |
|---|---|---|
| Physical Form | | Amber translucent spherical beads |
| Matrix | | Styrene-DVB, gel |
| Function group | | Sulfonic acid |
| Ionic form as shipped | | H+ form |
| Total volume capacity, min. | eq/L | 1.8 |
| | kgr/ft³ as CaCO₃ | 39.3 |
| Moisture retention capacity | % | 50-56 |
| Particle size | | |
| Uniformity coefficient, max. | | 1.1 |
| Harmonic mean diameter | pm | 600 ± 50 |
| Whole uncracked beads | % | 95-100 |
| Total swelling (Na⁺ → H⁺) | % | 8 |
| Particle density | g/mL | 1.2 |
| Shipping density | g/L | 800 |
| | lbs/ft³ | 50 |

In some embodiments, the catalyst can be an alkaline catalyst, an acidic catalyst, a catalytic resin, or a metal catalyst. In certain embodiments, the catalyst is an ion exchange resin, such as, e.g., AMBERLITE FPC11 Na, AMBERLITE FPC14 Na, DOWEX 88, DOWEX 88 H, DOWEX 88 MB, DOWEX 88 MB H, DOWEX FPC16UPS H, DOWEX FPC16UPS Na, DOWEX FPC23UPS H, DOWEX MAC-3, DOWEX MONOSPHERE 88, DOWEX MONOSPHERE 88 H, DOWEX MONOSPHERE 99 Ca/310, DOWEX MONOSPHERE 99 Ca/320, DOWEX MONOSPHERE 99 K/310, DOWEX MONOSPHERE 99 K/320, DOWEX MONOSPHERE 99 K/350, DOWEX™ PSR-2, DOWEX™ G-26 H, AMBERJET 1600 H, AMBERJET 2000 H, AMBERLITE IRN150, AMBERLITE IRN160, AMBERLITE IRN170, AMBERLITE IRN217, AMBERLITE IRN317, AMBERLITE IRN360, AMBERLITE IRN77, AMBERLITE IRN97 H, AMBERLITE IRN99 H, AMBERLITE IRN9652, AMBERLITEIRN9882, AMBERLITE IRN9687, AMBERSEP 252 H, DOWEX MONOSPHERE 1400PC H, DOWEX MONOSPHERE 650C H, AMBERLITE 200C Na, AMBERLITE IR120 H, AMBERLITE IR120 Na, AMBERLITE IRC83, AMBERLITE MB20, DOWEX MARATHON 1200 H, DOWEX MARATHON 1200 Na, DOWEX MARATHON 1300 H, DOWEX MARATHON 8300, DOWEX MARATHON C (DOWEX FPC16 UPS H), DOWEX MARATHON C-10, DOWEX MARATHON MR-3, DOWEX MARATHON MSC, DOWEX MARATHON MSC H, DOWEX™ HCR-S/S, IMAC™ HP333, AMBERJET UP1400, AMBERJET UP6040, AMBERJET UP6150, DOWEX MONOSPHERE MR-3 UPW, DOWEX MONOSPHERE MR-450 UPW, AMBERLITE CG50 Type 1, AMBERLITE COBALAMION, AMBERLITE FPC3500, AMBERLITE IRP476, AMBERLITE IRP64, AMBERLITE IRP69, AMBERLITE IRP88, DOWEX 50WX2 (H+), DOWEX 50WX4 (H+), DOWEX 50WX8 (H+), AMBERLITE BD10, AMBERLITE IRC84SPI H, AMBERLYST 123, AMBERLYST 125, AMBERLYST 131, AMBERLYST 15, AMBERLYST 16, AMBERLYST 19, AMBERLYST 33, AMBERLYST 35, AMBERLYST 36, AMBERLYST 39, AMBERLYST 40, AMBERLYST 45, AMBERLYST BD20, AMBERLYST CH28, AMBERSEP BD19, AMBERSEP 200 H, or other cation exchange resin in its protonated form.

In some cases, the oligosaccharide compositions described herein can be produced using a polymeric catalyst as described in WO 2012/118767, "POLYMERIC ACID CATALYSTS AND USES THEREOF" or by other suitable methods, e.g., as described in WO 2016/007778, "OLIGOSACCHARIDE COMPOSITIONS AND METHODS FOR PRODUCING THEREOF", each of which is incorporated herein by reference in its entirety. Other solid acid catalysts may also be used. In some embodiments, methods to prepare the polymeric and solid-supported catalysts described herein can be found in WO 2014/031956, "POLYMERIC AND SOLID-SUPPORTED CATALYSTS, AND METHODS OF DIGESTING CELLULOSIC MATERIALS USING SUCH CATALYSTS," which is incorporated herein by reference in its entirety.

In certain embodiments, non-limiting examples of acid catalysts that can be used to produce an oligosaccharide composition as described herein include: adipic acid, acetic acid, citric acid, fumaric acid, gluconic acid, itaconic acid, lactic acid, maleic acid, malic acid, succinic acid, tartaric acids, terephthalic acids, hydrochloric acid, sulfuric acid, sulfurous acid, thiosulfuric acid, dithionic acid, pyrosulfuric acid, selenic acid, selenious acid, nitric acid, phosphoric acid, phosphorous acid, hypophosphorous acid, pyrophosphoric acid, polyphosphoric acid, hypophosphoric acid, boric acid, perchloric acid, hypochlorous acid, hydrobromic acid. In some embodiments, the acid catalyst is an acidic alkali metal or alkaline earth metal salts of an inorganic acid. In some embodiments, the catalyst is a soluble acid catalyst, e.g., a soluble acid of any of the above.

In certain embodiments, the oligosaccharide polymerization reaction is loaded with an catalyst with acidic protons. In some embodiments, the molar ratio of acidic protons to total dextrose and galactose content (e.g., total dextrose monomers and galactose monomers) in the reaction is in a range of 0.01 to 0.1, 0.02 to 0.08, 0.03 to 0.06, or 0.05 to 0.06. In some embodiments, the molar ratio of acidic protons to total dextrose and galactose content (e.g., total dextrose and galactose monomers) in the reaction is in a range of 0.050 to 0.052.

In some embodiments, the starting material for the polymerization reaction to produce the oligosaccharide compositions includes one or more oligosaccharide units selected from an amino sugar, a deoxy sugar, an imino sugar, a sugar acid, a sugar amide, a sugar ether, a sugar alcohol, or any combination thereof. In some embodiments of the methods provided herein, the starting material for the polymerization reaction to produce the oligosaccharide compositions includes two or more monosaccharides (monomers), one or more disaccharides, one or more trisaccharides, one or more oligosaccharides, one or more polysaccharides comprising glucose and galactose, or a combination thereof. For example, the starting material for the polymerization reaction can be a dextrose preparation made up of dextrose monomers, dimers, and/or trimers, and a galactose preparation made up of galactose monomers, dimers, and/or trimers. In some embodiments, the starting material for the polymerization reaction includes dextrose monohydrate, galactose monohydrate, or a combination of dextrose monohydrate and galactose monohydrate. In some embodiments, the starting material for the polymerization reaction includes anhydrous dextrose. In some embodiments, the starting material for the polymerization reaction include anhydrous galactose. In some embodiments, the starting material for the polymerization reaction includes anhydrous dextrose and anhydrous galactose. In some embodiments, the starting material for the polymerization reaction includes dextrose monohydrate and anhydrous galactose. In some embodiments, the starting material for the polymerization reaction includes lactose, e.g., lactose monohydrate. In some embodiments of the method, the starting material for the polymerization reaction includes furanose sugar and/or pyranose sugar. In some embodiments, the starting material for the polymerization reaction is two or more oligosaccharide units selected from tetrose, pentose, hexose, and/or heptose, e.g., glucose and galactose tetroses, pentoses, hexoses, and/or heptoses. In some embodiments of the method, the starting material for the polymerization reaction includes glucose, optionally in either its L- or D-form, in alpha or beta configuration (for glucose dimers), and/or a deoxy-form, where applicable, and any combination thereof. In some embodiments of the method, the starting material for the polymerization reaction includes galactose, optionally in either its L- or D-form, in alpha or beta configuration (for galactose dimers), and/or a deoxy-form, where applicable, and any combination thereof. In one embodiment, the glucose/dextrose and galactose used as starting materials in the methods described herein can be C5 or C6 monosaccharides. In some embodiments, the glucose is a C5 monosaccharide. In some embodiments, the glucose is a C6 monosaccharide. In some embodiments the galactose is a C6 monosaccharide. In some embodiments, the galactose is a C5 monosaccharide. In some embodiments, the glucose and/or galactose is substituted or derivatized with one or more of an acetate ester, sulfate half-ester, phosphate ester, or a pyruvyl cyclic acetal group, or have been otherwise derivatized at, e.g., at one or more hydroxyl groups In some embodiments, the starting material for the polymerization reaction is a starch hydrolysate, e.g., a hydrolysate syrup. In some embodiments, the starting material for the polymerization reaction can be a hydrolysate syrup that contains glucose, galactose, and/or lactose, or any combination thereof. In some embodiments, the starting material can include a glucose syrup, a galactose syrup, or mixtures thereof. In some embodiments, the starting material for the polymerization reaction can include a dextrose syrup. In some embodiments, the starting material for the polymerization reaction is a lactose hydrolysate syrup. In some embodiments, the starting material can include a corn syrup. In some embodiments, the starting material can be a syrup chosen from any syrup within a range of dextrose equivalent (DE) syrups, e.g., a syrup chosen from 20-99DE syrups. In some embodiments, the dextrose monomers used may be dextrose monohydrate or 70DS corn syrup. In some embodiments, the starting material for the polymerization reaction to produce the oligosaccharide compositions includes dextrose and galactose monomers. In some embodiments, the ratio of dextrose monomer to galactose monomer in the reaction mixture is about 1:3, 1:2.8, 1:2.5, 1:2.4, 1:2.3, 1:2.2, 1:2.1, 1:2, 1:1.8, 1:1.5, 1:1.4, 1:1.3, 1:1.2, 1:1.1, 1:1, 1.1:1, 1.2:1, 1.3:1, 1.4:1, 1.5:1, 1.8:1, 2:1, 2.1:1, 2.2:1, 2.3:1, 2.4:1, 2.5:1, 2.8:1, or 3:1, respectively. In some embodiments, the ratio of dextrose monomer to galactose monomer is about 1:1. In some embodiments, between 5% and 95% of the sugars in the starting material for the polymerization reaction is dextrose, e.g., dextrose monohydrate or anhydrous dextrose. In some embodiments, between 5% and 95% of the sugars in the starting material for the polymerization reaction is galactose, e.g., galactose monohydrate or anhydrous galactose. In some embodiments, 5% of the starting material sugars is dextrose and 95% is galactose; 10% is dextrose and 90% is galactose; 20% is dextrose and 80% is galacose; 30% is dextrose and 70% is galactose; 40% is dextrose and 60% is galactose; 50% is dextrose and 50% is galactose; 60% is dextrose and 40% is galactose; 70% is dextrose and 30% is galactose; 80% is dextrose and 20% is galactose; 90% is dextrose and 10% is galactose; or 95% is dextrose and 5% is galactose. In a preferred embodiment, 50% of the sugars in the starting material for the polymerization reaction is dextrose and 50% of the sugars in the starting material for the polymerization reaction is galactose. In some embodiments, 50% of the starting material is dextrose and 50% of the starting material is galactose.

Reaction Conditions

In some embodiments, oligosaccharide compositions are produced by a process that initially involves heating a preparation comprising dextrose (e.g., dextrose monomers or monosaccharides) and galactose (e.g., galactose monomers or monosaccharides) to a temperature in a range of about 120° C. to about 160° C., e.g., about 120° C. to 130° C., about 120° C. to 140° C., about 125° C. to 135° C., about 130° C. to 140° C., about 130° C. to 135° C., about 135° C. to 145° C., about 135° C. to 155° C., or about 140° C. to 150° C., in the presence of catalyst. In certain embodiments, the catalyst is added at the same time as dextrose and galactose (e.g., preparations of dextrose and galactose, e.g., comprising dextrose and galactose monomers) in a reaction mixture for the polymerization of glycan units into oligosaccharides. In some embodiments, the dextrose and galactose preparations are heated first, and then the catalyst is loaded into the reaction mixture to promote acid catalyzed oligosaccharide formation. In some embodiments, heating is performed under agitation conditions. In some embodiments, heating involves gradually increasing the temperature (e.g., from room temperature to about 130° C., from room temperature to around 142° C., or from room temperature to about 148° C.) under suitable conditions to achieve homogeneity and uniform heat transfer.

In some embodiments, the pressure of the polymerization reaction is maintained in a certain range. The reaction pressure may be measured using any method known in the art, for example, in pounds per square inch (psi), millimeters of mercury (mmHg), Pascals (Pa), bar, or atmospheres (atm). In some embodiments, the reaction pressure is maintained in the range of about 0.1 psi to about 100 psi. For example, the pressure of the reaction may be maintained between about 1 psi and 75 psi, about 5 psi to about 50 psi, or about 10 psi to about 25 psi. In certain embodiments, the reaction pressure is greater than about 5 psi, about 10 psi, about 12 psi, about 15 psi, about 20 psi, about 25 psi, about 30 psi, about 35 psi, about 40 psi, about 45 psi, or about 50 psi. In other embodiments, the reaction pressure is lower than about 70 psi, about 60 psi, about 50 psi, about 40 psi, about 30 psi, about 20 psi, about 15 psi, about 10 psi, about 5 psi, or about 1 psi. In some embodiments, the pressure of the reaction is maintained lower than about 5 atm, e.g., between about 0.1 and 4 atm, between about 1 and 3 atm, or between about 0.5 and 1.5 atm. In certain embodiments, the reaction pressure may be measured in units of gauge pressure (e.g., relative to ambient atmospheric pressure) or in units of absolute pressure.

In some embodiments, the oligosaccharide preparations (e.g., dextrose and galactose monomers) and catalyst react for at least 30 minutes, at least 1 hour, at least 2 hours, at least 3 hours, at least 4 hours, at least 6 hours, at least 8 hours, at least 16 hours, at least 24 hours, at least 36 hours, or at least 48 hours; or between 1-24 hours, between 2-12 hours, between 2-5 hours, between 3-6 hours, between 1-96 hours, between 12-72 hours, or between 12-48 hours.

In some embodiments, the degree of polymerization of the oligosaccharide polymers of the oligosaccharide compositions produced according to the methods described herein can be regulated by the reaction time. For example, in some embodiments, the degree of polymerization of the oligosaccharide polymers is increased by increasing the reaction time, while in other embodiments, the degree of polymerization of the oligosaccharide polymers is decreased by decreasing the reaction time.

The amount of the glycan units in the starting material of the reaction used in the methods described herein relative to the amount solvent used may affect the rate of reaction and yield. In certain embodiments, the amount of the glycan units used may be characterized by the dry solids content. In certain embodiments, dry solids content refers to the total solids of a slurry as a percentage on a dry weight basis. In some embodiments, the dry solids content of the glycan units (e.g., dextrose and galactose monomers) is between about 5 wt % to about 95 wt %, between about 10 wt % to about 80 wt %, between about 15 wt % to about 75 wt %, or between about 15 wt % to about 50 wt %.

The viscosity of the reaction mixture may be measured and/or altered over the course of the reaction. In general, viscosity refers to a measurement of a fluid's internal resistance to flow (e.g., "thickness") and is expressed in centipoise (cP) or pascal-seconds. In some embodiments, the viscosity of the reaction mixture is between about 100 cP and about 95,000 cP, about 5,000 cP and about 75,000 cP, about 5,000 and about 50,000 cP, or about 10,000 and about 50,000 cP. In certain embodiments, the viscosity of the reaction mixture is between about 50 cP and about 200 cP.

In certain embodiments, the methods of using the catalyst are carried out in an aqueous environment. One suitable aqueous solvent is water, which may be obtained from various sources. Generally, water sources with lower concentrations of ionic species (e.g., salts of sodium, phosphorous, ammonium, or magnesium) may be used, in some embodiments, as such ionic species may reduce effectiveness of the catalyst. In some embodiments where the aqueous solvent is water, the water has less than 10% of ionic species (e.g., salts of sodium, phosphorous, ammonium, magnesium). In some embodiments where the aqueous solvent is water, the water has a resistivity of at least 0.1 megaohm-centimeters, of at least 1 megaohm-centimeters, of at least 2 megaohm-centimeters, of at least 5 megaohm-centimeters, or of at least megaohm-centimeters.

As the methods described herein promote oligosaccharide polymerization in the reaction mixture, water (such as evolved water) is produced with each coupling of the one or more monomers. In certain embodiments, the methods described herein may further include monitoring the amount of water present in the reaction mixture and/or the ratio of water to monomer or catalyst over a period of time. Thus, in some embodiments, the water content of the reaction mixture may be altered over the course of the reaction, for example, removing evolved water produced. Appropriate methods may be used to remove water (e.g., evolved water) in the reaction mixture, including, for example, by evaporation, such as via distillation. In certain embodiments, the method comprises removing water from the reaction mixture through evaporation. In some embodiments, the methods further include removing at least a portion of water produced in the reaction mixture (e.g., by removing at least about any of 10%, 20%, 30%, 40%, 50%, 60%, 70%, 80%, 90%, 95%, 97%, 99%, or 100%, such as by vacuum distillation). It should be understood, however, that the amount of water to monomer may be adjusted based on the reaction conditions and specific catalyst used.

In some embodiments, the water evolved over the course of the reaction is produced at a measurable rate. For example, the evolved water may be determined by measuring an amount of evolved water (e.g, milligrams, grams, or kilograms of water) per amount of input glycans (e.g., milligram, gram, kilogram of input glycan units) per unit of time (e.g., second, minute, hour, or day). In some embodiments, the water evolved is produced at a rate of at least about 0.1 g/kg input glycan unit/hour, e.g., at least about 0.5 g/kg, 1 g/kg, 2 g/kg, 3 g/kg, 4 g/kg, 5 g/kg, 6 g/kg, 7 g/kg, 8 g/kg, 9 g/kg, 10 g/kg, 12 g/kg, 15 g/kg, 18 g/kg, 20 g/kg, 25 g/kg, 30 g/kg, 33 g/kg, or 35 g/kg input glycan unit/hour. In some embodiments, the water evolved is produced at a rate of at least about 2 g/kg input glycan unit/hour. In some embodiments, the water evolved is produced at a rate of at least about 4 g/kg input glycan unit/hour. In some embodiments, the water evolved is produced at a rate of at least about 6 g/kg input glycan unit/hour. In some embodiments, the water evolved is produced at a rate of at least about 8 g/kg input glycan unit/hour. In some embodiments, the water evolved is produced at a rate of at least about 10 g/kg input glycan unit/hour. In some embodiments, the water evolved is produced at a rate of between at least 1 g/kg to 40 g/kg, e.g., between at least about 5 g/kg to 35 g/kg, between at least about 10 g/kg to 40 g/kg, between at least about 10 g/kg to 35 g/kg, or between at l;east about 15 g/kg and 35 g/kg. Evolved water may be measured by any known method in the art, e.g., by acquiring the mass or volume of the evolved water.

The water content of the reaction mixture may be altered over the course of the reaction, for example, by removing evolved water produced. Any method known in the art may be used to remove water (e.g., evolved water) in the reaction mixture, including, for example, by vacuum filtration, vacuum distillation, heating, and/or evaporation. In some embodiments, the method comprises including water in the reaction mixture.

In some embodiments, the degree of polymerization of the one or more glycan polymers produced according to the methods described herein can be regulated by adjusting or controlling the concentration of water present in the reaction mixture. For example, in some embodiments, the degree of polymerization of the one or more glycan polymers is increased by decreasing the water concentration, while in other embodiments, the degree of polymerization of the one or more glycan polymers is decreased by increasing the water concentration. In some embodiments, the water content of the reaction is adjusted during the reaction to regulate the degree of polymerization of the one or more glycan polymers produced.

Generally, the catalyst and the glycan units of the starting material are introduced into an interior chamber of a reactor, either concurrently or sequentially. Glycan synthesis can be performed in a batch process or a continuous process. For example, in one embodiment, glycan polymer synthesis is performed in a batch process, where the contents of the reactor are continuously mixed or blended, and all or a substantial amount of the products of the reaction are removed (e.g. isolated and/or recovered). In one variation, glycan polymer synthesis is performed in a batch process, where the contents of the reactor are initially mixed but no further physical mixing is performed. In another variation, glycan polymer synthesis is performed in a batch process, wherein once further mixing of the contents, or periodic mixing of the contents of the reactor, is performed (e.g., at one or more times per hour), all or a substantial amount of the products of the reaction are removed (e.g. isolated and/or recovered) after a certain period of time.

In other embodiments, glycan polymer synthesis is performed in a continuous process, where the contents flow through the reactor with an average continuous flow rate. After introduction of the catalyst and glycan units of the starting material into the reactor, the contents of the reactor are continuously or periodically mixed or blended, and after a period of time, less than all of the products of the reaction are removed (e.g. isolated and/or recovered). In one variation, glycan polymer synthesis is performed in a continuous process, where the mixture containing the catalyst and glycan units is not actively mixed. Additionally, mixing of catalyst and the glycan units may occur as a result of the redistribution of catalysts settling by gravity, or the non-active mixing that occurs as the material flows through a continuous reactor. In another variation, the reactor is continuously fed by a reactant stream, while a product stream is continuously removed from the reactor. In yet another variation, the reactor is operated in steady state, wherein the reactant stream and product stream are held at fixed flow rates. In other variations, a fraction of the reactor contents are continuously pumped through an external recycle loop, e.g. for the purpose of controlling or measuring properties of the reactor contents such as temperature, density, pH, viscosity, water content, and/or chemical composition. In some variations, mixing of the reactor contents is achieved by the action of pumping a fraction of the reactor contents through such an external recycle loop. In a particular variation, the external recycle loop contains an in-line heat exchanger, flash, or blowdown tank. In another variation, the external recycle loop contains a static mixing element or mixing chamber.

In some embodiments, the reaction mixture is maintained at its boiling point until the weight percent of dextrose (e.g., dextrose monomer) and galactose (e.g., galactose monomer) in the synthesized composition is in a particular range, e.g., once the weight percent of dextrose monomer and galactose monomer in the synthesized oligosaccharide composition is 30% or less (e.g., 28% or less, 25% or less, 22% or less, 20% or less, 19% or less, 18% or less, 17% or less, 16% or less, 15% or less, 14% or less, 13% or less, 12% or less, 11% or less, or 10% or less). In some embodiments, once the weight percent of dextrose monomer and galactose monomer in the oligosaccharide composition produced according to the methods described herein is in a particular range, e.g., a range between 5-30%, the reaction mixture is quenched (e.g., 10%-20%, 12%-22%, 14%-22%, 14%-20%, 14%-18%, or 16%-24%). Quenching typically involves using water (e.g., deionized water) to dilute the reaction mixture, and gradually decreasing the temperature of the reaction mixture to 100° C. or below, e.g., between about 60° C. to about 100° C. or between about 55° C. to 95° C. In some embodiments, the water used for quenching is about 95° C. The water may be added to the reaction mixture under conditions sufficient to avoid solidifying the mixture. In certain embodiments, water may be removed from the reaction mixture by evaporation. In some embodiments, the reaction mixture may contain 93-94 weight percent dissolved solids. In some embodiments, the reaction mixture is quenched when the weight percent of dextrose and galactose monomers in the oligosaccharide composition is between 5-25%, between 15-30%, between 10-25%, between 12-22%, between 14-20%, between 15-25%, or between 12-18%.

In some embodiments, the reaction mixture is maintained at its boiling point until the molar ratio of net water condensate to the total dextrose and galactose that was present in the reaction mixture prior to heating is in a particular range, e.g., a range of 0.1 to 5.0, e.g., a range of 0.35 to 1.0, 0.35 to 0.8, 0.4 to 0.9, 0.5 to 0.9, 0.5 to 0.8, 0.6 to 0.9, 0.6 to 0.8, or 0.7 to 0.9. For example, in some embodiments, the reaction mixture is maintained at its boiling point until the molar ratio of net water condensate to total dextrose monomer and galactose monomer in a reaction mixture prior to heating is 0.4 to 0.9 (e.g., about 0.6 to 0.8).

In some embodiments, once the molar ratio of net water condensate to the total dextrose and galactose that was present in the reaction mixture prior to heating is in a particular range, e.g., a range of 0.1 to 5.0, e.g., a range of 0.35 to 1.0, 0.35 to 0.8, 0.4 to 0.9, 0.5 to 0.9, 0.5 to 0.8, 0.6 to 0.9, 0.6 to 0.8, or 0.7 to 0.9, the reaction mixture is quenched. For example, in some embodiments, once the molar ratio of net water condensate to total dextrose monomer and galactose monomer in a reaction mixture prior to heating is 0.4 to 0.9 (e.g., about 0.6 to 0.8), the reaction mixture is quenched. In some embodiments, quenching involves using water (e.g., deionized water) to dilute the reaction mixture, and gradually decrease the temperature of the reaction mixture to 100° C. or below.

In some embodiments, the reaction mixture is stopped or quenched when the molar ratio of net water condensate produced by the reaction mixture (maintained at its boiling point at a pressure in the range of 0.5-1.5 atm) relative to the total dextrose and galactose in the reaction starting material (e.g., the total dextrose and galactose monomers in the starting material of the reaction before the acid catalyst is loaded) is in a range of 0.1-1.0, e.g., in a range of 0.15-1.0, in a range of 0.2-1.0, in a range of 0.3-0.9, in a range of 0.3-0.8, in a range of 0.2-0.9, or in a range of 0.2-0.8.

In some embodiments, aa oligosaccharide composition as described herein comprises a plurality of oligosaccharides selected from Formula (I) and Formula (II):

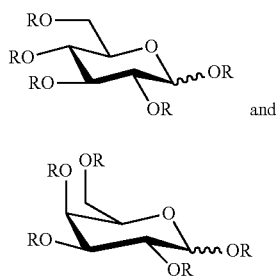

and

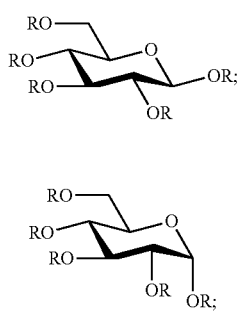

wherein R in Formula (I) and Formula (II) is independently selected from hydrogen, and Formulae (Ia), (Ib), (Ic), (Id), (IIa), (IIb), (IIc), (IId):

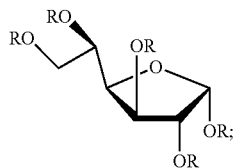

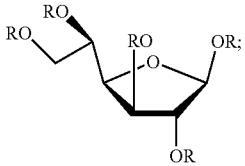

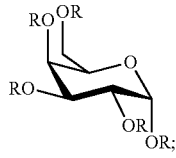

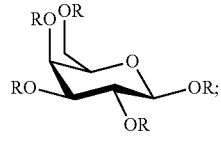

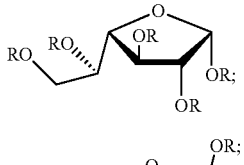

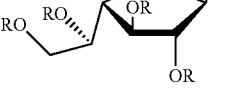

wherein R in Formulae (Ia), (Ib), (Ic), (Id), (IIa), (IIb), (IIc), and (IId) is independently defined as above in Formula (I) and Formula (II). In some embodiments, the oligosaccharide composition is produced by a process comprising:

(a) heating a preparation comprising dextrose, e.g., dextrose monomer, and galactose, galactose monomer, wherein the molar ratio of glucose to galactose is about 1:1 under agitation conditions, to a temperature in a range of 110° C. to 160° C., e.g., 130° C. to 148° C.;

(b) loading the preparation with a catalyst comprising acidic protons (e.g., a soluble acid catalyst or a solid acid catalyst), in an amount such that the molar ratio of acidic protons to total dextrose and galactose content is in a range of 0.001-0.25, e.g., 0.050 to 0.052, thereby forming a reaction mixture; and (c) maintaining the reaction mixture at atmospheric pressure (e.g., at around 1 atm), at a temperature in a range of 110° C. to 160° C., e.g., 128° C. to 150° C., under conditions that promote acid catalyzed glycan formation, until the weight percent of dextrose monomer and galactose monomer in the oligosaccharide composition is in a range of 12-16;

(d) quenching the reaction mixture, for example, using water while bringing the temperature of the reaction mixture to 100° C. or below (e.g., a temperature in the range of 55° C. to 95° C. (e.g., 85° C. or 90° C.)); and (e) separating oligosaccharides from the acid catalyst; thereby obtaining the oligosaccharide composition. In certain embodiments, steps (a) and (b) occur simultaneously. In some embodiments, step (a) comprises gradually increasing the temperature (e.g., from room temperature) to about 148° C., under suitable conditions to achieve homogeneity and uniform heat transfer.

Additional Processing Steps

Optionally, the oligosaccharide compositions described herein may undergo additional processing steps. Additional processing steps may include, for example, purification steps. In some embodiments, the oligosaccharide compositions may undego one or more processing steps that include, e.g., separation, dilution, concentration, filtration, desalting or ion-exchange, chromatographic separation, or decolorization, or any combination thereof. In some embodiments, the oligosacchide compositions described herein may undergo one or more demonomerization steps, wherein the DP1 fractions (the glucose and/or galactose monomers) of the oligosaccharide compositions are partially or completely removed.

In some embodiments, the oligosaccharide compositions produced according to the methods described herein can be subjected to one or more purification steps, such as one or more chromatography purification steps, e.g., using chromatography columns. In some embodiments, the oligosaccharide compositions can be run through one or more chromatographic resins to purify the oligosaccharide compositions and/or to isolate a particular portion of oligosaccharides (e.g., of a particular size range) from the oligosaccharide compositions. In some embodiments, the oligosaccharide compositions are run through a series of chromatographic resins than can include one or more cationic exchange resins, anionic exchange resins, and/or decolorizing polymer resins, in any combination or order. In some embodiments, the oligosaccharide compositions are run through a cationic exchange resin, followed by an anionic exchange resin, followed by a decolorizing polymer resin. In some embodiments, any or all of the types of resins may be used one or more times in any order.

Separation and Concentration

In some embodiments, the methods described herein further include isolating or separating an oligosaccharide composition described herein or a portion of the oligosaccharide composition (e.g., comprising one or more glycan polymers or a particular fraction of glycan polymers) from the catalyst or a portion of the catalyst, using a method known in the art, including, for example, centrifugation, filtration (e.g., vacuum filtration, membrane filtration), and gravity settling. In some embodiments, isolating the oligosaccharide composition comprises separating at least a portion of the oligosaccharide composition from at least a portion of any unreacted sugar, using any method known in the art, including, for example, filtration (e.g., membrane filtration), chromatography (e.g., chromatographic fractionation), differential solubility, and centrifugation (e.g., differential centrifugation).

In some embodiments, the methods described herein further include a concentration step. For example, in some embodiments, an oligosaccharide composition is subjected to evaporation (e.g., vacuum evaporation) to produce a concentrated oligosaccharide composition. In other embodiments, the oligosaccharide compositions may be subjected to a spray drying step to produce an oligosaccharide powder. In certain embodiments, the oligosaccharide compositions may be subjected to both an evaporation step and a spray drying step. In some embodiments, the oligosaccharide compositions be subjected to a lyophilization (e.g., freeze drying) step to remove water and produce powdered product. In some embodiments, the total percent water content of the oligosaccharide composition is 10% or lower, e.g., 9% or lower, 7% or lower, 5% or lower, 4% or lower, or 3% or lower.

In some embodiments, the oligosaccharide composition is separated from the acid catalyst (e.g., a solid acid catalyst), e.g., by diluting the quenched reaction mixture with water and/or by running the quenched reaction mixture through a filter. In some embodiments, deionized water is used for dilution. In certain embodiments, USP purified water is used for dilution. In certain embodiments, after dilution, the oligosaccharide composition comprises water in a range of about 5-75, 25-65, 35-65, 45-55, or 47-53 weight percent. In certain embodiments, after dilution, the oligosaccharide composition comprises water in a range of about 45-55 weight percent. In some embodiments, the quenched reaction mixture is diluted with water to a concentration of about 45-55 weight percent and a temperature of below about 85° C. and then passed through a filter or a series of chromatographic resins. In certain embodiments, the filter used is a 0.45 µm filter.

In some embodiments, an oligosaccharide composition described herein is not separated from the catalyst, e.g., when the catalyst is non-toxic to a subject, e.g., a human subject, and when the catalyst does not negatively affect the stability of the oligosaccharide composition or the use of the oligosaccharide composition for its intended purpose, e.g., in the treatment of a disease or disorder in a human subject.

Decolorization

In some embodiments, the methods described herein further include a decolorization step. The oligosaccharide compositions described herein may undergo a decolorization step using appropriate methods, including, for example, treatment with an absorbent (e.g., activated carbon). In certain embodiments, the oligosaccharide compositions are contacted with a color-adsorbing material at a particular temperature, at a particular concentration, and/or for a particular duration of time. In some embodiments, the mass of the color adsorbing species contacted with the oligosaccharide compositions is less than 50% of the mass of the oligosaccharide compositions, less than 35% of the mass of the oligosaccharide compostions, less than 20% of the mass of the oligosaccharide compositions, less than 10% of the mass of the oligosaccharide compositions, less than 5% of the mass of the oligosaccharide compositions, less than 2% of the mass of the oligosaccharide compositions, or less than 1% of the mass of the oligosaccharide compositions. In certain embodiments, the oligosaccharide compositions are made to flow through a fixed or packed bed of color-adsorbing material at a particular temperature and at a particular flow rate. In some embodiments, the oligosaccharide composition is flowed through a chromatography column, e.g., a chromatography column with an absorbent, and.or subjected to filtration (e.g., microfitration).

In some embodiments, the oligosaccharide compositions are contacted with a color adsorbing material. In certain embodiments, the oligosaccharide compositions are contacted with a color adsorbing material for less than 10 hours, less than 5 hours, less than 1 hour, or less than 30 minutes. In a particular embodiment, the oligosaccharide compositions are contacted with a color adsorbing material for 1 hour. In certain embodiments, the oligosaccharide compositions are contacted with a color adsorbing material at a temperature from 20 to 100 degrees Celsius, 30 to 80 degrees Celsius, 40 to 80 degrees Celsius, or 40 to 65 degrees Celsius. In a particular embodiment, the oligosaccharide compositions are contacted with a color adsorbing material at a temperature of 50 degrees Celsius.

In certain embodiments, the color adsorbing material is activated carbon. In one embodiment, the color adsorbing material is powdered activated carbon. In other embodiments, the color adsorbing material is an ion exchange resin. In one embodiment, the color adsorbing material is a strong base cationic exchange resin in a chloride form. In another embodiment, the color adsorbing material is cross-linked polystyrene. In yet another embodiment, the color adsorbing material is cross-linked polyacrylate. In certain embodiments, the color adsorbing material is Amberlite FPA91, Amberlite FPA98, Dowex 22, Dowex Marathon MSA, or Dowex Optipore SD-2.

Ion-Exchange/De-Salting (Demineralization)

In some embodiments, the oligosaccharide compositions produced according to the methods described herein are contacted with a material to remove salts, minerals, and/or other ionic species. For example, in certain embodiments, the oligosaccharide compositions produced are flowed through an anioic exchange column. In other embodiments, oligosaccharide compositions produced are flowed through an anionic/cationic exchange column pair. In one embodiment, the anionic exchange column contains a weak base exchange resin in a hydroxide form and the cationic exchange column contains a strong acid exchange resin in a protonated form. In certain embodiments, the oligosaccharide compositions produced are flowed through the ion exchange resin columns at a specified temperature and flow rate determined for the particular column and/or exchange medium. In a particular embodiment, the oligosaccharide compositions produced are flowed through the ion exchange resin columns for a period of time, after which the ion exchange media are regenerated. In a certain embodiment, the anionic exchange resin is Dowex 66 or Dowex 77.

Fractionation

In some embodiments, the methods described herein further include a fractionation step. Oligosaccharide compositions prepared and purified may be subsequently separated by molecular weight using any method known in the art, including, for example, high-performance liquid chromatography, adsorption/desorption (e.g. low-pressure activated carbon chromatography), or filtration (for example, ultrafiltration or diafiltration). In certain embodiments, oligosaccharide compositions are separated into pools representing 60%, 65%, 70%, 75%, 80%, 85%, 90%, 95%, 97%, 98%, or greater than 98% short (about DP1-2), medium (about DP3-10), long (about DP11-18), or very long (about DP>18) species.

In certain embodiments, prepared oligosaccharide compositions are fractionated by adsorption onto a carbonaceous material and subsequent desorption of fractions by washing the material with mixtures of an organic solvent in water at a concentration of 1%, 5%, 10%, 20%, 50%, or 100%. In one embodiment, the adsorption material is activated charcoal. In another embodiment, the adsorption material is a mixture of activated charcoal and a bulking agent such as diatomaceous earth or Celite 545 in 5%, 10%, 20%, 30%, 40%, or 50% portion by volume or weight.

In further embodiments, prepared oligosaccharide compositions are separated by passage through a high-performance liquid chromatography system. In certain variations, prepared oligosaccharide compositions are separated by ion-affinity chromatography, hydrophilic interaction chromatography, or size-exclusion chromatography including gel-permeation and gel-filtration.

In some embodiments, catalyst is removed by filtration. In certain embodiments, a filter (such as a 10 µm, 20 µm, or 50 µm filter) is used to remove catalyst during filtration. In other embodiments, low molecular weight materials are removed by filtration methods. In certain variations, low molecular weight materials may be removed by dialysis, ultrafiltration, diafiltration, or tangential flow filtration. In certain embodiments, the filtration is performed in static dialysis tube apparatus. In other embodiments, the filtration is performed in a dynamic flow filtration system. In other embodiments, the filtration is performed in centrifugal force-driven filtration cartridges. In certain embodiments, the reaction mixture is cooled to below about 85° C. before filtration.

De-monomerization

For some applications, it is desirable to reduce the level of residual saccharide monomers in the oligosaccharide composition to below that achieved during the synthesis of the oligosaccharide composition, e.g., to below a residual saccharide monomer content of about 25% monomer or less, 20% monomer or less, 15% monomer or less, 10% monomer or less, 5% monomer or less, 2% monomer or less, or 1% monomer or less. In some embodiments, the oligosaccharide compositions described herein may be de-monomerized. In some embodiments, de-monomerization involves the removal of residual saccharide monomers, e.g., some or all of the monosaccharide monomers (the DP1 component) in an oligosaccharide composition. In some embodiments, de-monomerization is performed using chromatographic resin. Accordingly, in some embodiments, different oligosaccharide compositions can be prepared depending upon the percent of monomer present. In some embodiments, the oligosaccharide compositions are de-monomerized to a monomer content of about 1%, about 3%, about 5%, about 8%, about 10%, about 12%, about 14%, about 15%, about 18%, about 20%, about 22%, about 25%, about 28%, or about 30%. In some embodiments, the oligosaccharide compositions are de-monomerized to a monomer content of between about 2-10%, 5-15%, 4-12%, 6-20%, 8-22%, 12-24%, 12-18%, 8-18%, 10-22%, 14-24%, 16-28%, or 18-30%. In one embodiment, the oligosaccharide compositions are de-monomerized to a monomer content of less than about 30%, less than 28%, less than 26%, less than 24%, less than 22%, less than 20%, less than 18%, less than 16%, less than 15%, less than 14%, less than 12%, less than 10%, less than 8%, less than 5%, less than 2%, or less than 1%. In one embodiment, the oligosaccharide compositions are de-monomerized to a monomer content of less than about 1%. In one embodiment, the oligosaccharide compositions are de-monomerized to a monomer content between about 12% and 18%. In one embodiment, the oligosaccharide compositions are de-monomerized to a monomer content between about 13% and 17%. In one embodiment, de-monomerization is achieved by osmotic separation. In a second embodiment de-monomerization is achieved by tangential flow filtration (TFF). In a third embodiment de-monomerization is achieved by ethanol precipitation. In some embodiments, the oligosaccharide compositions described herein are de-monomerized according to the procedures described in Example 4.

Various chemical characteristics of the oligosaccharide compositions as described herein can be affected by the saccharide monomer (DP1) content present in the oligosaccharide compositions, For example, the MWw, MWn, PDI, DP2+ content, average % bond distributions, NMR peaks (including areas under the curve), total dietary fiber content, and dextrose equivalent (DE) can be affected by the saccharide monomer content of the oligosaccharide composition. In some embodiments, the oligosaccharide composition is de-monomerized before values for these chemical characteristics are determined. In some embodiments, the monomer content of the oligosaccharide composition is determined before or at the time values for any of these chemical characteristics are determined, e.g., the monomer content of the oligosaccharide composition can be 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% at the time the MWw, MWn, PDI, DP2+ content, average % bond distributions, NMR peaks (including areas under the curve), total dietary fiber content, and/or dextrose equivalent (DE) is determined for the oligosaccharide composition. In some embodiments, the saccharide monomer content is less than 25%, less than 22%, less than 20%, less than 18%, less than 15%, less than 12%, less than 10%, less than 5%, less than 2%, or less than 1%. In some embodiments, the saccharide monomer content is between about 2-10%, 5-15%, 4-12%, 6-20%, 8-22%, 12-24%, 12-18%, 8-18%, 10-22%, 14-24%, 16-28%, or 18-30%.

Properties of Oligosaccharide Compositions

Various analytical methods can be used to determine the MWw, MWn, PDI, monomer content (DP1) and/or DP2+ content values for an oligosaccharide composition as described herein. In some embodiments, size exclusion chromatography (SEC) is used to determine the MWw, MWn, DP, PDI, monomer content (DP1) and/or DP2+ content values for the oligosaccharide composition. In some embodiments, the MWw, MWn, PDI, monomer content (DP1) and/or DP2+ content values of the oligosaccharides in the oligosaccharide composition are determined using the SEC method described in Example 5. In other embodiments, the SEC method described in Example 17 is used to determine the MWw and MWn of the oligosaccharide composition.

In some embodiments, the mean degree of polymerization (DP) of all of the glycans in the oligosaccharide composition is between about 6-14, e.g., 7-14. In some embodiments, the mean degree of polymerization of the glycans in the oligosaccharide composition is between about 6-7, 7-8, 8-9, 9-10, 10-11, 12-13, or 13-14. In some embodiments, the mean degree of polymerization (DP) of the glycans in the oligosaccharide composition is between about 6-14, 6-13, 6-12, 6-11, 7-14, 7-11, 8-12, 8-13, 8-14, 8-10, 8-9, 8-11, 9-11, 9-12, 9-14, 10-14, 10-13, or 10-11. In some embodiments, the mean degree of polymerization (DP) of glycans in the oligosaccharide composition is between about 6-14. In some embodiments, the mean degree of polymerization (DP) of glycans in the oligosaccharide composition is between about 6-12. In some embodiments, the mean degree of polymerization (DP) of glycans in the oligosaccharide composition is between about 6-11. In some embodiments, the mean degree of polymerization (DP) of glycans in the oligosaccharide composition is between about 8-14. In some embodiments, the mean degree of polymerization of the glycans in the oligosaccharide composition is about 6, about 7, about 8, about 8.5, about 9, about 9.5, about 10, about 10.5, about 11, about 11.5, about 12, about 12.5, about 13, about 13.5, or about 14.

In some embodiments, the oligosaccharide composition comprises glycans that have a MWw (weight-average molecular weight) (g/mol) in between about 950-2300, e.g., between about 1000-2300, between about 970-2270, between 1000-2000, between about 1100-2300, between about 1135-2271, between about 1150-2200, between about 1175-2190, between about 1200-2100, between about 1298-2110, between about 1300-2000, between about 970-1950, between about 1400-2000, between about 1460-1946, between about 1500-2050, between about 1600-2250, between about 1300-1800, between about 1250-1600, between about 1300-1450, or between about 1300-1550. In some embodiments, the oligosaccharide composition comprises glycans that have a MWw (weight-average molecular weight) (g/mol) in between 1150-2200. In some embodiments, the oligosaccharide composition comprises glycans that have a MWw (g/mol) in between 1175-2190. In some embodiments, the oligosaccharide composition comprises glycans that have a MWw (g/mol) in between 1000-1800. In some embodiments, the oligosaccharide composition comprises glycans that have a MWw (g/mol) in between 1300 and 1500. In some embodiments, the oligosaccharide composition comprises glycans that have a MWw (g/mol) in between 1060-1780. In some embodiments, the oligosaccharide composition comprises glycans that have a MWw (g/mol) in between 1250-1600. In some embodiments, the oligosaccharide composition comprises glycans that have a MWw (g/mol) in between 1300-1550. In some embodiments, the oligosaccharide composition comprises glycans that have a MWw (g/mol) of about 1525. In some embodiments, the oligosaccharide composition comprises glycans that have a MWw (g/mol) of about 1400.

In some embodiments, the oligosaccharide composition comprises glycans that have a MWn (number-average molecular weight) (g/mol) in a range of 650-1250. In some embodiments, the oligosaccharide composition comprises glycans that have a MWn (number-average molecular weight) (g/mol) in a range of 700-1250. In some embodiments, the oligosaccharide composition comprises glycans that have a MWn (g/mol) in a range of 735-1215. In some embodiments, the oligosaccharide composition comprises glycans that have a MWn (g/mol) in a range of 850-1100. In some embodiments, the oligosaccharide composition comprises glycans that have a MWn (g/mol) in a range of 900-1000. In some embodiments, the oligosaccharide composition comprises glycans that have a MWn (g/mol) in a range of 500-1200. In some embodiments, the oligosaccharide composition comprises glycans that have a MWn (g/mol) in a range of 690-1080. In some embodiments, the oligosaccharide composition comprises glycans that have a MWn (number-average molecular weight) (g/mol) in a range of 800-900. In some embodiments, the oligosaccharide composition comprises glycans that have a MWn (g/mol) in a range of 750-1000. In some embodiments, the oligosaccharide composition comprises glycans that have a MWn (g/mol) in a range of 800-975. In some embodiments, the oligosaccharide composition comprises glycans that have a MWn (g/mol) of about 940.

In some embodiments, the oligosaccharide composition has a pH in between 1.50-6.00. In some embodiments, the oligosaccharide composition has a pH in between 1.50-5.00. In some embodiments, the oligosaccharide composition has a pH in between of 2.00-4.00. In some embodiments, the oligosaccharide composition has a pH in between of 2.50-3.50. In some embodiments, the oligosaccharide composition has a pH in between 2.5-7.5, e.g., a pH in between 2.5-5.0 or 3.0-4.0.

In some embodiments, the oligosaccharide composition comprises oligosaccharides having two or more saccharide monomers (DP2+) in a range of 70-99 weight percent (dry basis). In some embodiments, the oligosaccharide composition comprises oligosaccharides having two or more saccharide monomers (DP2+) in a range of 75-95% weight percent (dry basis), 85-95 weight percent (dry basis), 80-95 weight percent (dry basis), 82-95 weight percent (dry basis), 80-90 weight percent (dry basis), 83-89 weight percent (dry basis), or 84-92 weight percent (dry basis). In some embodiments, the oligosaccharide composition comprises oligosaccharides having two or more saccharide monomers (DP2+) in a range of 84-weight percent. In some embodiments, the oligosaccharide composition comprises oligosaccharides having two or more saccharide monomers (DP2+) in a range of 85-87 weight percent. In some embodiments, the oligosaccharide composition comprises oligosaccharides having two or more saccharide monomers (DP2+) in a range of 83-91 weight percent. In some embodiments, the oligosaccharide composition comprises oligosaccharides having two or more saccharide monomers (DP2+) in a range of 83-85, 84-86, 85-87, 86-92, 86-88, 87-89, 88-90, or 89-91 weight percent (dry basis). In some embodiments, the oligosaccharide composition comprises oligosaccharides having over 75%, 78%, 80%, 82%, 84%, 85%, 88%, 90%, 92%, or 95% weight percent (dry basis) DP2+.

In certain embodiments, the weight percent of dextrose monomer and galactose monomer in the oligosaccharide composition is in a range of 5-20, e.g., 9-17. In certain embodiments, the weight percent of dextrose monomer and galactose monomer in the oligosaccharide composition is in a range of 10-18. In certain embodiments, the weight percent of dextrose monomer and galactose monomer in the oligosaccharide composition is in a range of 11-17. In certain embodiments, the weight percent of dextrose monomer and galactose monomer in the oligosaccharide composition is in a range of 12-16. In certain embodiments, the weight percent of dextrose monomer and galactose monomer in the oligosaccharide composition is in a range of 12-15. In certain embodiments, the weight percent of dextrose monomer and galactose monomer in the oligosaccharide composition is in a range of 13-14. In certain embodiments, the weight percent of dextrose monomer and galactose monomer in the oligosaccharide composition is in a range of 13-15.

In some embodiments, the oligosaccharide composition comprises water in a range of 5-75 weight percent. In some embodiments, the oligosaccharide composition comprises water in a range of 25-65 weight percent. In some embodiments, the oligosaccharide composition comprises water in a range of 35-65 weight percent. In some embodiments, the oligosaccharide composition comprises water in a range of 45-55 weight percent. In some embodiments, the oligosaccharide composition comprises water at a level below that which is necessary for microbial growth upon storage at room temperature.

In some embodiments, the oligosaccharide composition has a polydispersity index (PDI) of 1.2-1.8, e.g., 1.4-1.8. In some embodiments, the oligosaccharide composition has a PDI of 1.0-1.2, 1.2-1.3, 1.3-1.4, 1.4-1.5, 1.5-1.6, 1.7-1.8, or 1.8-2.0. In some embodiments, the oligosaccharide composition has a PDI of about 1.2, about 1.3, about 1.4, about 1.5, about 1.6, about 1.7, or about 1.8. In some embodiments, the amount of monosaccharides (DP1), disaccharides (DP2), and trisaccharides and above (DP3+) in the oligosaccharide composition is determined using size exclusion chromatography (SEC), e.g., the SEC method described in Example 15. In some embodiments, the oligosaccharide composition comprises between about 4% to 11% DP1, e.g., between about 5% to 10% DP1, between about 6% to 10% DP1 or between about 7% to 9% DP1. In some embodiments, the oligosaccharide composition comprises between about 6% to 15% DP2, e.g., between about 7% to 14% DP2, between about 8% to 13% DP2, or between about 9% to 11% DP2.

In some embodiments, the oligosaccharide composition comprises between about 74% to 90% DP3+, e.g., between about 75% to 90% DP3+, between about 76-88% DP3+, between about 75-85% DP3+, or between about 78% to 84% DP3+. In some embodiments, the oligosaccharide composition comprises at least 75% and less than 90% DP3+.

In some embodiments, the oligosaccharide compositions described herein can be analyzed to determine whether they contain certain impurities. In some embodiments, the presence and amount of impurities in the oligosaccharide compositions can be determined, e.g., by SEC HPLC (e.g., as described in Example 16). In some embodiments, the oligosaccharide composition contains 3.0% total impurities or less (excluding monomer (DP1) content), e.g., less than 3.0%, less than 2.5%, less than 2.0%, less than 1.5%, less than 1.0%, or less than 0.5% impurities. In some embodiments, the oligosaccharide composition comprises less than 0.3%, less than 0.2%, less than 0.15%, less than 0.1%, or less than 0.05% total impurities (excluding monomer (DP1)). In some embodiments, the total impurities in the oligosaccharide composition can include, e.g., levoglucosan, levoglucosan isomer, lactic acid, and/or formic acid. In some embodiments, the oligosaccharide composition contains less than about 1% w/w levoglucosan (e.g., less than about 1%, 0.9%, 0.8%, 0.7%, 0.6%, 0.5%, 0.4%, 0.3%, 0.2%, or 0.1% w/w levoglucosan); and/or less than abut 0.3% lactic acid (e.g., less than about 0.3%, 0.2%, 0.1%, 0.08%, 0.06%, or 0.04% w/w lactic acid); and/or less than about 0.3% formic acid (e.g., less than about 0.3%, 0.2%, 0.1%, 0.08%, 0.06%, or 0.04% w/w formic acid). In some embodiments, the oligosaccharide composition comprises less than about 0.5% w/w levoglucosan (e.g., less than about 0.4% or less than about 0.5% w/w levoglucosan); and/or less than about 0.15% w/w lactic acid (e.g., less than about 0.1% or less than about 0.05% w/w lactic acid); and/or less than about 0.15% w/w formic acid (e.g., less than about 0.1% w/w formic acid). In some embodiments, the oligosaccharide composition has lower than quantifiable amounts of lactic acid. In some embodiments, the oligosaccharide composition has lower than quantifiable amounts of formic acid.

In some embodiments, the oligosaccharide composition comprises 0.44% w/w levoglucosan, 0.06% w/w lactic acid, and/or 0.06% w/w formic acid. In some embodiments, the oligosaccharide composition comprises 0.42-0.47% w/w levoglucosan, 0.05-0.08% w/w lactic acid, and/or 0.00-0.11% w/w formic acid.

Dietary Fiber and Dextrose Equivalent (DE)

In some embodiments, oligosaccharide compositions with different monomer contents may also have different measurements for total dietary fiber, moisture, total dietary fiber (dry basis), or percent Dextrose Equivalent DE (dry basis). In some embodiments, total dietary fiber is measured according to the methods of AOAC 2011.25. In some embodiments, moisture is measured by using a vacuum oven, e.g., a vacuum oven at 60° C. In some embodiments, total dietary fiber is (dry basis) is calculated. In some embodiments, the percent DE is measured according to the Food Chemicals Codex (FCC).

In some embodiments, the oligosaccharide compositions described herein have a total dietary fiber content of at least 50% (on dry basis). For example, the oligosaccharide compositions described herein can have a total dietary fiber (dry basis) content of at least 55%, at least 60%, at least 65%, at least 70%, at least 75%, at least 80%, at least 85%, or at least 90%. In some embodiments, the oligosaccharide compositions have a total dietary fiber (dry basis) content of about 50%, about 55%, about 60%, about 65%, about 70%, about 75%, about 80%, about 85%, or about 90%. In some embodiments, the oligosaccharide compositions have a total dietary fiber (dry basis) content of about 60%, 65%, 70%, 71%, 72%, 73%, 74%, 75%, 76%, 77%, 78%, 79%, 80%, 81%, 82%, 83%, 84%, or 85%. In some embodiments, the oligosaccharide compositions have a total dietary fiber (dry basis) content of between about 50-95%, 55-90%, 60-80%, 70-90%, 70-80%, 75-90%, 75-85%, 80-85%, or 85-90%. In some embodiments, the oligosaccharide composition has a total dietary fiber (dry basis) content of at least 75% and less than 90%.

In some embodiments, an oligosaccharide composition as described herein contains a soluble dietary fiber precipitate (SDFP) that is below the limits of quantification. In some embodiments, the oligosaccharide composition contains insoluble dietary fiber (IDF) that is below the limits of quantification. In some embodiments, the oligosaccharide composition contains a high molecular weight dietary fiber (HMWDF), which is the SDFP and the IDF together, that is below the limits of quantification.

In some embodiments, an oligosaccharide composition described herein has between about 5 to 40 percent DE (on dry basis). For example, an oligosaccharide composition described herein can have between about 5 to 20 percent DE (dry basis), 10 to 30 percent DE (dry basis), 20 to 40 percent DE (dry basis), 15 to 25 percent DE (dry basis), 20 to 30 percent DE (dry basis), or 30 to 40 percent DE (dry basis). In some embodiments, an oligosaccharide composition described herein has less than 50% DE (dry basis), less than 40% DE (dry basis), less than 35% DE (dry basis), less than 30% DE (dry basis), less than 25% DE (dry basis), less than 20% DE (dry basis), less than 15% DE (dry basis), or less than 10% DE (dry basis). In some embodiments, an oligosaccharide composition has about 21 percent DE (on dry basis).

In some embodiments, oligosaccharide compositions are provided herein that contain a plurality of oligosaccharides that are minimally digestible in humans. In some embodiments, the oligosaccharides are resistant to degradation by human digestive enzymes (e.g., amylases, glucosidases, galactosidases and other digestive enzymes encoded by human cells), and/or are resistant to hydrolytic digestion, e.g., in the upper GI tract (e.g., the small intestines and stomach).

Characterization by Permethylation Analysis

The oligosaccharide compositions described herein, and prepared according to methods described herein, can be characterized and distinguished from prior art compositions using permethylation analysis. See, e.g., Zhao, Y., et al. 'Rapid, sensitive structure analysis of oligosaccharides,' PNAS Mar. 4, 1997 94 (5) 1629-1633; Kailemia, M. J., et al. 'Oligosaccharide analysis by mass spectrometry: A review of recent developments,' Anal Chem. 2014 Jan. 7; 86(1): 196-212. Accordingly, in some embodiments, an oligosaccharide composition comprises a plurality of oligosaccharides comprising monomer radicals. The molar percentages of different types of monomer radicals in the plurality of oligosaccharides can be quantified using a permethylation assay. In some embodiments, the oligosaccharide composition is minimally digestible in humans. In some embodiments, the permethylation assay is performed on an oligosaccharide composition sample that has been de-monomerized, e.g., using the method described in Example 4. In some embodiments, the permethylation assay is performed on an oligosaccharide composition sample that has a saccharide monomer content (e.g., containing glucose and galactose monomers) of 30% or less, 25% or less, 22% or less, 18% or less, 15% or less, 12% or less, 10% or less, 8% or less, 5% or less, or 2% or less.

In some embodiments, the oligosaccharide composition comprises a plurality of oligosaccharides comprising at least one (e.g., at least two, at least three, at least four, at least five, at least six, at least seven, at least eight, at least nine, or at least ten) monomer radical selected from radicals (1)-(36):

(1) t-glucopyranose monoradicals, representing 11.1-22.9 mol % of monomer radicals in the plurality of oligosaccharides;

(2) t-galactofuranose monoradicals, representing 1.7-8.2 mol % of monomer radicals in the plurality of oligosaccharides;

(3) t-galactopyranose monoradicals, representing 9.3-15.4 mol % of monomer radicals in the plurality of oligosaccharides;

(4) 3-glucopyranose monoradicals, representing 3.1-5.5 mol % of monomer radicals in the plurality of oligosaccharides;

(5) 2-glucopyranose monoradicals, representing 2.7-3.8 mol % of monomer radicals in the plurality of oligosaccharides;

(6) 2-galactofuranose and/or 2-glucofuranose monoradicals, representing 0-3.8 mol % of monomer radicals in the plurality of oligosaccharides;

(7) 3-glucofuranose monoradicals, representing 0-0.6 mol % of monomer radicals in the plurality of oligosaccharides;

(8) 3-galactopyranose monoradicals, representing 2.4-4.5 mol % of monomer radicals in the plurality of oligosaccharides;

(9) 3-galactofuranose monoradicals, representing 1.3-3.1 mol % of monomer radicals in the plurality of oligosaccharides;

(10) 2-galactopyranose monoradicals, representing 1.4-3.6 mol % of monomer radicals in the plurality of oligosaccharides;

(11) 6-glucopyranose monoradicals, representing 7.3-14.0 mol % of monomer radicals in the plurality of oligosaccharides;

(12) 4-galactopyranose and/or 5-galactofuranose monoradicals, representing 2.6-4.4 mol % of monomer radicals in the plurality of oligosaccharides;

(13) 4-glucopyranose and/or 5-glucofuranose monoradicals, representing 2.9-5.0 mol % of monomer radicals in the plurality of oligosaccharides;

(14) 2,3-galactofuranose diradicals, representing 0-0.8 mol % of monomer radicals in the plurality of oligosaccharides;

(15) 6-glucofuranose monoradicals, representing 0-1.8 mol % of monomer radicals in the plurality of oligosaccharides;

(16) 6-galactofuranose monoradicals, representing 1.4-4.7 mol % of monomer radicals in the plurality of oligosaccharides;

(17) 6-galactopyranose monoradicals, representing 5.6-10.1 mol % of monomer radicals in the plurality of oligosaccharides;

(18) 3,4-galactopyranose and/or 3,5-galactofuranose and/or 2,3-galactopyranose diradicals, representing 0.4-1.9 mol % of monomer radicals in the plurality of oligosaccharides;

(19) 3,4-glucopyranose and/or 3,5-glucofuranose diradicals, representing 0-1.3 mol % of monomer radicals in the plurality of oligosaccharides;

(20) 2,3-glucopyranose diradicals, representing 0-1.3 mol % of monomer radicals in the plurality of oligosaccharides;

(21) 2,4-glucopyranose and/or 2,5-glucofuranose and/or 2,4-galactopyranose and/or 2,5-galactofuranose diradicals, representing 0.9-1.6 mol % of monomer radicals in the plurality of oligosaccharides;

(22) 3,6-glucopyranose diradicals, representing 1.5-2.9 mol % of monomer radicals in the plurality of oligosaccharides;

(23) 3,6-glucofuranose diradicals, representing 0-0.6 mol % of monomer radicals in the plurality of oligosaccharides;

(24) 2,6-glucopyranose and/or 4,6-glucopyranose and/or 5,6-glucofuranose diradicals, representing 0.6-4.4 mol % of monomer radicals in the plurality of oligosaccharides;

(25) 3,6-galactofuranose diradicals, representing 0.8-1.6 mol % of monomer radicals in the plurality of oligosaccharides;

(26) 4,6-galactopyranose and/or 5,6-galactofuranose diradicals, representing 1.2-4.0 mol % of monomer radicals in the plurality of oligosaccharides;

(27) 2,3,4-glucopyranose and/or 2,3,5-glucofuranose triradicals, representing 0-0.4 mol % of monomer radicals in the plurality of oligosaccharides;

(28) 3,6-galactopyranose diradicals, representing 1.4-3.2 mol % of monomer radicals in the plurality of oligosaccharides;

(29) 2,6-galactopyranose diradicals, representing 0.6-1.6 mol % of monomer radicals in the plurality of oligosaccharides;

(30) 3,4,6-galactopyranose and/or 3,5,6-galactofuranose and/or 2,3,6-galactofuranose triradicals, representing 0.1-1.7 mol % of monomer radicals in the plurality of oligosaccharides;

(31) 3,4,6-glucopyranose and/or 3,5,6-glucofuranose triradicals, representing 0-0.1 mol % of monomer radicals in the plurality of oligosaccharides;

(32) 2,3,6-glucofuranose triradicals, representing 0-0.1 mol % of monomer radicals in the plurality of oligosaccharides;

(33) 2,4,6-glucopyranose and/or 2,5,6-glucofuranose triradicals, representing 0-1.0 mol % of monomer radicals in the plurality of oligosaccharides;

(34) 2,3,6-galactopyranose and/or 2,4,6-galactopyranose and/or 2,5,6-galactofuranose triradicals, representing 0-1.4 mol % of monomer radicals in the plurality of oligosaccharides;

(35) 2,3,6-glucopyranose triradicals, representing 0-0.9 mol % of monomer radicals in the plurality of oligosaccharides; and

(36) 2,3,4,6-glucopyranose and/or 2,3,5,6-glucofuranose tetraradicals, representing 0-0.5 mol % of monomer radicals in the plurality of oligosaccharides.

In some embodiments, the oligosaccharide composition comprises a plurality of oligosaccharides comprising at least one (e.g., at least two, at least three, at least four, at least five, at least six, at least seven, at least eight, at least nine, or at least ten) monomer radical selected from radicals (1)-(36):

(1) t-glucopyranose monoradicals, representing 7.2-26.77 mol % of monomer radicals in the plurality of oligosaccharides;

(2) t-galactofuranose monoradicals, representing 0.0-10.3 mol % of monomer radicals in the plurality of oligosaccharides;

(3) t-galactopyranose monoradicals, representing 7.3-17.4 mol % of monomer radicals in the plurality of oligosaccharides;

(4) 3-glucopyranose monoradicals, representing 2.3-6.2 mol % of monomer radicals in the plurality of oligosaccharides;

(5) 2-glucopyranose monoradicals, representing 2.4-4.1 mol % of monomer radicals in the plurality of oligosaccharides;

(6) 2-galactofuranose and/or 2-glucofuranose monoradicals, representing 0.0-5.2 mol % of monomer radicals in the plurality of oligosaccharides;

(7) 3-glucofuranose monoradicals, representing 0.0-0.9 mol % of monomer radicals in the plurality of oligosaccharides;

(8) 3-galactopyranose monoradicals, representing 1.7-5.1 mol % of monomer radicals in the plurality of oligosaccharides;

(9) 3-galactofuranose monoradicals, representing 0.8-3.6 mol % of monomer radicals in the plurality of oligosaccharides;

(10) 2-galactopyranose monoradicals, representing 0.8-4.2 mol % of monomer radicals in the plurality of oligosaccharides;

(11) 6-glucopyranose monoradicals, representing 5.1-16.2 mol % of monomer radicals in the plurality of oligosaccharides;

(12) 4-galactopyranose and/or 5-galactofuranose monoradicals, representing 2.1-4.9 mol % of monomer radicals in the plurality of oligosaccharides;

(13) 4-glucopyranose and/or 5-glucofuranose monoradicals, representing 2.2-5.6 mol % of monomer radicals in the plurality of oligosaccharides;

(14) 2,3-galactofuranose diradicals, representing 0.0-1.2 mol % of monomer radicals in the plurality of oligosaccharides;

(15) 6-glucofuranose monoradicals, representing 0.0-2.4 mol % of monomer radicals in the plurality of oligosaccharides;

(16) 6-galactofuranose monoradicals, representing 0.4-5.7 mol % of monomer radicals in the plurality of oligosaccharides;

(17) 6-galactopyranose monoradicals, representing 4.2-11.5 mol % of monomer radicals in the plurality of oligosaccharides;

(18) 3,4-galactopyranose and/or 3,5-galactofuranose and/or 2,3-galactopyranose diradicals, representing 0.3-2.3 mol % of monomer radicals in the plurality of oligosaccharides;

(19) 3,4-glucopyranose and/or 3,5-glucofuranose diradicals, representing 0.0-1.8 mol % of monomer radicals in the plurality of oligosaccharides;

(20) 2,3-glucopyranose diradicals, representing 0.0-1.8 mol % of monomer radicals in the plurality of oligosaccharides;

(21) 2,4-glucopyranose and/or 2,5-glucofuranose and/or 2,4-galactopyranose and/or 2,5-galactofuranose diradicals, representing 0.7-1.7 mol % of monomer radicals in the plurality of oligosaccharides;

(22) 3,6-glucopyranose diradicals, representing 1.1-3.3 mol % of monomer radicals in the plurality of oligosaccharides;

(23) 3,6-glucofuranose diradicals, representing 0.0-0.8 mol % of monomer radicals in the plurality of oligosaccharides;

(24) 2,6-glucopyranose and/or 4,6-glucopyranose and/or 5,6-glucofuranose diradicals, representing 0.0-5.6 mol % of monomer radicals in the plurality of oligosaccharides;

(25) 3,6-galactofuranose diradicals, representing 0.6-1.8 mol % of monomer radicals in the plurality of oligosaccharides;

(26) 4,6-galactopyranose and/or 5,6-galactofuranose diradicals, representing 0.4-4.8 mol % of monomer radicals in the plurality of oligosaccharides;

(27) 2,3,4-glucopyranose and/or 2,3,5-glucofuranose triradicals, representing 0.0-0.5 mol % of monomer radicals in the plurality of oligosaccharides;

(28) 3,6-galactopyranose diradicals, representing 0.9-3.7 mol % of monomer radicals in the plurality of oligosaccharides;

(29) 2,6-galactopyranose diradicals, representing 0.4-1.9 mol % of monomer radicals in the plurality of oligosaccharides;

(30) 3,4,6-galactopyranose and/or 3,5,6-galactofuranose and/or 2,3,6-galactofuranose triradicals, representing 0.0-2.2 mol % of monomer radicals in the plurality of oligosaccharides;

(31) 3,4,6-glucopyranose and/or 3,5,6-glucofuranose triradicals, representing 0.0-1.6 mol % of monomer radicals in the plurality of oligosaccharides;

(32) 2,3,6-glucofuranose triradicals, representing 0.0-0.2 mol % of monomer radicals in the plurality of oligosaccharides;

(33) 2,4,6-glucopyranose and/or 2,5,6-glucofuranose triradicals, representing 0.0-1.2 mol % of monomer radicals in the plurality of oligosaccharides;

(34) 2,3,6-galactopyranose and/or 2,4,6-galactopyranose and/or 2,5,6-galactofuranose triradicals, representing 0.0-1.8 mol % of monomer radicals in the plurality of oligosaccharides;

(35) 2,3,6-glucopyranose triradicals, representing 0.0-1.2 mol % of monomer radicals in the plurality of oligosaccharides; and

(36) 2,3,4,6-glucopyranose and/or 2,3,5,6-glucofuranose tetraradicals, representing 0.0-0.7 mol % of monomer radicals in the plurality of oligosaccharides.

In some embodiments, an oligosaccharide composition is provided, comprising a plurality of oligosaccharides comprising or consisting essentially of monomer radicals (1)-(36), as described herein. In some embodiments, an oligosaccharide composition is provided, comprising a plurality of oligosaccharides comprising at least one (e.g., at least two, at least three, at least four, at least five, at least six, at least seven, at least eight, at least nine, or at least ten) monomer radical selected from radicals (1)-(36) with at least one (e.g., at least two, at least three, at least four, at least five, at least six, at least seven, at least eight, at least nine, or at least ten) corresponding molar percentage shown in Table 2. In some embodiments, an oligosaccharide composition is provided, comprising a plurality of oligosaccharides comprising or consisting of monomer radicals (1)-(36) with the molar percentages shown in Table 2.

TABLE 2

Permethylation Data for the selected oligosaccharide produced using Marathon C catalyst

| Radicals | Mean mol % + 5 STD | Mean mol % + 3 STD | Mean mol % | Mean mol % − 3 STD | Mean mol % − 5 STD |
|---|---|---|---|---|---|
| t-glucopyranose monoradicals | 26.77% | 22.86% | 16.99% | 11.12% | 7.21% |
| t-galactofuranose monoradicals | 10.27% | 8.13% | 4.91% | 1.70% | 0.00% |
| t-galactopyranose monoradicals | 17.42% | 15.40% | 12.38% | 9.36% | 7.34% |
| 3-glucopyranose monoradicals | 6.24% | 5.46% | 4.29% | 3.12% | 2.34% |
| 2-glucopyranose monoradicals | 4.13% | 3.77% | 3.24% | 2.70% | 2.35% |
| 2-galactofuranose and/or 2-glucofuranose monoradicals | 5.19% | 3.76% | 1.63% | 0.00% | 0.00% |
| 3-glucofuranose monoradicals | 0.92% | 0.57% | 0.06% | 0.00% | 0.00% |
| 3-galactopyranose monoradicals | 5.14% | 4.45% | 3.43% | 2.41% | 1.73% |
| 3-galactofuranose monoradicals | 3.61% | 3.05% | 2.20% | 1.36% | 0.79% |
| 2-galactopyranose monoradicals | 4.24% | 3.55% | 2.52% | 1.48% | 0.79% |
| 6-glucopyranose monoradicals | 16.18% | 13.96% | 10.63% | 7.30% | 5.08% |
| 4-galactopyranose and/or 5-galactofuranose monoradicals | 4.89% | 4.32% | 3.47% | 2.62% | 2.06% |
| 4-glucopyranose and/or 5-glucofuranose monoradicals | 5.62% | 4.94% | 3.92% | 2.90% | 2.22% |
| 2,3-galactofuranose diradicals | 1.15% | 0.76% | 0.16% | 0.00% | 0.00% |
| 6-glucofuranose monoradicals | 2.38% | 1.77% | 0.87% | 0.00% | 0.00% |
| 6-galactofuranose monoradicals | 5.69% | 4.62% | 3.02% | 1.42% | 0.35% |
| 6-galactopyranose monoradicals | 11.52% | 10.06% | 7.86% | 5.66% | 4.19% |
| 3,4-galactopyranose and/or 3,5-galactofuranose and/or 2,3-galactopyranose diradicals | 2.27% | 1.82% | 1.15% | 0.47% | 0.03% |
| 3,4-glucopyranose and/or 3,5-glucofuranose diradicals | 1.76% | 1.29% | 0.57% | 0.00% | 0.00% |
| 2,3-glucopyranose diradicals | 1.79% | 1.23% | 0.41% | 0.00% | 0.00% |
| 2,4-glucopyranose and/or 2,5-glucofuranose and/or 2,4-galactopyranose and/or 2,5-galactofuranose diradicals | 1.71% | 1.51% | 1.21% | 0.91% | 0.71% |
| 3,6-glucopyranose diradicals | 3.27% | 2.84% | 2.20% | 1.56% | 1.13% |
| 3,6-glucofuranose diradicals | 0.77% | 0.59% | 0.31% | 0.03% | 0.00% |
| 2,6-glucopyranose and/or 4,6-glucopyranose and/or 5,6-glucofuranose diradicals | 5.57% | 4.34% | 2.50% | 0.66% | 0.00% |
| 3,6-galactofuranose diradicals | 1.84% | 1.58% | 1.19% | 0.80% | 0.55% |
| 4,6-galactopyranose and/or 5,6-galactofuranose diradicals | 4.78% | 3.91% | 2.60% | 1.29% | 0.42% |
| 2,3,4-glucopyranose and/or 2,3,5-glucofuranose triradicals | 0.52% | 0.32% | 0.03% | 0.00% | 0.00% |

TABLE 2-continued

Permethylation Data for the selected oligosaccharide produced using Marathon C catalyst

| Radicals | Mean mol % + 5 STD | Mean mol % + 3 STD | Mean mol % | Mean mol % − 3 STD | Mean mol % − 5 STD |
|---|---|---|---|---|---|
| 3,6-galactopyranose diradicals | 3.65% | 3.11% | 2.30% | 1.49% | 0.94% |
| 2,6-galactopyranose diradicals | 1.87% | 1.57% | 1.11% | 0.66% | 0.36% |
| 3,4,6-galactopyranose and/or 3,5,6-galactofuranose and/or 2,3,6-galactofuranose triradicals | 2.20% | 1.69% | 0.92% | 0.14% | 0.00% |
| 3,4,6-glucopyranose and/or 3,5,6-glucofuranose triradicals | 1.57% | 1.09% | 0.36% | 0.00% | 0.00% |
| 2,3,6-glucofuranose triradicals | 0.15% | 0.10% | 0.01% | 0.00% | 0.00% |
| 2,4,6-glucopyranose and/or 2,5,6-glucofuranose triradicals | 1.23% | 0.93% | 0.49% | 0.05% | 0.00% |
| 2,3,6-galactopyranose and/or 2,4,6-galactopyranose and/or 2,5,6-galactofuranose triradicals | 1.81% | 1.35% | 0.67% | 0.00% | 0.00% |
| 2,3,6-glucopyranose triradicals | 1.21% | 0.86% | 0.35% | 0.00% | 0.00% |
| 2,3,4,6-glucopyranose and/or 2,3,5,6-glucofuranose tetraradicals | 0.68% | 0.43% | 0.05% | 0.00% | 0.00% |

In some embodiments, the oligosaccharide composition comprises a plurality of oligosaccharides comprising at least one (e.g., at least two, at least three, at least four, at least five, at least six, at least seven, at least eight, at least nine, or at least ten) monomer radical selected from radicals (1)-(36):

(1) t-glucopyranose monoradicals, representing 17.77-30.95 mol % of monomer radicals in the plurality of oligosaccharides;

(2) t-galactofuranose monoradicals, representing 5.19-8.49 mol % of monomer radicals in the plurality of oligosaccharides;

(3) t-galactopyranose monoradicals, representing 9.82-21.45 mol % of monomer radicals in the plurality of oligosaccharides;

(4) 3-glucopyranose monoradicals, representing 3.24-4.52 mol % of monomer radicals in the plurality of oligosaccharides;

(5) 2-glucopyranose monoradicals, representing 2.92-3.74 mol % of monomer radicals in the plurality of oligosaccharides;

(6) 2-galactofuranose and/or 2-glucofuranose monoradicals, representing 1.67-2.26 mol % of monomer radicals in the plurality of oligosaccharides;

(7) 3-glucofuranose monoradicals, representing 0.14-0.50 mol % of monomer radicals in the plurality of oligosaccharides;

(8) 3-galactopyranose monoradicals, representing 2.16-3.66 mol % of monomer radicals in the plurality of oligosaccharides;

(9) 3-galactofuranose monoradicals, representing 1.55-1.97 mol % of monomer radicals in the plurality of oligosaccharides;

(10) 2-galactopyranose monoradicals, representing 1.77-2.45 mol % of monomer radicals in the plurality of oligosaccharides;

(11) 6-glucopyranose monoradicals, representing 6.55-12.07 mol % of monomer radicals in the plurality of oligosaccharides;

(12) 4-galactopyranose and/or 5-galactofuranose monoradicals, representing 1.52-3.11 mol % of monomer radicals in the plurality of oligosaccharides;

(13) 4-glucopyranose and/or 5-glucofuranose monoradicals, representing 1.70-3.97 mol % of monomer radicals in the plurality of oligosaccharides;

(14) 2,3-galactofuranose diradicals, representing 0.14-0.35 mol % of monomer radicals in the plurality of oligosaccharides;

(15) 6-glucofuranose monoradicals, representing 0.06-0.45 mol % of monomer radicals in the plurality of oligosaccharides;

(16) 6-galactofuranose monoradicals, representing 1.78-3.56 mol % of monomer radicals in the plurality of oligosaccharides;

(17) 6-galactopyranose monoradicals, representing 4.70-7.13 mol % of monomer radicals in the plurality of oligosaccharides;

(18) 3,4-galactopyranose and/or 3,5-galactofuranose and/or 2,3-galactopyranose diradicals, representing 0.59-1.33 mol % of monomer radicals in the plurality of oligosaccharides;

(19) 3,4-glucopyranose and/or 3,5-glucofuranose diradicals, representing 0.09-0.75 mol % of monomer radicals in the plurality of oligosaccharides;

(20) 2,3-glucopyranose diradicals, representing 0.04-0.57 mol % of monomer radicals in the plurality of oligosaccharides;

(21) 2,4-glucopyranose and/or 2,5-glucofuranose and/or 2,4-galactopyranose and/or 2,5-galactofuranose diradicals, representing 0.41-1.18 mol % of monomer radicals in the plurality of oligosaccharides;

(22) 3,6-glucopyranose diradicals, representing 0.77-2.06 mol % of monomer radicals in the plurality of oligosaccharides;

(23) 3,6-glucofuranose diradicals, representing 0.03-0.31 mol % of monomer radicals in the plurality of oligosaccharides;

(24) 2,6-glucopyranose and/or 4,6-glucopyranose and/or 5,6-glucofuranose diradicals, representing 1.20-3.30 mol % of monomer radicals in the plurality of oligosaccharides;

(25) 3,6-galactofuranose diradicals, representing 0.35-1.08 mol % of monomer radicals in the plurality of oligosaccharides;

(26) 4,6-galactopyranose and/or 5,6-galactofuranose diradicals, representing 0.92-2.67 mol % of monomer radicals in the plurality of oligosaccharides;

(27) 2,3,4-glucopyranose and/or 2,3,5-glucofuranose triradicals, representing 0-0.12 mol % of monomer radicals in the plurality of oligosaccharides;

(28) 3,6-galactopyranose diradicals, representing 1.01-2.18 mol % of monomer radicals in the plurality of oligosaccharides;

(29) 2,6-galactopyranose diradicals, representing 0.59-1.02 mol % of monomer radicals in the plurality of oligosaccharides;

(30) 3,4,6-galactopyranose and/or 3,5,6-galactofuranose and/or 2,3,6-galactofuranose triradicals, representing 0.23-0.90 mol % of monomer radicals in the plurality of oligosaccharides;

(31) 3,4,6-glucopyranose and/or 3,5,6-glucofuranose triradicals, representing 0.02-0.48 mol % of monomer radicals in the plurality of oligosaccharides;

(32) 2,3,6-glucofuranose triradicals, representing 0.02-0.07 mol % of monomer radicals in the plurality of oligosaccharides;

(33) 2,4,6-glucopyranose and/or 2,5,6-glucofuranose triradicals, representing 0.11-0.31 mol % of monomer radicals in the plurality of oligosaccharides;

(34) 2,3,6-galactopyranose and/or 2,4,6-galactopyranose and/or 2,5,6-galactofuranose triradicals, representing 0.28-0.67 mol % of monomer radicals in the plurality of oligosaccharides;

(35) 2,3,6-glucopyranose triradicals, representing 0.16-0.42 mol % of monomer radicals in the plurality of oligosacharides; and

(36) 2,3,4,6-glucopyranose and/or 2,3,5,6-glucofuranose tetraradicals, representing 0.07-0.12 mol % of monomer radicals in the plurality of oligosacharides.

TABLE 3

Permethylation Data for the selected oligosaccharide produced using citric acid catalyst

| Radicals | Mean mol % + 5 STD | Mean mol % + 3 STD | Mean mol % | Mean mol % − 3 STD | Mean mol % − 5 STD |
| --- | --- | --- | --- | --- | --- |
| t-glucopyranose monoradicals | 35.34% | 30.95% | 24.36% | 17.77% | 13.38% |
| t-galactofuranose monoradicals | 8.47% | 7.58% | 6.23% | 4.89% | 3.99% |
| t-galactofuranose monoradicals | 1.12% | 0.91% | 0.60% | 0.30% | 0.09% |
| t-galactopyranose monoradicals | 25.33% | 21.45% | 15.64% | 9.82% | 5.94% |
| 3-glucopyranose monoradicals | 4.95% | 4.52% | 3.88% | 3.24% | 2.82% |
| 2-glucopyranose monoradicals | 4.01% | 3.74% | 3.33% | 2.92% | 2.64% |
| 2-galactofuranose and/or 2-glucofuranose monoradicals | 2.45% | 2.26% | 1.96% | 1.67% | 1.48% |
| 3-glucofuranose monoradicals | 0.62% | 0.50% | 0.32% | 0.14% | 0.02% |
| 3-galactopyranose monoradicals | 4.16% | 3.66% | 2.91% | 2.16% | 1.66% |
| 3-galactofuranose monoradicals | 2.11% | 1.97% | 1.76% | 1.55% | 1.41% |
| 2-galactopyranose monoradicals | 2.68% | 2.45% | 2.11% | 1.77% | 1.54% |
| 6-glucopyranose monoradicals | 13.91% | 12.07% | 9.31% | 6.55% | 4.71% |
| 4-galactopyranose and/or 5-galactofuranose monoradicals | 3.64% | 3.11% | 2.32% | 1.52% | 0.99% |
| 4-glucopyranose and/or 5-glucofuranose monoradicals | 4.73% | 3.97% | 2.84% | 1.70% | 0.95% |
| 2,3-galactofuranose diradicals | 0.42% | 0.35% | 0.24% | 0.14% | 0.07% |
| 6-glucofuranose monoradicals | 0.58% | 0.45% | 0.26% | 0.06% | −0.06% |
| 6-galactofuranose monoradicals | 4.16% | 3.56% | 2.67% | 1.78% | 1.18% |
| 6-galactopyranose monoradicals | 7.95% | 7.13% | 5.91% | 4.70% | 3.88% |
| 3,4-galactopyranose and/or 3,5-galactofuranose and/or 2,3-galactopyranose diradicals | 1.57% | 1.33% | 0.96% | 0.59% | 0.34% |
| 3,4-glucopyranose and/or 3,5-glucofuranose diradicals | 0.97% | 0.75% | 0.42% | 0.09% | −0.13% |
| 2,3-glucopyranose diradicals | 0.75% | 0.57% | 0.31% | 0.04% | −0.14% |
| 2,4-glucopyranose and/or 2,5-glucofuranose and/or 2,4-galactopyranose and/or 2,5-galactofuranose diradicals | 1.43% | 1.18% | 0.79% | 0.41% | 0.16% |
| 3,6-glucopyranose diradicals | 2.49% | 2.06% | 1.41% | 0.77% | 0.34% |
| 3,6-glucofuranose diradicals | 0.34% | 0.26% | 0.15% | 0.03% | −0.04% |
| 2,6-glucopyranose and/or 4,6-glucopyranose and/or 5,6-glucofuranose diradicals | 0.40% | 0.31% | 0.17% | 0.03% | −0.07% |

TABLE 3-continued

Permethylation Data for the selected oligosaccharide produced using citric acid catalyst

| Radicals | Mean mol % + 5 STD | Mean mol % + 3 STD | Mean mol % | Mean mol % − 3 STD | Mean mol % − 5 STD |
|---|---|---|---|---|---|
| 3,6-galactofuranose diradicals | 3.99% | 3.30% | 2.25% | 1.20% | 0.50% |
| 4,6-galactopyranose and/or 5,6-galactofuranose diradicals | 1.32% | 1.08% | 0.71% | 0.35% | 0.10% |
| 2,3,4-glucopyranose and/or 2,3,5-glucofuranose triradicals | 3.26% | 2.67% | 1.79% | 0.92% | 0.33% |
| 3,6-galactopyranose diradicals | 0.17% | 0.12% | 0.05% | −0.02% | −0.06% |
| 2,6-galactopyranose diradicals | 2.57% | 2.18% | 1.59% | 1.01% | 0.62% |
| 3,4,6-galactopyranose and/or 3,5,6-galactofuranose and/or 2,3,6-galactofuranose triradicals | 1.17% | 1.02% | 0.81% | 0.59% | 0.45% |
| 3,4,6-glucopyranose and/or 3,5,6-glucofuranose triradicals | 1.12% | 0.90% | 0.56% | 0.23% | 0.01% |
| 2,3,6-glucofuranose triradicals | 0.63% | 0.48% | 0.25% | 0.02% | −0.13% |
| 2,4,6-glucopyranose and/or 2,5,6-glucofuranose triradicals | 0.09% | 0.07% | 0.05% | 0.02% | 0.00% |
| 2,3,6-galactopyranose and/or 2,4,6-galactopyranose and/or 2,5,6-galactofuranose triradicals | 0.38% | 0.31% | 0.21% | 0.11% | 0.04% |
| 2,3,6-glucopyranose triradicals | 0.80% | 0.67% | 0.47% | 0.28% | 0.14% |
| 2,3,4,6-glucopyranose and/or 2,3,5,6-glucofuranose tetraradicals | 0.51% | 0.42% | 0.29% | 0.16% | 0.07% |

In some embodiments, an oligosacharide composition is provided, comprising a plurality of oligosaccharides comprising or consisting essentially of monomer radicals (1)-(36), as described herein. In some embodiments, an oligosaccharide composition is provided, comprising a plurality of oligosaccharides comprising at least one (e.g., at least two, at least three, at least four, at least five, at least six, at least seven, at least eight, at least nine, or at least ten) monomer radical selected from radicals (1)-(36) with at least one (e.g., at least two, at least three, at least four, at least five, at least six, at least seven, at least eight, at least nine, or at least ten) corresponding molar percentage shown in Table 3. In some embodiments, an oligosaccharide composition is provided, comprising a plurality of oligosaccharides comprising or consisting of monomer radicals (1)-(36) with the molar percentages shown in Table 3.

In certain embodiments, the oligosaccharide compositions are free from monomer. In some embodiments, the oligosaccharide compositions are de-monomerized, e.g., using the method described in Example 4. In some embodiments, the oligosaccharide compositions have 5% or less monomer (glucose and/or galactose monomers), e.g., 5% or less monomer, 4% or less monomer, 3% or less monomer, 2% or less monomer, or 1% or less monomer. In some embodiments, the oligosaccharide compositions are not de-monomerized using the method described in Example 4. In some embodiments, the oligosaccharide compositions have 30% or less monomer (glucose and/or galactose monomers), e.g., 30% or less monomer, 25% or less monomer, 20% or less monomer, 18% or less monomer, 15% or less monomer, 12% or less monomer, 10% or less monomer, or 8% or less monomer. In other embodiments, the oligosaccharide compositions comprise glucose and/or galactose monomers.

Characterization by 2DNMR Analysis

The oligosaccharide compositions described herein, and prepared according to the methods described herein, can be characterized and distinguished from prior art compositions using two-dimensional heteronuclear NMR. Accordingly, oligosaccharide compositions are provided that comprise a plurality of oligosaccharides (e.g., that are minimally digestible in humans), the compositions being characterized by a $^1$H-$^{13}$C heteronuclear single quantum correlation (HSQC) NMR spectrum comprising at least one (e.g., 1, 2, 3, 4, 5, 6, 7, 8, 9, 10, or 11) signals selected from the following, each signal having a center position, a $^1$H integral region, and a $^{13}$C integral region, as defined in Table 4. In some embodiments, the oligosaccharide compositions have a $^1$H-$^{13}$C heteronuclear single quantum correlation (HSQC) NMR spectrum comprising at least two signals selected from the signals of Table X, each signal having a center position, a $^1$H integral region, and a $^{13}$C integral region, as defined in Table X. In some embodiments, oligosaccharide compositions are provided that comprise a plurality of oligosaccharides (e.g., that are minimally digestible in humans), the compositions being characterized by a $^1$H-$^{13}$C heteronuclear single quantum correlation (HSQC) NMR spectrum comprising the 11 signals of Table 4. In some embodiments, a signal may be referred to as a peak.

TABLE 4

HSQC NMR signals/peaks and $^1$H and $^{13}$C integral regions belonging to oligosaccharide compositions

| | $^1$H Position (ppm) | | | $^{13}$C Position (ppm) | | |
|---|---|---|---|---|---|---|
| | Center | $^1$H Integral Region | | Center | $^{13}$C Integral Region | |
| Signal | Position | from | to | Position | From | to |
| 1 | 3.67 | 3.607 | 3.742 | 63.35 | 63.78 | 62.92 |
| 2 | 3.97 | 3.925 | 4.008 | 66.25 | 66.78 | 65.73 |
| 3 | 3.88 | 3.848 | 3.910 | 67.13 | 67.50 | 66.76 |
| 4 | 3.71 | 3.674 | 3.753 | 67.34 | 68.02 | 66.65 |
| 5 | 3.83 | 3.791 | 3.864 | 71.27 | 71.70 | 70.84 |
| 6 | 3.96 | 3.906 | 4.014 | 71.58 | 71.91 | 71.24 |
| 7 | 3.72 | 3.669 | 3.777 | 72.4 | 72.78 | 72.02 |
| 8 | 3.33 | 3.262 | 3.404 | 73.76 | 74.29 | 73.23 |
| 9 | 4.06 | 4.022 | 4.108 | 77.39 | 77.89 | 76.90 |
| 10 | 4.11 | 4.066 | 4.147 | 81.73 | 82.15 | 81.32 |
| 11 | 4.51 | 4.461 | 4.556 | 103.34 | 103.95 | 102.72 |

In certain embodiments, the NMR spectrum is obtained by subjecting a sample of the composition to heteronuclear single quantum coherence (HSQC) NMR, wherein the sample is a solution in a deuterated solvent. Suitable deuterated solvents include deuterated acetonitrile, deuterated acetone, deuterated methanol, D$_2$O, and mixtures thereof. In a particular embodiment, the deuterated solvent is D$_2$O.

The area under the curve (AUC) of an individual signal (or peak) is determined using peak integration that is centered around a $^1$H position (ppm) and $^{13}$C position (ppm) relative to the total AUC of all signals of a defined group (e.g., total AUC of all signal positions provided in Table 4). In some embodiments, the total area is the sum of the areas of each of signals 1-11 of Table 4. In some embodiments, the area under the curve (AUC) of each individual signal 1, 2, 3, 4, 5, 6, 7, 8, 9, 10, and/or 11 is defined as a percentage of the total area of signals 1-11 provided in Table 4. In some embodiments, the percentage (%) of total areas of signals 1-11 are provided which represent the percentage that an area of a particular signal is relative to the total areas of signals (e.g., the sum of the areas of each of signals 1-11 of Table 4). In some embodiments, this percentage may be referred to as an area under the curve (AUC) parameter. In some embodiments, such parameters may be specified as a range within which a particular sample or composition falls. In some embodiments, the term "signal" is used interchangeably with the term "peak" when referring to NMR spectra. In some embodiments, the area under the curve for an individual signal or peak is derived from an integral region (e.g., an elliptical integral region). In some embodiments, an integral region (e.g., an elliptical integral region) for an individual signal or peak is defined by the expressed positions (e.g., $^1$H position (ppm) and $^{13}$C position (ppm)) provided in Table 4.

In certain embodiments, the spectrum comprises any one or more signals (e.g., two or more, three or more, four or more, five or more, six or more, seven of more, eight or more, nine or more, ten or more, or eleven signals) selected from Table 5, each signal having a center position and an area under the curve selected from Table 5. In some embodiments, the spectrum contains the eleven signals of Table 5, each signal having a center position and an area under the curve selected from Table 5.

TABLE 5

HSQC NMR signals/peaks and AUCs belonging to oligosaccharide compositions

| | Center Position (ppm) | | Area under the curve (AUC) (% of total areas of all signals |
| Signal | $^1$H | $^{13}$C | of Table 4) |
|---|---|---|---|
| 1 | 3.67 | 63.35 | 21.85-24.25 |
| 2 | 3.97 | 66.25 | 5.44-6.31 |
| 3 | 3.88 | 67.13 | 3.17-3.81 |
| 4 | 3.71 | 67.34 | 7.04-7.74 |
| 5 | 3.83 | 71.27 | 6.64-7.85 |
| 6 | 3.96 | 71.58 | 6.49-7.39 |
| 7 | 3.72 | 72.4 | 7.45-9.65 |
| 8 | 3.33 | 73.76 | 14.89-16.63 |
| 9 | 4.06 | 77.39 | 6.13-7.85 |
| 10 | 4.11 | 81.73 | 5.07-5.89 |
| 11 | 4.51 | 103.34 | 9.12-10.42 |

In certain embodiments, the spectrum comprises any one or more signals (e.g., two or more, three or more, four or more, five or more, six or more, seven of more, eight or more, nine or more, ten or more, or eleven signals) selected from Table 6, each signal having a center position and an area under the curve selected from Table 6. In some embodiments, the spectrum contains the eleven signals of Table 6, each signal having a center position and an area under the curve selected from Table 6.

TABLE 6

HSQC NMR signals/peaks and AUCs belonging to oligosaccharide compositions

| | Center Position (ppm) | | Area under the curve (AUC) (% of total areas of all signals |
| Signal | $^1$H | $^{13}$C | of Table 4) |
|---|---|---|---|
| 1 | 3.67 | 63.35 | 20.25-24.97 |
| 2 | 3.97 | 66.25 | 5.03-6.76 |
| 3 | 3.88 | 67.13 | 2.82-4.09 |
| 4 | 3.71 | 67.34 | 6.59-8.15 |
| 5 | 3.83 | 71.27 | 5.91-8.11 |
| 6 | 3.96 | 71.58 | 5.99-7.78 |
| 7 | 3.72 | 72.4 | 6.83-10.61 |
| 8 | 3.33 | 73.76 | 13.78-17.80 |
| 9 | 4.06 | 77.39 | 5.25-8.42 |
| 10 | 4.11 | 81.73 | 4.57-6.25 |
| 11 | 4.51 | 103.34 | 8.75-11.07 |

In certain embodiments, the spectrum comprises any one or more signals (e.g., two or more, three or more, four or more, five or more, six or more, seven of more, eight or more, nine or more, ten or more, or eleven signals) selected from Table 7, each signal having a center position and an area under the curve selected from Table 7. In some embodiments, the spectrum contains the eleven signals of Table 7, each signal having a center position and an area under the curve selected from Table 7.

TABLE 7

HSQC NMR signals/peaks and AUCs belonging to oligosaccharide compositions

| | Center Position (ppm) | | Area under the curve (AUC) (% of total areas of all signals |
| Signal | $^1$H | $^{13}$C | of Table 4) |
|---|---|---|---|
| 1 | 3.67 | 63.35 | 18.67-26.54 |
| 2 | 3.97 | 66.25 | 4.46-7.34 |

TABLE 7-continued

HSQC NMR signals/peaks and AUCs belonging to oligosaccharide compositions

| Signal | Center Position (ppm) $^1$H | Center Position (ppm) $^{13}$C | Area under the curve (AUC) (% of total areas of all signals of Table 4) |
|---|---|---|---|
| 3 | 3.88 | 67.13 | 2.39-4.52 |
| 4 | 3.71 | 67.34 | 6.06-8.68 |
| 5 | 3.83 | 71.27 | 5.18-8.84 |
| 6 | 3.96 | 71.58 | 5.40-8.38 |
| 7 | 3.72 | 72.4 | 5.57-11.87 |
| 8 | 3.33 | 73.76 | 12.44-19.14 |
| 9 | 4.06 | 77.39 | 4.19-9.48 |
| 10 | 4.11 | 81.73 | 4.01-6.81 |
| 11 | 4.51 | 103.34 | 7.98-11.84 |

In certain embodiments, the spectrum comprises any one or more signals (e.g., two or more, three or more, four or more, five or more, six or more, seven of more, eight or more, nine or more, ten or more, or eleven signals) selected from Table 8, each signal having a center position and an area under the curve selected from Table 8. In some embodiments, the spectrum contains the eleven signals of Table 8, each signal having a center position and an area under the curve selected from Table 8.

TABLE 8

HSQC NMR signals/peaks and AUCs belonging to oligosaccharide compositions

| Signal | Center Position (ppm) $^1$H | Center Position (ppm) $^{13}$C | Area under the curve (AUC) (% of total areas of all signals of Table 4) |
|---|---|---|---|
| 1 | 3.67 | 63.35 | 20.45-21.19 |
| 2 | 3.97 | 66.25 | 5.59-5.98 |
| 3 | 3.88 | 67.13 | 3.28-3.46 |
| 4 | 3.71 | 67.34 | 6.89-7.16 |
| 5 | 3.83 | 71.27 | 7.28-7.91 |
| 6 | 3.96 | 71.58 | 7.06-7.35 |
| 7 | 3.72 | 72.4 | 9.51-10.23 |
| 8 | 3.33 | 73.76 | 16.46-16.98 |
| 9 | 4.06 | 77.39 | 5.83-6.25 |
| 10 | 4.11 | 81.73 | 4.81-4.92 |
| 11 | 4.51 | 103.34 | 10.20-10.73 |

In certain embodiments, the spectrum comprises any one or more signals (e.g., two or more, three or more, four or more, five or more, six or more, seven of more, eight or more, nine or more, ten or more, or eleven signals) selected from Table 9, each signal having a center position and an area under the curve selected from Table 9. In some embodiments, the spectrum contains the eleven signals of Table 9, each signal having a center position and an area under the curve selected from Table 9.

TABLE 9

HSQC NMR signals/peaks and AUCs belonging to oligosaccharide compositions

| Signal | Center Position (ppm) $^1$H | Center Position (ppm) $^{13}$C | Area under the curve (AUC) (% of total areas of all signals of Table 4) |
|---|---|---|---|
| 1 | 3.67 | 63.35 | 20.23-21.61 |
| 2 | 3.97 | 66.25 | 5.26-6.25 |

TABLE 9-continued

HSQC NMR signals/peaks and AUCs belonging to oligosaccharide compositions

| Signal | Center Position (ppm) $^1$H | Center Position (ppm) $^{13}$C | Area under the curve (AUC) (% of total areas of all signals of Table 4) |
|---|---|---|---|
| 3 | 3.88 | 67.13 | 3.13-3.57 |
| 4 | 3.71 | 67.34 | 6.72-7.41 |
| 5 | 3.83 | 71.27 | 6.96-8.43 |
| 6 | 3.96 | 71.58 | 6.84-7.62 |
| 7 | 3.72 | 72.4 | 9.07-10.88 |
| 8 | 3.33 | 73.76 | 16.01-17.29 |
| 9 | 4.06 | 77.39 | 5.56-6.60 |
| 10 | 4.11 | 81.73 | 4.75-5.02 |
| 11 | 4.51 | 103.34 | 9.78-11.14 |

In certain embodiments, the spectrum comprises any one or more signals (e.g., two or more, three or more, four or more, five or more, six or more, seven of more, eight or more, nine or more, ten or more, or eleven signals) selected from Table 10, each signal having a center position and an area under the curve selected from Table 10. In some embodiments, the spectrum contains the eleven signals of Table 10, each signal having a center position and an area under the curve selected from Table 10.

TABLE 10

HSQC NMR signals/peaks and AUCs belonging to oligosaccharide compositions

| Signal | Center Position (ppm) $^1$H | Center Position (ppm) $^{13}$C | Area under the curve (AUC) (% of total areas of all signals of Table 4) |
|---|---|---|---|
| 1 | 3.67 | 63.35 | 19.51-22.13 |
| 2 | 3.97 | 66.25 | 4.93-6.59 |
| 3 | 3.88 | 67.13 | 2.99-3.72 |
| 4 | 3.71 | 67.34 | 6.49-7.64 |
| 5 | 3.83 | 71.27 | 6.47-8.92 |
| 6 | 3.96 | 71.58 | 6.59-7.88 |
| 7 | 3.72 | 72.4 | 8.47-11.48 |
| 8 | 3.33 | 73.76 | 15.59-17.72 |
| 9 | 4.06 | 77.39 | 5.22-6.94 |
| 10 | 4.11 | 81.73 | 4.66-5.11 |
| 11 | 4.51 | 103.34 | 9.32-11.60 |

Figure 10:
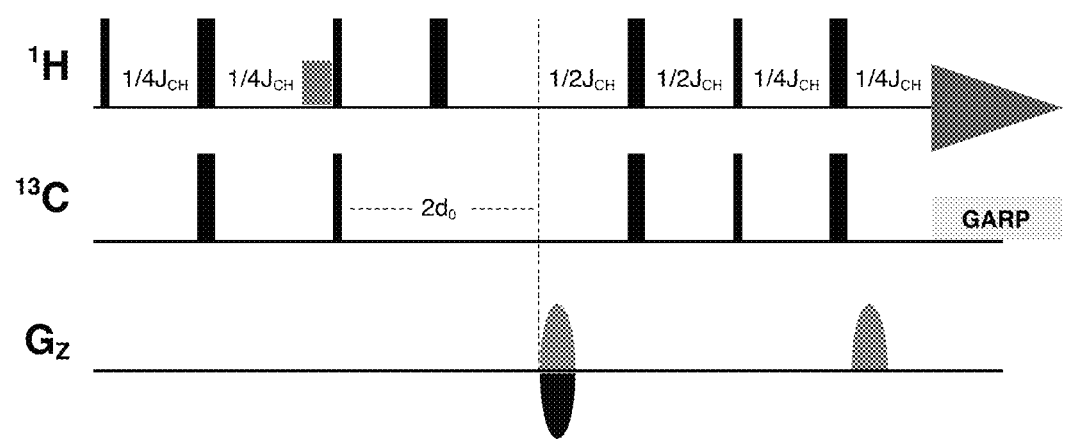
FIG. 10 depicts an HSQC NMR pulse sequence diagram.

In certain embodiments, the NMR spectrum is obtained using the conditions described in Example 15. In some embodiments, the NMR spectrum is obtained by subjecting a sample of the composition to a multiplicity-edited gradient-enhanced $^1$H-$^{13}$C heteronuclear single quantum coherence (HSQC) experiment using the echo-antiecho scheme for coherence selection using the pulse sequence diagram as described in FIG. 10, and the following acquisition parameters and processing parameters:

Acquisition Parameters
$^1$H Carrier Frequency=4 ppm
$^{13}$C Carrier Frequency=65 ppm
Number of points in acquisition dimension=596
Spectral range in acquisition dimension=6.00 ppm to 2.03 ppm
Number of points in indirect dimension=300 complex points
Spectral range in indirect dimension=120 ppm to 10 ppm
Recycle delay=1 second
One-bond $^1$H-$^{13}$C coupling constant=$J_{CH}$=146 Hz
Number of scans=8

Temperature=298 K
Solvent=D$_2$O
Processing Parameters
Window function in direct dimension=Gaussian broadening, 7.66 Hz
Window function in indirect dimension=Gaussian broadening 26.48 Hz
Processing=512 complex points in direct dimension, 1024 complex points in indirect dimension In certain embodiments, the oligosaccharide composition analyzed by NMR contains monosaccharide monomers (DP1), i.e., the DP1 component is not removed from the composition prior to NMR analysis. For example, in some embodiments, the oligosaccharide composition analyzed by NMR contains between 10%-25% DP1 monomers. In certain embodiments, the composition analyzed by NMR is de-monomerized, i.e., some or all of the DP1 component of the composition is removed prior to NMR analysis, e.g., by the method described in Example 4. For example, in some embodiments, the oligosaccharide composition analyze by NMR contains between 0.05% to 8% DP1 monomers.

Exemplary oligosaccharide compositions may be prepared according to the procedures described herein.

III. Pharmaceutical Compositions and Unit Dosage Forms

Provided herein are also methods of producing pharmaceutical compositions containing an oligosaccharide composition as described herein. Methods for formulating the oligosacharide composition into a pharmaceutical composition are known in the art and can include one or more, two or more, three or more, or four or more of the following steps: (i) formulating the composition into drug product, (ii) packaging the composition, (iii) labeling the packaged composition, and (iv) selling or offering for sale the packaged and labeled composition. Formulating the oligosaccharide composition into a drug product is known in the art and may include one or more, two or more, three or more, or four or more of the following steps: (i) removing unwanted constituents from the composition, (ii) reducing the volume of the composition, (iii) sterilizing the composition, (iv) admixing the composition with a pharmaceutically acceptable excipient or carrier, (v) admixing the composition with a another (e.g., a second) drug or pharmaceutical agent, (vi) formulating the composition into a suitable consistency, such as, e.g., aqueous diluted solution, a syrup or a solid, (vii) formulating the composition into a suitable dosage form, e.g. into a sachet, tablet, pill or capsule.

In some embodiments, the oligosaccharide composition undergoes further processing to produce either a syrup or powder. For example, in one variation, the oligosaccharide composition is concentrated to form a syrup. Any suitable methods known in the art to concentrate a solution may be used, such as the use of a vacuum evaporator. In another variation, the oligosaccharide composition is spray dried to form a powder. Any suitable methods known in the art to spray dry a solution to form a powder may be used.

Also provided herein are pharmaceutical compositions containing an oligosaccharide composition as described herein. Optionally, a pharmaceutical composition comprising an oligosaccharide composition further contains a second agent, e.g., a therapeutic agent or drug (e.g., an antibiotic), or a substance (e.g., a prebiotic substance, a probiotic bacterium, or a micronutrient such as a polyphenol, etc.). For example, in some embodiments, the pharmaceutical compositions containing an oligosaccharide composition further contains a micronutrient. Further, optionally, the pharmaceutical compositions comprising an oligosaccharide composition comprise one or more excipients or carriers, including diluents, binders, disintegrants, dispersants, lubricants, glidants, stabilizers, surfactants, flavoring agents, and colorants.

In some embodiments, the pharmaceutical compositions comprising an oligosaccharide composition comprise a second therapeutic agent or drug or preparation thereof. In some embodiments, the therapeutic agent is an antibiotic, an antifungal agent, an antiviral agent, or an anti-inflammatory agent (e.g., a cytokine, hormone, etc.). Antibiotics can include aminoglycosides, such as amikacin, gentamicin, kanamycin, neomycin, streptomycin, and tobramycin; cephalosporins, such as cefamandole, cefazolin, cephalexin, cephaloglycin, cephaloridine, cephalothin, cephapirin, and cephradine; macrolides, such as erythromycin and troleandomycin; penicillins, such as penicillin G, amoxicillin, ampicillin, carbenicillin, cloxacillin, dicloxacillin, methicillin, nafcillin, oxacillin, phenethicillin, and ticarcillin; polypeptide antibiotics, such as bacitracin, colistimethate, colistin, polymyxin B; tetracyclines, such as chlortetracycline, demeclocycline, doxycycline, methacycline, minocycline, tetracycline, and oxytetracycline; and miscellaneous antibiotics such as chloramphenicol, clindamycin, cycloserine, lincomycin, rifampin, spectinomycin, vancomycin, viomycin and metronidazole. In some embodiments, the antibiotic can be a rifamycin-based antibiotic. In some embodiments, the antibiotic can be rifamycin (CAS ID: 6998-60-3). In some embodiments, the antibiotic can be rifaximin (CAS ID: 80621-81-4). In some embodiments, the antibiotic can be rifampin (CAS ID: 13292-46-1). In some embodiments, the pharmaceutical composition contains an oligosaccharide composition as described herein and a rifamycin-based antibiotic. In some embodiments, the pharmaceutical composition contains an oligosaccharide composition as described herein and rifamycin. In some embodiments, the pharmaceutical composition contains an oligosaccharide composition as described herein and rifaximin. In some embodiments, the pharmaceutical composition contains an oligosaccharide composition as described herein and rifampin. In some embodiments, the pharmaceutical composition contains an oligosaccharide composition as described herein and neomycin.

In some embodiments, the therapeutic agent is lactulose. In some embodiments, the pharmaceutical composition contains an oligosaccharide composition as described herein and lactulose. In some embodiments, the therapeutic agent is lactitol. In some embodiments, the pharmaceutical composition contains an oligosaccharide composition as described herein and lactitol.

In some embodiments, the pharmaceutical compositions (and kits comprising same) comprise an oligosaccharide composition described herein and one or more micronutrient. In some embodiments, the micronutrient is selected from the group consisting of a trace mineral, choline, a vitamin, and a polyphenol.

In some embodiments, the micronutrient is a trace metal. Trace minerals suitable as a micronutrient include, but are not limited to, boron, cobalt, chromium, calcium, copper, fluoride, iodine, iron, magnesium, manganese, molybdenum, selenium, and zinc.

In some embodiments, the micronutrient is a vitamin. Vitamins suitable as a micronutrient include, but are not limited to, Vitamin B complex, Vitamin B1 (thiamin), Vitamin B2 (riboflavin), Vitamin B3 (niacin), Vitamin B5 (pantothenic acid), Vitamin B6 group (pyridoxine, pyridoxal, pyridoxamine), Vitamin B7 (biotin), Vitamin B8 (ergadenylic acid), Vitamin B9 (folic acid), Vitamin B12 (cyanocobalamin), Choline, Vitamin A (retinol), Vitamin C (ascorbic acid), Vitamin D, Vitamin E (tocopherol), Vitamin K, carotenoids (alpha carotene, beta carotene, cryptoxanthin, lutein, lycopene) and zeaxanthin.

In some embodiments, the micronutrient is a polyphenol. Polyphenols are chemical compounds or molecules that are characterized by having at least one aromatic ring with one or more hydroxyl groups. In some embodiments, the polyphenol is a synthetic polyphenol or a naturally occurring polyphenol. In some embodiments, the polyphenol is a naturally occurring polyphenol and is derived from plant source material. In some embodiments, the polyphenol is a flavonoid or catechin. In some embodiments, the flavonoid or catechin is selected from anthocyanins, chalcones, dihydrochalcones, dihydroflavonols, flavanols, flavanones, flavones, flavonols and isoflavonoids. In some embodiments, the polyphenol is a lignan. In some embodiments, the polyphenol is selected from alkylmethoxyphenols, alkylphenols, curcuminoids, furanocoumarins, hydroxybenzaldehydes, hydroxybenzoketones, hydroxycinnamaldehydes, hydroxycoumarins, hydroxyphenylpropenes, methoxyphenols, naphtoquinones, phenolic terpenes, and tyrosols. In some embodiments, the polyphenol is a tannin or tannic acid. In some embodiments, the polyphenol is selected from hydroxybenzoic acids, hydroxycinnamic acids, hydroxyphenylacetic acids, hydroxyphenylpropanoic acids, and hydroxyphenylpentanoic acids. In some embodiments, the polyphenol is a stilbene.

In some embodiments, the pharmaceutical compositions comprising an oligosaccharide composition described herein further comprise a prebiotic substance or preparation thereof. In some embodiments, prebiotics may be administered to a subject receiving the pharmaceutical compositions comprising an oligosaccharide composition described herein. Prebiotics are non-digestible substances that when consumed may provide a beneficial physiological effect on the host by selectively stimulating the favorable growth or activity of a limited number of indigenous bacteria in the gut (Gibson G R, Roberfroid M B. Dietary modulation of the human colonic microbiota: introducing the concept of prebiotics. J Nutr. 1995 June; 125(6):1401-12). A prebiotic such as a dietary fiber or prebiotic oligosaccharide (e.g. crystalline cellulose, wheat bran, oat bran, corn fiber, soy fiber, beet fiber and the like) may further encourage the growth of probiotic and/or commensal bacteria in the gut by providing a fermentable dose of carbohydrates to the bacteria and increase the levels of those microbial populations (e.g. lactobacilli and bifidobacteria) in the gastrointestinal tract.

Prebiotics can include, but are not limited to, various galactans and carbohydrate based gums, such as psyllium, guar, carrageen, gellan, lactulose, and konjac. In some embodiments, the prebiotic is one or more of galactooligosaccharides (GOS), lactulose, raffinose, stachyose, lactosucrose, fructo-oligosaccharides (FOS, e.g. oligofructose or oligofructan), inulin, isomalto-oligosaccharide, xylo-oligosaccharides (XOS), paratinose oligosaccharide, isomaltose oligosaccharides (IMOS), transgalactosylated oligosaccharides (e.g. transgalacto-oligosaccharides), transgalactosylate disaccharides, soybean oligosaccharides (e.g. soyoligosaccharides), chitosan oligosaccharide (chioses), gentiooligosaccharides, soy- and pectin-oligosaccharides, glucooligosaccharides, pecticoligosaccharides, palatinose polycondensates, difructose anhydride III, sorbitol, maltitol, lactitol, polyols, polydextrose, linear and branched dextrans, pullalan, hemicelluloses, reduced paratinose, cellulose, beta-glucose, beta-galactose, beta-fructose, verbascose, galactinol, xylan, inulin, chitosan, beta-glucan, guar gum, gum arabic, pectin, high sodium alginate, and lambda carrageenan, or mixtures thereof. In some embodiments, the pharmaceutical composition contains an oligosaccharide composition as described herein and lactulose.

Prebiotics can be found in certain foods, e.g. chicory root, Jerusalem artichoke, Dandelion greens, garlic, leek, onion, asparagus, wheat bran, wheat flour, banana, milk, yogurt, sorghum, burdock, broccoli, Brussels sprouts, cabbage, cauliflower, collard greens, kale, radish and rutabaga, and miso. In some embodiments, the glycan therapeutics described herein are administered to a subject in conjunction with a diet that includes foods rich in prebiotics. Suitable sources of soluble and insoluble fibers are commercially available.

In some embodiments, the pharmaceutical compositions comprising an oligosaccharide composition described herein further comprise a probiotic bacterium or preparation thereof, e.g., derived from bacterial cultures that are generally recognized as safe (GRAS) or known commensal or probiotic microbes. In some embodiments, to maximize the beneficial effect of endogenous commensal microbes or exogenously administered probiotic microorganisms, the pharmaceutical compositions comprising an oligosaccharide composition are administered to stimulate the growth and/or activity of advantageous bacteria in the GI tract.

Examples of suitable probiotics include, but are not limited to, organisms classified as genera *Bacteroides, Blautia, Clostridium, Fusobacterium, Eubacterium, Ruminococcus, Peptococcus, Peptostreptococcus, Akkermansia, Faecalibacterium, Roseburia, Prevotella, Bifidobacterium, Lactobacillus, Bacillus, Enterococcus, Escherichia, Streptococcus, Saccharomyces, Streptomyces*, and family Christensenellaceae. Non-exclusive examples of probiotic bacteria that can be used in the methods and compositions described herein include *L. acidophilus, Lactobacillus* species, such as *L. crispatus, L. casei, L. rhamnosus, L. reuteri, L. fermentum, L. plantarum, L. sporogenes*, and *L. bulgaricus*, as well as *Bifidobacterum* species, such as *B. lactis, B. animalis, B. bifidum, B. longum, B. adolescentis*, and *B. infantis*. Yeasts, such as *Saccharomyces boulardii*, are also suitable as probiotics for administration to the gut, e.g. via oral dosage forms or foods. For example, yogurt is a product which already contains bacteria species, such as *Lactobacillus bulgaricus* and *Streptococcus thermophilus*.

Beneficial bacteria for the modulation of the gastrointestinal microbiota may include bacteria that produce organic acids (lactic & acetic acids) or that produce cytotoxic or cytostatic agents (to inhibit pathogenic growth), such as, e.g., hydrogen peroxide ($H_2O_2$) and bacteriocins. Bacteriocins are small antimicrobial peptides which can kill both closely-related bacteria, or exhibit a broader spectrum of activity (e.g., nisin). Beneficial bacteria may include, but are not limited to, one or more of the genus *Akkermansia, Anaerofilum, Bacteroides, Blautia, Bifidobacterium, Butyrivibrio, Clostridium, Coprococcus, Dialister, Dorea, Fusobacterium, Eubacterium, Faecalibacterium, Lachnospira, Lactobacillus, Phascolarctobacterium, Peptococcus, Peptostreptococcus, Prevotella, Roseburia, Ruminococcus*, and *Streptococcus*, and/or one or more of the species *Akkermansia municiphilia, minuta, Clostridium coccoides, Clostridium leptum, Clostridium scindens, Dialister invisus, Eubacterium rectal, Eubacterium eligens, Faecalibacterium prausnitzii, Streptococcus salivarius*, and *Streptococcus thermophilus*.

In some embodiments, the probiotic bacteria are lyophilized vegetative cells. In some embodiments, the preparations of spores from sporulating probiotic bacteria are used.

In some embodiments, a pharmaceutical composition containing an oligosaccharide composition further comprises a prebiotic and probiotic. In one embodiment, the pharmaceutical composition comprises probiotics whose viability has been partially attenuated (e.g. a mixture comprising 10%, 20%, 30%, 40%, 50% or more non-viable bacteria), or probiotics consisting solely of non-viable microbes. The compositions may further comprise microbial membranes and/or cell walls that have been isolated and purified from killed microbes.

The oligosaccharide compositions described herein, other therapeutically active agents (e.g., therapeutic agents or drugs, such as an antibiotic), prebiotic substances, micronutrients and/or probiotics may be comingled or mixed in a single pharmaceutical composition. In other embodiments, they may be contained in separate containers (and/or in various suitable unit dosage forms) but packaged together in one or more kits. In some embodiments, the preparations or compositions are not packaged or placed together. A physician or other medical professional or caregiver may then administer the preparations or compositions together, e.g. prior to, concomitant with, or after one another. In some embodiments, the preparations or compositions act synergistically in modulating the microbiota in a subject, e.g., in the GI tract.

Further, if desired, the pharmaceutical compositions comprising an oligosaccharide composition described herein may comprise therapeutically active agents (e.g., therapeutic agents or drugs, such as an antibiotic), prebiotic substances and/or probiotic bacteria. Alternatively or in addition, therapeutically active agents, prebiotic substances and/or probiotic bacteria may be administered separately (e.g. prior to, concurrent with or after administration of the oligosaccharide composition) and not as a part of the pharmaceutical composition (e.g. as a co-formulation) of oligosaccharide compostions. In some embodiments, pharmaceutical compositions comprising an oligosaccharide composition are administered in combination with a recommended or prescribed diet, e.g. a diet that is rich in probiotic and/or prebiotic-containing foods, such as it may be determined by a physician or other healthcare professional. Therapeutically active agents, prebiotic substances and/or probiotic bacteria may be administered to modulate the gut microbiome of the subject. In some embodiments, the combined effect (e.g. on the number or intensity of the microbial, genomic or functional shifts) is additive. In other embodiments, the combined effect (e.g. on the number or intensity of the microbial, genomic or functional shifts) is synergistic.

In some embodiments, the pharmaceutical compositions comprising an oligosaccharide composition do not contain a second agent, e.g., a therapeutic agent or drug (e.g., an antibiotic), or a substance (e.g., a prebiotic substance, a probiotic bacterium, or a micronutrient such as a polyphenol). In some embodiments, the pharmaceutical compositions comprising an oligosaccharide composition do not contain a therapeutic agent or drug (e.g., an antibiotic). In some embodiments, the pharmaceutical compositions comprising an oligosaccharide composition do not contain a prebiotic substance. In some embodiments, the pharmaceutical compositions comprising an oligosaccharide composition do not contain a probiotic bacterium. In some embodiments, the pharmaceutical compositions comprising an oligosaccharide composition do not contain a micronutrient (e.g., a polyphenol).

IV. Methods of Use

As described herein, the oligosaccharide compositions may be used to reduce ammonia levels in a subject, e.g., in a human subject with an elevated ammonia level, such as a subject with a liver cirrhosis and/or a subject with hepatic encephalopathy (HE). In some embodiments, the oligosaccharide compositions can be used to prevent or treat a symptom or complication of a disease or disorder associated with elevated ammonia levels, such as cirrhosis and/or hepatic encephalopathy (e.g., overt hepatic encephalopathy and/or minimal hepatic encephalopathy). For example, in some embodiments, the oligosaccharide compositions can be used to prevent the onset of a hepatic encephalopathy (HE) event or prevent the reoccurrence of a hepatic encephalopathy (HE) event.

The oligosaccharide compositions described herein can also or optionally be used to reduce the abundance or level of a pathogen (e.g., a multi-drug resistant pathogen, such as CRE or VRE) in a subject, e.g., in a human subject, such as a subject infected with a pathogen. In some embodiments, the oligosaccharide compositions can be used to prevent the colonization of a subject by a pathogen (e.g., a multi-drug resistant pathogen, such as CRE or VRE), reduce the severity of the colonization of a subject by a pathogen (e.g., by reducing the degree to which the pathogen is able to colonize the subject or reducing the number of pathogens colonizing the subject), and/or reverse the colonization of a subject by the pathogen, e.g., by decolonizing the subject of the pathogen or some proportion of the pathogen.

In some embodiments, the oligosaccharide composition is formulated as powder, e.g., for reconstitution (e.g., in water) for oral administration.

Ammonia Reduction

The oligosaccharide compositions described herein are useful for reducing ammonia levels, e.g., blood ammonia levels, in a subject in need thereof, e.g., a human subject with elevated ammonia levels relative to the normal levels of ammonia in healthy humans. The oligosaccharide compositions can thus be used to treat, prevent, or alleviate a symptom of any disease or disorder associated with elevated ammonia levels in a human subject, e.g., in a human subject with hyperammonemia, hepatic encephalopathy (HE), and/or liver cirrhosis. In some embodiments, the oligosaccharide compositions described herein can be used to treat, prevent, or alleviate a symptom of hyperammonemia in a subject. In some embodiments, the oligosaccharide compositions can be used to treat, prevent, or alleviate a symptom of cirrhosis in a subject. In some embodiments, the oligosaccharide compositions described herein can be used to treat, prevent, or alleviate a symptom of hepatic encephalopathy (HE).

Presentation and Symptoms

In some embodiments, subjects with hepatic encephalopathy (HE) may be treated according to the methods provided herein. Hepatic encephalopathy covers a complex set of non-specific neuropsychiatric symptoms and clinical signs affecting the quality of life of both patients and their relatives. Hepatic encephalopathy is a common complication of advanced liver disease, including all forms of cirrhosis (e.g., decompensated cirrhosis or compensated cirrhosis), and up to 80% of cirrhotic patients have some form of HE, ranging from minimal hepatic encephalopathy (MHE) to overt hepatic encephalopathy (OHE). Hepatic encephalopathy includes multiple adverse neurological symptoms that occur when the liver is unable to remove toxic substances such as ammonia from the blood. Liver dysfunction can include: liver cirrhosis (and portal hypertension), e.g., Types A (resulting from acute liver failure (ALF), B (resulting predominantly from PSS) or C (resulting from cirrhosis) (Child-Pugh Score for severity of liver cirrhosis); an absence of cirrhosis with either spontaneous or surgically created portosystemic shunts (portosystemic shunt surgery); portal-systemic bypass, acute liver failure (ALF), or acute-on-chronic liver failure (ACLF). In some cases, inflammation may also play a role in exacerbating the neurological effects of HE. For example, inflammation caused by an inflamed or necrotic liver, or inflammation caused by pathogens in the gut (e.g., from translocation of pathogenic bacteria or microbial products through an impaired gut barrier) could impact HE symptoms.

The 2014 AASLD and EASL clinical practice guidelines for managing HE recommend classifying HE according to the underlying liver disease, the severity of the manifestations, the time course, and precipitating factors. The severity of HE may be graded based upon clinical manifestations: Minimal (abnormal results on psychometric or neurophysiological testing with no clinical manifestations); Grade I (mild confusion, slurred speech, disordered sleep, behavioral changes); Grade II (lethargy, mild confusion); Grade III (marked confusion (stupor), incoherent speech, sleeping but arousable); and Grade IV (coma, unresponsive to pain). HE may be further categorized based on the time course of the disease: episodic; recurrent (bouts of HE occur for 6 months or less); and persistent (patterns of behavioral alterations are always present and interspersed with relapses of overt HE).

Subjects with HE may suffer from a bout wherein the subject exhibits metal status abnormalities or cognitive deficits, referred to as a hepatic encephalopathy (HE) event or HE episode. HE events can be recurring and the frequency of events can vary, depending on the severity of the subject's underlying disease, e.g., liver cirrhosis. During an HE event, a subject may present with cognitive deficits including, for example: confusion, forgetfulness, anxiety or excitation, sudden changes in personality or behavior, changes in sleep patterns, disorientation, sweet or musty smelling breath, slurred speech, and/or difficulty controlling motor functions. The condition reflects a diffuse disturbance of brain functions due to advanced liver disease or large portosystemic shunts (e.g., TIPS). Patients may present with neuromuscular impairments including bradykinesia, hyperreflexia, rigidity, myoclonus, and asterixis. Disturbances in the diurnal sleep pattern (insomnia and hypersomnia) are common initial manifestations of hepatic encephalopathy and typically precede other mental status changes or neuromuscular symptoms.

'Minimal hepatic encephalopathy' (MHE) is defined as the presence of test-dependent or clinical signs of brain dysfunction in patients with chronic liver disease (CLD) who are not disoriented or display asterixis. The term "minimal" conveys that there is no clinical sign, cognitive sign, or other sign of HE. The term "covert hepatic encephalopathy (CHE)" includes minimal and grade 1 HE. Because the occurrence of MHE and CHE in patients with CLD may be as high as 50%, patients at risk should be tested. Patients with MHE have subtle symptoms that may only be detected using specialized psychometric tests and MHE is generally underdiagnosed. There is currently no common diagnostic paradigm in clinical practice to define MHE and there are no approved treatments for MHE. MHE can cause the loss of independent living skills (e.g., driving) and is predictive of subsequent development of OHE. Patients who have a single episode of OHE, often caused by a precipitant, and subsequently recover are also likely to have some level of MHE.

OHE is defined as neurologic abnormalities that are observable by a clinician without special testing. Symptoms can include shaking of the hands or arms, disorientation and slurred speech. OHE patients can progress into coma. OHE can develop in patients with liver disease, cirrhosis and in patients with a transjugular intrahepatic portosystemic shunt (TIPS). This condition may follow a gastrointestinal bleed or infection. Development of OHE is associated with increased mortality. Admissions for OHE are frequent among patients with end stage liver disease (ESLD).

Testing for Ammonia and Diagnosis of Subjects with Hyperammonemia (e.g., Hepatic Encephalopathy (HE))

a. Ammonia Testing

Subjects having, suspected of having, or at risk of having hyperammonemia (e.g., subjects with hepatic encephalopathy (HE)) can have elevated blood ammonia levels, e.g., plasma ammonia levels, serum ammonia levels, or whole blood ammonia levels, relative to a control subject (e.g., a subject who does not have, is not suspected of having, or is not at risk of having hyperammonemia, such as a subject without HE). In some embodiments, blood ammonia levels in healthy adult subjects (e.g., subjects who does not have, are not suspected of having, or at not at risk of having hyperammonemia) are less than 15, 20, 25, 30, 35, 40, 45, or 50 mol/L, e.g., less than 30 mol/L. In some embodiments, a blood ammonia level of about 0.5-fold, about 1-fold, about 1.5-fold, about 2-fold, about 2.5-fold, or about 3-fold or higher above normal (e.g., above the blood ammonia level in a subject not having, not suspected of having, or not at risk of having hyperammonemia, e.g., a subject not having HE) is suggestive of hyperammonemia, e.g., HE. In some embodiments, a subject having or suspected of having hyperammonemia, e.g., HE, has blood ammonia levels of greater than or equal to 90, 95, 100, 105, 110, 115, 120, 125, 130, 135, 140, 145, 150, 155, 160, 165, 170, 175, or 180 mol/L. In some embodiments, a subject having or suspected of having HE has blood ammonia levels of greater than or equal to 100, 105, 110, 115, 120, 125, 130, 135, 140, 145, or 150 mol/L. In some embodiments, a subject having or suspected of having hyperammonemia, e.g., HE, has blood ammonia levels of greater than or equal to 100 mol/L. In some embodiments, a subject having or suspected of having hyperammonemia, e.g., HE, has blood ammonia levels of greater than or equal to 150 µmol/L.

Newborns and children having, suspected of having, or at risk of having hyperammonemia (e.g., newborns or children with liver failure and/or HE) may have elevated blood ammonia levels, e.g., plasma ammonia levels, serum ammonia levels, or whole blood ammonia levels, relative to a healthy newborn or child. In some embodiments, a healthy newborn or child has an average blood ammonia concentration of 45±10 µmol/L. In some embodiments, a healthy newborn or child (e.g., a subject not having, not suspected of having, or not at risk of having hyperammonemia, e.g., a subject not having HE) has an average blood ammonia concentration of less than or equal to 70, 71, 72, 73, 74, 75, 76, 77, 78, 79, 80, 81, 82, 83, 84, 85, 86, 87, 87, 88, 89, 90, 91, 92, 93, 94, or 95 µmol/L, e.g., 80 or 90 µmol/L. In some embodiments, a newborn or child having or suspected of having hyperammonemia, e.g., a subject having or suspected of having HE, has blood ammonia levels of greater than or equal to 55, 60, 65, 70, 75, 80, 90, or 95, 100, 105, 110, 115, 120, 125, 130, 135, 140, 145, 150, 155, 160, 165, 170, 175, or 180 µmol/L. In some embodiments, an oligosaccharide composition described herein can be administered to a newborn or child having, suspected of having, or at risk of having hyperammonemia, e.g., a newborn or child with HE, that has blood ammonia levels of greater than or equal to 55, 60, 65, 70, 75, 80, 90, or 95, 100, 105, 110, 115, 120, 125, 130, 135, 140, 145, 150, 155, 160, 165, 170, 175, or 180 μmol/L.

In some embodiments, blood ammonia concentration can be measured in venous and arterial blood samples to determine whether a subject or subjects should be adminstered an oligosaccharide composition described herein. In some embodiments, subjects having hyperammonemia (e.g., subjects with HE) have elevated concentrations of blood ammonia relative to a control subject (e.g., a subject not having, not suspected of having, or not at risk of having hyperammonia, e.g., a subject not having HE). In some embodiments, blood ammonia concentration is measured in a venous or arterial blood sample from a subject to determine whether the subject has elevated ammonia levels and should be administered an oligosaccharide composition to reduce the ammonia levels. In some embodiments, measuring serum ammonia levels can be used for monitoring the efficacy of the oligosaccharide compositions described herein in reducing ammonia. For example, in some embodiments, serum ammonia levels are measured in a subject, e.g., a subject with elevated concentrations of ammonia, at a time point before the oligosaccharide composition is administered to the subject and at a time point after the oligosaccharide composition is administered to the subject. A decrease in the concentration of serum ammonia at the time point after the oligosaccharide composition was administered, relative to the time point before the oligosaccharide composition was administered, indicates that the oligosaccharide composition has some efficacy in reducing ammonia.

In some embodiments, the grade or severity of hyperammonemia can be assessed by measuring the partial pressure of gaseous ammonia (pNH3), e.g., in the brain. pNH3 values can be calculated from the total ammonia and pH. In some embodiments, subjects having hyperammonemia have elevated levels of pNH3 relative to a control subject (e.g., a subject not having, not suspected of having, or not at risk of having hyperammonemia, e.g., a subject not having HE).

In some embodiments, serum levels of 3-nitrotyrosine can be elevated in subjects having, suspected of having, or at risk for minimal hepatic encephalopathy (MHE). In some embodiments, a subject having, suspected of having, or at risk for MHE has serum 3-nitrotyrosine levels of greater than about 10 nM, 15 nM, 20 nM, 30 nM, 40 nM, 50 nM, 60 nM, 70 nM, 80 nM, 90 nM, or 100 nM. In some embodiments, a subject having, suspected of having, or at risk for MHE has serum 3-nitrotyrosine levels of greater than about 10 nM or about 15 nM. In some embodiments, serum levels of 3-nitrotyrosine can be elevated in subjects having, suspected of having, or at risk for overt hepatic encephalopathy (OHE).

In some embodiments, serum levels of 3-nitrotyrosine can be measured to determine whether a subject or subjects should be adminstered an oligosaccharide composition described herein. In some embodiments, subjects having hyperammonemia (e.g., subjects with HE) have elevated concentrations of serum levels of 3-nitrotyrosine relative to a control subject (e.g., a subject not having, not suspected of having, or not at risk of having hyperammonia, e.g., a subject not having HE). In some embodiments, serum levels of 3-nitrotyrosine are measured in a subject to determine whether the subject has elevated serum levels of 3-nitrotyrosine and should be administered an oligosaccharide composition. In some embodiments, measuring serum levels of 3-nitrotyrosine can be used for monitoring the efficacy of the oligosaccharide compositions described herein. For example, in some embodiments, serum levels of 3-nitrotyrosine are measured in a subject, e.g., a subject with elevated concentrations of ammonia, at a time point before the oligosaccharide composition is administered to the subject and at a time point after the oligosaccharide composition is administered to the subject. A decrease in the serum levels of 3-nitrotyrosine at the time point after the oligosaccharide composition was administered, relative to the time point before the oligosaccharide composition was administered, indicates that the oligosaccharide composition has some efficacy.

b. Diagnosis

Diagnosis of HE can be performed using tests for liver function, serum ammonia levels, EEG, and other blood and neurological tests. Psychometric tests for diagnosis include: Number Connection Test (Reitan Test) (timed connect-the-numbers test administered in two parts in which patients without hepatic encephalopathy should finish the test in a number of seconds less than or equal to their age in years); Psychometric Hepatic Encephalopathy Score (PHES) (five paper-pencil tests that evaluate cognitive and psychomotor processing speed and visuomotor coordination); Inhibitory Control Test (ICT) (computerized test of attention and response inhibition that has been used to characterize attention deficit disorder, schizophrenia, and traumatic brain injury); STROOP Task (test of psychomotor speed and cognitive flexibility that evaluates the functioning of the anterior attention system and is sensitive for the detection of cognitive impairment in minimal hepatic encephalopathy); Repeatable Battery for the Assessment of Neuropsychological Status (RBANS) (measures a wide range of neurocognitive functions relevant to minimal hepatic encephalopathy); and the Continuous Reaction Time (CRT) test (relies on repeated registration of the motor reaction time (pressing a button) to auditory stimuli (through headphones)).

Neurophysiological tests for diagnosis include the Critical Flicker Frequency (CFF) Test (psychophysiological tool defined as the frequency at which a fused light (presented from 60 Hz downward) appears to be flickering to the observer); Electroencephalography examination (which may detect changes in cortical cerebral activity across the spectrum of HE without patient cooperation or risk of a learning effect); and Evoked Potentials (externally recorded electrical signals that reflect synchronous volleys of discharges through neuronal networks in response to various afferent stimuli). In some embodiments, hepatic encephalopathy is diagnosed using any combination of two or more psychometric or neurophysiological tests. In some embodiments, an oligosaccharide composition as described herein is administered to a subject diagnosed as having HE using any combination of two or more psychometric or neurophysiological tests.

Treatment of Hyperammonemia and HE

Medical treatment of HE currently includes treatment of the underlying precipitant, if present, such as gastrointestinal bleeding or infection. Standard-of-care treatments for HE include lactulose, lactitol, and antibiotics (e.g., rifaximin or neomycin).

Lactulose is a non-absorbed disaccharide that has been used for several decades to reduce hyperammonemia in OHE patients. Lactulose's mechanism of action is thought to work primarily through purging of the stool and acidification of the colonic environment, leading to the conversion of ammonia to ammonium, which less readily crosses the colonic barrier and enters the bloodstream. Lactulose has also been shown to stimulate bacterial growth, thus promoting assimilation of ammonia into bacterial proteins. Lactulose reduces episodes of OHE by up to 50% compared to a placebo.

Rifaximin, a poorly-absorbed antibiotic derived from rifamycin, is currently approved as a second line treatment for OHE and is used in conjunction with lactulose when lactulose alone does not control OHE. When administered in combination with lactulose, rifaximin reduces episodes of OHE by approximately 50%. Neither lactulose nor rifaximin sufficiently reduces the risk of OHE recurrence, each episode of which significantly increases mortality risk.

Treatments may also include dietary modifications and probiotics. Treatment efficacy may be assessed by resolution of the symptoms or diagnostic criteria listed above (e.g., reduction in serum ammonia levels), decreased incidence of future episodes of HE (HE events), or, in subjects at risk for HE, by decreased occurrence of an initial episode of HE (HE event).

The oligosaccharide compositions described herein can be used to reduce ammonia concentration in a subject in need thereof, e.g., the blood ammonia concentration of a subject with a higher than normal concentration of blood ammonia. In some embodiments, the subject has, or is diagnosed as having, hyperammonemia, hepatic encephalopathy (HE), and/or cirrhosis (e.g., decompensated cirrhosis or compensated cirrhosis). In some embodiments, an oligosaccharide composition can be administered to a subject that has a blood ammonia level that is about 0.5-fold, about 1-fold, about 1.5-fold, about 2-fold, about 2.5-fold, or about 3-fold or higher above normal (a blood ammonia level of less than 15, 20, 25, 30, 35, 40, 45, or 50 µmol/L, e.g., less than 30 µmol/L) to reduce the blood ammonia level in the subject. In some embodiments, an oligosaccharide composition can be administered to a subject that has a blood ammonia level of greater than or equal to 90 mol/L, e.g., 90, 95, 100, 105, 110, 115, 120, 125, 130, 135, 140, 145, 150, 155, 160, 165, 170, 175, or 180 mol/L or higher. In some embodiments, the blood ammonia level in a human subject administered an oligosaccharide composition are reduced to a level close to the blood ammonia level of a healthy human subject, e.g., a blood ammonia level of 50 µmol/L or less, e.g., less than 15, 20, 25, 30, 35, 40, 45, or 50 µmol/L. In some embodiments, a subject diagnosed as having an elevated blood ammonia level (e.g., a subject with hyperammonemia, HE, and/or cirrhosis) is administered an oligosaccharide composition, thereby reducing the blood ammonia level in the subject to between 15-90 180 µmol/L, e.g., between 15-30, between 15-50, between 20-70, between 15-75, between 25-85, or between 30-90 µmol/L.

In some embodiments, an oligosaccharide composition described herein is administered to a subject with an elevated blood ammonia level, thereby reducing the blood ammonia level in the subject by at least 10%, e.g., at least 10, 20, 25, 30, 35, 40, 45, 50, 55, 60, 65, 70, 75, 80, 85, 90, 95% or more. In some embodiments, the blood ammonia level in the subject is reduced by between 10-90%, 15-85%, 20-80%, 25-75%, 15-65%, 25-50%, 10-30%, 50-90%, 50-75%, or 70-90%.

In some embodiments, an oligosaccharide composition described herein can be administered to a subject with serum 3-nitrotyrosine levels of greater than about 10 nM, 15 nM, nM, 30 nM, 40 nM, 50 nM, 60 nM, 70 nM, 80 nM, 90 nM, or 100 nM or higher, e.g., a subject subject having, suspected of having, or diagnosed as having MHE with serum 3-nitrotyrosine levels greater than about 10 nM, e.g., about 10 nM, 15 nM, 20 nM, 30 nM, 40 nM, 50 nM, 60 nM, nM, 80 nM, 90 nM, or 100 nM or higher. In some embodiments, a subject determined as having serum 3-nitrotyrosine levels of greater than about 10 nM, 15 nM, 20 nM, 30 nM, 40 nM, nM, 60 nM, 70 nM, 80 nM, 90 nM, or 100 nM or higher (e.g., a subject with HE (e.g., MHE or OHE) and/or cirrhosis) is administered an oligosaccharide composition, thereby reducing the serum 3-nitrotyrosine levels of the subject.

In some embodiments, the oligosaccharide compositions described herein can be used to reduce the frequency, and/or severity, of HE events in a subject, e.g., a subject with hepatic encephalopathy and/or cirrhosis. In some embodiments, an oligosaccharide composition can be administered to a subject (e.g., a subject with OHE) to reduce the frequency of HE events in the subject by at least 10% (e.g., at least 10%, 15%, 20%, 25%, 30%, 35%, 40%, 45%, 50%, 55%, 60%, 65%, 70%, 75%, 80%, 85%, 90%, or 95% or more) relative to the frequency of HE events in the subject prior to the administration of the oligosaccharide composition. In some embodiments, an oligosaccharide composition can be administered to a subject with hepatic encephalopathy (e.g., a subject with OHE or a subject undergoing an HE event) to reduce the severity of at least one symptom associated with HE (e.g., at least one neurological symptoms) by at least 10% (e.g., at least 10%, 15%, 20%, 25%, 30%, 35%, 40%, 45%, 50%, 55%, 60%, 65%, 70%, 75%, 80%, 85%, 90%, or 95%, or more) relative to the severity of the at least one symptom in subject prior to administration of the oligosaccharide composition. In some embodiments, an oligosaccharide composition is administered to a subject with HE or who is at risk of developing HE (e.g., a subject who is at risk of having an HE event, such as a subject with MHE, a subject with OHE, and/or a subject with cirrhosis) to prevent the occurrence of an HE event. In some embodiments, the oligosaccharide composition is administered to the subject to prevent a first HE event in the subject, e.g., a subject having, diagnosed as having or suspected as having MHE, OHE, and/or cirrhosis. In some embodiments, an oligosaccharide composition is administered to a subject with HE, e.g., a subject with OHE and/or cirrhosis, to prevent the reoccurrence of an HE event in the subject. In some embodiments, an oligosaccharide composition is administered to a subject with HE, e.g., a subject with MHE, a subject with OHE, and/or a subject with cirrhosis, to reduce the severity of an HE event should the subject experience one, e.g., by reducing the severity of at least one symptom of HE during the event.

In some embodiments, an oligosaccharide composition described herein is administered to a subject to treat, prevent, or alleviate at least one symptom or complication associated with liver cirrhosis, such as elevated blood ammonia level, a heptic encephalopathy (HE) event, and/or a neurological symptom or cognitive impairment. In some cases, the oligosaccharide composition reduces blood ammonia levels in the subject with liver cirrhosis. In some cases, the oligosaccharide composition prevents the occurrence of, prevents the reoccurrence of, or reduces the frequency of HE events in the subject with liver cirrhosis. In some embodiments, the oligosaccharide composition treats, prevents, or alleviates at least one symptom associated with HE, such as, e.g., confusion, forgetfulness, anxiety or excitation, sudden changes in personality or behavior, changes in sleep patterns, disorientation, sweet or musty smelling breath, slurred speech, and/or difficulty controlling motor functions. In some embodiments, the oligosaccharide composition can be used to treat or prevent an infection in a subject with liver cirrhosis, e.g., by reducing the abundance of a pathogen (e.g., a bacterial pathogen) in the subject with liver cirrhosis.

In some embodiments, the methods disclosed herein (e.g., methods for treating or preventing HE (e.g., MHE or OHE), methods for decreasing the level of a metabolite (e.g., ammonia), and methods for identifying or selecting treatment regimens, e.g., for HE (e.g., MHE or OHE)), may be combined with one or more (e.g., one, two, three, four, or more) existing therapeutic options, e.g., therapeutic options described herein, to treat subjects with having, suspected of having, or at risk of having hyperammonemia, e.g., subjects with HE (e.g., MHE or OHE).

In some embodiments, the methods disclosed herein may be combined with any appropriate standard-of-care for the treatment of HE. In some embodiments, the methods disclosed herein may be combined with lactulose for the treatment of HE. In some embodiments, the methods disclosed herein may be combined with an antibiotic, e.g., rifaximin, for the treatment of HE. In some embodiments, an oligosaccharide composition as described herein can be combined with lactulose and/or an antibiotic, e.g., rifaximin, for the treatment of hyperammonemia, HE, and/or cirrhosis in a subject.

In some embodiments, an oligosaccharide composition and lactulose are administered to a subject in need thereof, e.g., a subject with hyperammonemia, HE, and/or cirrhosis. In some embodiments, an oligosaccharide composition and an antibiotic (e.g., rifaximin) are administered to a subject in need thereof, e.g., a subject with hyperammonemia, HE, and/or cirrhosis. In some embodiments, an oligosaccharide composition and rifaximin are administered to a subject in need thereof, e.g., a subject with hyperammonemia, HE, and/or cirrhosis. In some embodiments, an oligosaccharide composition, lactulose, and rifaximin are administered to a subject in need thereof, e.g., a subject with hyperammonemia, HE, and/or cirrhosis. The oligosaccharide composition and lactulose and/or rifaximin can be administered to a subject in any sequence, e.g., the oligosaccharide composition can be administered before, substantially at the same time (co-administered), or after the lactulose and/or rifaximin are administered to the subject. In some embodiments, the oligosaccharide composition and lactulose and/or rifaximin can be administered orally to the subject. In some embodiments, one or more of the oligosaccharide composition, lactulose, and/or rifaximin can be administered orally to the subject (e.g., the oligosaccharide composition and rifaximin can be administered orally to the subject).

In some embodiments, a subject has been treated with lactulose and/or rifaximin prior to administration of the oligosaccharide composition. In some embodiments, a subject has been treated with lactulose and/or an antibiotic, e.g., rifaximin, concurrently with administration of the oligosaccharide composition. In some embodiments, a subject can be treated with lactulose and/or an antibiotic, e.g., rifaximin, after administration of the oligosaccharide composition. In some embodiments, the subject has been treated with rifaximin prior to administering the oligosaccharide composition. In some embodiments, a subject has been treated with rifaximin concurrently with administration of the oligosaccharide composition. In some embodiments, a subject can be treated with rifaximin after administration of the oligosaccharide composition. In some embodiments, the subject has been treated with lactulose prior to administering the oligosaccharide composition. In some embodiments, a subject has been treated with lactulose concurrently with administration of the oligosaccharide composition. In some embodiments, a subject can be treated with lactulose after administration of the oligosaccharide composition. In some embodiments, the subject has been treated with lactulose and rifaximin prior to administering the oligosaccharide composition. In some embodiments, a subject has been treated with lactulose and rifaximin concurrently with administration of the oligosaccharide composition. In some embodiments, a subject can be treated with lactulose and rifaximin after administration of the oligosaccharide composition. In some embodiments, the methods disclosed herein may be combined with lactitol for the treatment of HE.

In some embodiments, the methods disclosed herein may be combined with dietary modifications for the treatment of HE. In some embodiments, the methods disclosed herein may be combined with commensal bacteria or probiotics for the treatment of HE. In some embodiments, the oligosaccharide composition can be administered to the subject prior to, concurrently with, and/or after treatment of the subject with lactitol, dietary modification, and/or commensal bacteria or probiotics to treat HE.

In some embodiments, an oligosaccharide composition as described herein is administered to a subject with an elevated level of blood ammonia, wherein the subject is also infected with a pathogen, e.g., a bacterial pathogen. In some embodiments, the pathogen is a multi-drug resistant (MDR) pathogen, e.g., an MDR bacterial pathogen such as CRE or VRE. In some embodiments, the subject is colonized with the pathogen, e.g., an MDR bacterial pathogen such as CRE or VRE.

Patient Populations

In some embodiments, a subject is suffering from hyperammonemia. In some embodiments, a subject having hyperammonemia is suffering from hepatic encephalopathy (HE). In some embodiments, a subject is suffering from HE. In some embodiments, a subject having hyperammonemia is at risk of developing HE. In some embodiments, a subject having hepatic encephalopathy is at risk of developing hyperammonemia. In some embodiments, hyperammonemia is associated with, affected by, or caused by alcohol and/or alcoholic cirrhosis. In some embodiments, hyperammonemia is associated with, affected by, or caused by autoimmune hepatitis, chronic hepatitis B, or chronic hepatitis C. In some embodiments, hyperammonemia is associated with, affected by, or caused by fatty liver. In some embodiments, hyperammonemia is associated with, affected by, or caused by hepatitis C. In some embodiments, hyperammonemia is associated with, affected by, or caused by hepatitis C and alcohol. In some embodiments, hyperammonemia is associated with, affected by, or caused by iron overload and steatosis. In some embodiments, hyperammonemia is associated with, affected by, or caused by nonalcoholic steatohepatitis. In some embodiments, hyperammonemia is associated with, affected by, or caused by nonalcoholic steatohepatitis and hepatitis B. In some embodiments, hyperammonemia is associated with, affected by, or caused by primary biliary cirrhosis.

In some embodiments, a subject having hyperammonemia has been previously treated or administered with lactulose and/or rifaximin before an oligosaccharide composition described herein is administered to the subject. In some embodiments, a subject having hyperammonemia associated with, affected by, or caused by alcohol, alcoholic cirrhosis, hepatitis C and alcohol, or nonalcoholic steatohepatitis has been previously treated or administered with lactulose and/or rifaximin before an oligosaccharide composition described herein is administered to the subject.

In some embodiments, a subject having hyperammonemia has a Child-Pugh score of at least 5. In some embodiments, a subject having hyperammonemia has a Child-Pugh score of 5, 6, 7, 8, 9, 10, 11, 12, 13, 14, or 15. In some embodiments, a subject having hyperammonemia has a Child-Pugh score of 5-6. In some embodiments, a subject having hyperammonemia has a Child-Pugh score of 7-9. In some embodiments, a subject having hyperammonemia has a Child-Pugh score of 10-15. In some embodiments, a subject having a Child-Pugh score of at least 5, e.g., 6, 5, 7, 8, 9, 10, 11, 12, 13, 14, or 15, is administered an oligosaccharide described herein.

In some embodiments, a subject having hyperammonemia has high ammonia levels, e.g., blood ammonia levels, relative to a subject or subjects not having hyperammonemia, e.g., the ammonia levels in a healthy subject or the average ammonia levels in a population of healthy subjects without hyperammonemia.

In some embodiments, a subject having hyperammonemia has high Alanine Aminotransferase (ALT) levels relative to a subject or subjects not having hyperammonemia, e.g., the ALT levels in a healthy subject or the average ALT levels in a population of healthy subjects without hyperammonemia. In some embodiments, a subject having hyperammonemia does not have high Alanine Aminotransferase (ALT) levels relative to a subject or subjects not having hyperammonemia, e.g., the ALT levels in a healthy subject or the average ALT levels in a population of healthy subjects without hyperammonemia.

In some embodiments, a subject having hyperammonemia has high Gamma-Glutamyl Transferase (GGT) levels relative to a subject or subjects not having hyperammonemia, e.g., the GGT levels in a healthy subject or the average GGT levels in a population of healthy subjects without hyperammonemia. In some embodiments, a subject having hyperammonemia does not have high Gamma-Glutamyl Transferase (GGT) levels relative to a subject or subjects not having hyperammonemia, e.g., the GGT levels in a healthy subject or the average GGT levels in a population of healthy subjects without hyperammonemia.

In some embodiments, a subject has hyperammonemia that is associated with, affected by, or caused by alcohol or alcoholic cirrhosis, optionally wherein the subject has previously been treated with lactulose and/or rifaximin, and optionally wherein the subject has high ammonia, high ALT, and/or high GGT levels. In some embodiments, a subject having hyperammonemia that is associated with, affected by, or caused by alcohol or alcoholic cirrhosis, optionally wherein the subject has previously been treated with lactulose and/or rifaximin, and optionally wherein the subject has high ammonia, high ALT, and/or high GGT levels, is administered an oligosaccharide composition described herein.

In some embodiments, a subject has hyperammonemia that is associated with, affected by, or caused by autoimmune hepatitis, chronic hepatitis B, or chronic hepatitis C, wherein the subject has not previously been treated with lactulose and/or rifaximin, and wherein the subject does not have high ammonia, high ALT, or high GGT levels. In some embodiments, a subject having hyperammonemia that is associated with, affected by, or caused by autoimmune hepatitis, chronic hepatitis B, or chronic hepatitis C, wherein the subject has not previously been treated with lactulose and/or rifaximin, and wherein the subject does not have high ammonia, high ALT, or high GGT levels, is administered an oligosaccharide composition described herein.

In some embodiments, a subject has hyperammonemia that is associated with, affected by, or caused by fatty liver or fatty liver disease, wherein the subject has not previously been treated with lactulose and/or rifaximin, and optionally wherein the subject has high ALT and/or high GGT levels. In some embodiments, a subject having hyperammonemia that is associated with, affected by, or caused by fatty liver or fatty liver disease, wherein the subject has not previously been treated with lactulose and/or rifaximin, and optionally wherein the subject has high ALT and/or high GGT levels, is administered an oligosaccharide composition described herein.

In some embodiments, a subject has hyperammonemia that is associated with, affected by, or caused by hepatitis C, optionally wherein the subject has not previously been treated with lactulose and/or rifaximin, and optionally wherein the subject has high ammonia, high ALT, and/or high GGT levels. In some embodiments, a subject having hyperammonemia that is associated with, affected by, or caused by hepatitis C, optionally wherein the subject has not previously been treated with lactulose and/or rifaximin, and optionally wherein the subject has high ammonia, high ALT, and/or high GGT levels, is administered an oligosaccharide composition described herein.

In some embodiments, a subject has hyperammonemia that is associated with, affected by, or caused by iron overload and steatosis, wherein the subject has not previously been treated with lactulose and/or rifaximin, and wherein the subject has high ALT levels. In some embodiments, a subject having hyperammonemia that is associated with, affected by, or caused by iron overload and steatosis, wherein the subject has not previously been treated with lactulose and/or rifaximin, and wherein the subject has high ALT levels, is administered an oligosaccharide composition described herein.

In some embodiments, a subject has hyperammonemia that is associated with, affected by, or caused by nonalcoholic steatohepatitis, optionally wherein the subject has previously been treated with lactulose and/or rifaximin, and optionally wherein the subject has high ammonia, high ALT, and/or high GGT levels. In some embodiments, a subject having hyperammonemia that is associated with, affected by, or caused by nonalcoholic steatohepatitis, optionally wherein the subject has previously been treated with lactulose and/or rifaximin, and optionally wherein the subject has high ammonia, high ALT, and/or high GGT levels, is administered an oligosaccharide composition described herein.

In some embodiments, a subject has hyperammonemia that is associated with, affected by, or caused by primary biliary cirrhosis, wherein the subject has high GGT levels. In some embodiments, a subject having hyperammonemia that is associated with, affected by, or caused by primary biliary cirrhosis, wherein the subject has high GGT levels, is administered an oligosaccharide composition described herein.

Pathogen Reduction or Decolonization

In some embodiments, oligosaccharide compositions provided herein effectively reduce the abundance of, reduce colonization with, prevent colonization with, and/or reduce the risk of an adverse effect of a pathogen (e.g., a bacterial pathogen, e.g., a multi-drug resistant bacterial pathogen) to a subject in need thereof (e.g., a human subject infected with a pathogen or a human subject at risk of being infected with a pathogen, such as a subject with HE and/or cirrhosis). In some embodiments, oligosaccharide compostions provided herein effectively increase the abundance of at least one commensal microorganism (e.g., a commensal bacterium) in a subject (e.g., a human subject infected with a pathogen or a human subject at risk of being infected with a pathogen, such as a subject with HE and/or cirrhosis). In some embodiments, provided is a method of decolonizing the gastrointestinal tract (e.g., all of the GI tract or part of the GI tract, e.g. the small intestine and/or the large intestine) of a subject from a pathogen or an antibiotic resistance gene carrier. In some embodiments, the method comprises shifting the microbial community in the gastrointestinal tract toward a population dominated by a commensal community, e.g., thereby replacing (e.g., outcompeting) a pathogen or an antibiotic resistance gene carrier. In some embodiments, the method comprises increasing the abundance of a commensal microorganism, e.g., a commensal bacterium, relative to the abundance of a pathogen, e.g., a bacterial pathogen, in the gastrointestinal tract of a subject. In some embodiments, the oligosaccharide compositions described herein can restore a subject's gut microbiome to a less dysbiotic state, e.g., by increasing the abundance of at least one commensal microorganism (e.g., a bacterial commensal) and/or decreasing the abundance of at least one pathogen (e.g., a bacterial pathogen). In some embodiments, provided is a method of reducing dysbiosis or preventing dysbiosis in the gut of a subject in need thereof, e.g., in the small intestine, large intestine, and/or colon of the subject).

In some embodiments, an oligosaccharide composition described herein can be administered to a subject to modulate the abundance or the amount of a pathogen (e.g., a bacterial pathogen) in a subject. In some embodiments, an oligosaccharide composition described herein can be administered to a subject to reduce the abundance or the amount of a pathogen (e.g., a bacterial pathogen) in a human subject. In some embodiments, the oligosaccharide composition can reduce the abundance of the pathogen in the subject by at least 10%, at least 20%, at least 25%, at least 30%, at least 40%, at least 50%, at least 60%, at least 70%, at least 75%, at least 80%, at least 90%, or at least 95%, e.g., relative to the abundance of the pathogen in the subject prior to the administration of the oligosaccharide composition. In some embodiments, the oligosaccharide composition can reduce the abundance of the pathogen in the subject by about 1.5-fold, by about 2-fold, by about 2.5-fold, by about 3-fold, by about 3.5-fold, by about 4-fold, by about 4.5-fold, by about 5-fold, or by about 10-fold or more, e.g., relative to the abundance of the pathogen in the subject prior to the administration of the oligosaccharide composition. In some embodiments, the abundance of the pathogen is reduced relative to the abundance of one or more commensal bacteria in the subject.

In some embodiments, an oligosaccharide composition described herein can be administered to a subject to modulate the abundance or amount of a commensal microorganism (e.g., a commensal bacterium), including, e.g., the *Bacteroides* and/or *Parabacteroides* genera, in a subject. In some embodiments, an oligosaccharide composition described herein can be administered to a subject to increase the abundance or the amount of a commensal microorganism (e.g., a commensal bacterium) in a human subject. In some embodiments, the oligosaccharide composition can increase the abundance of the commensal microorganism in the subject by at least 10%, at least 20%, at least 25%, at least 30%, at least 40%, at least 50%, at least 60%, at least 70%, at least 75%, at least 80%, at least 90%, or at least 95%, e.g., relative to the abundance of the commensal microorganism in the subject prior to the administration of the oligosaccharide composition. In some embodiments, the oligosaccharide composition can increase the abundance of the commensal microorganism in the subject by about 1.5-fold, by about 2-fold, by about 2.5-fold, by about 3-fold, by about 3.5-fold, by about 4-fold, by about 4.5-fold, by about 5-fold, or by about 10-fold or more, e.g., relative to the abundance of the commensal microorganism in the subject prior to the administration of the oligosaccharide composition. In some embodiments, the abundance of the commensal microorganism is reduced relative to the abundance of one or more pathogens in the subject.

In some embodiments, an oligosaccharide composition can be administered to a subject to modulate the colonization of a subject (e.g., colonization of the gut of the subject) by a pathogen and/or modulate the decolonization of a pathogen in the subject (e.g., in the gut of the subject). In some embodiments, the oligosaccharide composition prevents or inhibits a pathogen from colonizing a subject. For example, in some embodiments, the oligosaccharide composition prevents a pathogen from colonizing the gastrointestinal tract of a subject, so that no pathogens or few pathogens detectably colonize the gastrointestinal tract of the subject. In some embodiments, the oligosaccharide composition can be used to decolonize a subject whose gastrointestinal tract is colonized with a pathogen. In some embodiments, the oligosaccharide composition is administered to a subject colonized with a pathogen to reduce the abundance of the pathogen in the subject, thereby decolonizing the subject of the pathogen. In some embodiments, an oligosaccharide composition decolonizes at least 10%, at least 20%, at least 25%, at least 30%, at least 40%, at least 50%, at least 60%, at least 70%, at least 75%, at least 80%, at least 90%, or at least 95% of a pathogen (e.g., a pathogen community) colonizing a subject, e.g., relative to the amount of pathogen colonizing the subject prior to administration of the oligosaccharide composition. In some embodiments, administration of an oligosaccharide composition results in a decolonization of a pathogen colonizing a subject by about 1.5-fold, by about 2-fold, by about 2.5-fold, by about 3-fold, by about 3.5-fold, by about 4-fold, by about 4.5-fold, by about 5-fold, or by about 10-fold or more, e.g., relative to the amount of pathogen colonizing the subject prior to the administration of the oligosaccharide composition.

In some embodiments, an oligosaccharide composition can be administered to a subject to reduce the risk of an adverse effect of a pathogen on the subject. In some embodiments, the oligosaccharide composition can reduce the risk of morbidity in a subject, reduce the severity of a symptom associated with morbidity in a subject, and/or decrease the risk of mortality in a subject in need thereof (e.g., a human subject infected with a pathogen or a human subject at risk of being infected with a pathogen, such as a subject with HE and/or cirrhosis).

In some embodiments, the oligosaccharide compositions provided herein are administered to a subject to reduce the spread of pathogen to other untreated subjects. In some embodiments, the oligosaccharide composition is administered in an effective amount and/or to a sufficient number of subjects that the spread of the pathogen, e.g., from a first subject to a second subject, is reduced. Such reduction might be measured by any of the methods described herein or any other conceivable method.

In some embodiments, provided is a method of reducing a pathogen reservoir in a subject by administering an oligosaccharide composition to the subject, e.g., in an effective amount and/or to a sufficient number of subjects that the pathogen reservoir is reduced. In some embodiments, the pathogen reservoir is reduced by about 1%, about 2%, about 3%, about 4%, about 5%, about 10%, about 15%, about 20%, about 30%, about 35%, about 40%, about 45%, about 50%, about 55%, about 60%, about 65%, about 70%, about 75%, about 80%, about 85%, about 90%, about 95%, about 99%, or about 100%, e.g., relative to a reference standard. In some embodiments, a pathogen reservoir may represent about 1%, about 5%, about 10%, about 15%, about 20%, about 30%, about 35%, about 40%, about 45%, about 50%, about 55%, about 60%, about 65%, about 70%, about 75%, about 80%, or about 85% of the total bacterial reservoir of a subject (e.g., about 5%, about 10%, about 15%, about 20%, about 30%, about 35%, about 40%, about 45%, about 50%, about 55%, about 60%, about 65%, about 70%, about 75%, about 80%, or about 85% of the total bacterial population in the gut or intestines of a subject). In some embodiments, the pathogen reservoir comprises the pathogen biomass. In some embodiments, the bacterial reservoir comprises the total bacterial biomass.

In some embodiments, methods described herein comprise administering an oligosaccharide composition to a subject in an effective amount to reduce the total pathogen reservoir from about 80% to about 5% of the total bacterial reservoir, from about 80% to about 10% of the total bacterial reservoir, from about 80% to about 20% of the total bacterial reservoir, from about 80% to about 30% of the total bacterial reservoir, from about 80% to about 40% of the total bacterial reservoir, or from about 80% to about 50% of the total bacterial reservoir. In some embodiments, methods described herein comprise administering an oligosaccharide composition to a subject in an effective amount to reduce the total pathogen reservoir from about 50-80% to about 5% of the total bacterial reservoir, from about 50-80% to about 10% of the total bacterial reservoir, from about 50-80% to about 20% of the total bacterial reservoir, from about 50-80% to about 30% of the total bacterial reservoir, or from about 50-80% to about 40% of the total bacterial reservoir.

In some embodiments, provided is a method of modulating the biomass of a pathogen or an antibiotic resistance gene carrier. In some embodiments, the modulating comprises increasing or decreasing, e.g., the biomass of a pathogen or an antibiotic resistance gene carrier. In some embodiments, the oligosaccharide composition is administered in an effective amount and/or to a sufficient number of subjects, that the reservoir or biomass of a pathogen is reduced. In some embodiments, the oligosaccharide composition is administered in an effective amount that pathogen biomass is modulated, e.g., reduced (e.g., the number of pathogens and/or the number of drug- or antibiotic-resistance gene or MDR element carriers is modulated). In some embodiments, provided is a method of modulating the number of pathogens or antibiotic resistance gene carriers (e.g., in a population, e.g., a microbial population).

Exemplary pathogens include, but are not limited to, Enterobacteriaciae (e.g., a family comprising genera *Escherichia, Klebsiella, Enterobacter, Plesiomonas, Shigella*, or *Salmonella*), *Clostridium* (e.g., a genus comprising *Clostridium difficile*), *Enterococcus, Staphylococcus, Campylobacter, Vibrio, Aeromonas, Norovirus, Astrovirus, Adenovirus, Sapovirus*, or *Rotavirus*. In some embodiments, exemplary pathogens include *Candida* fungi, e.g., *Candida albicans, Candida auris, Candida glabrata, Candida krusei, Candida tropicalis*, and *Candida lusitaniae*.

In some embodiments, the pathogen is a multi-drug resistant pathogen. In some embodiments, the pathogen is a multi-drug resistant bacterium. In some embodiments, the pathogen is a carbapenem-resistant Enterobacteriaceae (CRE). In some embodiments, the pathogen is a vancomycin-resistant Enterococci (VRE). In some embodiments, the pathogen is an extended-spectrum beta-lactamase (ESBL) producing organism, e.g., an ESBL-producing Enterobacteriaceae. In some embodiments, the pathogen is a *Candida*.

In some embodiments, the pathogen includes Enterobacteriaciae (e.g., a family comprising genera *Escherichia, Klebsiella, Enterobacter, Plesiomonas, Shigella*, or *Salmonella*). In some embodiments, the pathogen includes *Clostridium* (e.g., a genus comprising *Clostridium difficile*). In some embodiments, the pathogen includes *Enterococcus*. In some embodiments, the pathogen includes *Staphylococcus*. In some embodiments, the pathogen includes *Candida*.

In some embodiments, provided is a method of reducing the rate at which a pathogen causes infection or colonization (e.g., in a subject) by administering a oligosaccharide composition to the subject, e.g., in an effective amount and/or to a sufficient number of subjects that the rate of infection is reduced. In some embodiments, the oligosaccharide composition is administered in an effective amount and/or to a sufficient number of subject(s), that the rate at which a pathogen causes infection, or the severity of pathogen infection, as indicated by assessment of symptoms associated with infection, is reduced. In some embodiments, the rate of infection is reduced by about 1%, about 2%, about 3%, about 4%, about 5%, about 10%, about 15%, about 20%, about 30%, about 35%, about 40%, about 45%, about 50%, about 55%, about 60%, about 65%, about 70%, about 75%, about 80%, about 85%, about 90%, about 95%, about 99%, or about 100%, e.g., relative to a reference standard.

Reduction in the rate of infection or colonization using a method described herein may be prospective or retrospective, e.g., relative to an infection. In some embodiments, the method described herein comprises monitoring a subject or a population of subjects for a similar infection, e.g., through observation of similar symptoms or similar features to those known to be caused by or identified with a pathogen of interest. Rather than, or in addition to using clinical characteristics, any of the methods described herein might be used to more specifically determine the type of the pathogen involved, and its relationship—if any—to spread or a reservoir.

In some embodiments, provided is a method of modulating the gastrointestinal tract (e.g., all of the GI tract or a part thereof, e.g., the small intestine, the large intestine, and the like) of a subject. In some embodiments, the method comprises modulating the environment (e.g., chemical or physical environment) of the gastrointestinal tract of a subject to make the gastrointestinal tract (and the microbial community therein) less selective or less receptive for a pathogen or an antibiotic resistance gene carrier. In some embodiments, the method further comprises administering a second agent in combination with an oligosaccharide composition, e.g., charcoal or an antibiotic-degrading enzyme (e.g., beta-lactamase), or a symbiotic (e.g., an engineered beta-lactamase (e.g., a non-infectious beta-lactamase).

In some embodiments, the oligosaccharide composition is administered in an effective amount to shift the microbial community of a subject to displace or inhibit growth of a pathogen, an organism that can donate a drug or antibiotic resistance gene, or MDR element (donor microbes), or an organism that can receive a drug or antibiotic resistance gene, or MDR element (recipient microbes). In some embodiments, the oligosaccharide composition is administered in an effective amount to reduce the probability of donor microbes to spread a drug or antibiotic resistance gene, or MDR element.

In some embodiments, provided is a method of managing an infection by a pathogen. In some embodiments, managing an infection by a pathogen comprises treating, preventing, and/or reducing the risk of developing an infection by a pathogen. In some embodiments, treating an infection by a pathogen comprises administering an oligosaccharide composition to a subject or population upon detection of a pathogen. In some embodiments, preventing an infection by a pathogen comprises administering an oligosaccharide composition to a subject or population at risk of developing an infection. The subject or population may include those who may have been exposed to the pathogen directly and/or infected individuals. In some embodiments, reducing the risk of developing an infection by a pathogen comprises administering a oligosaccharide composition to a subject or population that may become exposed to a pathogen.

In some embodiments, provided is a method of modulating the microbial community composition and/or the metabolic output of the microbial community, e.g. modulating the environment, e.g., to modulate (e.g., reduce) pathogen growth. In some embodiments, a oligosaccharide composition is administered in an effective amount to modulate the microbial community and alter the environment of the GI tract, (e.g., altering pH, altering lactic acid, altering microbial density, etc.). In some embodiments, the method comprises outcompeting a pathogen or an antibiotic resistance gene carrier for space or nutrients in the gastrointestinal tract. In some embodiments, a oligosaccharide composition is administered in an effective amount to reduce the "space" for a pathogen to colonize, e.g., physical space. In some embodiments, the method comprises making non-pathogenic bacteria fitter (e.g., providing a more selective nutrient source or encouraging growth of fitter (e.g., faster) growing species/strains). In some embodiments, the method comprises outcompeting a pathogen or an antibiotic resistance gene carrier by increasing the population of a commensal bacterial strain, or by increasing an anti-microbial defense mechanism in a commensal bacterial strain, e.g., production of a bacteriocin, anti-microbial peptide, hydrogen peroxide, or low pH (e.g., through increased level of an acid (e.g., acetate, butyrate, and the like).

In some embodiments, provided are methods of reducing the abundance and/or spread of pathogens. In some embodiments, pathogens include bacterial pathogens (e.g., *Abiotrophia* spp., (e.g., *A.* defective), *Achromobacter* spp., *Acinetobacter* spp., (e.g., *A. baumanii*), *Actinobaculum* spp., (e.g., *A. schallii*), *Actinomyces* spp., (e.g., *A. israelii*), *Aerococcus* spp., (e.g., *A. urinae*), *Aeromonas* spp., (e.g., *A. hydrophila*), *Aggregatibacter* spp., e.g. *A. aphrophilus*, *Bacillus anthracis*, *Bacillus cereus* group, *Bordetella* spp., *Brucella* spp., e.g. *B. henselae*, *Burkholderia* spp., e.g., *B. cepaciae*, *Campylobacter* spp., e.g., *C. jejuni*, *Chlamydia* spp., *Chlamydophila* spp., *Citrobacter* spp., e.g., *C. freundii*, *Clostridium botulinum*, *Clostridium difficile*, *Clostridium perfringens*, *Corynebacterium* spp., e.g., *C. amycolatum*, *Cronobacter*, e.g., *C. sakazakii*, Enterobacteriaceae, including many of the genera below, *Enterobacter* spp., e.g., *E. cloacae*, *Enterococcus* spp., e.g. *E. faecium*, *Escherichia* spp., including enteropathogenic, uropathogenic, and enterohemorrhagic strains of *E. coli*, *Francisella* spp., e.g. *F. tularensis*, *Fusobacterium* spp., e.g. *F. necrophorum*, *Gemella* spp., e.g. *G. mobillorum*, *Granulicatella* spp., e.g. *G. adiaciens*, *Haemophilus* spp., e.g. *H. influenza*, *Helicobacter* spp., e.g. *H. pylori*, *Kingella* spp., e.g. *K. kingae*, *Klebsiella* spp., e.g. *K. pneumoniae*, *Legionella* spp., e.g. *L. pneumophila*, *Leptospira* spp., *Listeria* spp., e.g. *L. monocytogenes*, *Morganella* spp., e.g. *M. morganii*, *Mycobacterium* spp., e.g. *M. abcessus*, *Neisseria* spp., e.g. *N. gonorrheae*, *Nocardia* spp., e.g. *N. asteroids*, *Ochrobactrum* spp., e.g. *O. anthropic*, *Pantoea* spp., e.g. *P. agglomerans*, *Pasteurella* spp., e.g. *P. multocida*, *Pediococcus* spp., *Plesiomonas* spp., e.g. *P. shigelloides*, *Proteus* spp., e.g. *P. vulgaris*, *Providencia* spp., e.g. *P. stuartii*, *Pseudomonas* spp., e.g. *P. aeruginosa*, *Raoultella* spp., e.g. *R. ornithinolytica*, *Rothia* spp., e.g. *R. mucilaginosa*, *Salmonella* spp., e.g. *S. enterica*, *Serratia* spp., e.g. *S. marcesens*, *Shigella* spp., e.g. *S. flexneri*, *Staphylococcus aureus*, *Staphylococcus lugdunensis*, *Staphylococcus pseudintermedius*, *Staphylococcus saprophyticus*, *Stenotrophomonas* spp., e.g. *S. maltophilia*, *Streptococcus agalactiae*, *Streptococcus anginosus*, *Streptococcus constellatus*, *Streptococcus dysgalactiae*, *Streptococcus intermedius*, *Streptococcus milleri*, *Streptococcus pseudopneumoniae*, *Streptococcus pyogenes*, *Streptooccus pneumoniae*, *Treponema* spp., *Ureaplasma ureolyticum*, *Vibrio* spp., e.g. *V. cholerae*, and *Yersinia* spp., (e.g., *Y. enterocolitica*)); viral pathogens (e.g., *Adenovirus*, *Astrovirus*, *Cytomegalovirus*, *Enterovirus*, *Norovirus*, *Rotavirus*, and *Sapovirus*); and gastrointestinal pathogens (e.g., *Cyclospora* spp., *Cryptosporidium* spp., *Entamoeba histolytica*, *Giardia lamblia*, and Microsporidia, (e.g., *Encephalitozoon canaliculi*)). In some embodiments, the pathogens include CRE, VRE, and/or ESBL-producing Enterobacteriaceae.

In some embodiments, the method comprises reducing the abundance and/or spread of antibiotic resistant organisms. Antibiotic resistant organisms include: beta-lactamase producing Enterobacteriaceae (including extended spectrum beta-lactamase and carbapenemase producers, possessing genes such as TIM, OXA, VIM, SHV, CTX-M, KPC. NDM or AmpC); Vancomycin-resistant *Enterococcus* (e.g., possessing genes such as VanA or VanB); Fluoroquinolone-resistant Enterobacteriaceae (e.g., with genes such as Qnr); carbapenem-resistant and multidrug resistant *Pseudomonas*; methicillin-resistant *Staphylococcus aureus* and *Streptococcus pneumoniae* (e.g., possessing the MecA gene); multi-drug resistant *Acinetobacter* (often containing beta-lactamase); trimethoprim resistant organisms (e.g., dihydrofolate reductase); sulfamethoxazole resistant organisms (e.g., dihydropteroate synthetase); and aminoglycoside resistant organisms (e.g., ribosomal methyltransferase).

In some embodiments, the subject is critically ill and/or a transplant patient. Critically ill subjects and/or transplant patients are prone to infections (e.g. have a high rate of infections), such as bloodstream infections. In some embodiments, infectious pathogens causing infections are carried in the gut (e.g., can be acquired through colonization) and include *E. coli*, *Klebsiella*, other Enterobacteriaceae, and *Enterococcus*. In some embodiments, the microbes (e.g., pathogens) are drug resistant (e.g. carbapenem-resistant Enterobacteriaceae, vancomycin-resistant *Enterococcus*).

In some embodiments, assessment of colonization (e.g., with pathogens) is used to predict the risk of infection (e.g., bloodstream infection, urinary tract infection (UTI), or respiratory infection, bacteremia), e.g., by correlating levels of colonization (e.g., by assessing a suitable sample for presence or absence of predetermined bacterial taxa and/or assessing pathogen load) with risk of infection, wherein evidence of colonization is correlated with an increased risk of infection, wherein culture-negative subjects are at lower risk of infection. In some embodiments, higher levels of bacteria lead to higher rates of infection. In some embodiments, intestinal colonization (e.g. by a pathogen, e.g. VRE) precedes infection in other tissues (e.g., bloodstream). Examples of gastrointestinal tract-colonizing pathogens may include: Enterobacteriaceae (e.g. *E. coli*, *Klebsiella*, *Enterobacter*, *Proteus*) and *Enterococcus*. In some embodiments, gastrointestinal tract-colonizing pathogens further include multidrug resistant bacteria (e.g., carbapenem resistant Enterobacteriaceae, Vancomycin resistant *Enterococcus*).

In some embodiments, the outcome of screening subject populations for pathogen status determines the course of bloodstream infection management. In some embodiments, screening methods comprise stool sampling (e.g. by rectal swab) of subjects. In some embodiments, the method comprises assessing the presence/absence (abundance) of drug/antibiotic resistant pathogens (e.g., VRE) in the stool. In some embodiments, the level of pathogens within the gut is correlated with infection risk. In some embodiments, intensive care unit (ICU) subjects, transplant subjects, chemotherapy-receiving subjects, and antibiotic-receiving subjects have a higher risk of having pathogen colonization from antibiotic resistant bacteria such as carbapenem resistant Enterobacteriaciae and Vancomycin-resistant *Enterococcus*. In some embodiments, reducing the level of pathogens within the gut reduces risk (e.g., by administering an oligosaccharide composition if desired in combination with an antibiotic). In some embodiments, if the drug resistant pathogen is absent, the subject is administered a oligosaccharide composition to prevent infection (e.g., bloodstream infection) or bacteremia. In some embodiments, if the drug resistant pathogen is present, the subject is administered a oligosaccharide composition to reduce infection (e.g., bloodstream infection) or bacteremia.

In some embodiments, provided is a method to reduce the colonization level or prevalence of antibiotic resistant pathogens carried in the GI tract of high-risk subjects (e.g. subjects with HE and/or cirrhosis). Exemplary antibiotic resistant pathogens include Carbapenem-resistant Enterobacteriaciae (e.g., extended spectrum beta lactamase (ESBL) producing Enterobacteriaciae) and Vancomycin-resistant *Enterococcus*.

In some embodiments, provided is a method to reduce the rate of infections (e.g., from pathogens that colonize the GI tract) in critically ill or high-risk subjects (e.g. subjects with HE and/or cirrhosis). In some embodiments, the method comprises reducing the rate of urinary tract infections. In some embodiments, the method comprises reducing the rate of bloodstream infections. In some embodiments, the method comprises reducing the rate of respiratory tract infections.

In some embodiments, the method comprises managing infections in subjects. Examples of subject groups with infections (bacteremia) include: subjects with cirrhosis, subjects with urinary infections (e.g., infected with *Enterococcus*, Enterobacteriaciae), subjects with bloodstream infections (e.g., infected with *Enterococcus*, Enterobacteriaciae), transplant subjects (e.g., bone marrow (e.g., undergoing hematopoietic stem cell transplantation), solid organ (e.g., liver)), intensive care patients (e.g., infected with Carbapenem resistant Enterobacteriaciae and ESBL producing pathogens), pre-transplant liver failure patients (e.g., infected with Vancomycin resistant *Enterococcus*), post-transplant liver failure patients (e.g., infected with Vancomycin resistant *Enterococcus*). Subjects undergoing chemotherapy experience high levels of enteric pathogen bacteremia, *C. difficile* infection (CDI)C, and chemotherapy-induced diarrhea compared to other subjects (e.g., the general hospital patient population). In some embodiments, antibiotic-treated subjects comprise higher pathogen loads, including antibiotic resistant pathogens. In some embodiments, subjects undergoing or about to undergo a transplant, subjects with cancer, subjects with liver disease (e.g., end-stage renal disease), or subjects with suppressed immune system (e.g., immunocompromised subjects) may have high risk of developing infections, e.g., gut-derived infections. In some embodiments, the method comprises prophylactic treatment, e.g., with an oligosaccharide composition, of a subject, e.g., a subject with a high risk of developing an infection. In some embodiments, subjects who are undergoing chemotherapy or antibiotic treatment have reduced diversity of commensal bacteria. In some embodiments, the method comprises treatment of a subject to reduce the colonization of pathogens, e.g., multidrug resistant pathogens, in a subject, e.g., subjects in a facility, e.g., a hospital or long-term care facility. In some embodiments, bacteria that pose a risk of colonization in subjects (or a capable of colonizing the GI tract of subjects) comprise resistant subpopulations of Enterobacteriaceae (e.g., *E. cloacae* and *Enterococcus*), *C. difficile* (including Nap1 (pandemic hypervirulent) *C. difficile* strain), and bacteria that cause infectious diarrhea (e.g., *Campylobacter, Salmonella, Shigella*, enterohemorrhagic *E. coli* (EHEC), enterotoxigenic *E. coli* (ETEC), enteropathogenic *E. coli* (EPEC), enteroinvasive *E. coli* (EIEC), enteroaggregative *E. coli* (EAEC), diffusely adherent *E. coli* (DAEC), and uropathogenic *E. coli*).

In some embodiments, the method comprises managing infections in subjects with other disorders. In some embodiments, the method comprises managing infections in subjects with excess ammonia levels. In some embodiments, subjects with hepatic encephalopathy (HE) may be treated according to the methods provided herein. In some embodiments, the subject has HE as a consequence of liver cirrhosis. In some embodiments, such subjects display hepatic multiple adverse neurological symptoms that occur when the liver is unable to remove toxic substances such as ammonia from the blood. In some embodiments, the subjects have or are suspected of having minimal HE. In some embodiments, the subjects have or are suspected of having overt HE. Standard-of-care treatments for overt HE include lactulose, lactitol, and antibiotics (e.g., rifaximin or neomycin). Treatments may also include dietary modifications and probiotics. In some embodiments, such methods result in decreased incidence of future episodes of ammonia crisis, or, in subjects at risk of HE, by decreased occurrence of an initial episode of ammonia crisis.

In some embodiments, the method comprises managing infections in subjects who are in need of an organ transplant, e.g., a liver or bone marrow transplant. In some embodiments, the method comprises managing infections in subjects immediately, or shortly, before said subject receives an organ transplant, e.g., a liver or bone marrow transplant. In some embodiments, the method comprises managing infections in subjects immediately, or shortly, after said subject receives an organ transplant, e.g., a liver or bone marrow transplant. In some embodiments, the method comprises managing infections in subjects who have, are suspected of having, or at risk of having end-stage liver disease (ESLD).

In some embodiments, efficacy of a treatment provided herein may be assessed by resolution of the symptoms or diagnostic criteria listed above (e.g., reduction in serum ammonia levels). In some embodiments, one or both of the following is reduced: i) the number of ammonia crises over a period of 1 year (e.g., by at least 1, 2, or at least 3 crises), ii) the severity of complications from ammonia crises, including neurodevelopmental delays and/or cognitive declines (e.g., compared to a suitable control group not receiving the oligosaccharide composition). In some embodiments, the time period between ammonia crises is increased, e.g., by at least 15%, 30%, 60%, 100%, or 200%

(e.g., compared to a suitable control group not receiving the oligosaccharide composition).

In some embodiments, the method reduces the abundance of pathogens and increases the relative of abundance of commensal bacteria, e.g., in a subject, e.g., in the gastrointestinal tract of the subject (e.g, the colon). In some embodiments, the method increases the alpha-diversity (e.g., a high degree of diversity) of a microbial community (e.g., a community of commensal bacteria), e.g., of the gut of a subject.

In some embodiments, oligosaccharide compositions are substantially fermented or consumed by commensal bacteria and are not fermented or consumed by pathogens. In some embodiments, oligosaccharide compositions are substantially fermented or consumed by commensal bacteria and are fermented or consumed by pathogens at low levels. In some embodiments, a oligosaccharide composition that is substantially consumed by commensal bacteria may increase the diversity and biomass of the commensal microbiota and lead to a reduction in the relative abundance of a pathogen(s), such as a bacterial pathogen (e.g., a pathogenic taxa). In some embodiments, an oligosaccharide composition is substantially non-fermented or not consumed by VRE or CRE species or ESBL-producing species. In some embodiments, an oligosaccharide composition is substantially non-fermented or not consumed by *C. difficile*.

In some embodiments, an oligosaccharide composition supports the growth of commensal or probiotic bacteria, e.g., in a gut microbiome. In some embodiments, an oligosaccharide composition does not support the growth of at least one pathogen, e.g., does not support the growth of a CRE, VRE, a *C. difficile* species and/or a *Candida* species.

In some embodiments, administration of an oligosaccharide composition may increase the concentration, amount or relative abundance of commensal bacteria relative to pathogenic bacteria in the microbiome of a subject (e.g., a human patient). In some embodiments, administration of an oligosaccharide composition and a population of viable commensal or probiotic bacteria may increase the concentration, amount, or relative abundance of commensal bacteria relative to pathogenic bacteria in the microbiome of a subject (e.g., a human patient). In some embodiments, administration of an oligosaccharide composition that supports the growth of commensal or probiotic bacteria, e.g., in a gut microbiome, may increase the concentration, amount or relative abundance of commensal bacteria relative to pathogenic bacteria in the microbiome of a subject (e.g., a human patient). In some embodiments, administration of an oligosaccharide composition that does not support the growth of at least one pathogen, e.g., does not support the growth of a CRE, VRE, and/or *C. difficile* species, e.g., in a gut microbiome, may increase the concentration, amount or relative abundance of commensal bacteria relative to pathogenic bacteria in the microbiome of a subject (e.g., a human patient). In some embodiments, administration of an oligosaccharide composition that supports the growth of commensal or probiotic bacteria and does not support the growth of at least one pathogen, e.g., does not support the growth of a CRE, VRE, and/or *C. difficile* species, e.g., in a gut microbiome, may increase the concentration, amount or relative abundance of commensal bacteria relative to pathogenic bacteria in the microbiome of a subject (e.g., a human patient).

In embodiments, an oligosaccharide composition described herein is co-administered with commensal or probiotic bacterial taxa and bacteria that are generally recognized as safe (GRAS) or known commensal or probiotic microbes. In some embodiments, probiotic or commensal bacterial taxa (or preparations thereof) may be administered to a subject before or after administration of an oligosaccharide composition to the subject. In some embodiments, an oligosaccharide composition and commensal or probiotic bacterial taxa are administered to a subject with a depleted microbiome, e.g., a subject with few or no detectable gut commensals, to try to restore greater gut microbiome diversity in the subject. In some embodiments, the subject's gut microbiome has been depleted through the use of an antibiotic, e.g., by the prior administration of one or more courses of antibiotics to the subject.

A commensal or probiotic bacteria is also referred to a probiotic. Probiotics can include the metabolites generated by the probiotic bacteria during fermentation. These metabolites may be released to the medium of fermentation, e.g., into a host organism (e.g., subject), or they may be stored within the bacteria. Probiotic bacteria includes bacteria, bacterial homogenates, bacterial proteins, bacterial extracts, bacterial ferment supernatants and combinations thereof, which perform beneficial functions to the host animal, e.g., when given at a therapeutic dose.

Useful probiotics include at least one lactic acid and/or acetic acid and/or propionic acid producing bacteria, e.g., microbes that produce lactic acid and/or acetic acid and/or propionic acid by decomposing carbohydrates such as glucose and lactose. Preferably, the probiotic bacteria is a lactic acid bacterium. In embodiments, lactic acid bacteria include *Lactobacillus, Leuconostoc, Pediococcus, Streptococcus*, and *Bifidobacterium*. Suitable probiotic bacteria can also include other bacterias which beneficially affect a host by improving the hosts intestinal microbial balance, such as, but not limited to yeasts such as *Saccharomyces, Debaromyces, Candida, Pichia* and *Torulopsis*, molds such as *Aspergillus, Rhizopus, Mucor*, and *Penicillium* and *Torulopsis*, and other bacteria such as but not limited to the genera *Bacteroides, Clostridium, Fusobacterium, Melissococcus, Propionibacterium, Enterococcus, Lactococcus, Staphylococcus, Peptostreptococcus, Bacillus, Pediococcus, Micrococcus, Leuconostoc, Weissella, Aerococcus*, and *Oenococcus*, and combinations thereof.

Commensal or probiotic bacteria which are particularly useful in the present disclosure include those which (for human administration) are of human origin (or of the origin of the mammal to which the probiotic bacteria is being administered), are non-pathogenic to the host, resist technological processes (i.e. can remain viable and active during processing and in delivery vehicles), are resistant to gastric acidity and bile toxicity, adhere to gut epithelial tissue, have the ability to colonize the gastrointestinal tract, produce antimicrobial substances, modulate immune response in the host, and influence metabolic activity (e.g. cholesterol assimilation, lactase activity, vitamin production).

The commensal or probiotic bacteria can be used as a single strain or a combination of multiple strains, wherein the total number of bacteria in a dose of probiotic bacteria is from about $1 \times 10^3$ to about $1 \times 10^{14}$, or from about $1 \times 10$ to about $1 \times 10^{12}$, or from about $1 \times 10^7$ to about $1 \times 10^{11}$ CFU per dose.

The commensal or probiotic bacteria can be formulated with the oligosaccharide compositions while the probiotic bacteria are alive but in a state of "suspended animation" or somnolence. Once freeze-dried, the viable cultures(s) of probiotic bacteria are handled so as to minimize exposure to moisture that would reanimate the cultures because, once reanimated, the cultures can experience high rates of morbidity unless soon cultured in a high moisture environment or medium. Additionally, the cultures are handled to reduce possible exposure to high temperatures (particularly in the presence of moisture) to reduce morbidity.

The probiotic bacterias can be used in a powdered, dry form. The probiotic bacterias can also be administered in the oligosaccharide composition or in a separate oligosaccharide composition, administered at the same time or different time as the oligosaccharide compositions.

In embodiments, a commensal bacterial taxa that can be used in and/or in combination with an oligosaccharide composition described herein comprises *Akkermansia, Anaerococcus, Bacteroides, Bifidobacterium* (including *Bifidobacterium lactis, B. animalis, B. bifidum, B. longum, B. adolescentis, B. breve,* and *B. infantis*), *Blautia, Clostridium, Corynebacterium, Dialister, Eubacterium, Faecalibacterium, Finegoldia, Fusobacterium, Lactobacillus* (including, *L. acidophilus, L. helveticus, L. bifidus, L. lactis, L. fermentii, L. salivarius, L. paracasei, L. brevis, L. delbruekii, L. thermophiles, L. crispatus, L. casei, L. rhamnosus, L. reuteri, L. fermentum L. plantarum, L. sporogenes,* and *L. bulgaricus*), *Peptococcus, Peptostreptococcus, Peptoniphilus, Prevotella, Roseburia, Ruminococcus, Staphylococcus,* and/or *Streptococcus* (including *S. lactis, S. cremoris, S. diacetylactis, S. thermophiles*).

In embodiments, a commensal bacterial taxa, e.g., GRAS strain, that can be used in and/or in combination with an oligosaccharide composition described herein comprises *Bacillus coagulans* GBI-30, 6086; *Bifidobacterium animalis* subsp. *Lactis* BB-12; *Bifidobacterium breve* Yakult; *Bifidobacterium infantis* 35624; *Bifidobacterium animalis* subsp. *Lactis* UNO 19 (DR10); *Bifidobacterium longum* BB536; *Escherichia coli* M-17; *Escherichia coli* Nissle 1917; *Lactobacillus acidophilus* DDS-1; *Lactobacillus acidophilus* LA-5; *Lactobacillus acidophilus* NCFM; *Lactobacillus casei* DN 114-001 (*Lactobacillus casei* Immunitas(s)/Defensis); *Lactobacillus casei* CRL431; *Lactobacillus casei* F19; *Lactobacillus paracasei* Stl 1 (or NCC2461); *Lactobacillus johnsonii* Lai (*Lactobacillus* LCI, *Lactobacillus johnsonii* NCC533); *Lactococcus lactis* L1A; *Lactobacillus plantarum* 299V; *Lactobacillus reuteri* ATTC 55730 (*Lactobacillus reuteri* SD2112); *Lactobacillus rhamnosus* ATCC 53013; *Lactobacillus rhamnosus* LB21; *Saccharomyces cerevisiae* (*boulardii*) lyo; mixture of *Lactobacillus rhamnosus* GR-1 and *Lactobacillus reuteri* RC-14; mixture of *Lactobacillus acidophilus* NCFM and *Bifidobacterium lactis* BB-12 or BL-04; mixture of *Lactobacillus acidophilus* CL1285 and *Lactobacillus casei*; and a mixture of *Lactobacillus helveticus* R0052, *Lactobacillus rhamnosus* R0011, and/or *Lactobacillus rhamnosus* GG (LGG).

In some embodiments, the method comprises the administration of an oligosaccharide composition and the administration of a commensal or probiotic bacterial species. In some embodiments, the combined administration of oligosaccharide compositions and commensal bacteria may be used to benefit patients with depleted microbiomes (e.g., patients with few or no detectable commensal bacteria), e.g., patients who are undergoing chemotherapy or receiving antibiotics. In some embodiments, a subject or patient may have a gut microbiome devoid of any detectable commensal bacteria. In some embodiments, the method comprises combined administration of oligosaccharide compositions and commensal bacteria to a subject or patient who has a gut microbiome devoid of any detectable commensal bacteria.

IV. Kits

Kits also are contemplated. For example, a kit can comprise unit dosage forms of the oligosaccharide composition, and a package insert containing instructions for use of the composition in treatment, e.g., of a disease associated with hyperammonemia. In some embodiments, the composition is provided in a dry powder format. In some embodiments, the composition is provided in solution. The kits include an oligosaccharide composition in suitable packaging for use by a subject in need thereof. Any of the compositions described herein can be packaged in the form of a kit. A kit can contain an amount of an oligosaccharide composition sufficient for an entire course of treatment, or for a portion of a course of treatment. Doses of an oligosaccharide composition can be individually packaged, or the oligosaccharide composition can be provided in bulk, or combinations thereof. Thus, in one embodiment, a kit provides, in suitable packaging, individual doses of an oligosaccharide composition that correspond to dosing points in a treatment regimen, wherein the doses are packaged in one or more packets.

In some embodiments, a kit can contain an oligosaccharide composition described herein and one or more additional therapeutic agents, drugs, or substances (e.g., one, two, three, four, or five additional therapeutic agents, drugs, or substances). In some embodiments, the kit contains an oligosaccharide composition and a second therapeutic agent, drug, or substance. In some embodiments, the second therapeutic agent, drug, or substance reduces ammonia levels when administered to a subject, e.g., a human subject with hyperammonemia. In some embodiments, the second therapeutic agent, drug, or substance is an antibiotic. In some embodiments, the second therapeutic agent, drug, or substance is rifaximin (CAS ID: 80621-81-4). In some embodiments, the second therapeutic agent is lactulose. In some embodiments, the kit contains doses of an oligosaccharide composition and rifaximin. In some embodiments, the kit contains doses of an oligosaccharide composition and lactulose. In some embodiments, the kit contains doses of an oligosaccharide composition, rifaximin, and lactulose. Doses of the oligosaccharide composition and an additional therapeutic agent, drug, or substance can co-formulated in a bulk container or co-formulated in individual packages (e.g., individual doses of the oligosaccharide composition and the additional therapeutic agent packaged together in packets). Alternatively, doses of the oligosaccharide composition and an additional therapeutic agent, drug, or substance can be packaged in separate bulk containers or in separate packages or packets.

Kits can further include written materials, such as instructions, expected results, testimonials, explanations, warnings, clinical data, information for health professionals, and the like. In one embodiment, the kits contain a label or other information indicating that the kit is only for use under the direction of a health professional. The container can further include scoops, syringes, bottles, cups, applicators or other measuring or serving devices.

EXAMPLES

Example 1: Production of an Exemplary Oligosaccharide Composition at 10 kg Scale from Dextrose Monohydrate and Galactose To a reaction vessel (22 L Littleford-Day horizontal plow mixer) was added 5 kg of dextrose monohydrate, 4.5 kg of galactose and 0.892 kg (0.450 kg on a dry solid basis) of solid acid catalyst (styrene-divinylbenzene comprising sulfonic acid moieties, e.g., Dowex® Marathon® C resin). The contents were agitated at approximately 30 RPM and the vessel temperature was gradually increased over a two hour period to about 130° C. at atmospheric pressure. The mixture was maintained at temperature for one hour, after which the heating was stopped and pre-heated water was gradually added to the reaction mixture at a rate of 60 mL/min until the temperature of the reactor contents decreased to 120° C., then at a rate of 150 mL/min until the temperature of the reactor contents decreased to 110° C., then at a rate of 480 mL/min until the temperature of the reactor contents decreased below 100° C. and a total of 6 kg of water was added. The reaction mixture was drained from the vessel and the solids were removed by filtration, resulting in 12 kg of product material as a syrup.

The glycan composition was further diluted to a concentration of about 35 wt % in de-ionized water and then purified by flowing through a cationic exchange resin (Dowex® Monosphere® 88H) column, an anionic exchange resin (Dowex® Monosphere® 77WBA) column, and a decolorizing polymer resin (Dowex® OptiPore® SD-2). The resulting purified material was then concentrated to a final concentration of about 75 wt % solids by vacuum rotary evaporation to yield the purified glycan composition.

Example 2: Production of an Exemplary Oligosaccharide Composition at 10 kg Scale from Dextrose Monohydrate and Galactose (10 kg Scale) with Serial Catalyst Addition The present example demonstrates the synthesis of oligosaccharide composition comprising glucose and galactose sub-units at 10 kg scale (dry oligosaccharide composition) for two replicate batches in a 22 L horizontal-mixed reactor.

About 5 kg of food grade dextrose monohydrate and 4.5 kg of food grade galactose were charged into a 22 L horizontal plough mixer (Littleford-Day, Lexington, Ky.) equipped with a hot-oil jacket. The dextrose and galactose mixture was melted by gradually heating to a temperature of about 120° C. with continuous mixing at 30 RPM. Thirty minutes later, 0.892 kg (0.450 kg on a dry solid basis) of solid acid catalyst (styrene-divinylbenzene comprising sulfonic acid moieties, e.g., Dowex® Marathon® C resin) was added to the reaction mixture to form a mixed suspension. The reaction temperature was gradually increased to about 130° C. at atmospheric pressure over a two hour period with continuous mixing (maintained at 30 RPM). Fifteen minutes later (2.5 hours after addition of catalyst), preheated water was gradually added to the reaction mixture at a rate of 60 mL/min until the temperature of the reactor contents decreased to 120° C., then at a rate of 150 mL/min until the temperature of the reactor contents decreased to 110° C., then at a rate of 480 mL/min until the temperature of the reactor contents decreased below 100° C. and a total of 6 kg of water was added. The reactor contents were further cooled to below 85° C., and filtered to remove the solid acid catalyst from the oligosaccharide composition. Approximately 12 kg of product material were recovered.

The oligosaccharide composition was further diluted to a concentration of about 35 wt % in de-ionized water and then purified by flowing through a cationic exchange resin (Dowex® Monosphere 88H) column, an anionic exchange resin (Dowex® Monosphere 77WBA) column, a decolorizing polymer resin (Dowex® OptiPore SD-2), and then an anionic exchange resin (Dowex® Monosphere 77WBA) column. The resulting purified material was then concentrated to a final concentration of about 75 wt % solids to yield the purified oligosaccharide composition.

Example 3: Production of an Exemplary Oligosaccharide Composition at 10 kg Scale from Dextrose Monohydrate and Galactose A 22 L reactor (22 L Littleford Reactor) equipped with a condenser, oil heater (SterlCo oil heater), and air-cooled chiller (Silverstar air-cooled chiller) was used in the synthesis of oligosaccharide compositions. The oil heater was set to a temperature of 300° F. and the air-cooled chiller was set to 5° C. The reactor mixing element was set to 30 Hz.

About 5.0 kg of dextrose monohydrate, 4.5 kg of anhydrous galactose, and then 0.90 kg of catalyst were sequentially added into the reactor. A condenser was attached to the top port of the reactor.

After 2.5 hours from the time the reactor began being charged with dextrose monohydrate, 6 kg of USP water were heated to 95° C. At 3 hours 10 minutes from the start of the reaction, the reactor temperature was set to 150° F. At 3 hours 15 minutes from the start of the reaction, the reaction was quenched by adding preheated water to the reaction mixture at a rate of 60 mL/min until the temperature of the reactor contents decreased to 120° C., then at a rate of 150 mL/min until the temperature of the reactor contents decreased to 110° C., then at a rate of 480 mL/min until the temperature of the reactor contents decreased below 100° C. and a total of 6 kg of water was added. The reactor contents were further cooled to below 85° C.

Once the quench was finished, the USP water for quenching container was removed and replaced with USP water for dilution (about 4.6 kg, in order to obtain a total of 10.6 kg of USP water added between quenching and dilution). At 84±1° C. internal reactor temperature, the reactor was drained through a wire mesh screen, to help remove catalyst, and into the receiving vessel. The receiving vessel containing the diluted crude glycan composition was further cooled. The glycan composition was further purified by filteration through a 0.45 μm filter.

The oligosaccharide composition was further diluted to a concentration of about 35 wt % in de-ionized water and then purified by flowing through a cationic exchange resin (Dowex® Monosphere 88H) column, a decolorizing polymer resin (Dowex® OptiPore SD-2), a decolorizing polymer resin (Dowex® OptiPore SD-2), and then an anionic exchange resin (Dowex® Monosphere 77WBA) column.

Example 4: De-Monomerization Procedure

Individual batches of oligosaccharide composition, as produced in Examples 1-3 and 16, were concentrated on a rotatory evaporator to approximately 50 Brix as measured by a Brix refractometer. The resulting syrup (200 mg) was loaded onto a Teledyne ISCO RediSep Rf Gold Amine column (11 grams stationary phase) using a luer-tip syringe. Other similar columns such as the Biotage SNAP KP-NH Catridges may also be used. The sample was purified on a Biotage Isolera equipped with an ELSD detector using a 20/80 to 50/50 (v/v) deionized water/ACN mobile phase gradient over 55 column volumes. Other flash chromatography systems such as the Teledyne ISCO Rf may also be used. The flow rate was set in accordance with the manufacturer's specifications for the column and system. After the monomer fraction completely eluted at ~20 column volumes, the mobile phase was set to 100% water until the remainder of the oligosaccharide eluted and was collected.

The non-monomer containing fractions were concentrated by rotary evaporation to afford the de-monomerized product.

Example 5. Size Exclusion Chromatography

The weight-average molecular weight (MWw), number-average molecular weight (MWn), and polydispersity index (PDI) of 39 batches and samples of the selected oligosaccharide composition, as described in Examples 6-12, were determined by SEC HPLC.

Method

These methods involved the use of an Agilent 1100 with refractive index (RI) detector equipped with two Agilent PL Aquagel-OH 20 (7.5×300 mm, 5 μm) columns in series.

The mobile phase (0.2 M NaNO3) was prepared by weighing 34 g of NaNO3 (ACS grade reagent) and dissolving in 2000 mL of deionized (DI) water (from MiliQ water filter). The solution was filtered through a 0.2 m filter.

Polymer standard solutions (10.0 mg/mL) of each of D-(+) Glucose (analytical standard, Sigma-Aldrich, Cat number 47829), PPS-pul342 (Mp: 342), PPS-pul1.3 k (Mp: 1080), PPS-pul6 k (Mp: 6100), PPS-pul10 k (Mp: 9600), and PPS-pul22 k (Mp: 22000) were prepared by weighing 20 mg of a standard into a separate 20 mL scintillation vial and adding 2.0 mL of DI water to each vial.

Sample A was prepared in duplicate. Approximately 300 mg of oligosaccharide sample was weighed into a 20 mL scintillation vail and 10 mL of DI water was added. The solution was mixed and filtered through a Acrodisc 25 mm syringe filter with a 0.2 m polyethersulfone membrane.

Sample B was prepared in duplicate. Approximately 210 mg of oligosaccharide sample was weighed into a 20 mL scintillation vail and 10 mL of DI-water was added. The solution was mixed and filtered a Acrodisc 25 mm syringe filter with a 0.2 m polyethersulfone membrane.

The flow rate was set to 0.9 mL/min at least 2 hours before running samples with the column temperature and RI detector each set to 40° C. with the RI detector purge turned on.

Before running samples wherein the injection volume for all samples was 10 μL and run time was 28 minutes, the detector purge was turned off and the pump was run at 0.9 mL/min until an acceptable baseline was obtained.

A blank sample consisting of DI water was run. Samples of each standard were run. Sample A was run. Sample B was run.

The peaks between 15 and 22 minutes were integrated. The monomer and the broad peak (the product) were integrated as shown in the sample chromatogram. The calibration curve fit type in Empower 3 software was set to $3^{rd}$ order. The molecular weight distributions and polydispersity were calculated using Empower 3 software for the broad peak. The Mw, Mn and polydispersity of the product peak (DP2+) were reported.

Results

Three batches of the selected oligosaccharide composition produced using the process in Example 18, thirty batches of the selected oligosaccharide composition produced at the 22 L scale using the processes described in Examples 1 or 3, five batches of the selected oligosaccharide composition produced at the 22 L scale using the process described in Example 21, and one batch of the selected oligosaccharide produced using the process of Example 20, were analyzed using the SEC methods described above. The 22 L batches produced according to the processes of Example 1 or 3 were analyzed twice.

The three batches of oligosaccharide composition produced according to Example comprised oligosaccharides with an average MWw of 1514 (with a min/max range of 1114-MWw). The 22 L batches of oligosaccharide composition produced according to the processes of Examples 1 or 3 comprised oligosaccharides with an average MWw of 1528 g/mol (with a min/max range of 1174 g/mol to 2187 g/mol), an average MWn of 942 g/mol (with a min/max range of 735 g/mol to 1213 g/mol), and an average PDI of 1.6 (with a min/max range of 1.53 to 1.86). These batches had an average monomer content of about 13.5% (with a min/max range of about 9% to 17.2%). The SEC data collected from the 22 L batches produced according to the process of Example 21 is presented in Table 11. The oligosaccharide composition batch produced according to the process described in Example 20 comprises oligosaccharides with a MWw of 1617 g/mol and an MWn of 889 g/mol (with a saccharide monomer content of 13.8% monomer).

TABLE 11

SEC data for selected production batches of oligosaccharide

| Batch Number | 22 Liter Oligosaccharide Composition Batches (Example 21) | | | | |
|---|---|---|---|---|---|
| | 1 | 2 | 3 | 4 | 5 |
| Polydisperity | 1.7 | 1.7 | 1.7 | 1.7 | 1.7 |
| MWw | 1441 | 1409 | 1401 | 1417 | 1383 |
| MWn | 841 | 829 | 828 | 831 | 821 |
| % Monomer | 13.3 | 13.3 | 13.3 | 13.5 | 13.9 |

Example 6: Ex Vivo Screen of Fecal Samples from Patients with Minimal Hepatic Encephalopathy (MHE) and Healthy Subjects to Test the Efficacy of Glycans for Ammonia Patients with advanced liver disease often fail to fully detoxify blood ammonia, thus leading to a condition known as hyperammonemia. This elevated blood ammonia is thought to give rise to several symptoms in this patient population, including cognitive impairment, loss of consciousness, and death. Identification of compounds capable of lowering blood ammonia levels is therefore critical to reducing the morbidity associated with liver disease. Currently, patients diagnosed with overt hepatic encephalopathy (OHE) are treated with lactulose (4-O-β-D-Galactosyl-D-fructose), a non-digestible disaccharide thought to reduce blood ammonia by limiting the contribution of gut bacteria to overall ammonia levels. Those patients who do not tolerate lactulose well are treated with rifaximin, a non-absorbable antibiotic. The efficacy of these treatments suggests that the gut microbiota have an appreciable impact on blood ammonia levels. For this reason, an ex vivo screen was conducted that identified glycans that reduce the amount of ammonia contributed by gut bacteria. A selected oligosaccharide that exhibited significant ammonia reduction in this screen was selected for further testing to determine whether it could reduce ammonia produced by microbiota isolated from healthy subjects and from patients with minimal hepatic encephalopathy (MHE).

Test and control articles were created as 5% (w/v) stock solutions and tested at a final concentration of 0.5%. All stock solutions were stored in 50 mL conicals and maintained at 4° C. Molecular biology grade water was added to growth medium at a 1:10 (v/v) ratio to serve as a no added carbon (NAC) control.

Human fecal samples were stored at −80° C. To prepare working stocks, the fecal samples were transferred into the anaerobic chamber and allowed to thaw. The 20% w/v fecal slurries were centrifuged at 2,000×g for about 5 minutes, supernatant was removed, and the pellet was resuspended in PBS pH 7.4. To make a 1% fecal slurry, 700 µL of each fecal slurry was added to 13.30 mL of a medium containing 900 mg/L sodium chloride, 26 mg/L calcium chloride dihydrate, 20 mg/L magnesium chloride hexahydrate, 10 mg/L manganese chloride tetrahydrate, 40 mg/L ammonium sulfate, 4 mg/L iron sulfate heptahydrate, 1 mg/L cobalt chloride hexahydrate, 300 mg/L potassium phosphate dibasic, 1.5 g/L sodium phosphate dibasic, 5 g/L sodium bicarbonate, 0.125 mg/L biotin, 1 mg/L pyridoxine, 1 m/L pantothenate, 75 mg/L histidine, 75 mg/L glycine, 75 mg/L tryptophan, 150 mg/L arginine, 150 mg/L methionine, 150 mg/L threonine, 225 mg/L valine, 225 mg/L isoleucine, 300 mg/L leucine, 400 mg/L cysteine, and 450 mg/L proline (Theriot C M et al. Nat Commun. 2014; 5:3114) supplemented with 750 µM urea.

The resulting 1% w/v fecal slurries were added to 96-well plates containing 35 µL of the selected oligosaccharide composition or a control, at a 350 µL final volume per well, and incubated anaerobically at 37° C. for 45 hours. After incubation, plates containing the fecal samples with the selected oligosaccharide or control were maintained outside the anaerobic chamber on wet ice during sample processing. This experiment was performed in triplicate. Absorption measurements were obtained by making a 1 to 10 dilution of all samples in water and then obtaining a spectrophotometer reading of each sample using a spectrophotometer set to a wavelength of 600 nm. After the OD600 readings were taken, all plates were spun at 3062×g (4150×rpm) for 10 minutes and the supernatants were collected and stored at −80° C. Cell pellets were resuspended, transferred into DNA extraction plates, and stored at −80° C. until shallow shotgun sequencing was performed on the samples.

A modified ammonia colorimetric assay kit (BioVision, catalog #K470-100) was used to analyze the collected supernatants. This non-enzymatic assay detects the formation of indophenol from ammonia, forming a colored product that is easily quantifiable by colorimetry using a plate reader. Thawed culture supernatants were filtered using 10 kD filter plates (Pall corporation, cat #8034), centrifuged at 1500×g for 15 mins, and then diluted 1:100 with molecular biology grade water. One hundred µL of this 1:100 dilution was transferred into black microplates with flat bottoms (Corning 3631). Reagents were added and the plates were incubated, per manufacturer's instructions, the plates were then read at OD670, and the resulting values were compared to a standard curve to obtain mM ammonia values.

Figure 9:
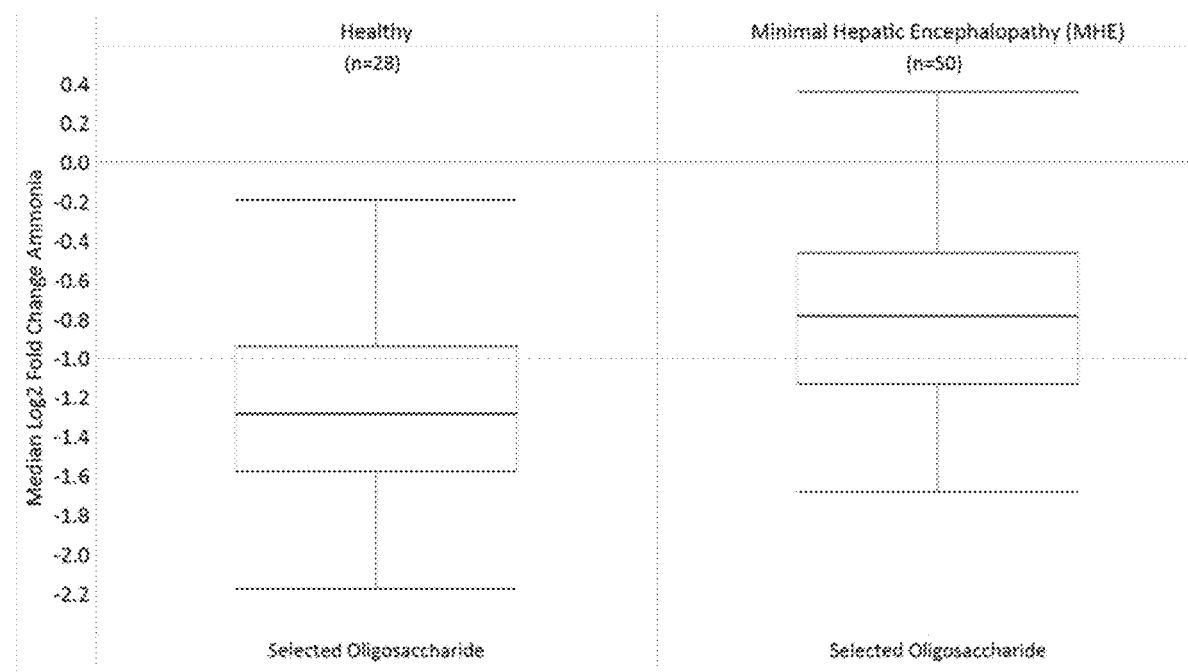
FIG. 9 depicts graphs showing reduction in ammonia levels in an ex vivo assay where fecal samples from human subjects (healthy subjects and subjects with Minimal Hepatic Encephalopathy) were incubated with the selected oligosaccharide composition.

FIG. 9 shows that the selected oligosaccharide reduced ammonia levels in the fecal samples of healthy subjects and in the fecal samples of subjects with MHE 45 hours after being introduced to the samples in an ex vivo assay. After 45 hours, the selected oligosaccharide composition reduced ammonia levels in all of the fecal samples from healthy subjects and in 47 out of 50 mHE patient fecal samples. The selected oligosaccharide composition produced a greater than about 50% reduction in ammonia levels compared to control in 21 out of 28 healthy subject samples and in 17 out of 50 mHE subject samples, demonstrating that this oligosaccharide can decrease ammonia levels produced by gut microbial communities in healthy and hyperammonemia subjects.

Example 7: Reduction of Pathogen Abundance in a Defined Microbial Community in the Presence of Oligosaccharide Compositions Approximately four hundred fifteen different oligosaccharide compositions were tested for their ability to modulate (e.g., reduce) the relative abundance of pathogens and to support the growth of commensal bacteria in a defined microbial community (comprising 46 different commensal bacterial strains). This screening was conducted by spiking the defined microbial community with three drug-resistant bacteria (CRE *Klebsiella pneumoniae*, CRE *Escherichia coli*, or VRE *Enterococcus faecium*) and subsequently growing the spiked microbial community in the presence of a single test oligosaccharide composition, wherein the single test oligosaccharide composition represented the sole carbon source.

The defined microbial community was constructed by combining 46 strains that belonged to phyla Actinobacteria, Firmicutes, and Bacteroidetes: *Blautia producta, Blautia hansenii, Clostridium celatum, Bacteroiodes cellulosilyticus, Odoribacter splanchnicus, Bifidobacterium catenulatum, Eubacterium hallii, Bacteroides dorei, Bifidobacterium pseudocatenulatum, Bifidobacterium adolescentis, Bacteroides coprophilus, Lactobacillus casei, Coprococcus catus, Bifidobacterium angulatum, Eubacterium ventriosum, Lachnospira multipara, Parabacteroides merdae, Bacteroides finegoldii, Parabacteroides distasonis, Bacteroides thetaiotaomicron, Blautia hydrogenotrophica, Blautia coccoides, Clostridium bolteae, Clostridium scindens, Holdemanella biformis, Bifidobacterium longum* sub. *Infantalis, Ruminococcus obeum, Dorea formicigenerans, Collinsella aerofaciens, Eubacterium eligens, Faecalibacterium prausnitzii, Bifidobacterium longum, Prevotella copri, Eubacterium rectale, Bacteroides uniformis, Succinivibrio dextrinosolvens, Roseburia intestinalis, Clostridium nexile, Bacteroides caccae, Bacteroides vulgatus, Dorea longicatena, Akkermansia muciniphila, Bacteroides thetaiotaomicron, Bacteroides cellulosilyticus, Clostridium symbiosum,* and *Ruminococcus gnavus*.

To prepare the defined microbial community, each of the 46 different commensal bacterial strains were independently grown in standard chopped meat glucose media (CMG) for 18-48 hours, depending on the strain. After growth, the optical density ($OD_{600}$) of each bacterial strain was adjusted to 0.2 and equal volumes of each of the 46 strains were combined into one bottle. 1.5-mL aliquots of the defined microbial community were frozen at −80° C. with a final glycerol concentration of 15%. The CRE *Klebsiella pneumoniae*, CRE *Escherichia coli*, and VRE *Enterococcus faecium* strains for use in this Example were obtained from the Centers for Disease Control (CDC) and were grown aerobically in BHI media for 12 hours at 37° C. prior to their addition to the defined microbial community.

Frozen aliquots of defined microbial community sample were later thawed and washed with a media consisting of 900 mg/L sodium chloride, 26 mg/L calcium chloride dihydrate, 20 mg/L magnesium chloride hexahydrate, 10 mg/L manganese chloride tetrahydrate, 40 mg/L ammonium sulfate, 4 mg/L iron sulfate heptahydrate, 1 mg/L cobalt chloride hexahydrate, 300 mg/L potassium phosphate dibasic, 1.5 g/L sodium phosphate dibasic, 5 g/L sodium bicarbonate, 0.125 mg/L biotin, 1 mg/L pyridoxine, 1 mg/L pantothenate, 75 mg/L histidine, 75 mg/L glycine, 75 mg/L tryptophan, 150 mg/L arginine, 150 mg/L methionine, 150 mg/L threonine, 225 mg/L valine, 225 mg/L isoleucine, 300 mg/L leucine, 400 mg/L cysteine, and 450 mg/L proline (Theriot C M et al. Nat Commun. 2014; 5:3114) that was further supplemented with 0.1% peptone and 0.75 mM urea in order to adjust the defined microbial community sample to an $OD_{600}$ of 0.01. CRE *Klebsiella pneumoniae*, CRE *Escherichia coli*, and VRE *Enterococcus faecium*, all at $OD_{600}$ of 0.01, were then added to (i.e., used to spike) the defined microbial community sample. Each spiked aliquot was provided one of the four hundred and fifteen different oligosaccharide compositions (as the sole carbon source present in the aliquot) at a final concentration of 0.5% w/v or 0.05% w/v and incubated for 24 hours in the anaerobic chamber at 37° C. Water was used as a negative control (i.e., no carbon source). Each oligosaccharide composition was replicated up to 3 times. After 24 hours of incubation, the $OD_{600}$ of each spiked microbial community was measured to provide an approximation of total anaerobic growth.

To determine the level of pathogens in each spiked microbial community, a 200× dilution of each community was made in fresh Luria-Bertani (LB) media, and incubated aerobically for 24 hours at 37° C. $OD_{600}$ was measured every 15 minutes to generate growth curves using a Biotek plate reader. The time to mid-log growth was calculated and used to determine the total pathogen load at the end of the anaerobic phase of the experiment. Lesser times to mid-log growth corresponded to higher pathogen levels.

To identify oligosaccharide compositions that supported overall community growth, while reducing pathogen growth, both $OD_{600}$ at the end of the anaerobic phase (higher is a sign of more commensals) and time to mid-log growth during the secondary aerobic growth were normalized within their respective metrics from 0 to 1. These two values were multiplied and subtracted from 1 (i.e., 1−(anerobic growth*aerobic growth)). These final values, representative of individual oligosaccharide compositions, were normalized to negative control (water) to identify oligosaccharide compositions that reduced levels of pathogenic bacteria and promoted levels of commensal bacteria.

Example 8: Reduction of Pathogen Abundance in a Fecal Slurries from Humans in the Presence of Oligosaccharide Compositions One hundred and thirty-five oligosaccharide compositions that reduced the abundance of pathogens and supported commensal growth in the spiked microbial community of Example 6 were further assessed for their abilities to similarly function in ex vivo fecal slurries from humans that were spiked with single pathogen strains (VRE *E. faecium*, CRE *K. pneumoniae*, or CRE *E. coli*). Oligosaccharide compositions were prepared at 5% w/v in water, filter-sterilized and added to 96-well deep well microplates assay plates for a final concentration of 0.5% or 0.05% w/v in the assay, with water supplied as a negative control.

A human fecal sample donation was stored at −80° C. To prepare working stocks of fecal slurry, the fecal sample was transferred into the anaerobic chamber and allowed to thaw. The fecal sample was then prepared in 20% w/v in phosphate buffered saline (PBS) pH 7.4 (P0261, Teknova Inc., Hollister, Calif.), 15% glycerol. The 20% w/v fecal slurry+ 15% glycerol was centrifuged at 2,000×g, supernatant was removed, and the pellet was suspended in 1% PBS prior to dilution in a CM media consisting of 900 mg/L sodium chloride, 26 mg/L calcium chloride dihydrate, 20 mg/L magnesium chloride hexahydrate, 10 mg/L manganese chloride tetrahydrate, 40 mg/L ammonium sulfate, 4 mg/L iron sulfate heptahydrate, 1 mg/L cobalt chloride hexahydrate, 300 mg/L potassium phosphate dibasic, 1.5 g/L sodium phosphate dibasic, 5 g/L sodium bicarbonate, 0.125 mg/L biotin, 1 mg/L pyridoxine, 1 m/L pantothenate, 75 mg/L histidine, 75 mg/L glycine, 75 mg/L tryptophan, 150 mg/L arginine, 150 mg/L methionine, 150 mg/L threonine, 225 mg/L valine, 225 mg/L isoleucine, 300 mg/L leucine, 400 mg/L cysteine, and 450 mg/L proline (Theriot C M et al. Nat Commun. 2014; 5:3114) that was further supplemented with 750 µM urea to provide a final dilution of 1% w/v fecal slurry.

One day prior to the start of the experiment, a single strain of CRE *K. pneumoniae*, a single strain of CRE *E. coli*, and a single strain of VRE were independently grown overnight in CM media with 0.5% D-glucose in an anaerobic chamber. On the day of the experiment, aliquots of the pathogenic cultures were washed with PBS and the optical density ($OD_{600}$) of each pathogenic culture and the 1% fecal slurry were adjusted to OD 0.1 in CM media. Each of the three pathogen cultures was then separately added to three aliquots of the fecal slurry such that the pathogen cultures comprised 8% of the final volume of the fecal slurry/ pathogen mixture. Each of the three fecal slurry/pathogen mixtures were exposed to the 96-well plates of oligosaccharide compositions at a final concentration of 0.05% w/v or 0.5% w/v, 350 µL final volume per well, at 37° C. for 45 hours, anaerobically.

Following the ex vivo incubation, the plates were removed from the anaerobic chamber and a 200× dilution of each culture in fresh Luria-Bertani (LB) media was made. These diluted cultures were incubated aerobically for 24 hours at 37° C. $OD_{600}$ was measured every 15 minutes for 24 hours to generate growth curves using a Biotek plate reader. The time to mid-log growth was calculated and used to determine the total pathogen load at the end of the anaerobic phase of the experiment. Lower time to mid-log values corresponded to higher levels of pathogens at the end of the anaerobic phase of the experiment.

Commensal strains in the fecal slurry communities are strict anaerobes and thus do not grow under aerobic conditions. The $OD_{600}$ measured at the end of anaerobic incubation (referred to as anaerobic $OD_{600}$) and time to mid-log growth as calculated from aerobic growth curves allowed for the identification of a selected oligosaccharide composition that exclusively supports commensal growth (e.g., high anaerobic $OD_{600}$ and long time to midlog).

Example 9: Testing the Ability Oligosaccharide Compositions to Support the Growth of Single Pathogens A total of fifty-five oligosaccharide compositions from Example 7A were further selected for investigation in an additional assay designed to directly test whether the oligosaccharide compositions can support the growth of single pathogens.

Individual pathogenic bacterial strains, including CRE *Escherichia coli*, CRE *Klebsiella pneumoniae*, and *Clostridium difficile*, were grown in CM, and single strain of VRE *Enterococcus faecium* was grown in mega medium (MM) prior to the addition of a single glycan preparation or water (a no carbon control). Mega Media (MM) contains 10 g/L tryptone peptone, 5 g/L yeast extract, 4.1 mM L-cysteine, 100 mM potassium phosphate buffer (pH 7.2), 0.008 mM magnesium sulfate, 4.8 mM sodium bicarbonate, 1.37 mM sodium chloride, 5.8 mM vitamin K, 0.8% calcium chloride, 1.44 mM iron (II) sulfate heptahydrate, 4 mM resazurin, 0.1% histidine-hematin, 1% ATCC trace mineral supplement, 1% ATCC vitamin supplement, 29.7 mM acetic acid, 0.9 mM isovaleric acid, 8.1 mM propionic acid, 4.4 mM N-butyric acid with the pH adjusted to 7 using sodium hydroxide. This media was filter sterilized using a 0.2 um filter and stored in an anaerobic chamber prior to use to allow any dissolved oxygen to dissipate. The single strains of *E. coli* (BAA-2340, BAA-97, 4 strains isolated from patients), *K. pneumoniae* (ATCC 33259, BAA-1705, BAA-2342, and 7 strains isolated from patients), and *C. difficile* were grown in isolation overnight in CM with 0.5% D-glucose in a COY anaerobic chamber. Single strains of *E. faecium* (ATCC 700221 and 9 strains isolated from patients, and EFM.70), were grown in isolation overnight in MM with 0.5% D-glucose in a COY anaerobic chamber. 1 mL of each overnight culture was washed with PBS and the optical density ($OD_{600}$) of each culture was measured. Each culture was adjusted to $OD_{600}$ 0.01 in media (e.g., CM or MM).

Inside of the COY anaerobic chamber, the normalized single strain cultures of *E. coli, K. pneumoniae*, or *C. difficile* were added to 96 well microplates with one of the oligosaccharide compositions as the sole carbon source in each well. Water added to media (e.g., CM or MM) without any carbon source functioned as a control. These microplates were then incubated at 37° C. in the COY anaerobic chamber for a total of 45 hours and the $OD_{600}$ was measured every 15 minutes to generate a growth curve for each experimental well. Each oligosaccharide composition was tested in three replicates against each bacterial pathogen.

The area under the curve (AUC) was calculated for the growth curve and a time-to-midlog was determined for each experiment.

A selected oligosaccharide composition did not support the growth of CRE *E. coli*, CRE *K. pneumoniae*, VRE *E. faecium*, or *C. difficile*. These results further demonstrated that the selected oligosaccharide composition does not support the growth of pathogens, and thereby disadvantages pathogen growth and abundance in microbial communities by selectively favoring the growth of commensal bacteria.

Example 10: Reduction of Pathogen Growth and Abundance in the Presence of a Selected Oligosaccharide Composition in Cultures of Single Pathogen Strains A selected oligosaccharide composition comprised of a plurality of glycans selected from Formula (I) and Formula (II) and produced by a process as described in Examples 1-3 and 16 was further tested for its ability to reduce growth and abundance of single strains of pathogens that frequently encountered in critically ill and immunocompromised patients.

The selected oligosaccharide composition was tested for its ability to reduce the growth and abundance of individual strains of CRE *Escherichia coli*, CRE *Klebsiella pneumoniae*, and VRE *E. faecium*. Single strains of *E. coli* (one strain obtained from the CDC's Enterobacteriaceae-carbapenem-breakpoint panel, the other isolated from a patient) and *K. pneumoniae* (one strain from CDC panel, the other isolated from a patient) were grown in isolation overnight in CM media with 0.5% D-glucose in a COY anaerobic chamber. Single strains of *E. faecium* (ATCC 700221 and 2 strains isolated from patients) were grown in isolation overnight in MM media with 0.5% D-glucose in a COY anaerobic chamber. The media was filter sterilized using a 0.2 μm filter and stored in an anaerobic chamber prior to use to allow any dissolved oxygen to dissipate. 1 mL of each overnight culture was washed with PBS and the $OD_{600}$ of each culture was measured. Each culture was adjusted to an $OD_{600}$ of 0.01 and then incubated with glucose, fructooligosaccharide (FOS), or a sample of the selected oligosacchride composition. Water was added to media without any added carbon source as a negative control. The final concentration of glucose, FOS, or the selected oligosacchride composition in each assay was 0.5% w/v and each assay was replicated 3 times within each growth plate. Plates were incubated at 37° C. in an anaerobic chamber for a total of 45 hours. Optical density was determined for each strain every 15 minutes for 48 hours.

Figure 2:
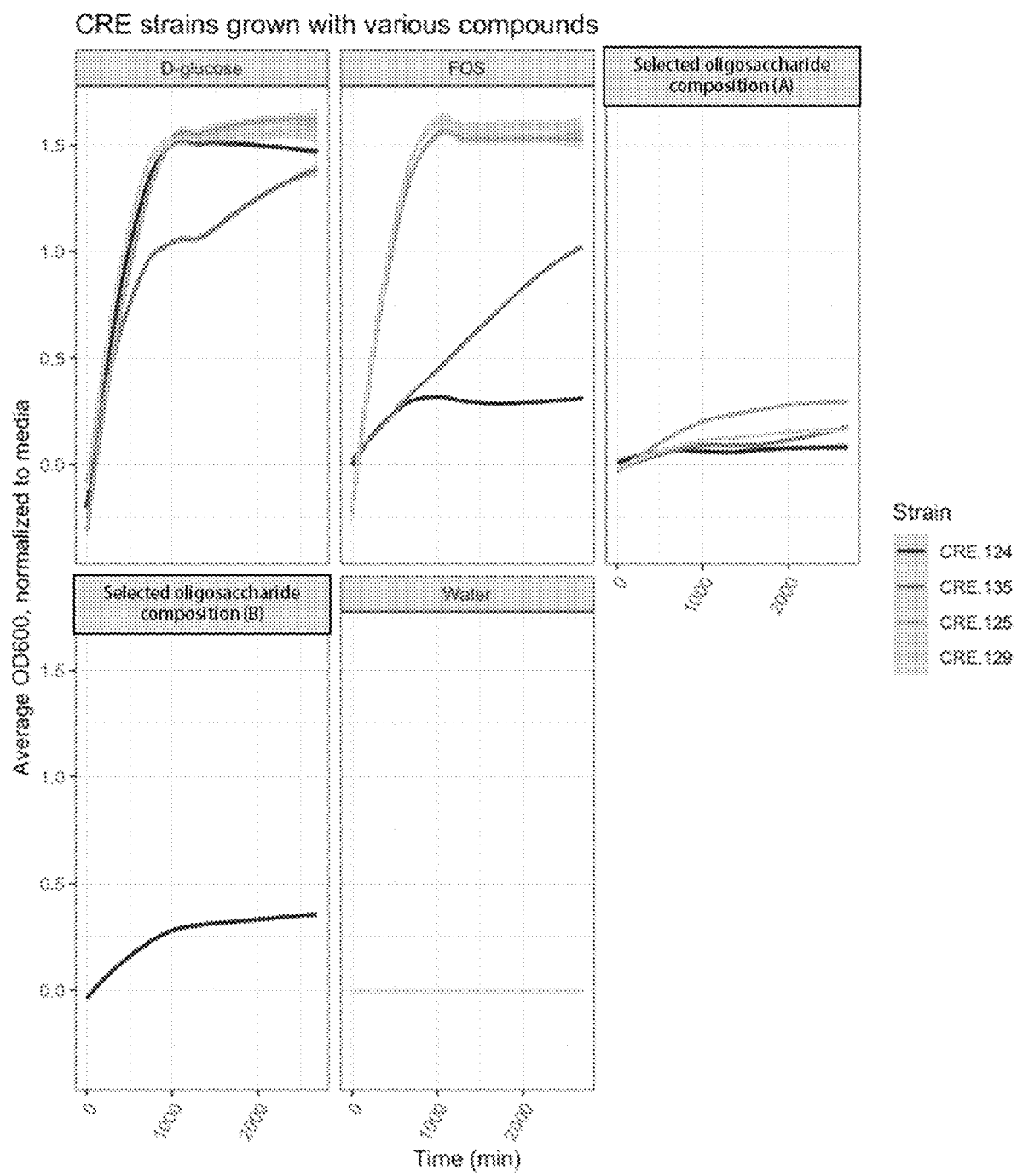
FIG. 2 provides graphs showing reduction in pathogen growth in cultures of single pathogen strains (CRE *Escherichia coli*, CRE *Klebsiella pneumoniae*) incubated in the presence of samples of a selected oligosaccharide composition.
Figure 3:
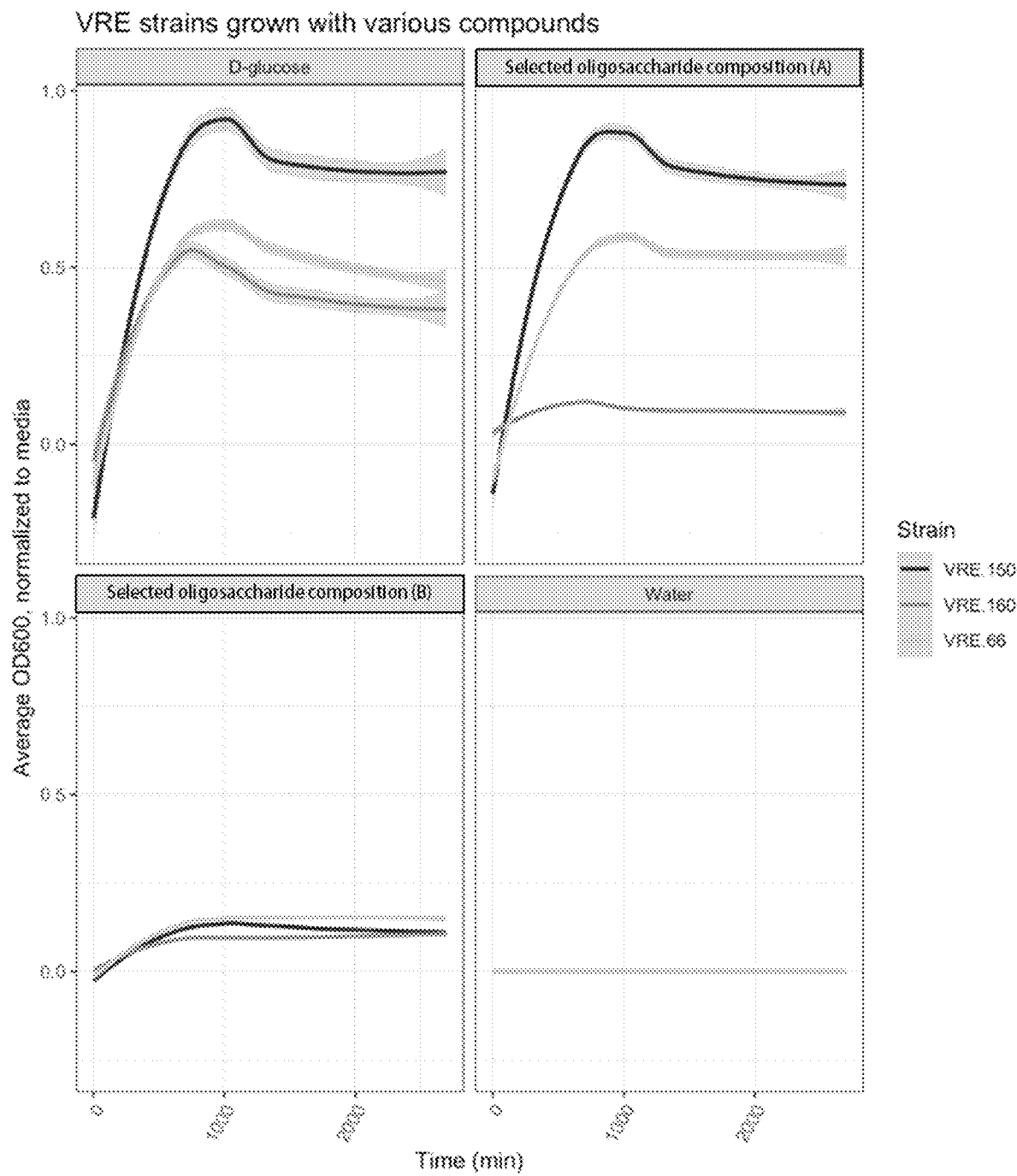
FIG. 3 provides graphs showing reduction in pathogen growth in cultures of single pathogen strains (VRE *Enterococcus faecium*) incubated in the presence of samples of a selected oligosaccharide composition.

The CRE and VRE pathogens exhibited little-to-no growth in the presence of samples of the selected oligosaccharide composition, similar to the growth of pathogens in the presence of the water control (FIG. 2 and FIG. 3).

The selected oligosaccharide composition was tested for its ability to reduce the growth and abundance of individual strains of fungal pathogens (*Candida albicans, Candida glabrata, Candida krusei*, and *Candida tropicalis*). Each of four strains of *Candida albicans, Candida glabrata, Candida krusei*, and *Candida tropicalis* were obtained from ATCC (ATCC MYA-2950, ATCC 14243, ATCC 201380 and ATCC MYA-2876). All *Candida* strains were grown aerobically in modified Sabouraud broth (10 g/L peptone solution) with glucose at 2% final concentration at 37° C. for 24 hours until each strain achieved optical density ($OD_{600}$) of about 1. 200 μL of each culture was diluted in 3 mL of modified Sabouraud broth and 120 μL was added to each well of a 96 well plate containing 80 μL of one of the following 5% w/v solutions per well: glucose, FOS, or a sample of the selected oligosaccharide composition. Water was used as a negative control. The final concentration of glucose, FOS, or the selected oligosaccharide composition in each assay to test *Candida albicans, Candida glabrata, Candida krusei*, or *Candida tropicalis* was 2%, each assay was replicated 3 times, and plates were incubated at 37° C. for a total of 65 hours. Optical density data was collected for each of the *Candida albicans, Candida glabrata, Candida krusei*, or *Candida tropicalis* strains every 15 minutes.

Figure 4:
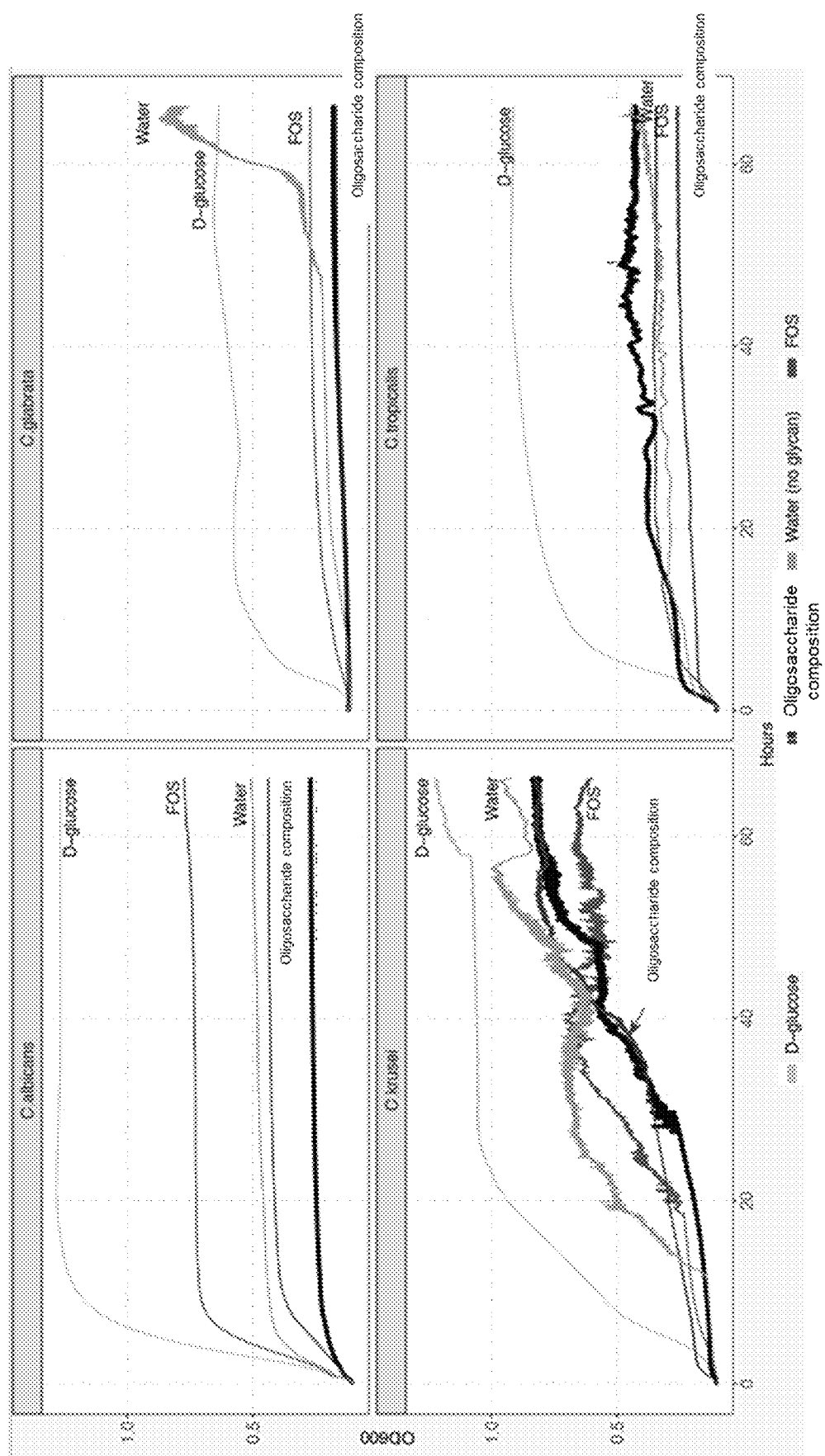
FIG. 4 provides graphs showing reduction in pathogen growth in cultures of single pathogen strains (*Candida albicans, Candida glabrata, Candida krusei, Candida tropicalis*) incubated in the presence of samples of a selected oligosaccharide composition.

Each of the *Candida albicans, Candida glabrata, Candida krusei*, or *Candida tropicalis* strains grew minimally in the presence of the samples of selected oligosaccharide composition (FIG. 4). Meanwhile, each of these strains grew to high $OD_{600}$ in the presence of glucose. Further, growth of each *Candida* strain in the presence of the selected oligosaccharide composition was similar to the amount of growth in the presence of water (negative control, no carbon source).

These data collectively demonstrate that the selected oligosaccharide composition as produced according to Examples 1-3 and 16 does not support growth and abundance of pathogenic microbes (bacteria and fungi), as evidenced by the inability of any of the tested VRE (*E. faecium*) and CRE (CRE *E. coli*, CRE *K. pneumoniae*), and *Candida* strains. By contrast, all of the tested strains exhibited significant growth in the presence of glucose and/or FOS.

Example 11: Assessment of Selected Oligosaccharide Compositions in Fecal Slurries from Hospitalized Patients The ability of a selected oligosaccharide composition comprised of a plurality of glycans selected from Formula (I) and Formula (II) as produced by a process as described in Examples 1-3 and 16 to reduce pathogen growth in microbiome samples from fecal slurries of thirteen hospitalized patients receiving antibiotic treatment from an Intensive Care Unit (ICU) facility was assessed.

Fecal samples from ICU patients and healthy subjects were collected and stored at −80° C. To prepare the fecal material for use in the ex vivo assay, aliquots of a 20% w/v slurry in phosphate buffered saline (PBS) and glycerol were thawed in a COY anaerobic chamber. This slurry was then further diluted into a 1% solution of Mega Media (MM).

This media was filter sterilized using a 0.2 μm filter and stored in an anaerobic chamber prior to use to allow any dissolved oxygen to dissipate.

A single strain of Carbapenem-resistant Enterobacteriaceae (CRE) and vancomycin-resistant Enterococcaceae (VRE) were grown in isolation overnight in MM with 0.5% D-glucose in a COY chamber. On the day of the experiment, aliquots of the overnight cultures were washed with PBS and the optical density ($OD_{600}$) of the cultures was measured. The culture was adjusted to $OD_{600}$ of 0.1 in MM and added to the 1% fecal slurries. Fecal slurries mixed with either Carbapenem-resistant Enterobacteriaceae (CRE) and vancomycin-resistant Enterococcaceae (VRE) were then subjected to 16S sequencing to determine the initial relative abundance of pathogen and commensal bacteria. The cultures were then added to 96-well microplates with one of the following carbon sources (final concentration of 0.5% w/v) in each well: maltodextrin, fructooligosaccharide, a sample of the selected oligosaccharide composition, or water (negative control, i.e., no carbon source). These microplates were then incubated at 37° C. in the COY chamber for a total of 45 hours, with each experimental condition being tested in three replicates on each plate.

At the end of the 45-hour incubation, a sample of the culture from each well was subjected to 16S sequencing to determine the final relative abundance of pathogen and commensal bacteria in the community after intervention with oligosaccharide composition.

For the 16S sequencing, genomic DNA was extracted from the fecal slurries and variable region 4 of the 16S rRNA gene was amplified and sequenced (Earth Microbiome Project protocol www.earthmicrobiome.org/emp-standard-protocols/16s/ and Caporaso J G et al. Ultra-high-throughput microbial community analysis on the Illumina HiSeq and MiSeq platforms. ISME J. (2012) August; 6(8): 1621-4). Raw sequences were demultiplexed, and each sample was processed separately with UNOISE2 (Robert Edgar UNOISE2: improved error-correction for Illumina 16S and ITS amplicon sequencing. bioRxiv (2016) Oct. 15). Reads from 16S rRNA amplicon sequencing data were rarefied to 5000 reads, without replacement, and resulting OTU table used in downstream calculations.

Figure 5A:
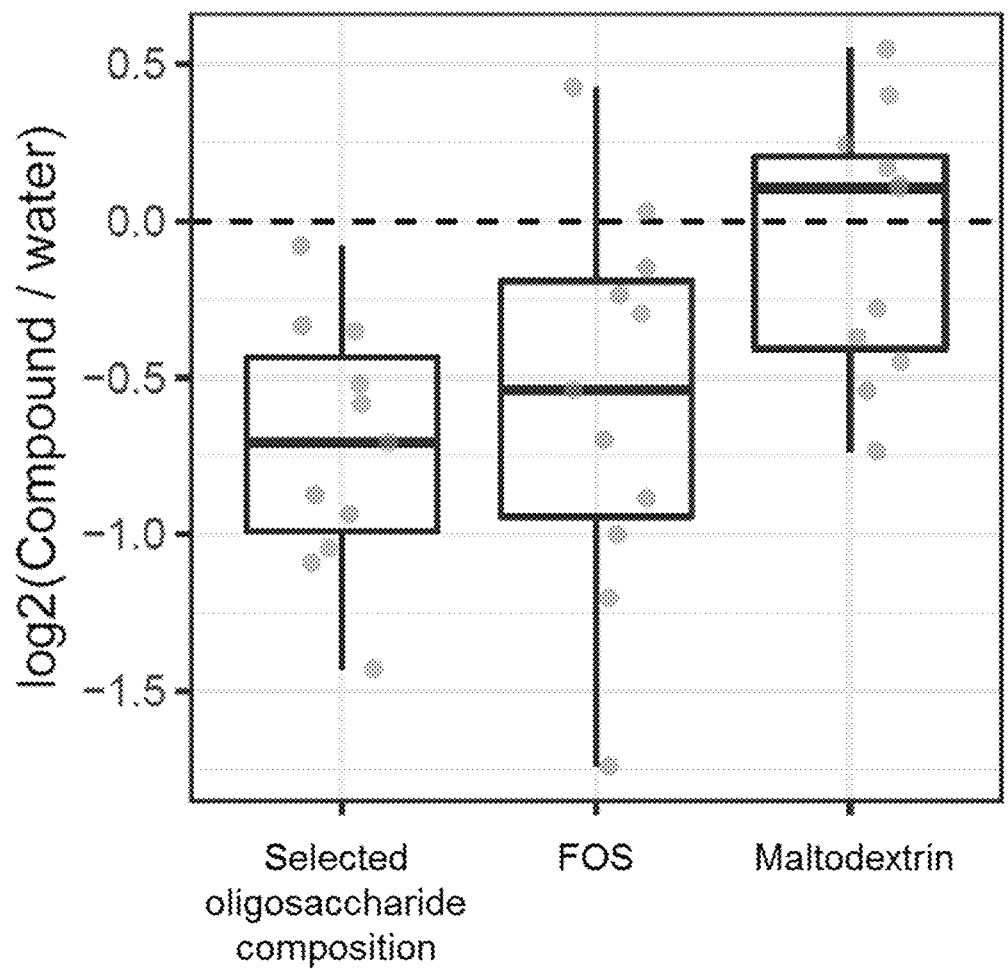
FIGS. 5A-5B provide graphs showing reduction in pathogen growth (normalized to water controls) in an ex vivo pathogen reduction assay where fecal samples from ICU patients were incubated with the selected oligosaccharide composition.
Figure 5B:
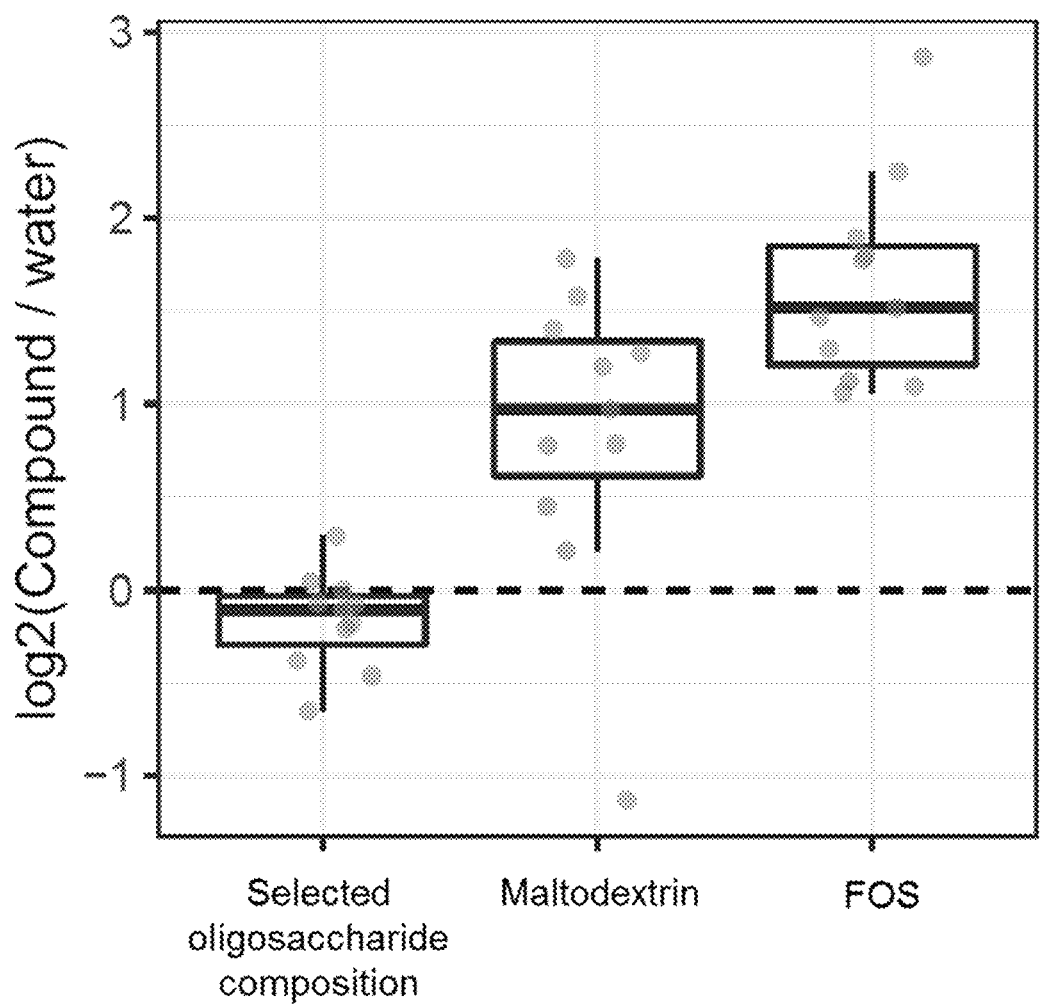

The selected oligosaccharide composition reduced the abundance of Carbapenem-resistant Enterobacteriaceae (FIG. 5A) and vancomycin-resistant Enterococcaceae (FIG. 5B) in spiked fecal slurries from ICU patients, as assessed by 16S sequencing. The abundance of each of these pathogens was greater in those spiked fecal slurries that were incubated in the presence of FOS (a commercial fiber) or maltodextrin. This demonstrates that a selected oligosaccharide composition comprised of a plurality of glycans selected from Formula (I) and Formula (II) as produced by a process as described in Examples 1-3 and 16 is capable of reducing or preventing the growth of pathogens such as Carbapenem-resistant Enterobacteriaceae (CRE) and vancomycin-resistant Enterococcaceae (VRE) in a clinically relevant model.

Example 12: Assessment of Selected Oligosaccharide Compositions in Fecal Slurries from Hepatic Encephalopathy (HE) Patients In some cases, pathogen infection could potentially be a precipitating factor of hepatic encephalopathy (HE) in certain patients. Further, HE patients can be immunocompromised and susceptible to pathogen infection. The ability of a selected oligosaccharide composition comprised of a plurality of glycans selected from Formula (I) and Formula (II) as produced by a process as described in Examples 1-3 and 16 to reduce pathogen abundance in patients with HE was testes. Microbiome samples from 44 HE patients were spiked with a single pathogen strain (CRE *E. coli* or VRE *E. faecium*) and then grown in the presence of selected oligosaccharide composition, FOS, or water (negative control, i.e., no carbon source).

Fecal samples from HE patients and a healthy subject were collected and stored at −80° C. To prepare the fecal material for use in the ex vivo assay, it was moved into a COY anaerobic chamber and made into a 20% w/v slurry in phosphate buffered saline (PBS) with 15% glycerol. Aliquots of each fecal slurry were stored at −80° C. For this experiment, an aliquot of each slurry was thawed at ambient temperature within the COY chamber. The aliquots were centrifuged at 2000×g for 5 minutes and the supernatant was discarded. The cell pellet was resuspended in PBS and was then further diluted into a 1% solution in Mega Media (MM). This media was filter sterilized using a 0.2 μm filter and stored in an anaerobic chamber prior to use to allow any dissolved oxygen to dissipate.

A single strain of Carbapenem-resistant Enterobacteriaceae (CRE) and vancomycin-resistant Enterococcaceae (VRE) were grown in isolation overnight in MM with 0.5% D-glucose in a COY chamber. On the day of the experiment, aliquots of the overnight cultures were washed with PBS and the optical density ($OD_{600}$) of the cultures and fecal slurries were measured. The $OD_{600}$ measurements were used to normalize the bacterial cultures to either an $OD_{600}$ of 0.01 or an $OD_{600}$ of 0.1 and the fecal slurries to an $OD_{600}$ of 0.1 in MM. After normalization, the CRE strain or VRE strain was added to the fecal slurries at 8% (v/v) of the total culture. Each batch of CRE strain and VRE strain that was normalized to an $OD_{600}$ of 0.01 was added to 12 of the fecal slurries. The remaining 32 fecal slurries were supplemented with cultures of these pathogens that were normalized to an $OD_{600}$ of 0.1. A sample of each pathogen-supplemented fecal slurry was then subjected to shallow shotgun sequencing (16S sequencing) to determine the initial relative abundance of pathogen and commensal bacteria. The mixed culture was then added to 96-well microplates with one of the following carbon sources (final concentration of 0.5% w/v) in each well: selected oligosaccharide composition, FOS, or water. These microplates were then incubated at 37° C. in the COY chamber for a total of 45 hours. Each oligosaccharide composition was tested in three replicates on each plate, with each experimental condition being tested in three replicates on each plate.

After incubation, 16S sequencing was performed as in Example 9 to determine the relative abundance of pathogen in each fecal slurry sample.

Figure 6A:
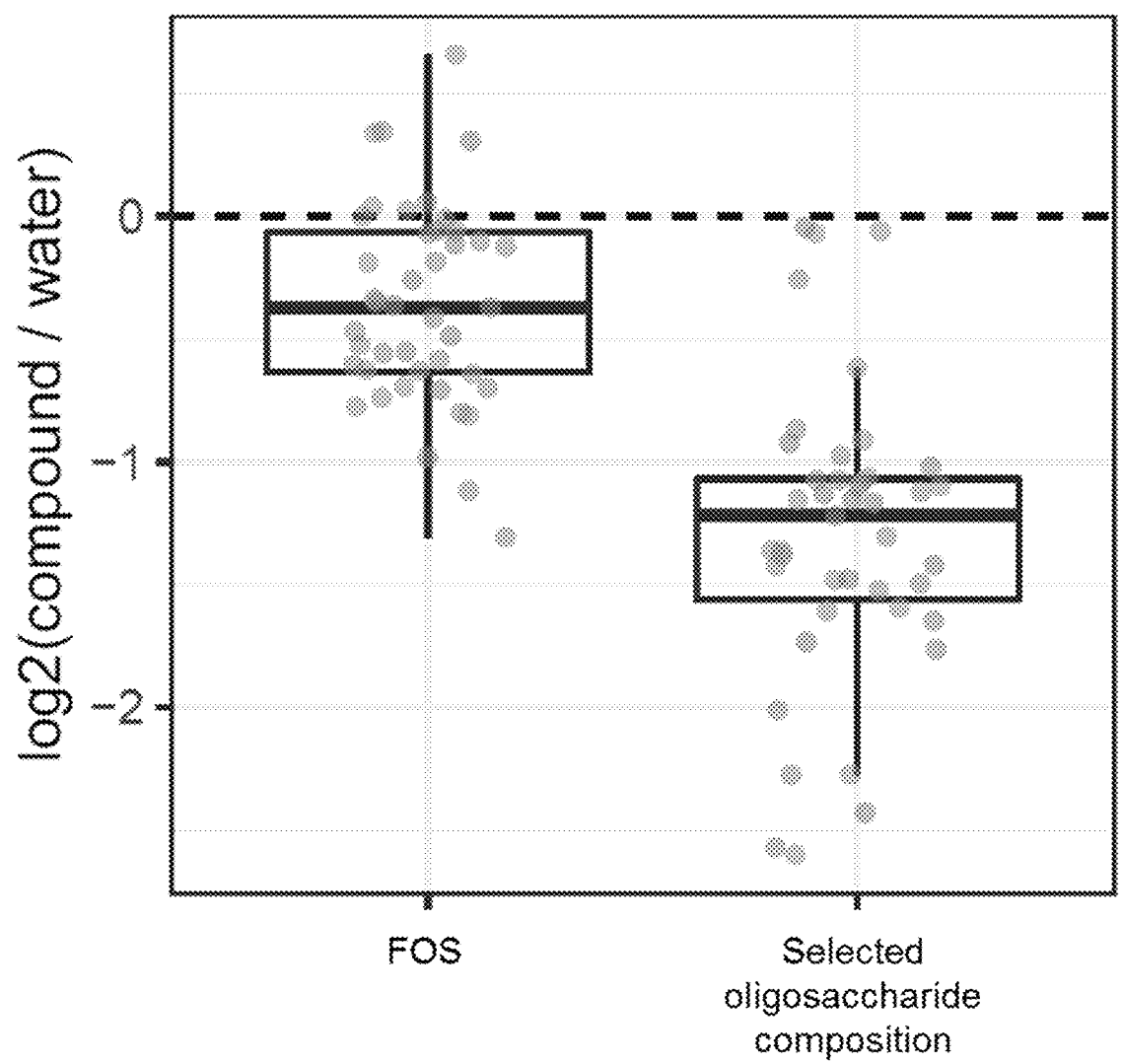
FIGS. 6A-6B provide graphs showing reduction in pathogen growth (normalized to water controls) in an ex vivo pathogen reduction assay where fecal samples from hepatic encephalopathy (HE) patients were incubated with the selected oligosaccharide composition.
Figure 6B:
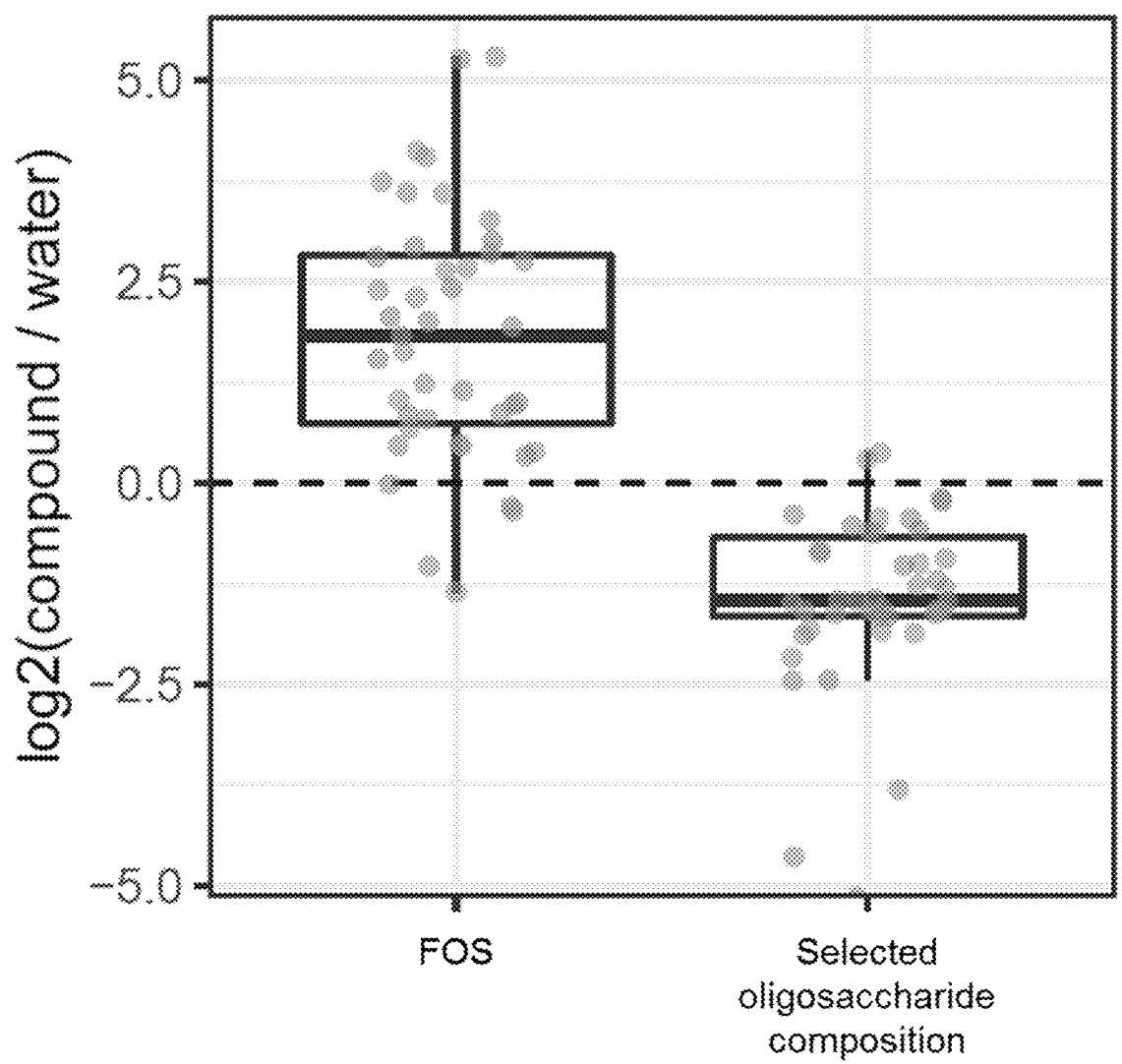
Figure 7:
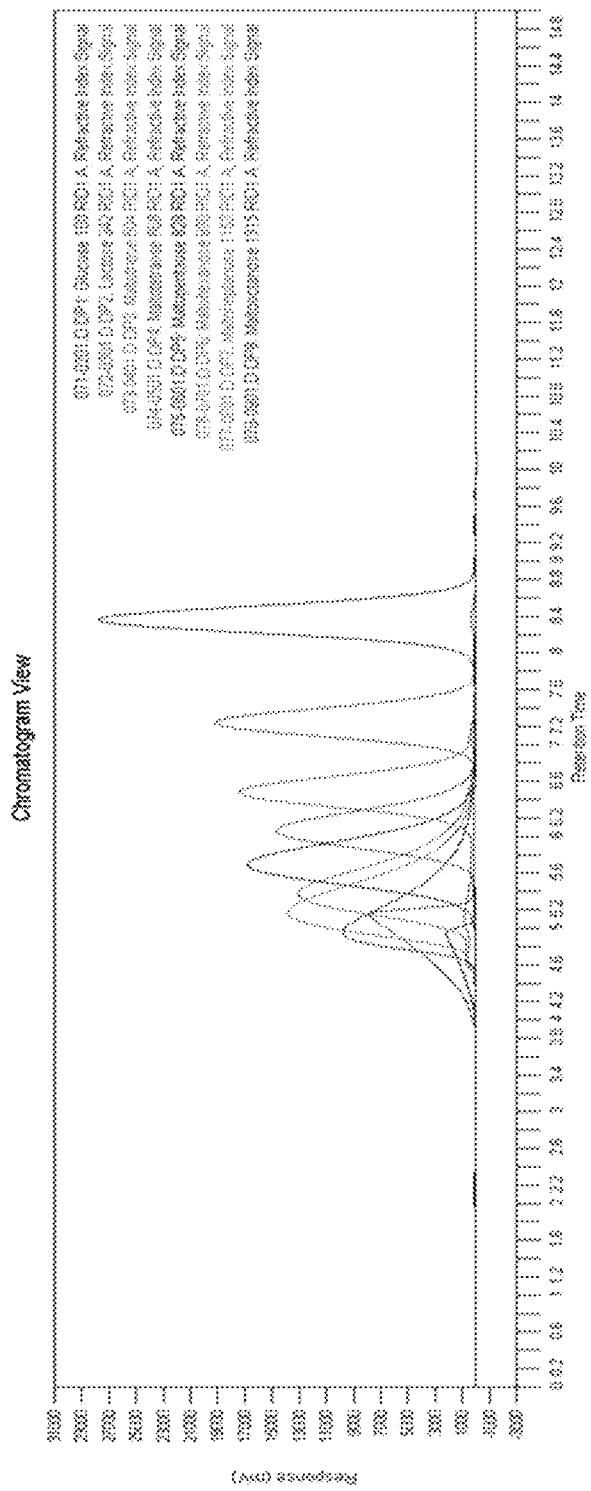
FIG. 7 depicts an overlay of SEC-HPLC chromatograms of standard glycans for use in Example 17.

The fold reduction in abundance of CRE pathogen or VRE pathogen for each experimental composition and patient sample was determined relative to water (negative control). The selected oligosaccharide composition reduced the abundance of both Carbapenem-resistant Enterobacteriaceae (FIG. 6A) and vancomycin-resistant Enterococcaceae (FIG. 6B) to a greater degree than FOS, a commercially available fiber. These results demonstrate that the selected oligosaccharide composition comprised of a plurality of glycans selected from Formula (I) and Formula (II) as produced by a process as described in Examples 1-3 and 16 is capable of reducing or preventing the growth of pathogens such as Carbapenem-resistant Enterobacteriaceae (CRE) and vancomycin-resistant Enterococcaceae (VRE) in a relevant model of HE.

Example 13: Collection of Fecal Samples

Fecal samples were collected by providing subjects with the Fisherbrand Commode Specimen Collection System (Fisher Scientific) and associated instructions for use. Collected samples were stored with ice packs or at −80° C. until processing (McInnes & Cutting, Manual of Procedures for Human Microbiome Project: Core Microbiome Sampling Protocol A, v12.0, 2010, hmpdacc.org/doc/HMP_MOP_Version12_0_072910.pdf). Alternative collection devices may also be used. For example, samples may be collected into the Faeces Tube 54×28 mm (Sarstedt AG, 25 ml SC Feces Container w/Scoop), Globe Scientific Screw Cap Container with Spoon (Fisher Scientific) or the OMNIgene-GUT collection system (DNA Genotek, Inc.), which stabilizes microbial DNA for downstream nucleic acid extraction and analysis. Aliquots of fecal samples were stored at −20° C. and −80° C. following standard protocols known to one skilled in the art.

Example 14: Determining the Level of Pathogens in Subjects

To determine the titer of pathogens carried in the gastrointestinal tract, fecal samples or rectal swabs are collected by a suitable method. Sample material is cultured on, e.g., i) Cycloserine-Cefoxitin Fructose Agar (available for instance from Anaerobe Systems) cultured anaerobically to selectively and differentially grow *Clostridium difficile*; ii) Eosin Methylene Blue Agar (available for instance from Teknova) cultured aerobically to titer *Escherichia coli* and other Gram-negative enteric bacteria, most of which are opportunistic pathogens; iii) Bile Esculin Agar (BD) cultured aerobically to titer *Enterococcus* species; iv) phenyl-ethylalcohol blood agar (Becton Dickinson), or Colistin-Nalidixic Acid (CNA) blood agar (for instance, from Hardy Diagnostics) cultured aerobically to grow *Enterococcus* and/or *Streptococcus* species; v) *Bifidobacterium* Selective Agar (Anaerobe Systems) to titer *Bifidobacterium* species; vi) or MacConkey Agar (Fisher Scientific) to titer *E. coli* and other Gram-negative enteric bacteria. Additional antibiotics can be used as appropriate to select drug-resistant subsets of these bacteria, for instance vancomycin (e.g., for vancomycin-resistant *Enterococcus*), cefoxitin (e.g., for extended spectrum beta lactamases or *Enterococcus*), ciprofloxacin (e.g., for fluoroquinolone resistance), ampicillin (e.g., for ampicillin resistant bacteria), and ceftazidime (e.g., for cephalosporin resistant bacteria). Additionally, chromogenic substrates may be added to facilitate the differentiation of pathogens from commensal strains, such as with ChromID plates (Biomerieux) or ChromAgar (Becton Dickinson). Plates are incubated at 35-37° C. under aerobic, anaerobic or microaerophilic conditions as appropriate for the pathogen. After 16-48 hours, colonies are counted and used to back-calculate the concentration of viable cells in the original sample.

For quantitative assessment, the subjects sample volume or weight is measured, and serial 1:10 dilutions prepared in phosphate buffered saline or other diluent, followed by plating, growth and counting of colonies to determine the level of a pathogen in a sample.

Alternatively, the quantity of a pathogen is measured by quantitative PCR. For this method, primers specific to one or more of the pathogens (including bacterial pathogens, viral pathogens and pathogenic protozoa) described herein are designed and used in a real-time quantitative PCR (for instance, using a PCR reaction to which a double-stranded-specific fluorescent dye such as Sybr Green, or a sequence-specific Taqman probe (Applied Biosystems/Thermo Scientific). Genomic DNA is extracted from each sample using the Mo Bio Powersoil®-htp 96 Well Soil DNA Isolation Kit (Mo Bio Laboratories, Carlsbad, Calif.) or QIAamp PowerFecal DNA Kit (Qiagen) according to the manufacturer's instructions or by bead beating, e.g., performed for 2 minutes using a BioSpec Mini-Beadbeater-96 (BioSpec Products, Bartlesville, Okla.). Alternatively, the genomic DNA is isolated using the Mo Bio Powersoil® DNA Isolation Kit (Mo Bio Laboratories, Carlsbad, Calif.) or the QIAamp DNA Stool Mini Kit (QIAGEN, Valencia, Calif.) according to the manufacturer's instructions. The cycle threshold of a sample of a subject in quantitative PCR is then compared to a standard curve of known quantities of pathogens to determine the level of pathogen in the sample. The development of assays is described (e.g., in "Application of the fluorogenic probe technique (TaqMan PCR) to the detection of *Enterococcus* spp. and *Escherichia coli* in water samples", Edith Frahm and Ursala Obst, J. Microbiol. Meth. 2003 January; 52(1):123-31.). Alternatively, to simplify assay design, analyte-specific reagents are available for many of the pathogens, for instance from Luminex, Inc (www.luminexcorp.com). Alternatively, or in addition, universal ribosomal primers are used to quantitatively measure the total copy number of genomes from pathogens to determine relative instead of absolute abundance of pathogens. If desired, the ratio of pathogen to total copies is calculated. The colony counts can be normalized (e.g., a ratio is calculated) to the total DNA content of the sample, or to the quantitative measure, e.g., determined by a qPCR using universal ribosomal primers.

Alternatively, the colony count of a pathogen, or all pathogens combined, is compared to the total colony count of the sample cultured under non-selective conditions. Samples are cultured on rich media or agar such as *Brucella* Blood Agar (Anaerobe Systems), Brain Heart Infusion Broth (Teknova), or chocolate agar (Anaerobe Systems). The maximum number of colonies on these media, grown anaerobically are used as the denominator in a normalized ratio of pathogens to commensals as a relative measure.

The amount of pathogen may also be estimated by 16s ribosomal DNA profiling. Genomic DNA is extracted from subject samples (e.g. fecal samples, rectal swabs, skin or mucosal swabs, biopsies or tissue samples), and variable region 4 of the 16S rRNA gene is amplified and sequenced (Earth Microbiome Project protocol www.earthmicrobiome.org/emp-standard-protocols/16s/ and Caporaso J G et al. 2012. Ultra-high-throughput microbial community analysis on the Illumina HiSeq and MiSeq platforms. ISME J.). Operational Taxonomic Units (OTUs) are generated by aligning 16S rRNA sequences at 97% identity, or lower as appropriate. Then the OTUs potentially representing pathogenic species are assessed by aligning the OTUs to known taxonomic structures such as those maintained by NCBI (ncbi.nlm.nih.gov) or the Ribosomal Database Project (https://rdp.cme.msu.edu), and their abundance estimated, for instance as a ratio of number of pathogen sequences to total number of sequences.

Example 15. HSQC NMR Analysis Procedure Using a Varian Unity Inova NMR Machine A determination of HSQC NMR spectra of samples of the selected oligosaccharide composition described in Examples 6-12, and produced as described in Examples 1-3 (10 batches were analyzed) and 21 (5 batches were analyzed), was performed using a Varian Unity Inova NMR, according to the protocol described below.

Method

Sample Preparation:

25 mg of a previously lyophilized solid sample of the oligosaccharide composition was dissolved in 300 uL of D2O with 0.1% acetone as internal standard. The solution was then placed into a 3 mm NMR tube.

NMR Experiment:

Each sample was analyzed in a Varian Unity Inova operating at 499.83 MHz (125.69 MHz 13C) equipped with a XDB broadband probe with Z-axis gradient, tuned to 13C, and operating at 25° C. Each sample was subjected to a multiplicity-edited gradient-enhanced 1H-13C heteronuclear single quantum coherence (HSQC) experiment using the echo-antiecho scheme for coherence selection. The pulse sequence diagram as described in FIG. 10, and acquisition and processing parameters as shown below were used to obtain the NMR spectrum for each sample Acquisition Parameters 1H Carrier Frequency=4 ppm 13C Carrier Frequency=65 ppm Number of points in acquisition dimension=596

Spectral range in acquisition dimension=6.00 ppm to 2.03 ppm

Number of points in indirect dimension=300 complex points

Spectral range in indirect dimension=120 ppm to 10 ppm

Recycle delay=1 second

One-bond 1H-13C coupling constant=JCH=146 Hz

Number of scans=8

Temperature=298 K

Solvent=D2O

Processing Parameters

Window function in direct dimension=Gaussian broadening, 7.66 Hz

Window function in indirect dimension=Gaussian broadening 26.48 Hz

Processing=512 complex points in direct dimension, 1024 complex points in indirect dimension Spectral Analysis:

The resulting spectra were analyzed using the MNova software package from Mestrelab Research (Santiago de Compostela, Spain). The spectra were referenced to the internal acetone signal (1H—2.22 ppm; 13C—30.8 ppm) and phased using the Regions2D method in both the F2 and F1 dimension. Apodization using 90 degree shifted sine was applied in both the F2 and F1 dimension. For each spectrum, individual signals (C—H correlations) were quantified by integration of their respective peaks using "predefined integral regions" with elliptical integration shapes. The resulting table of integral regions and values from the spectra were normalized to a sum of 100 in order for the value to represent a percentage of the total. The peak integral regions were selected to avoid peaks associated with monomers.

Results

Fifteen batches of the selected oligosaccharide composition (10 batches produced according to the processes described in Examples 1 or 3, and 5 batches produced according to the process of Example 21) were analyzed using the above NMR methods. Collectively, these batches comprised the following NMR peak signals (Table 4)

TABLE 4

HSQC NMR peaks of the selected oligosaccharide composition

| | 1H Position (ppm) | | | 13C Position (ppm) | | |
|---|---|---|---|---|---|---|
| | Center | 1H Integral Region | | Center | 13C Integral Region | |
| Signal | Position | from | to | Position | from | to |
| 1 | 3.67 | 3.607 | 3.742 | 63.35 | 63.78 | 62.92 |
| 2 | 3.97 | 3.925 | 4.008 | 66.25 | 66.78 | 65.73 |
| 3 | 3.88 | 3.848 | 3.910 | 67.13 | 67.50 | 66.76 |
| 4 | 3.71 | 3.674 | 3.753 | 67.34 | 68.02 | 66.65 |
| 5 | 3.83 | 3.791 | 3.864 | 71.27 | 71.70 | 70.84 |
| 6 | 3.96 | 3.906 | 4.014 | 71.58 | 71.91 | 71.24 |
| 7 | 3.72 | 3.669 | 3.777 | 72.4 | 72.78 | 72.02 |
| 8 | 3.33 | 3.262 | 3.404 | 73.76 | 74.29 | 73.23 |
| 9 | 4.06 | 4.022 | 4.108 | 77.39 | 77.89 | 76.90 |
| 10 | 4.11 | 4.066 | 4.147 | 81.73 | 82.15 | 81.32 |
| 11 | 4.51 | 4.461 | 4.556 | 103.34 | 103.95 | 102.72 |

The area under the curve (AUC) of each individual signal of signals 1-11 were determined relative to the total AUC of all signals 1-11. The AUC for each of the signals 1-11 were determined for the 10 batches of the selected oligosaccharide composition produced according to the methods of Examples 1-3 (and described in Example 5). Statistics that summarize the aggregated results of HSQC NMR analyses of the 10 batches are presented in Table 12.

TABLE 12

AUCs for peak signals of the selected oligosaccharide composition

| | Center Position (ppm) | | Mean | Maximum | Minimum |
|---|---|---|---|---|---|
| Signal | 1H | 13C | AUC | AUC | AUC |
| 1 | 3.67 | 63.35 | 22.61 | 24.25 | 21.85 |
| 2 | 3.97 | 66.25 | 5.90 | 6.31 | 5.44 |
| 3 | 3.88 | 67.13 | 3.46 | 3.81 | 3.17 |
| 4 | 3.71 | 67.34 | 7.37 | 7.74 | 7.04 |
| 5 | 3.83 | 71.27 | 7.01 | 7.85 | 6.64 |
| 6 | 3.96 | 71.58 | 6.89 | 7.39 | 6.49 |
| 7 | 3.72 | 72.4 | 8.72 | 9.65 | 7.45 |
| 8 | 3.33 | 73.76 | 15.79 | 16.63 | 14.39 |
| 9 | 4.06 | 77.39 | 6.83 | 7.85 | 6.13 |
| 10 | 4.11 | 81.73 | 5.41 | 5.89 | 5.07 |
| 11 | 4.51 | 103.34 | 9.91 | 10.42 | 9.12 |

The AUC for each of the signals 1-11 was determined for the 5 batches of the selected oligosaccharide composition produced according to the method of Example 21 (and described in Example 5). Statistics that summarize the aggregated results of HSQC NMR analyses of the 5 batches are presented in Table 13.

TABLE 13

AUCs for peak signals of the selected oligosaccharide composition

| | Center Position (ppm) | | Mean | Maximum | Minimum |
|---|---|---|---|---|---|
| Signal | 1H | 13C | AUC | AUC | AUC |
| 1 | 3.67 | 63.35 | 20.82 | 21.19 | 20.45 |
| 2 | 3.97 | 66.25 | 5.76 | 5.98 | 5.59 |
| 3 | 3.88 | 67.13 | 3.35 | 3.46 | 3.38 |
| 4 | 3.71 | 67.34 | 7.07 | 7.16 | 6.89 |
| 5 | 3.83 | 71.27 | 7.70 | 7.91 | 7.28 |
| 6 | 3.96 | 71.58 | 7.23 | 7.35 | 7.06 |
| 7 | 3.72 | 72.4 | 9.98 | 10.23 | 9.51 |
| 8 | 3.33 | 73.76 | 16.65 | 16.98 | 16.46 |

TABLE 13-continued

AUCs for peak signals of the selected oligosaccharide composition

| Signal | Center Position (ppm) $^1$H | Center Position (ppm) $^{13}$C | Mean AUC | Maximum AUC | Minimum AUC |
|---|---|---|---|---|---|
| 9 | 4.06 | 77.39 | 6.08 | 6.25 | 5.83 |
| 10 | 4.11 | 81.73 | 4.89 | 4.92 | 4.81 |
| 11 | 4.51 | 103.34 | 10.46 | 10.73 | 10.20 |

Figure 8A:
FIGS. 8A-8B depict representative HSQC NMR spectra.
Figure 8B:
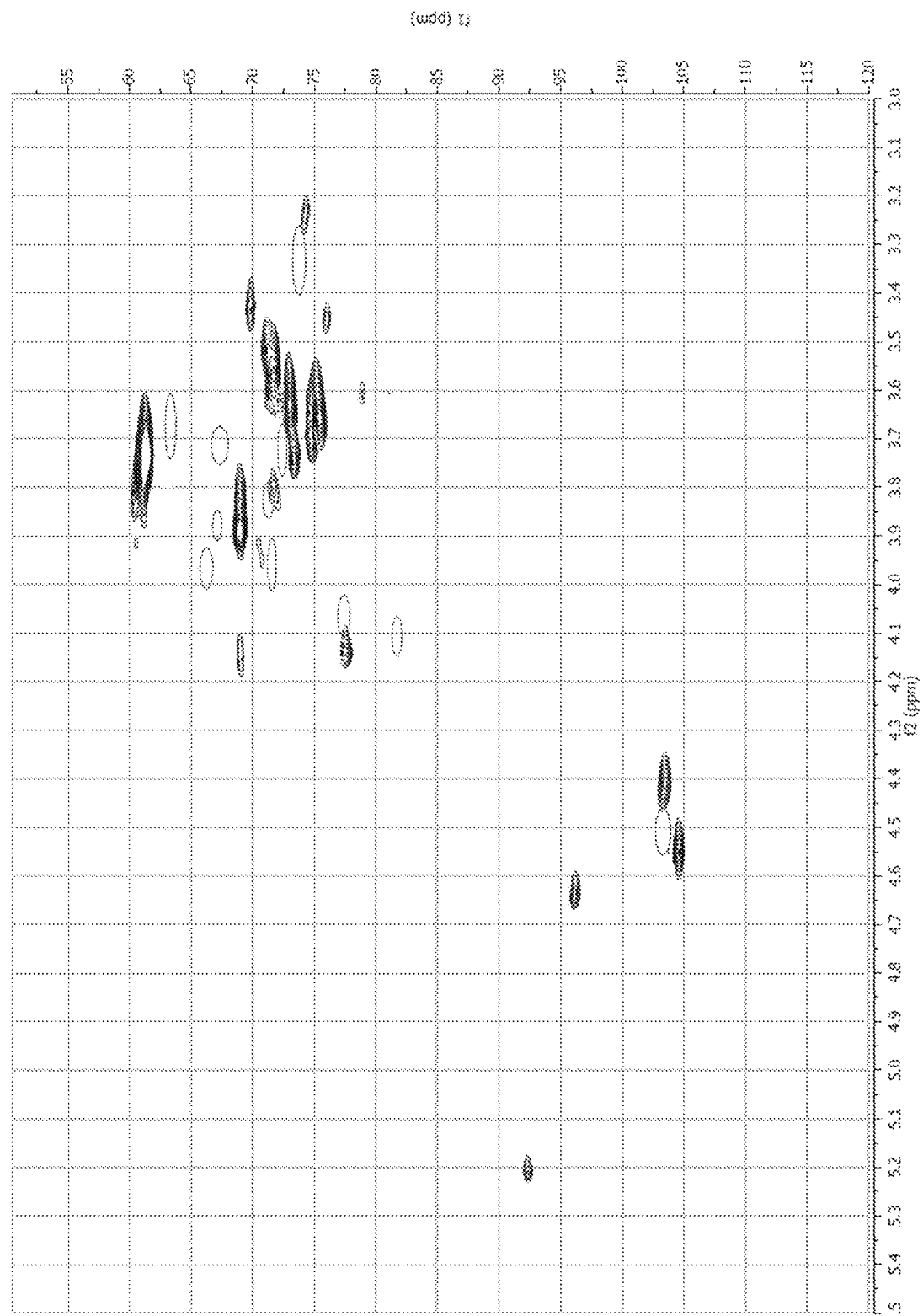

A representative HSQC NMR spectra of the selected oligosaccharide composition is provided in FIG. 8A. The integrated peaks for the HSQC spectra of the selected oligosaccharide composition, as denoted in Table 4, are circled. For comparative analyses, a HSQC NMR spectra of a known oligosaccharide, Galacto-oligosaccharide (GOS), was determined using the NMR methods described above. None of the integrated peaks of the selected oligosaccharide composition denoted in Table 4 overlap with the peaks in the NMR spectra of GOS (FIG. 8B).

Example 16: SEC HPLC Methodology for Determination of Impurities

SEC HPLC was used to determine the presence of residual organic acid impurities and related substances in samples of the selected oligosaccharide composition described in Examples 6-12 and produced by the processes described in Examples 1 or 3 and 21.

These methods involved the use of an Agilent 1100 with refractive index (RI) detector equipped with a guard column (Bio-Rad MicroGuard Cation H+ Cartridge, PIN 125-0129, or equivalent) and a Bio-Rad Aminex HPX-87H, 300×7.8 mm, 9 m, PIN 125-0140 column, or equivalent.

The mobile phase (25 mM $H_2SO_4$ in water) was prepared by filling a bottle with 2000 mL DI-water and slowly adding 2.7 mL of $H_2SO_4$. The solution was filtered through a 0.2 μm filter.

A standard solution was prepared by measuring 50±2 mg of reference standard into a 100-mL volumetric flask, adding mobile phase to 100-mL mark and mixing well.

A sample of a selected oligosaccharide composition (Sample A) was prepared in duplicate. Approximately 1000 mg of oligosaccharide sample was weighed into a 10 mL volumetric flask and mobile phase was added up to the mark. The solution was mixed and filtered through a PES syringe filter with a 0.2 m polyethersulfone membrane.

A sample of a selected oligosaccharide composition (Sample B) was prepared in duplicate. Approximately 700 mg of oligosaccharide sample was weighed into a 10 mL volumetric flask and mobile phase was added up to the mark. The solution was mixed and filtered through a PES syringe filter with a 0.2 m polyethersulfone membrane.

The flow rate was set to 0.65 mL/min at least 2 hours before running samples with the column temperature set to 50° C. and the RI detector temperature set to 50° C. with the RI detector purge turned on.

Before running samples wherein the injection volume for all samples was 50 μL and run time was 40 minutes, the detector purge was turned off and the pump was run at 0.65 mL/min until an acceptable baseline was obtained.

A blank sample consisting of DI water was run. The standard, sample A, and sample B were each independently run.

The peaks at 11.3 min (Levoglucosan), 11.9 min (Lactic Acid), and 13.1 min (Formic Acid) were integrated. The calibration curve fit type in Empower 3 software was set to $3^{rd}$ order.

Results

Thirty batches of the selected oligosaccharide composition described in Examples 1-4 and produced by the process described in Examples 1 or 3, and five batches of the selected oligosaccharide composition described in Examples 1-4 and produced by the process described in Example 21, were tested using the HPLC method described above. These batches had an average saccharide monomer content of 11.2%. The combined results of this analysis are presented in Table 14.

TABLE 14

Impurities data for selected production batches of oligosaccharide composition

| Impurity | Mean | Standard Dev. | Minimum-Maximum | +/−3SD | +/−5SD |
|---|---|---|---|---|---|
| Levoglucosan | 0.43% | 0.02 | 0.42%-0.49% | 0.57%-0.49% | 0.33%-0.53% |
| Lactic Acid | 0.06% | 0.01 | 0.04%-0.08% | 0.03%-0.09% | 0.01%-0.11% |
| Formic Acid | 0.06% | 0.02 | 0.0%-0.09% | 0.0%-0.12% | 0.0%-0.16% |
| Monomer (% DP1) | 11.2% | 1.1 | 8.5%-12.5% | 7.9%-14.5% | 5.7%-16.7% |

The five batches of the oligosaccharide composition produced according to the process described in Example 21 contain a mean of 0.38% levoglucosan (with a maximum of 0.39% and a minimum of 0.38% levoglucosan); a mean of 0.06% lactic acid (with a maximum of 0.07% and a minimum of 0.06% lactic acid); and a mean of 0.00% formic acid.

Example 17: HPLC Methodology for Determination of DP1 to DP7

The relative amounts of oligosaccharides with a degree of polymerization (DP) of 1, 2, and 3+ in samples of a selected oligosaccharide composition, as produced by the processes in Examples 1 and 3, were determined by SEC HPLC.

These methods involved the use of an Agilent 1100 with refractive index (RI) detector equipped with a guard column (Shodex SUGAR SP-G 6B Guard Column 6×50 mm, 10 μm, P/N F6700081, or equivalent) and a chromatography column (Shodex Sugar SP0810, 8.0×300 mm, 8 μm, P/N F6378105, or equivalent).

The mobile phase (0.1 M NaNO3) was prepared by weighing 42.5 g of NaNO3 (ACS grade reagent) and dissolving in 5000 mL of deionized (DI) water (from MiliQ water filter). The solution was filtered through a 0.2 m filter.

Polymer standard solutions (10.0 mg/mL) of each of D-(+) Glucose Mp 180, Carbosynth Ltd Standard, or equivalent (CAS #50-99-7) (DP1); Maltose Mp 342, Carbosynth Ltd Standard, or equivalent (CAS #69-79-4) (DP2); Maltotriose Mp 504, Carbosynth Ltd Standard, or equivalent (CAS #1109-28-0) (DP3); Maltotetraose Mp 667, Carbosynth Ltd Standard, or equivalent (CAS #34612-38-9) (DP4); Maltopentaose Mp 828, Carbosynth Ltd Standard, or equivalent (CAS #34620-76-3) (DP5); Maltohexaose Mp 990, Carbosynth Ltd Standard, or equivalent (CAS #34620-77-4) (DP6); Maltoheptaose Mp 1153, Carbosynth Ltd Standard, or equivalent (CAS #34620-78-5) (DP7); and Maltooctaose Mp 1315, Carbosynth Ltd Standard, or equivalent (CAS #6156-84-9) (DP8), were prepared by weighing 10 mg of a standard into an individual 1.5 mL centrifuge tube and adding DI water to make 10 mg/mL solution.

Samples of the selected oligosaccharide composition were prepared as 10 mg/mL concentrated samples or dilute aqueous samples to 2.5-3.5 Brix.

The flow rate was set to 1.0 mL/min at least 2 hours before running samples with the column temperature set to 70° C. and the RI detector temperature set to 40° C. with the RI detector purge turned on.

Before running samples wherein the injection volume for all samples was 5 µL and run time was 15 minutes, the detector purge was turned off and the pump was run at 1.0 mL/min until an acceptable baseline was obtained.

A blank sample consisting of DI water, individual standards, and sample were independently run.

Each peak between 4 and 9.2 minutes in the sample run, corresponding to individual standards, was integrated. An overlay of the standards in shown in FIG. 10. The calibration curve fit type in Empower 3 software was set to $3^{rd}$ order. The DP1, DP2, and DP3+ values of the samples (samples of selected oligosaccharide composition) were determined using these methods.

Results

Ten samples of selected oligosaccharide composition were assayed using this method. The selected oligosaccharide composition comprised 7.78% (±1.14%) monomer (DP1), 10.66% (±1.41%) disaccharide (DP2), and 81.56% (±2.53%) oligomers having three or more repeat units (DP3+).

Example 18: Production of an Exemplary Oligosaccharide Composition at 100 g Scale from Dextrose Monohydrate and Galactose The present example demonstrates the synthesis of oligosaccharide composition comprising glucose and galactose sub-units at 100 g scale (dry oligosaccharide composition) in a three-neck round-bottomed flask.

The flask was placed in a heating mantle, and one side arm was fitted with a stoppered thermocouple. The other side arm was fitted with an ethylene glycol-cooled vertical condenser distillation head connected to a vacuum manifold and receiving flask. The center neck was connected to an overhead stirrer via stirring rod and half-moon style stirring paddle.

50.0 g of D-glucose and 50.0 g of D-galactose were added to the flask, followed by 50 g anhydrous glucose and 9.4 g of wet catalyst (4.4 g dry basis) (poly-styrene-co-divinyl-benzene comprising >3.0 mmol/g sulfonic acid moieties, e.g., Dowex® Marathon® C resin). The solids were stirred at 100 rpm, reaction heating was initiated, and 25 mL DI water was added to the mixture.

Upon reaching 100° C. (internal temperature), the sugar-water mixture began to melt. After reaching 120° C. the reaction mixture homogenized and the catalyst dispersed completely. Vacuum (700 mbar) was then applied and the reaction proceeded with distillation of water.

After two and a half hours, the heat source was removed. After the mixture had cooled to 100° C., 300 mL of DI water was added and stirred under ambient conditions until complete dissolution occurred.

The catalyst was removed by filtration and rinsed with 150 mL of DI water. The combined liquids were collected and passed through a serial array of three purification columns in the following order: DOWEX Monosphere 88 Strong Acid Cation (H+), DOWEX Monosphere 77 Weak Base Anion (OH−), DOWEX Optipore SD-2 Adsorbent resin. The purified oligosaccharide composition was passed through a filter and concentrated to 25 brix via rotary evaporation.

Example 19: Determination of Glycosidic Bond Distribution Using Permethylation Analysis A determination of the glycosidic bond distribution of samples of the selected oligosaccharide composition, as described in Examples 6-12, was performed using permethylation analysis, according to the protocol described below. Samples of the selected oligosaccharide composition made using the production methods of Examples 1 or 3, 20, and 21 were analyzed using this procedure.

The reagents used in this procedure included methanol, acetic acid, sodium borodeuteride, sodium carbonate, dichloromethane, isopropanol, trifluoroacetic acid (TFA), and acetic anhydride. The equipment used in this procedure included a heating block, drying apparatus, gas chromatograph equipped for capillary columns and with a RID/MSD detector, and a 30 meter RTX®-2330 (RESTEK). All derivation procedures were done in a fume hood.

Preparation of Alditol Acetates

A. Standard Preparation 1 mg/mL solutions of the following standard analytes were prepared: arabinose, rhamnose, fucose, xylose, mannose, galactose, glucose, and inositol. The standard was prepared by mixing 50 µL of each of arabinose, xylose, fucose, glucose, mannose, and galactose with 20 µL of inositol in a vial. The standard was subsequently lyophilized.

B. Sample Preparation

Each sample was prepared by mixing 100-500 µg of of the selected oligosaccharide composition (as weighed on an analytical balance) with 20 µg (20 µL) of inositol in a vial.

C. Hydrolysis

200 µL of 2 M tifluoroacetic acid (TFA) was added to the each of the oligosaccharide sample(s). The vial containing the sample was capped tightly and incubated on a heating block for 2 hours at 121° C. After 2 hours, the sample was removed from the heating block and allowed to cool to room temperature. The sample was then dried down with $N_2$/air. µL of IPA (isopropanol) was added and dried down again with $N_2$/air. This hydrolysis step (addition of TFA for two hours at 121° C.; washing with isopropanol) was repeated twice.

The standard was similarly subjected to hydrolysis using TFA, as described for the sample.

D. Reduction and Acetylation

A 10 mg/mL solution of sodium borodeuteride was prepared in 1 M ammonium hydroxide. 200 µL of this solution was added to each oligosaccharide sample. The sample was then incubated at room temperature for at least one hour or overnight. After incubation with sodium borodeuteride solution, 5 drops of glacial acetic acid were added to the sample, followed by 5 drops of methanol. The sample was then dried down. 500 μL of 9:1 MeOH:HOAc was added to the sample and subsequently dried down (twice repeated). 500 μL MeOH was then added to the sample and subsequently dried down (once repeated). This produced a crusty white residue on the side of the sample vial.

250 μL acetic anhydride was then added to each sample vial and the sample was vortexed to dissolve. 230 μL of concentrated TFA was added to the sample and the sample was incubated at 50° C. for 20 minutes. The sample was removed from the heat and allowed to cool to room temperature. Approximately 1 mL isopropanol was added and the sample was dried down. Then, approximately 200 μL isopropanol was added and the sample was dried down again. Approximately 1 mL of 0.2M sodium carbonate was then added to the sample and it was mixed gently. Approximately 2 mL dichloromethane was finally added to the sample, after which it was vortexed and centrifuged briefly. The aqueous top layer was discarded. 1 mL water was added and the sample was vortexed and centrifuged briefly. This step was repeated before the organic layer (bottom) was removed and transferred to another vial. The sample was concentrated using $N_2$/air to a final volume of about 100 μL. 1 μL of final sample was then injected on GC-MS.

The GC temperature program SP2330 was utilized for GC-MS analysis. The initial temperature was 80° C. and the initial time was 2.0 minutes. The first ramp was at a rate of 30° C./min with a final temperature of 170° C. and a final time of 0.0 minutes. The second ramp was at a rate of 4° C./min with a final temperature of 240° C. and a final time of 20.0 minutes.

Glycosyl-Linkage Analysis of Poly- and Oligosaccharides by Hakomori Methylation

A. Preparation of NaOH Base

In a glass screw top tube, 100 μL of a 50/50 NaOH solution and 200 μL of dry MeOH were combined. Plastic pipets were used for the NaOH and glass pipets were used for the MeOH. The solution was vortexed briefly, approximately 4 mL dry DMSO was added, and the solution was vortexed again. The tube was centrifuged to concentrate the solution and the DMSO and salts were pipetted off from the pellet. The previous two steps were repeated about four times in order to remove all the water from the pellet. All white residue was removed from the sides of the tube. Once all the residue was removed and the pellet was clear, about 1 mL dry DMSO was added and the solution was vortexed. The base was then ready to use. The base was prepared fresh each time it was needed.

B. Permethylation

Each sample was prepared by mixing 600-1000 μg of the selected oligosaccharide composition (as weighed on an analytical balance) with 200 μL DMSO. The sample was stirred overnight until the oligosaccharide composition dissolved.

An equal amount of NaOH base (400 μL) was added to the sample, after which the sample was placed back on the stirrer and mixed well for 10 minutes. 100 μL of iodomethane ($CH_3I$) was added to the sample. The sample was mixed on the stirrer for 20 minutes, and then the previous steps (addition of NaOH base and iodomethane) were repeated.

Approximately 2 mL ultrapure water was added to the sample and the sample was mixed well, such that it turned cloudy. The tip of a pipette was placed into the sample solution at the bottom of the tube and $CH_3I$ was bubbled off with a very low flow of air. The sample became clear as the $CH_3I$ was bubbled off. The pipette was moved around the solution to make certain that all the $CH_3I$ was gone. Approximately 2 mL methylene chloride was then added and the solution was mixed well by vortex for 30 seconds. The sample was then centrifuged and the top aqueous layer was removed. Approximately 2 mL of water were added and the sample was mixed, then briefly centrifuged, then the top aqueous layer was removed. The additions of methylene chloride and water were repeated. The organic bottom layer was removed and transferred into another tube and dried down using $N_2$. The analysis was continued with Alditol Acetates.

C. Hydrolysis

200 μL of 2 M tifluoroacetic acid (TFA) was added to the sample(s). The vial containing the sample was capped tightly and incubated on a heating block for 2 hours at 121° C. After 2 hours, the sample was removed from the heating block and allowed to cool to room temperature. The sample was then dried down with $N_2$/air. 200 μL of IPA (isopropanol) was added and dried down again with $N_2$/air. This hydrolysis step (addition of TFA for two hours at 121° C.; washing with isopropanol) was repeated twice.

D. Reduction and Acetylation

A 10 mg/mL solution of sodium borodeuteride was prepared in 1 M ammonium hydroxide. 200 μL of this solution was added to each oligosaccharide sample. The sample was then incubated at room temperature for at least one hour or overnight. After incubation with sodium borodeuteride solution, 5 drops of glacial acetic acid were added to the sample, followed by 5 drops of methanol. The sample was then dried down. 500 μL of 9:1 MeOH:HOAc was added to the sample and subsequently dried down (twice repeated). 500 μL MeOH was then added to the sample and subsequently dried down (once repeated). This produced a crusty white residue on the side of the sample vial.

250 μL acetic anhydride was then added to each sample vial and the sample was vortexed to dissolve. 230 μL concentrated TFA was added to the sample and the sample was incubated at 50° C. for 20 minutes. The sample was removed from the heat and allowed to cool to room temperature. Approximately 1 mL isopropanol was added and the sample was dried down. Then, approximately 200 μL isopropanol was added and the sample was dried down again. Approximately 1 mL of 0.2M sodium carbonate was then added to the sample and it was mixed gently. Approximately 2 mL dichloromethane was finally added to the sample, after which it was vortexed and centrifuged briefly. The aqueous top layer was discarded. 1 mL water was added and the sample was vortexed and centrifuged briefly. This step was repeated before the organic layer (bottom) was removed and transferred to another vial. The sample was concentrated using $N_2$/air to a final volume of about 100 μL. 1 μL of final sample was then injected on GC-MS.

The GC temperature program SP2330 was utilized for GC-MS analysis. The initial temperature was 80° C. and the initial time was 2.0 minutes. The first ramp was at a rate of 30° C./min with a final temperature of 170° C. and a final time of 0.0 minutes. The second ramp was at a rate of 4° C./min with a final temperature of 240° C. and a final time of 20.0 minutes.

Results

Permethylation data was collected using the methods described above for ten batches of de-monomerized oligosaccharide composition (four batches produced by the process of Example 18 (each analyzed two times), and six batches produced by the process of Example 1 or Example 3 (five batches analyzed two times and one batch analyzed one time). These batches were demonomerized according to the method described in Example 4. Averaged data relating to the radicals present in these batches of de-monomerized oligosaccharide composition are provided in Table 2 below.

TABLE 2

Permethylation Data for selected oligosaccharide produced using Marathon C catalyst

| Monomer Radicals | Mean mol % + 5 STD | Mean mol % + 3 STD | Mean mol % | Mean mol % − 3 STD | Mean mol % − 5 STD |
|---|---|---|---|---|---|
| t-glucopyranose monoradicals | 26.77% | 22.86% | 16.99% | 11.12% | 7.21% |
| t-galactofuranose monoradicals | 10.27% | 8.13% | 4.91% | 1.70% | 0.00% |
| t-galactopyranose monoradicals | 17.42% | 15.40% | 12.38% | 9.36% | 7.34% |
| 3-glucopyranose monoradicals | 6.24% | 5.46% | 4.29% | 3.12% | 2.34% |
| 2-glucopyranose monoradicals | 4.13% | 3.77% | 3.24% | 2.70% | 2.35% |
| 2-galactofuranose and/or 2-glucofuranose monoradicals | 5.19% | 3.76% | 1.63% | 0.00% | 0.00% |
| 3-glucofuranose monoradicals | 0.92% | 0.57% | 0.06% | 0.00% | 0.00% |
| 3-galactopyranose monoradicals | 5.14% | 4.45% | 3.43% | 2.41% | 1.73% |
| 3-galactofuranose monoradicals | 3.61% | 3.05% | 2.20% | 1.36% | 0.79% |
| 2-galactopyranose monoradicals | 4.24% | 3.55% | 2.52% | 1.48% | 0.79% |
| 6-glucopyranose monoradicals | 16.18% | 13.96% | 10.63% | 7.30% | 5.08% |
| 4-galactopyranose and/or 5-galactofuranose monoradicals | 4.89% | 4.32% | 3.47% | 2.62% | 2.06% |
| 4-glucopyranose and/or 5-glucofuranose monoradicals | 5.62% | 4.94% | 3.92% | 2.90% | 2.22% |
| 2,3-galactofuranose diradicals | 1.15% | 0.76% | 0.16% | 0.00% | 0.00% |
| 6-glucofuranose monoradicals | 2.38% | 1.77% | 0.87% | 0.00% | 0.00% |
| 6-galactofuranose monoradicals | 5.69% | 4.62% | 3.02% | 1.42% | 0.35% |
| 6-galactopyranose monoradicals | 11.52% | 10.06% | 7.86% | 5.66% | 4.19% |
| 3,4-galactopyranose and/or 3,5-galactofuranose and/or 2,3-galactopyranose diradicals | 2.27% | 1.82% | 1.15% | 0.47% | 0.03% |
| 3,4-glucopyranose and/or 3,5-glucofuranose diradicals | 1.76% | 1.29% | 0.57% | 0.00% | 0.00% |
| 2,3-glucopyranose diradicals | 1.79% | 1.23% | 0.41% | 0.00% | 0.00% |
| 2,4-glucopyranose and/or 2,5-glucofuranose and/or 2,4-galactopyranose and/or 2,5-galactofuranose diradicals | 1.71% | 1.51% | 1.21% | 0.91% | 0.71% |
| 3,6-glucopyranose diradicals | 3.27% | 2.84% | 2.20% | 1.56% | 1.13% |
| 3,6-glucofuranose diradicals | 0.77% | 0.59% | 0.31% | 0.03% | 0.00% |

TABLE 2-continued

Permethylation Data for selected oligosaccharide produced using Marathon C catalyst

| Monomer Radicals | Mean mol % + 5 STD | Mean mol % + 3 STD | Mean mol % | Mean mol % − 3 STD | Mean mol % − 5 STD |
|---|---|---|---|---|---|
| 2,6-glucopyranose and/or 4,6-glucopyranose and/or 5,6-glucofuranose diradicals | 5.57% | 4.34% | 2.50% | 0.66% | 0.00% |
| 3,6-galactofuranose diradicals | 1.84% | 1.58% | 1.19% | 0.80% | 0.55% |
| 4,6-galactopyranose and/or 5,6-galactofuranose diradicals | 4.78% | 3.91% | 2.60% | 1.29% | 0.42% |
| 2,3,4-glucopyranose and/or 2,3,5-glucofuranose triradicals | 0.52% | 0.32% | 0.03% | 0.00% | 0.00% |
| 3,6-galactopyranose diradicals | 3.65% | 3.11% | 2.30% | 1.49% | 0.94% |
| 2,6-galactopyranose diradicals | 1.87% | 1.57% | 1.11% | 0.66% | 0.36% |
| 3,4,6-galactopyranose and/or 3,5,6-galactofuranose and/or 2,3,6-galactofuranose triradicals | 2.20% | 1.69% | 0.92% | 0.14% | 0.00% |
| 3,4,6-glucopyranose and/or 3,5,6-glucofuranose triradicals | 1.57% | 1.09% | 0.36% | 0.00% | 0.00% |
| 2,3,6-glucofuranose triradicals | 0.15% | 0.10% | 0.01% | 0.00% | 0.00% |
| 2,4,6-glucopyranose and/or 2,5,6-glucofuranose triradicals | 1.23% | 0.93% | 0.49% | 0.05% | 0.00% |
| 2,3,6-galactopyranose and/or 2,4,6-galactopyranose and/or 2,5,6-galactofuranose triradicals | 1.81% | 1.35% | 0.67% | 0.00% | 0.00% |
| 2,3,6-glucopyranose triradicals | 1.21% | 0.86% | 0.35% | 0.00% | 0.00% |
| 2,3,4,6-glucopyranose and/or 2,3,5,6-glucofuranose tetraradicals | 0.68% | 0.43% | 0.05% | 0.00% | 0.00% |

Permethylation data was also collected using the methods described above for 5 batches of de-monomerized oligosaccharide composition produced according to the process described in Example 21. These batches were demonomerized according to the method described in Example 4. Averaged data relating to the radicals present in these batches of de-monomerized oligosaccharide composition are provided in Table 3 below.

TABLE 3

Permethylation Data for selected oligosaccharide produced using citric acid catalyst

| Radicals | Mean mol % + 5 STD | Mean mol % + 3 STD | Mean mol % | Mean mol % − 3 STD | Mean mol % − 5 STD |
|---|---|---|---|---|---|
| t-glucopyranose monoradicals | 35.34% | 30.95% | 24.36% | 17.77% | 13.38% |
| t-galactofuranose monoradicals | 8.47% | 7.58% | 6.23% | 4.89% | 3.99% |
| t-galactofuranose monoradicals | 1.12% | 0.91% | 0.60% | 0.30% | 0.09% |
| t-galactopyranose monoradicals | 25.33% | 21.45% | 15.64% | 9.82% | 5.94% |
| 3-glucopyranose monoradicals | 4.95% | 4.52% | 3.88% | 3.24% | 2.82% |
| 2-glucopyranose monoradicals | 4.01% | 3.74% | 3.33% | 2.92% | 2.64% |
| 2-galactofuranose and/or 2-glucofuranose monoradicals | 2.45% | 2.26% | 1.96% | 1.67% | 1.48% |
| 3-glucofuranose monoradicals | 0.62% | 0.50% | 0.32% | 0.14% | 0.02% |
| 3-galactopyranose monoradicals | 4.16% | 3.66% | 2.91% | 2.16% | 1.66% |
| 3-galactofuranose monoradicals | 2.11% | 1.97% | 1.76% | 1.55% | 1.41% |
| 2-galactopyranose monoradicals | 2.68% | 2.45% | 2.11% | 1.77% | 1.54% |
| 6-glucopyranose monoradicals | 13.91% | 12.07% | 9.31% | 6.55% | 4.71% |
| 4-galactopyranose and/or 5-galactofuranose monoradicals | 3.64% | 3.11% | 2.32% | 1.52% | 0.99% |
| 4-glucopyranose and/or 5-glucofuranose monoradicals | 4.73% | 3.97% | 2.84% | 1.70% | 0.95% |
| 2,3-galactofuranose diradicals | 0.42% | 0.35% | 0.24% | 0.14% | 0.07% |
| 6-glucofuranose monoradicals | 0.58% | 0.45% | 0.26% | 0.06% | −0.06% |
| 6-galactofuranose monoradicals | 4.16% | 3.56% | 2.67% | 1.78% | 1.18% |
| 6-galactopyranose monoradicals | 7.95% | 7.13% | 5.91% | 4.70% | 3.88% |
| 3,4-galactopyranose and/or 3,5-galactofuranose and/or 2,3-galactopyranose diradicals | 1.57% | 1.33% | 0.96% | 0.59% | 0.34% |
| 3,4-glucopyranose and/or 3,5-glucofuranose diradicals | 0.97% | 0.75% | 0.42% | 0.09% | −0.13% |
| 2,3-glucopyranose diradicals | 0.75% | 0.57% | 0.31% | 0.04% | −0.14% |
| 2,4-glucopyranose and/or 2,5-glucofuranose and/or 2,4-galactopyranose and/or 2,5-galactofuranose diradicals | 1.43% | 1.18% | 0.79% | 0.41% | 0.16% |
| 3,6-glucopyranose diradicals | 2.49% | 2.06% | 1.41% | 0.77% | 0.34% |
| 3,6-glucofuranose diradicals | 0.34% | 0.26% | 0.15% | 0.03% | −0.04% |
| 2,6-glucopyranose and/or 4,6-glucopyranose and/or 5,6-glucofuranose diradicals | 0.40% | 0.31% | 0.17% | 0.03% | −0.07% |
| 3,6-galactofuranose diradicals | 3.99% | 3.30% | 2.25% | 1.20% | 0.50% |
| 4,6-galactopyranose and/or 5,6-galactofuranose diradicals | 1.32% | 1.08% | 0.71% | 0.35% | 0.10% |
| 2,3,4-glucopyranose and/or 2,3,5-glucofuranose triradicals | 3.26% | 2.67% | 1.79% | 0.92% | 0.33% |
| 3,6-galactopyranose diradicals | 0.17% | 0.12% | 0.05% | −0.02% | −0.06% |
| 2,6-galactopyranose diradicals | 2.57% | 2.18% | 1.59% | 1.01% | 0.62% |
| 3,4,6-galactopyranose and/or 3,5,6-galactofuranose and/or 2,3,6-galactofuranose triradicals | 1.17% | 1.02% | 0.81% | 0.59% | 0.45% |
| 3,4,6-glucopyranose and/or 3,5,6-glucofuranose triradicals | 1.12% | 0.90% | 0.56% | 0.23% | 0.01% |
| 2,3,6-glucofuranose triradicals | 0.63% | 0.48% | 0.25% | 0.02% | −0.13% |
| 2,4,6-glucopyranose and/or 2,5,6-glucofuranose triradicals | 0.09% | 0.07% | 0.05% | 0.02% | 0.00% |
| 2,3,6-galactopyranose and/or 2,4,6-galactopyranose and/or 2,5,6-galactofuranose triradicals | 0.38% | 0.31% | 0.21% | 0.11% | 0.04% |
| 2,3,6-glucopyranose triradicals | 0.80% | 0.67% | 0.47% | 0.28% | 0.14% |
| 2,3,4,6-glucopyranose and/or 2,3,5,6-glucofuranose tetraradicals | 0.51% | 0.42% | 0.29% | 0.16% | 0.07% |

Example 20. Production of the Oligosaccharide Composition at 900 kg Scale from Dextrose Monohydrate and Galactose Using a Soluble Acid Catalyst (Citric Acid)

The selected oligosaccharide composition described in Examples 6-12 was synthesized at 900 kg scale in a 2,840 L (750-gallon) reactor with overhead agitation. The reactor was equipped with a heat jacket and a condenser.

To initiate production, about 200 kg (±20 kg) of purified water was added to the reactor and heated to about 90° C. (±5° C.). The reactor was then charged with about 675 kg (±10 kg) of food grade dextrose monohydrate. The dextrose was stirred until it dissolved. The reactor was then charged with about 619 kg (±10 kg) of galactose, which was then stirred until dissolved. About 37 kg (±0.5 kg) of citric acid was then added to the reactor as a catalyst and then stirred until it dissolved. The reactor was then heated while stirring until the internal baffle temperature was 130° C. (using a jacket temperature of not more than 148° C. as a set point), and the distillate was condensed into a condensation collection tank. The reactor was held at approximately 130° C. for about 30 minutes (±5 minutes). The molar ratio of condensate to feed sugar (glucose and galactose) was between 0.4 and 0.9, generally. The reaction was then quenched by charging the reactor with about 730 kg (±30 kg) of purified water by a spray ring. The purified water was heated to about 90° C. (±5° C.) in a heated tank equipped with a heat jack (with a jacket set point of 100° C.) before it was added to the reactor to quench the reaction. The reactor material was then cooled to about 55° C. (±5° C.) and purified water was added to adjust the material to about a 45-55% solids concentration (measured as Brix).

The resulting solution was then sequentially processed through ion-exchange resins to reduce trace metal ions, improve color, and reduce organic acids. The material was first transferred under controlled flow (240 kg/hr) to a first column of adsorbent chromatography resin (Dowex Optipore SD-2), and then through a second 75 kg of adsorbent resin (Dowex Optipore SD-2). The material was then transferred to a column of 66 kg of anion exchange resin (Dowex Monosphere 77), and then through a second column of 66 kg anion exchange resin (Dowex Monosphere 77). The resulting material was then cooled to about 30° C. (±5° C.) and discharged through a 0.45 micron filter into containers for storage at 2-8° C. The yield of the reaction was approximately 900 kg of oligosaccharide composition on a solid basis (about 1,800 kg of 50% solids solution). The oligosaccharide composition can be stored under these conditions until it is ready to be spray dried.

The purified oligosaccharide composition can be converted to solid powder by mixing the composition and United States Pharmacopeia (USP) purified grade water in a vessel until a 50% solids concentration is obtained. The solution can then be spray dried, and the resulting powder transferred into a container, e.g., a low-density polyethylene (LDPE) bag. This material can be packaged, e.g., in twist-tied double LDPE bags with approximately 280 g desiccant placed between two LDPE bags, and stored, e.g., in a 30-gallon high density polyethylene (HDPE) container at controlled room temperature.

Example 21: Production of an Exemplary Oligosaccharide Composition at 10 kg Scale from Dextrose Monohydrate and Galactose Using Soluble Catalyst A 22 L reactor (22 L Littleford Reactor) equipped with a condenser, oil, and air-cooled chiller was used in the synthesis of oligosaccharide compositions. The reactor mixing element was set to 30 Hz. The oil heater is set to an appropriate temperature to bring the reactor contents to 136° C.

About 5.0 kg of dextrose monohydrate, 4.5 kg of anhydrous galactose, and 0.27 kg of anhydrous citric acid along with 0.38 kg of USP purified water was added into the reactor. A condenser was attached to the top port of the reactor. The internal temperature of the reactor was monitored, and a timer initiated when the contents reached 100° C. The reaction mixture continued to be mixed and heated for 3.5 hours or until the internal temperature reaches 138.0° C.

At that point, the oil heater temperature was reduced and 6 kg of USP purified water previously heated to 95° C. was used to quench the reaction by adding preheated water to the reaction mixture at a rate of 60 mL/min until the temperature of the reactor contents decreased to 120° C., then at a rate of 150 mL/min until the temperature of the reactor contents decreased to 110° C., then at a rate of 480 mL/min until the temperature of the reactor contents decreased below 100° C. and a total of 6 kg of water was added. The reactor contents were further cooled to below 85° C.

Once the quench was finished, the USP purified water for quenching container was removed and replaced with USP purified water for dilution (about 2.2 kg, in order to obtain a total of 8.2 kg of USP water added between quenching and dilution). At an internal reactor temperature of 80° C. or below, the reactor was drained into the receiving vessel. The receiving vessel containing the diluted crude glycan composition was further cooled. The glycan composition was further purified by filtration through a 0.45 μm filter.

The oligosaccharide composition was then purified by flowing through a decolorizing polymer resin (Dowex® OptiPore SD-2) and then an anionic exchange resin (Dowex® Monosphere 77WBA) column.

EQUIVALENTS AND TERMINOLOGY

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, optional features, modification and variation of the concepts herein disclosed may be resorted to by those skilled in the art, and that such modifications and variations are considered to be within the scope of this disclosure.

In addition, where features or aspects of the disclosure are described in terms of Markush groups or other grouping of alternatives, those skilled in the art will recognize that the disclosure is also thereby described in terms of any individual member or subgroup of members of the Markush group or other group.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

What is claimed is:

1. An oligosaccharide composition comprising a plurality of oligosaccharides that comprise Formula (I) and Formula (II):

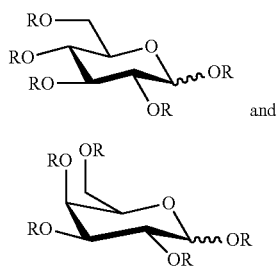

(I)

and

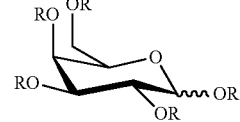

(II)

wherein R in Formula (I) and Formula (II) is independently selected from hydrogen, and Formulae (Ia), (Ib), (Ic), (Id), (IIa), (IIb), (IIc), (IId):

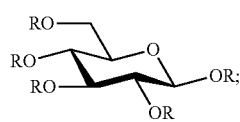

(Ia)

(Ib)

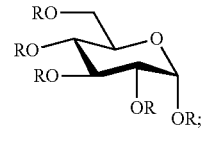

(Ic)

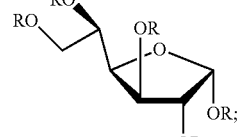

(Id)

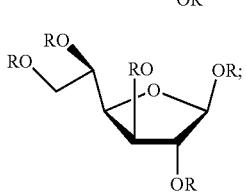

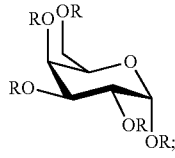

(IIa)

(IIb)

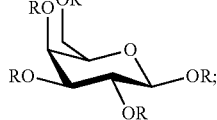

(IIc)

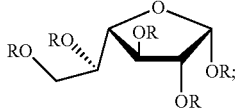

(IId)

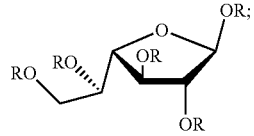

wherein R in Formulae (Ia), (Ib), (Ic), (Id), (IIa), (IIb), (IIc), and (IId) is independently defined as above in Formula (I) and Formula (II);

wherein the oligosaccharide composition is produced by a process comprising:
(a) forming a reaction mixture comprising a dextrose preparation and a galactose preparation with a catalyst comprising positively charged hydrogen ions; and
(b) promoting acid catalyzed oligosaccharide formation in the reaction mixture by transferring sufficient heat to the reaction mixture to maintain the reaction mixture at its boiling point until the weight percent of dextrose monomer and galactose monomer in the oligosaccharide composition is in a range of 5%-20% w:w; and wherein the plurality of oligosaccharides is characterized by a multiplicity-edited gradient-enhanced $^1$H-$^{13}$C heteronuclear single quantum correlation (HSQC) NMR spectrum comprising signals 1 to 11:

| Signal | Center Position (ppm) $^1$H | Center Position (ppm) $^{13}$C | Area under the curve (AUC) (% of total areas of signals 1-11) |
|---|---|---|---|
| 1 | 3.67 | 63.35 | 18.67-26.54 |
| 2 | 3.97 | 66.25 | 4.46-7.34 |
| 3 | 3.88 | 67.13 | 2.39-4.52 |
| 4 | 3.71 | 67.34 | 6.06-8.68 |
| 5 | 3.83 | 71.27 | 5.18-8.84 |
| 6 | 3.96 | 71.58 | 5.40-8.38 |
| 7 | 3.72 | 72.4 | 5.57-11.87 |
| 8 | 3.33 | 73.76 | 12.44-19.14 |
| 9 | 4.06 | 77.39 | 4.19-9.48 |
| 10 | 4.11 | 81.73 | 4.01-6.81 |
| 11 | 4.51 | 103.34 | 7.98-11.84. |

2. The oligosaccharide composition of claim 1, wherein step (b) further comprises removing water from the reaction mixture by evaporation.

3. The oligosaccharide composition of claim 1, wherein the reaction mixture is maintained at its boiling point until the molar ratio of net water condensate produced by the reaction mixture relative to the total dextrose and galactose in the dextrose and galactose preparations prior to loading in (a) is in a range of 0.1-1.0.

4. The oligosaccharide composition of claim 1, wherein, prior to step (b), the temperature of the reaction mixture is gradually increased from room temperature to the boiling point of the reaction mixture under suitable conditions to achieve homogeneity and uniform heat transfer.

5. The oligosaccharide composition of claim 1, wherein the reaction mixture in step (a) comprises a molar ratio of dextrose to galactose of about 1:1.

6. The oligosaccharide composition of claim 1, wherein the process further comprising:
   (c) quenching the reaction mixture using water while bringing the temperature of the reaction mixture to below 100° C.

7. The oligosaccharide composition of claim 6, wherein in step (c) the water has a temperature of about 60-100° C.

8. The oligosaccharide composition of claim 7, wherein the process further comprises: (d) separating at least a portion of the oligosaccharides from the catalyst.

9. The oligosaccharide composition of claim 8, wherein the process further comprises one or more of steps (e) to (g):
   (e) passing the diluted composition through a cationic exchange resin;
   (f) passing the diluted composition through an anionic exchange resin; and
   (g) passing the diluted composition through a decolorizing polymer resin;
wherein each of (e), (f), and (g) can be performed one or more times in any order.

10. The oligosaccharide composition of claim 1, wherein the catalyst is a soluble acid catalyst.

11. The oligosaccharide composition of claim 10, wherein the soluble acid catalyst is citric acid.

12. The oligosaccharide composition of claim 1, wherein the oligosaccharide composition has been subjected to a demonomerization process, optionally wherein the oligosaccharide composition comprises less than 2% monomer.

13. The oligosaccharide composition of claim 1, wherein less than 10% of the oligosaccharide composition or the plurality of oligosaccharides comprise monomers or oligomer subunits that are different from Formula (I), Formula (II), or Formulae (Ia), (Ib), (Ic), (Id), (IIa), (IIb), (IIc), and (IId).

14. The oligosaccharide composition of claim 1, wherein about 75 to 95 weight percent (dry basis) of the oligosaccharide composition comprises oligosaccharides having a degree of polymerization of two or more monomers (DP2+).

15. The oligosaccharide composition of claim 1, wherein the oligosaccharide composition comprises less than 15% monomer (DP1).

16. The oligosaccharide composition of claim 1, wherein the oligosaccharide composition comprises less than 3% w/w impurities.

17. The oligosaccharide composition of claim 16, wherein the impurities comprise levoglucosan, lactic acid, and/or formic acid.

18. The oligosaccharide composition of claim 1, wherein the plurality of oligosaccharides comprises 55% to 95% total dietary fiber (dry basis).

19. The oligosaccharide composition of claim 1, wherein any or all of NMR signals 1-11 are defined as follows:

| Signal | Center Position (ppm) $^1H$ | Center Position (ppm) $^{13}C$ | Area under the curve (AUC) (% of total areas of signals 1-11) |
|---|---|---|---|
| 1 | 3.67 | 63.35 | 20.25-24.97 |
| 2 | 3.97 | 66.25 | 5.03-6.76 |
| 3 | 3.88 | 67.13 | 2.82-4.09 |
| 4 | 3.71 | 67.34 | 6.59-8.15 |
| 5 | 3.83 | 71.27 | 5.91-8.11 |
| 6 | 3.96 | 71.58 | 5.99-7.78 |
| 7 | 3.72 | 72.4 | 6.83-10.61 |
| 8 | 3.33 | 73.76 | 13.78-17.80 |
| 9 | 4.06 | 77.39 | 5.25-8.42 |
| 10 | 4.11 | 81.73 | 4.57-6.25 |
| 11 | 4.51 | 103.34 | 8.75-11.07. |

20. The oligosaccharide composition of claim 1, wherein signals 1-11 are each further characterized by an $^1H$ integral region and a $^{13}C$ integral region, defined as follows:

| Signal | $^1H$ Position (ppm) Center Position | $^1H$ Integral Region from | $^1H$ Integral Region To | $^{13}C$ Position (ppm) Center Position | $^{13}C$ Integral Region from | $^{13}C$ Integral Region to |
|---|---|---|---|---|---|---|
| 1 | 3.67 | 3.607 | 3.742 | 63.35 | 63.78 | 62.92 |
| 2 | 3.97 | 3.925 | 4.008 | 66.25 | 66.78 | 65.73 |
| 3 | 3.88 | 3.848 | 3.910 | 67.13 | 67.50 | 66.76 |
| 4 | 3.71 | 3.674 | 3.753 | 67.34 | 68.02 | 66.65 |
| 5 | 3.83 | 3.791 | 3.864 | 71.27 | 71.70 | 70.84 |
| 6 | 3.96 | 3.906 | 4.014 | 71.58 | 71.91 | 71.24 |
| 7 | 3.72 | 3.669 | 3.777 | 72.4 | 72.78 | 72.02 |
| 8 | 3.33 | 3.262 | 3.404 | 73.76 | 74.29 | 73.23 |
| 9 | 4.06 | 4.022 | 4.108 | 77.39 | 77.89 | 76.90 |
| 10 | 4.11 | 4.066 | 4.147 | 81.73 | 82.15 | 81.32 |
| 11 | 4.51 | 4.461 | 4.556 | 103.34 | 103.95 | 102.72 |

21. The oligosaccharide composition of claim 1, wherein the NMR spectrum is obtained by subjecting a sample of the composition to a multiplicity-edited gradient-enhanced $^1H$-$^{13}C$ heteronuclear single quantum coherence (HSQC) experiment using an echo-antiecho scheme for coherence selection using the pulse sequence diagram as set forth in FIG. 10; and the following acquisition parameters and processing parameters:
   (i) $^1H$ Carrier Frequency=4 ppm;
   (ii) $^{13}C$ Carrier Frequency=65 ppm;
   (iii) Number of points in acquisition dimension=596;
   (iv) Spectral range in acquisition dimension=6.00 ppm to 2.03 ppm;
   (v) Number of points in indirect dimension=300 complex points;
   (vi) Spectral range in indirect dimension=120 ppm to 10 ppm;
   (vii) Recycle delay=1 second;
   (viii) One-bond $^1H$-$^{13}C$ coupling constant=$J_{CH}$=146 Hz;
   (ix) Number of scans=8;
   (x) Temperature=298 K;
   (xi) Solvent=$D_2O$;
   (xii) Window function in direct dimension=Gaussian broadening, 7.66 Hz;
   (xiii) Window function in indirect dimension=Gaussian broadening 26.48 Hz; and
   (xiv) Processing=512 complex points in direct dimension, 1024 complex points in indirect dimension.

22. The oligosaccharide composition of claim 1, wherein the NMR spectrum is obtained by subjecting a sample of the composition to HSQC NMR, wherein the sample is dissolved in D$_2$O.

* * * * *